United States Patent  
Miyazaki et al.

(10) Patent No.: US 10,787,457 B2
(45) Date of Patent: Sep. 29, 2020

(54) FUSED PYRIMIDINE COMPOUND OR SALT THEREOF

(71) Applicant: TAIHO PHARMACEUTICAL CO., LTD., Chiyoda-ku, Tokyo (JP)

(72) Inventors: Isao Miyazaki, Tsukuba (JP); Tadashi Shimamura, Tsukuba (JP); Masanori Kato, Tsukuba (JP); Hidenori Fujita, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 16/203,749

(22) Filed: Nov. 29, 2018

(65) Prior Publication Data
US 2019/0092776 A1 Mar. 28, 2019

Related U.S. Application Data

(60) Division of application No. 15/700,800, filed on Sep. 11, 2017, now Pat. No. 10,233,189, which is a continuation of application No. PCT/JP2016/076354, filed on Sep. 7, 2016.

(30) Foreign Application Priority Data

Sep. 8, 2015 (JP) .................................. 2015-177073

(51) Int. Cl.
A61K 31/519 (2006.01)
A61K 31/5377 (2006.01)
A61P 35/04 (2006.01)
C07D 487/04 (2006.01)
C07D 519/00 (2006.01)

(52) U.S. Cl.
CPC .......... *C07D 487/04* (2013.01); *A61K 31/519* (2013.01); *A61K 31/5377* (2013.01); *A61P 35/04* (2018.01); *C07D 519/00* (2013.01)

(58) Field of Classification Search
CPC ............................ C07D 487/04; C07D 31/519
USPC ........................................ 544/280; 514/265.1
See application file for complete search history.

(56) References Cited

U.S. PATENT DOCUMENTS

| | | | |
|---|---|---|---|
| 5,665,721 A | 9/1997 | Bhagwat et al. | |
| 2016/0115168 A1 | 4/2016 | Iguchi et al. | |
| 2017/0217970 A1 | 8/2017 | Kawai et al. | |
| 2018/0009818 A1 | 1/2018 | Miyazaki et al. | |

FOREIGN PATENT DOCUMENTS

| JP | 2007-521334 A | 8/2007 |
|---|---|---|
| JP | 2008-508358 A | 3/2008 |
| JP | 2009-518434 A | 5/2009 |
| JP | 2015505555 A | 2/2015 |
| WO | 96/40686 A1 | 12/1995 |
| WO | 2004056830 A1 | 7/2004 |
| WO | 2005047289 A1 | 5/2005 |
| WO | 2005062795 A2 | 7/2005 |
| WO | 2006017443 A2 | 2/2006 |
| WO | 2007067781 A2 | 6/2007 |
| WO | 2011018894 A1 | 2/2011 |
| WO | 2013059740 A1 | 4/2013 |
| WO | 2013114113 A1 | 8/2013 |
| WO | 2014130975 A1 | 8/2014 |
| WO | 2014184069 A1 | 11/2014 |
| WO | 2015022926 A1 | 2/2015 |
| WO | 2015078417 A1 | 6/2015 |
| WO | 2017038838 A1 | 3/2017 |
| WO | 2017146116 A1 | 8/2017 |

OTHER PUBLICATIONS

Mulligan, "RET revisited: expanding the oncogenic portfolio", Nature Reviews, 14(3):pp. 173-186, (2014).
Ibanez, "Structure and Physiology of the RET Receptor Tyrosine Kinase", Cold Spring Harbor Perspectives in Biology, 5(2) a009134:pp. 1-10, (2013).
Kohno et al., "KIF5B-RET fusions in lung adenocarcinoma", Nature Medicine, 18(3) :pp. 375-377, (2012).
Santoro et al, "RET/PTC activation in papillary thyroid carcinoma: European Journal of Endocrinology Prize Lecture", European Journal of Endocrinology, 155:pp. 645-653, (2006).
Yeganeh et al, "RET Proto Oncogene Mutation Detection and Medullary Thyroid Carcinoma Prevention", Asian Pacific Journal of Cancer Prevention, 16(6):pp. 2107-2117, (2015).
Gattelli et al.,"Ret inhibition decreases growth and metastatic potential of estrogen receptor positive breast cancer cells", EMBO Molecular Medicine, 5:pp. 1335-1350, (2013).
Ito et al., "Expression of glial cell line—derived neurotrophic factor family members and their receptors in pancreatic cancers", Surgery, 138(4):pp. 788-794, (2005).

(Continued)

*Primary Examiner* — Susanna Moore
(74) *Attorney, Agent, or Firm* — Rothwell, Figg, Ernst & Manbeck, P.C.

(57) ABSTRACT

The present invention provides a novel RET inhibitor comprising, as an active ingredient, a compound or a salt thereof that have not been known for their RET inhibitory activity, and also provides an agent for preventing or treating diseases (e.g., malignant tumors) that can be prevented or treated by RET inhibitory activity. The RET inhibitor comprises, as an active ingredient, a compound represented by Formula (I) below or a salts thereof:

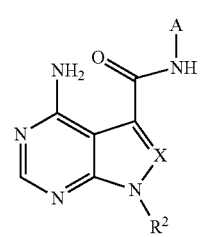

(I)

wherein A, $R^1$ to $R^3$, X, and n are as defined in the specification.

3 Claims, 2 Drawing Sheets

(56) References Cited

OTHER PUBLICATIONS

Dawson et al., "Altered Expression of RET Proto-oncogene Product in Prostatic Intraepithelial Neoplasia and Prostate Cancer", Journal of the National Cancer Institute, 90(7):pp. 519-523, (1998).
Cai et al., "KIF5B-RET Fusions in Chinese Patients With Non-Small Cell Lung Cancer", Cancer, 119:pp. 1486-1494, (2013).
Elisei et al., "Prognostic Significance of Somatic RET Oncogene Mutations in Sporadic Medullary Thyroid Cancer: A 10-Year Follow-Up Study", The Journal of Clinical Endocrinology & Metabolism, 93(3):pp. 682-687, (2008).
Zeng et al., "The Relationship between Over-expression of Glial Cell-derived Neurotrophic Factor and Its RET Receptor with Progression and Prognosis of Human Pancreatic Cancer", The Journal of International Medical Research, 36:pp. 656-664, (2008).
Carlomagno et al, "The Kinase Inhibitor PP1 Blocks Tumorigenesis Induced by RET Oncogenes1" Cancer Research, 62(4):pp. 1077-1082, (2002).
Waltenberger et al, "A Dual Inhibitor of Platelet-Derived Growth Factor b-Receptor and Src Kinase Activity Potently Interferes With Motogenic and Mitogenic Responses to PDGF in Vascular Smooth Muscle Cells a Novel candidate for Prevention of Vascular Remodeling", Circulation Research, 85(1):pp. 12-22, (1999).
Tatton et al., "The Src-selective Kinase Inhibitor PP1 Also Inhibits Kit and Bcr-Abl Tyrosine Kinases*", The Journal of Biological Chemistry, 278(7):pp. 4847-4853, (2003).
Warmuth et al., "Dual-specific Src and Abl kinase inhibitors, PP1 and CGP76030, inhibit growth and survival of cells expressing imatinib mesylate—resistant Bcr-Abl kinases", Blood, 101(2):pp. 664-672, (2003).
Lowe et al., "Osteopetrosis in Src-deficient mice is due to an autonomous defect of osteoclasts", Proceedings of the National Academy of Sciences of the United States of America, 90(10):pp. 4485-4489, (1993).
Molina et al., "Profound block in thymocyte development in mice lacking p56", Nature, 357(6374):pp. 161-164, (1992).
McClellan et al., "Discovery of potent and selective thienopyrimidine inhibitors of Aurora kinases". Bioorganic & Medicinal Chemistry Letters 21, 2011, pp. 5620-5624.
Bavetsias et al., "Aurora Kinase Inhibitors: Current Status and Outlook", Frontiers in Oncology, 2015, vol. 5, Art.278.
Keefe et al., "Tumor control versus adverse events with targeted anticancer therapies" Nature Reviews Clinical Oncology, 2012, vol. 9, No. 2, pp. 98-109.
International Search Repot cited in PCT/JP2016/076354 dated Nov. 1, 2016, 4 pages.
F. Hidenori et al., "4784 / 13—TAS0286/HM05, A Novel Highly Selective RET Inhibitor, Prominently Inhibits Various RET Defective Tumor Growth", AACR Annual Meeting 2018 Online Proceedings and Itinerary Planner Home, Abstract, Apr. 17, 2018, 1 page.
F. Hidenori et al., "TAS0286/HMO5, A Novel Highly Selective RET Inhibitor, Prominently Inhibits Various RET Defective Tumor Growth", 4784 Abstract, Mar. 14, 2018, 1 page.
Fujita et al. (AACR Annual Meeting 2018 Online Proceedings and Itinerary Planner Home, Abstract 4784—TAS0286/HM05, a novel highly selective RET inhibitor, prominently inhibits various RET defective tumor growth, <http://www.abstractsonline.com/pp8/> downloaded Jul. 10, 2018).
Fujita et al. (AACR Annual Meeting 2018 Abstract 4784, Poster #13—TAS0286/H M05, a novel highly selective RET inhibitor, prominently inhibits various RET defective tumor growth, Apr. 17, 2018).
Extended European Search Report dated Jan. 12, 2018, cited in the related European application No. 17756554.6, 6 pages.
Dyson G, "Chemistry of Synthetic Medical Substances", M.: Mir, 1964, pp. 12-19.
Belikov, Pharmaceutical Chemistry in Two Parts, "Pharmaceutical Chemistry", 1993, pp. 43-47.
Mashkovsky, "MD Medicines", 1993, Part 1-S.1,8.
Patani et al., "Bioisosterism: A Rational Approach in Drug Design", Chemical Reviews, 1996, vol. 96, No. 8, pp. 3147-3176.
Office Action for the related RU patent application No. 2018112252, dated Dec. 14, 2018, 20 pages.
Office Action for the related TW patent application No. 105128898, dated Jan. 3, 2019, 8 pages.
Vaughan et al., "Cytoplasmic Dynein Binds Dynactin through a Direct Interaction between the Intermediate Chains and p150 Glued" The Journal of Cell Biology, 1995, Vo. 131, No. 6, pp. 1507-1516.
Wang et al., Fusion of dynactin 1 to anaplastic lymphoma kinase in inflammatory myofibroblastic tumor, Human Pathology, 2012, vol. 43, pp. 2047-2052.
Chen et al., "Increasing Incidence of Differentiated Thyroid Cancer in the United States, 1988-2005", Cancer, 2009, vol. 115, No. 16, pp. 3801-3807.
Yoh et al., Vandetanib in patients with previously treated RET-rearranged advanced non-small-cell lung cancer (LURET): an open-label, multicentre phase 2 trial, Lancet Respiratory Medicine, 2017, vol. 5, pp. 42-50.
Soares et al., "BRAF mutations and RET/PTC rearrangements are alternative events in the etiopathogenesis of PTC" Oncogene, 2003, vol. 22, No. 29, pp. 4578-4580.
"Integrated Genomic Characterization of Papillary Thyroid Carcinoma", Cell, 2014, vol. 159, No. 3, pp. 676-690.
Drilon et al., "Response to Cabozantinib in Patients with RET Fusion-Positive Lung Adenocarcinomas", Cancer Discovery, 2013, vol. 3, No. 6, pp. 630-635.
"Comprehensive molecular profiling of lung adenocarcinoma", Nature, 2014, vol. 511, No. 7511, pp. 543-550.

FUSED PYRIMIDINE COMPOUND OR SALT THEREOF

CROSS-REFERENCE TO RELATED PATENT APPLICATIONS

The present application is a divisional of U.S. Ser. No. 15/700,800 filed Sep. 11, 2017, which is a continuation of PCT/JP2016/076354, filed Sep. 7, 2016, which claims priority to Japanese Patent Application No. 2015-177073 filed on Sep. 8, 2015, which are incorporated by reference in their entirety.

TECHNICAL FIELD

The present invention relates to a novel fused pyrimidine compound having RET inhibitory activity or a salt thereof, and to a pharmaceutical composition containing the compound or salt.

BACKGROUND ART

Various protein kinases are present in vivo and are known to be involved in a wide range of functional regulations. RET is a receptor tyrosine kinase identified as one of the proto-oncogenes. RET binds to the glial cell line-derived neurotrophic factor (GDNF) and GDNF receptor to form a complex, which enables RET to perform physiological functions through intracellular phosphorylation signaling (Non-patent Literature 1). A study reports that in normal tissues, RET contributes to kidney development and neurogenesis during fetal life (Non-patent Literature 2). Some studies indicate that in cancers, such as lung cancer, thyroid cancer, breast cancer, pancreas cancer, and prostate cancer, the translocation, mutation, or overexpression of the RET gene enhances its activation to thereby contribute to cell growth, tumor formation, or tissue infiltration (Non-patent Literature 3, 4, 5, 6, 7, and 8). In addition, RET is known to be an adverse prognostic factor of cancer, as indicated in some reports that the translocation of RET and its enhanced activation level are also inversely correlated with prognosis in cancer (Non-patent Literature 9, 10, 11, and 12).

Therefore, an inhibitor capable of inhibiting RET activity is thought to be useful as a therapeutic agent for diseases associated with abnormally enhanced RET signaling pathways.

It is expected, for example, that in cancers involving translocated, mutated, and overexpressed RET genes, the administration of a medicament capable of specifically inhibiting RET will selectively and intensively suppress the proliferation of cancer cells and contribute to the treatment, life prolongation, and improvement in quality of life of cancer patients.

As an example of such compounds having RET inhibitory activity, PP1 is known (Non-patent Literature 13). PP1 is known to exhibit high inhibitory activity against not only RET but also SRC (Non-patent Literature 14), c-Kit, Bcr-Abl (Non-patent Literature 15 and 16), and others. For example, as side effects, the inhibition of SRC may lead to abnormally enhanced bone formation, and the inhibition of LCK may suppress T cells (Non-patent Literature 17 and 18). Since multikinase inhibitors inhibit not only RET but also various signaling pathways, inhibiting cell growth and other functions, the inhibitors raise concerns about possible various side effects, which may require dose reduction or drug holidays, thus leading to insufficient RET inhibitory activity. From the standpoint of side effect reduction, there has been a demand for a RET inhibitor having high inhibitory activity against RET while exhibiting low inhibitory activity against other kinases.

CITATION LIST

Patent Literature

Patent Literature 1: U.S. Pat. No. 5,665,721
Patent Literature 2: WO96/40686A1

Non-Patent Literature

Non-patent Literature 1: Lois M. Mulligan, Nature Rev., 14(3): pp. 173-186, (2014)
Non-patent Literature 2: Carlos F. Ibanez, Cold Spring Harb Perspect Biol., 5(2): pp. 1-10, (2013)
Non-patent Literature 3: Takashi Kohno, Nature Med., 18(3): pp. 375-377, (2012)
Non-patent Literature 4: Massimo Santoro, Eur J Endocrinol., 155: pp. 645-653, (2006)
Non-patent Literature 5: Marjan Zarif Yeganeh, Asian Pac J Cancer Prev., 16(6): pp. 2107-2117, (2015)
Non-patent Literature 6: Albana Gattelli, EMBO Mol Med., 5: pp. 1335-1350, (2013)
Non-patent Literature 7: Yoshinori Ito, Surgery, 138: pp. 788-794, (2005)
Non-patent Literature 8: Dawn M. Dawson, J Natl Cancer Inst., 90(7): pp. 519-523, (1998)
Non-patent Literature 9: Weijing Cai, Cancer, 119: pp. 1486-1494, (2013)
Non-patent Literature 10: Rossella Elisei, J Clin Endocrinol Metab., 93(3): pp. 682-687, (2008)
Non-patent Literature 11: Albana Gattelli, EMBO Mol Med., 5: pp. 1335-1350, (2013)
Non-patent Literature 12: Q Zeng, J. Int. Med. Res., 36: pp. 656-664, (2008)
Non-patent Literature 13: Francesca Carlomagno, Cancer Res., 62(4): pp. 1077-1082, (2002)
Non-patent Literature 14: Johannes Waltenberger, Circ Res., 85(1): pp. 12-22, (1999)
Non-patent Literature 15: Louise Tatton, J Biol Chem., 278(7): pp. 4847-4853, (2003)
Non-patent Literature 16: Markus Warmuth, Blood. 101(2): pp. 664-672, (2003)
Non-patent Literature 17: Carolyn Lowe, Proc Natl Acad Sci USA, 90(10): pp. 4485-4489, (1993)
Non-patent Literature 18: Thierry Molina, Nature, 357 (6374): pp. 161-164, (1992)

SUMMARY OF INVENTION

Technical Problem

An object of the present invention is to provide a novel RET inhibitor comprising, as an active ingredient, a compound or a salt thereof that have not been known for their RET inhibitory activity, and to also provide an agent for preventing or treating diseases (e.g., malignant tumors) that can be prevented or treated by RET inhibitory activity. Another object of the present invention is to provide a novel compound or a salt thereof that selectively and potently inhibit RET.

Solution to Problem

The present inventors conducted extensive research to achieve the above objects, and consequently found that a compound group represented by Formulas (I) and (I') below showed excellent inhibitory activity against RET and kinase selectivity, and was useful as a pharmaceutical preparation for treating RET-related diseases, such as malignant tumors. Thus, the present invention has been completed.

Specifically, the present invention provides a compound represented by Formula (I) below or a salt thereof:

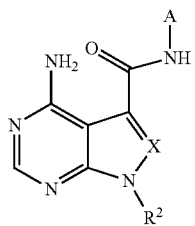
(I)

wherein A is pyrazolyl substituted with n-number of $R^1$;
$R^1$ is
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
$R^2$ is
substituted or unsubstituted C1-C10 alkyl,
substituted or unsubstituted C3-C7 cycloalkyl,
substituted or unsubstituted C2-C6 alkenyl,
substituted or unsubstituted C3-C7 cycloalkenyl,
substituted or unsubstituted C4-C12 bridged cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
X is
N or
$CR^3$, wherein $R^3$ is
　hydrogen,
　halogen,
　cyano,
　substituted or unsubstituted C1-C6 alkyl,
　substituted or unsubstituted C2-C6 alkenyl,
　substituted or unsubstituted C2-C6 alkynyl,
　substituted or unsubstituted C1-C6 alkoxy,
　substituted or unsubstituted amino,
　substituted or unsubstituted C6-C14 aromatic hydrocarbon, or
　a substituted or unsubstituted C3-C10 monocyclic or polycyclic unsaturated heterocyclic group containing 1 to 3 identical or different heteroatoms selected from nitrogen, oxygen, and sulfur; and
n is an integer of 0 to 3,
wherein when n is 2 or 3, $R^1$ may be identical or different from each other.

The present invention also provides a compound represented by Formula (I') below or a salt thereof:

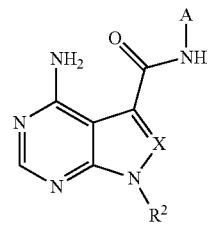
(I')

wherein A is pyrazolyl substituted with n-number of $R^1$;
$R^1$ is
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
$R^2$ is
substituted or unsubstituted C1-C10 alkyl,
substituted or unsubstituted C3-C4 cycloalkyl,
substituted or unsubstituted C2-C6 alkenyl,
substituted or unsubstituted C3-C4 cycloalkenyl,
substituted or unsubstituted C4-C12 bridged cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
X is
N or
$CR^3$, wherein $R^3$ is
　hydrogen,
　halogen,
　cyano,
　substituted or unsubstituted C1-C6 alkyl,
　substituted or unsubstituted C2-C6 alkenyl,
　substituted or unsubstituted C2-C6 alkynyl,
　substituted or unsubstituted C1-C6 alkoxy,
　substituted or unsubstituted amino,
　substituted or unsubstituted C6-C14 aromatic hydrocarbon, or
　a substituted or unsubstituted C3-C10 monocyclic or polycyclic unsaturated heterocyclic group containing 1 to 3 identical or different heteroatoms selected from nitrogen, oxygen, and sulfur; and
n is an integer of 0 to 3,
wherein when n is 2 or 3, $R^1$ may be identical or different from each other.

The present invention also provides a RET inhibitor comprising a compound represented by Formula (I) or (I') above or a salt thereof as an active ingredient.

The present invention also provides a pharmaceutical composition comprising a compound represented by Formula (I) or (I') above or a salt thereof.

The present invention also provides a pharmaceutical composition comprising a compound represented by Formula (I) or (I') above or a salt thereof, wherein the pharmaceutical composition prevents or treats a disease that can be treated by RET inhibition.

The present invention also provides an antitumor agent comprising a compound represented by Formula (I) or (I') above or a salt thereof.

The present invention also provides an antitumor agent comprising a compound represented by Formula (I) or (I') above or a salt thereof, wherein the antitumor agent treats a malignant tumor with enhanced activation of RET.

The present invention also provides a compound represented by Formula (I) or (I') above or a salt thereof for use in prevention or treatment of a malignant tumor.

The present invention also provides a compound represented by Formula (I) or (I') above or a salt thereof for use in prevention or treatment of a malignant tumor, wherein the malignant tumor is a malignant tumor with enhanced activation of RET.

The present invention also provides use of a compound represented by Formula (I) or (I') above or a salt thereof for producing an antitumor agent.

The present invention also provides use of a compound represented by Formula (I) or (I') above or a salt thereof for producing an antitumor agent, wherein the antitumor agent is an antitumor agent for treating a malignant tumor with enhanced activation of RET.

The present invention also provides use of a compound represented by Formula (I) or (I') above or a salt thereof for producing a RET inhibitor.

The present invention also provides a method for preventing or treating a malignant tumor, comprising administering a compound represented by Formula (I) or (I') above or a salt thereof to a mammal.

The present invention also provides a method for preventing or treating a malignant tumor, comprising administering a compound represented by Formula (I) or (I') above or a salt thereof to a mammal, wherein the malignant tumor is a malignant tumor with enhanced activation of RET.

The present invention also provides a method of inhibiting RET comprising administering a compound represented by Formula (I) or (I') above or a salt thereof to a mammal.

Patent Literature 1 and 2 do not suggest RET inhibitory activity or antitumor effects.

PP1 mentioned above is known as a compound having RET inhibitory activity. In PP1, a p-toluyl group is bonded to a fused ring pyrimidine skeleton; however, its structure is significantly different from the present invention in that PP1 does not have a pyrazolyl group continuous with an amide bond, which is the feature of the compound of the present invention. Moreover, as shown in Test Examples provided later, the compound or a salt thereof of the present invention has the characteristic of a high RET selectivity, which is different from PP1.

Advantageous Effects of Invention

The present invention can provide a novel RET inhibitor and an agent for preventing or treating diseases (e.g., malignant tumors) that can be prevented or treated by RET inhibitory activity, by using, as their active ingredients, compounds represented by Formulas (I) and (I') or salts thereof, which have not been known for their RET inhibitory activity. In particular, a novel compound represented by Formula (I') or a salt thereof, etc., are preferred.

It was revealed that the compound or a salt thereof of the present invention has excellent RET-selective inhibitory activity and a cancer cell growth inhibitory effect.

RET is known as an oncogene and known to be activated by the translocation, mutation, or overexpression of the RET gene in many types of cancer (Non-patent Literature 3, 4, 5, 6, 7, and 8). Thus, the compound or a salt thereof of the present invention, both of which have a high RET inhibitory activity, is useful as an agent for preventing and/or treating cancer.

Further, the compound or a salt thereof of the present invention selectively and potently inhibits RET, rather than other kinases, such as SRC and LCK; therefore, side effects can be reduced, and improvement in safety can be expected.

Moreover, the compound or a salt thereof of the present invention is advantageous in that it has excellent stability in hepatic microsomes, excellent exposure in the blood can be expected, and there is no concern about Cyp inhibition.

DESCRIPTION OF EMBODIMENTS

Figure 1:
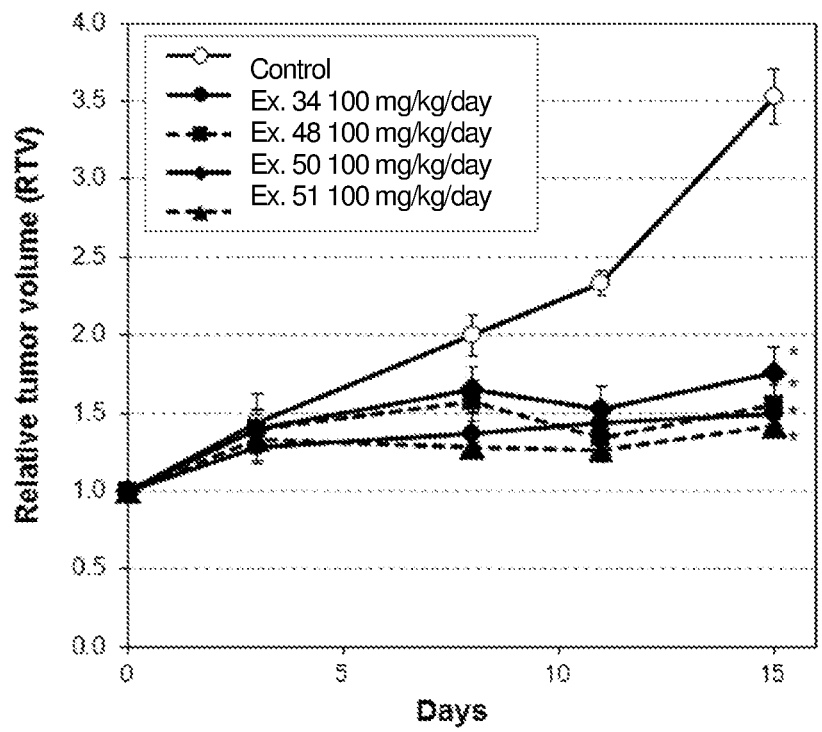
FIG. 1 illustrates changes in relative tumor volume during the test in Test Example 5.

The compounds of the present invention represented by Formulas (I) and (I') above are compounds having a fused ring pyrimidine skeleton with a pyrazolyl group via an amide bond, and they have not been known for their RET inhibitory activity. In particular, the compound represented by Formula (I') above or a salt thereof, etc., are novel compounds that are not disclosed in any of the above prior art documents.

In the present invention, the compounds represented by Formulas (I) and (I') are also referred to simply as "Compound (I)" and "Compound (I')," respectively.

In the present specification, unless otherwise specified, examples of the "substituent" include halogen, hydroxy, cyano, nitro, alkyl, halogenoalkyl, hydroxyalkyl, alkoxyalkyl, cycloalkyl, cycloalkyl-alkyl, bridged cycloalkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or dialkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, saturated heterocyclic oxy, etc. (These substituents are also referred to as "Substituents B.") When a substituent listed above is present, the number thereof is typically one, two, or three.

In the present specification, examples of the "halogen" include fluorine, chlorine, bromine, and iodine.

In the present specification, the "alkyl" may be linear or branched. Examples include methyl, ethyl, n-propyl, isopropyl, n-butyl, isobutyl, tert-butyl, 1-methylpropyl, n-pentyl, isopentyl, n-hexyl, 1,1-dimethylpropyl, 1,1,2,2-tetramethylethyl, n-heptyl, 1,1,2,2-tetramethylpropyl, n-octyl, n-nonyl, n-decyl, etc.; and specifically include C1-C10 alkyl, C1-C6 alkyl, etc.

In the present specification, examples of the "halogenoalkyl" include C1-C10 linear or branched alkyl having one or more (e.g., 1 to 10, 1 to 7, or 1 to 5) halogen atoms (halogeno C1-C10 alkyl). Examples include fluoromethyl, difluoromethyl, trifluoromethyl, trichloromethyl, fluoroethyl, 1,1,1-trifluoroethyl, monofluoro-n-propyl, perfluoro-n-propyl, perfluoroisopropyl, monofluoro-n-butyl, monofluoro-n-pentyl, monofluoro-n-hexyl, etc.; and specifically include halogeno C1-C6 alkyl, halogeno C1-C4 alkyl, etc.

In the present specification, examples of the "hydroxyalkyl" include C1-C10 linear or branched alkyl having one or more (e.g., 1 to 5, 1 to 3, or 1) hydroxy groups (hydroxy C1-C10 alkyl). Examples include hydroxymethyl, hydroxyethyl (1-hydroxyethyl or 2-hydroxyethyl), hydroxypropyl, hydroxybutyl, hydroxypentyl, hydroxyhexyl, etc.; and specifically include hydroxy C1-C6 alkyl, hydroxy C1-C4 alkyl, etc.

In the present specification, examples of the "alkoxyalkyl" include alkoxyalkyl in which the alkoxy moiety is C1-C6 linear or branched alkoxy, and the alkyl moiety is C1-C10 linear or branched alkyl (C1-C6 alkoxy C1-C10 alkyl). Examples of C1-C6 linear or branched alkoxy include those in which the alkyl moiety is C1-C6 alkoxy among the examples of the alkyl mentioned above. Examples of the alkoxyalkyl include methoxymethyl, ethoxymethyl, n-propoxymethyl, n-butoxymethyl, 2-methoxyethyl, 1-methoxy-n-propyl, 3-methoxy-n-propyl, 2-ethoxy-n-butyl, 4-methoxy-n-butyl, 5-methoxy-n-pentyl, 6-methoxy-n-hexyl, etc.; and specifically include C1-C4 alkoxy C1-C6 alkyl, C1-C4 alkoxy C1-C4 alkyl, etc.

In the present specification, specific examples of the "cycloalkyl" include cyclopropyl, cyclobutyl, cyclopentyl, cyclohexyl, cycloheptyl, etc.; and specifically include C3-C7 cycloalkyl, C3-C5 cycloalkyl, C3-C4 cycloalkyl, etc. In the present invention, the "cycloalkyl" should be specified independently from "bridged cycloalkyl," described later. Therefore, in the present invention, the "bridged cycloalkyl" is excluded from the "cycloalkyl".

In the present specification, examples of the "cycloalkylalkyl" include cyclopropylmethyl, cyclobutylmethyl, cyclopentylmethyl, cyclohexylmethyl, cycloheptylmethyl, etc.; and specifically include C3-C7 cycloalkyl-substituted C1-C10 alkyl, C3-C5 cycloalkyl-substituted C1-C6 alkyl, etc.

In the present specification, the "bridged cycloalkyl" refers to bridged cyclic hydrocarbon in which the carbocyclic ring constituting the bridged cyclic hydrocarbon has a saturated structure. In the present specification, examples of the "bridged cycloalkyl" include bicyclo[1.1.0]butyl (bicyclo[1.1.0]butan-1-yl or bicyclo[1.1.0]butan-2-yl), bicyclo[1.1.1]pentyl (bicyclo[1.1.1]pentan-1-yl or bicyclo[1.1.1]pentan-2-yl), bicyclo[3.1.0]hexyl (bicyclo[3.1.0]hexan-1-yl, bicyclo[3.1.0]hexan-2-yl, bicyclo[3.1.0]hexan-3-yl, or bicyclo[3.1.0]hexan-6-yl), bicyclo[2.2.1]heptyl (bicyclo[2.2.1]heptan-1-yl, bicyclo[2.2.1]heptan-2-yl, or bicyclo[2.2.1]heptan-7-yl), bicyclo[3.1.1]heptyl (bicyclo[3.1.1]heptan-1-yl, bicyclo[3.1.1]heptan-2-yl, bicyclo[3.1.1]heptan-3-yl, or bicyclo[3.1.1]heptan-6-yl), adamanthyl (adamantan-1-yl or adamantan-2-yl), etc.; and specifically include C4-C12 bridged cycloalkyl, etc.

In the present specification, examples of the "aralkyl" include benzyl, phenethyl, naphthylmethyl, fluorenylmethyl, etc.; and specifically include C7-C14 aralkyl, etc.

In the present specification, the "alkenyl" may be linear or branched, and refers to unsaturated aliphatic hydrocarbon having at least one (e.g., 1 or 2, or 1) double bond. Examples include vinyl, allyl, 1-propenyl, 2-methyl-2-propenyl, isopropenyl, 1-, 2- or 3-butenyl, 2-, 3-, or 4-pentenyl, 2-methyl-2-butenyl, 3-methyl-2-butenyl, 5-hexenyl, 1-cyclopentenyl, 1-cyclohexenyl, 3-methyl-3-butenyl, etc.; and specifically include C2-C6 alkenyl, C2-C4 alkenyl, etc.

In the present specification, the "cycloalkenyl" refers to unsaturated alicyclic hydrocarbon having at least one (e.g., 1 or 2, or 1) double bond. Examples include cyclopropenyl (e.g., 2-cyclopropen-1-yl), cyclobutenyl (e.g., 2-cyclobuten-1-yl), cyclopentenyl (e.g., 2-cyclopenten-1-yl and 3-cyclopenten-1-yl), cyclopentadienyl (e.g., 2,4-cyclopentadien-1-yl), cyclohexenyl (e.g., 3-cyclohexen-1-yl), cycloheptenyl (e.g., 3-cyclohepten-1-yl), etc.; and specifically include C3-C7 cycloalkenyl, C3-C5 cycloalkenyl, C3-C4 cycloalkenyl, etc.

In the present specification, the "alkynyl" may be linear, branched, or cyclic, and refers to unsaturated hydrocarbon having at least one triple bond. Examples include ethynyl, 1- or 2-propynyl, 1-, 2- or 3-butynyl, 1-methyl-2-propynyl, etc.; and specifically include C2-C6 alkynyl, C2-C4 alkynyl, etc.

In the present specification, the "alkoxy" may be linear or branched. Examples include methoxy, ethoxy, propoxy, isopropoxy, butoxy, isobutoxy, tert-butoxy, pentyloxy, isopentyloxy, hexyloxy, etc.; and specifically include C1-C6 alkoxy, C1-C4 alkoxy, etc.

In the present specification, the "halogenoalkoxy" refers to C1-C6 linear or branched alkoxy having one or more (e.g., 1 to 10, 1 to 7, or 1 to 5) halogen atoms (halogeno C1-C6 alkoxy). Examples include fluoromethoxy, difluoromethoxy, trifluoromethoxy, trichloromethoxy, fluoroethoxy, 1,1,1-trifluoroethoxy, monofluoro-n-propoxy, perfluoro-n-propoxy, perfluoro-isopropoxy, etc.; and specifically include halogeno C1-C6 alkoxy, halogeno C1-C4 alkoxy, etc.

In the present specification, specific examples of the "cycloalkoxy" include cyclopropoxy, cyclobutoxy, cyclopenthyloxy, cyclohexyloxy, cycloheptyloxy, etc.; and specifically include C3-C7 cycloalkoxy.

In the present specification, examples of the "cycloalkylalkoxy" include cyclopropylmethoxy, cyclobutylmethoxy, cyclopentylmethoxy, cyclohexylmethoxy, cycloheptylmethoxy, etc.; and specifically include C3-C7 cycloalkyl-substituted C1-C4 alkoxy, etc.

In the present specification, examples of the "aralkyloxy" include benzyloxy, phenethyloxy, naphthylmethyloxy, fluorenylmethyloxy, etc.; and specifically include C7-C14 aralkyloxy, etc.

In the present specification, the "alkylthio" may be linear or branched. Examples include methylthio, ethylthio, n-propylthio, isopropylthio, n-butylthio, isobutylthio, tert-butylthio, n-pentylthio, isopentylthio, hexylthio, etc.; and specifically include C1-C6 alkylthio, C1-C4 alkylthio, etc.

In the present specification, examples of the "cycloalkylalkylthio" include cyclopropylmethylthio, cyclobutylmethylthio, cyclopentylmethylthio, cyclohexylmethylthio, cycloheptylmethylthio, etc.; and specifically include C3-C7 cycloalkyl-substituted C1-C4 alkylthio, etc.

In the present specification, examples of the "monoalkylamino" include methylamino, ethylamino, n-propylamino, isopropylamino, n-butylamino, isobutylamino, tert-butylamino, n-pentylamino, isopentylamino, hexylamino, etc.; and specifically include amino mono-substituted with linear or branched C1-C6 alkyl.

In the present specification, examples of the "dialkylamino" include dimethylamino, ethylmethylamino, diethylamino, di(n-propyl)amino, diisopropylamino, di(n-butyl)amino, diisobutylamino, di(tert-butyl)amino, di(n-pentyl)amino, diisopentylamino, dihexylamino, etc.; and specifically include amino di-substituted with linear or branched C1-C6 alkyl.

In the present specification, examples of the "cycloalkylalkylamino" include cyclopropylmethylamino, cyclobutylmethylamino, cyclopentylmethylamino, cyclohexylmethyl-amino, cycloheptylmethylamino, etc.; and specifically include C3-C7 cycloalkyl-substituted C1-C4 alkylamino, etc.

In the present specification, the "acyl" refers to alkylcarbonyl or arylcarbonyl.

In the present specification, examples of the "alkylcarbonyl" include methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, hexylcarbonyl, etc.; and specifically include linear or branched (C1-C6 alkyl)carbonyl, etc.

In the present specification, examples of the "arylcarbonyl" include phenylcarbonyl, naphthylcarbonyl, fluorenylcarbonyl, anthrylcarbonyl, biphenylylcarbonyl, tetrahydronaphthylcarbonyl, chromanylcarbonyl, 2,3-dihydro-1,4-dioxanaphthalenylcarbonyl, indanylcarbonyl, phenanthrylcarbonyl, etc.; and specifically include (C6-C14 aryl)carbonyl, etc.

In the present specification, the "acyloxy" refers to alkylcarbonyloxy or arylcarbonyloxy.

In the present specification, examples of the "alkylcarbonyloxy" include methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, hexylcarbonyloxy, etc.; and specifically include linear or branched (C1-C6 alkyl)carbonyloxy, etc.

In the present specification, examples of the "arylcarbonyloxy" include phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, phenanthrylcarbonyloxy, etc.; and specifically include (C6-C14 aryl)carbonyloxy, etc.

In the present specification, the "alkoxycarbonyl" may be linear or branched. Examples include methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, hexyloxycarbonyl, etc.; and specifically include (C1-C6 alkoxy)carbonyl, etc.

In the present specification, examples of the "aralkyloxycarbonyl" include benzyloxycarbonyl, phenethyloxycarbonyl, naphthylmethyloxycarbonyl, fluorenylmethyloxycarbonyl, etc.; and specifically include (C7-C14 aralkyl) oxycarbonyl, etc.

In the present specification, the "saturated heterocyclic group" refers to a monocyclic or polycyclic saturated heterocyclic group having a heteroatom selected from nitrogen, oxygen, and sulfur. Specific examples include morpholino, 1-pyrrolidinyl, piperidino, piperazinyl, 4-methyl-1-piperazinyl, tetrahydrofuranyl, tetrahydropyranyl, tetrahydrothiophenyl, thiazolidinyl, oxazolidinyl, 7-azabicyclo[2.2.1]hept-2-yl, 2,6-dioxabicyclo[3.2.1]oct-7-yl, etc. In the present invention, examples of the saturated heterocyclic group include a "C3-C10 monocyclic or polycyclic saturated heterocyclic group containing 1 to 3 identical or different heteroatoms selected from nitrogen, oxygen, and sulfur," a "C3-C6 monocyclic saturated heterocyclic group containing 1 to 3 identical or different heteroatoms selected from nitrogen, oxygen, and sulfur," and a "C4-C5 monocyclic saturated heterocyclic group containing 1 to 3 identical or different heteroatoms selected from nitrogen and oxygen."

In the present specification, the "unsaturated heterocyclic group" refers to a monocyclic or polycyclic, completely or partially unsaturated heterocyclic group having a heteroatom selected from nitrogen, oxygen, and sulfur. Specific examples include imidazolyl, thienyl, furanyl, pyrrolyl, oxazolyl, isoxazolyl, triazolyl, isothiazolyl, thiadiazolyl, pyrazolyl, triazolyl, tetrazolyl, pyridyl, pyrazyl, pyrimidinyl, pyridazinyl, indolyl, isoindolyl, indazolyl, triazolopyridyl, benzoimidazolyl, benzoxazolyl, benzothiazolyl, benzothienyl, benzofuranyl, purinyl, quinolyl, isoquinolyl, quinazolinyl, quinoxalinyl, methylenedioxyphenyl, ethylenedioxyphenyl, dihydrobenzofuranyl, etc. In the present invention, examples of the unsaturated heterocyclic group include a "C3-C10 monocyclic or polycyclic unsaturated heterocyclic group containing 1 to 3 identical or different heteroatoms selected from nitrogen, oxygen, and sulfur," a "C3-C6 monocyclic unsaturated heterocyclic group containing 1 to 3 identical or different heteroatoms selected from nitrogen, oxygen, and sulfur," a "C4-C5 monocyclic unsaturated heterocyclic group containing 1 or 2 identical or different heteroatoms selected from nitrogen, oxygen, and sulfur," a "C4-C5 monocyclic unsaturated heterocyclic group containing one nitrogen atom, one oxygen atom, or one sulfur atom," a "C4-C5 monocyclic unsaturated heterocyclic group containing one oxygen atom or one sulfur atom," and a "C3-C6 monocyclic unsaturated heterocyclic group containing 1 to 3 nitrogen atoms."

In the present specification, the "aromatic hydrocarbon" (aryl) include phenyl, tolyl, xylyl, naphthyl, anthracenyl, phenanthryl, fluorenyl, tetrahydronaphthyl, etc.; and specifically include C6-C14 aromatic hydrocarbon, etc.

In the present specification, the "saturated heterocyclic oxy" refers to oxy to which a saturated heterocyclic ring having a heteroatom selected from nitrogen, oxygen, and sulfur is bonded. Specific examples include morpholinyloxy, 1-pyrrolidinyloxy, piperidinooxy, piperazinyloxy, 4-methyl-1-piperazinyloxy, tetrahydrofuranyloxy, tetrahydropyranyloxy, tetrahydrothiophenyloxy, thiazolidinyloxy, and oxazolidinyloxy.

The term "Ca-Cb" in the description regarding the substituent in the present specification indicates that the substituent has a- to b-number of carbon atoms. For example, "C1-C6 alkyl" refers to alkyl having 1 to 6 carbon atoms, and "C6-C14 aromatic hydrocarbon oxy" refers to oxy to which C6-C14 aromatic hydrocarbon is bonded. Further, the term "a- to b-membered" indicates that the number of atoms (number of ring members) that constitute the ring is a to b. For example, a "4- to 10-membered saturated heterocyclic group" refers to a saturated heterocyclic group with a 4- to 10-membered ring.

In Formulas (I) and (I'), A is pyrazolyl substituted with n-number of $R^1$. Examples of the pyrazolyl represented by A include pyrazol-1-yl, pyrazol-3-yl, pyrazol-4-yl, and pyrazol-5-yl. Pyrazol-3-yl is preferred in the present invention.

In Formulas (I) and (I'), examples of the "halogen" represented by $R^1$ include those mentioned above, preferably chlorine and bromine, and more preferably bromine.

In Formulas (I) and (I'), examples of the "C1-C6 alkyl" in the "substituted or unsubstituted C1-C6 alkyl" represented by $R^1$ include those mentioned above, and preferably C1-C4 alkyl. Specific examples include methyl, ethyl, n-propyl, isopropyl, etc.; more preferably methyl and ethyl; and even more preferably methyl.

Examples of the "substituent" in the "substituted or unsubstituted C1-C6 alkyl" represented by $R^1$ include those mentioned above, and preferably halogen and C1-C4 alkoxy. Specific examples include fluorine, methoxy, etc.; more preferably halogen; and even more preferably fluorine.

When the C1-C6 alkyl is substituted, the number of substituents is not particularly limited, but is preferably 1 to 3. When the substituent is halogen, the number of substituents is preferably 2 or 3. When the substituent is C1-C4 alkoxy, the number of substituents is preferably 1.

The "substituted or unsubstituted C1-C6 alkyl" represented by $R^1$ is preferably C1-C6 alkyl that may be substituted with halogen or C1-C4 alkoxy. Specific examples include methyl, ethyl, n-propyl, isopropyl, trifluoromethyl, difluoromethyl, methoxymethyl, etc.; more preferably C1-C6 alkyl that may be substituted with halogen; even more preferably C1-C4 alkyl that may be substituted with halogen; still more preferably C1-C4 alkyl that may be substituted with fluorine; further still more preferably C1-C4 alkyl; and further still more preferably methyl.

In Formulas (I) and (I'), examples of the "C3-C7 cycloalkyl" in the "substituted or unsubstituted C3-C7 cycloalkyl" represented by $R^1$ include those mentioned above; preferably cyclopropyl, cyclobutyl, and cyclopentyl; and more preferably cyclopropyl.

Examples of the "substituent" in the "substituted or unsubstituted C3-C7 cycloalkyl" represented by $R^1$ include those mentioned above.

The "substituted or unsubstituted C3-C7 cycloalkyl" represented by $R^1$ is preferably C3-C7 cycloalkyl. Specific examples include cyclopropyl, cyclobutyl, cyclopentyl, etc.; more preferably C3-C5 cycloalkyl; and even more preferably cyclopropyl.

In Formulas (I) and (I'), examples of the "C6-C14 aromatic hydrocarbon" in the "substituted or unsubstituted C6-C14 aromatic hydrocarbon" represented by $R^1$ include those mentioned above, and preferably phenyl.

Examples of the "substituent" in the "substituted or unsubstituted C6-C14 aromatic hydrocarbon" represented by $R^1$ include those mentioned above.

The "substituted or unsubstituted C6-C14 aromatic hydrocarbon" represented by $R^1$ is preferably phenyl.

In Formulas (I) and (I'), the "C3-C10 monocyclic or polycyclic saturated or unsaturated heterocyclic group containing 1 to 3 identical or different heteroatoms selected from nitrogen, oxygen, and sulfur" in the "substituted or unsubstituted C3-C10 monocyclic or polycyclic saturated or unsaturated heterocyclic group containing 1 to 3 identical or different heteroatoms selected from nitrogen, oxygen, and sulfur" represented by $R^1$ is preferably a C3-C6 monocyclic unsaturated heterocyclic group containing one oxygen atom or one sulfur atom; more preferably a C4-C5 monocyclic unsaturated heterocyclic group containing one oxygen atom or one sulfur atom; even more preferably thienyl and furanyl; still more preferably the following:

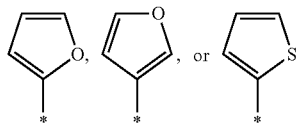

wherein * represents a bonding position (hereinafter the same) and further still more preferably the following:

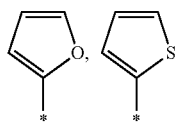

Examples of the "substituent" in the "substituted or unsubstituted C3-C10 monocyclic or polycyclic saturated or unsaturated heterocyclic group containing 1 to 3 identical or different heteroatoms selected from nitrogen, oxygen, and sulfur" represented by $R^1$ include those mentioned above.

The "substituted or unsubstituted C3-C10 monocyclic or polycyclic saturated or unsaturated heterocyclic group containing 1 to 3 identical or different heteroatoms selected from nitrogen, oxygen, and sulfur" represented by $R^1$ is preferably a C3-C6 monocyclic unsaturated heterocyclic group containing one oxygen atom or one sulfur atom; more preferably a C4-C5 monocyclic unsaturated heterocyclic group containing one oxygen atom or one sulfur atom; even more preferably thienyl or furanyl; still more preferably the following:

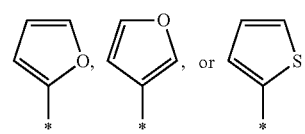

and further still more preferably the following:

[Formula 6]

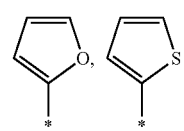

In Formulas (I) and (I'), $R^1$ is preferably
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur.
$R^1$ is more preferably
halogen;
cyano;
C1-C6 alkyl that may be substituted with halogen or C1-C4 alkoxy;
C3-C7 cycloalkyl;
phenyl; or
a C3-C6 monocyclic unsaturated heterocyclic group containing one oxygen atom or one sulfur atom.
$R^1$ is even more preferably
halogen;
cyano;
C1-C6 alkyl that may be substituted with halogen;
C3-C7 cycloalkyl;
phenyl; or
a C3-C6 monocyclic unsaturated heterocyclic group containing one oxygen atom or one sulfur atom.
$R^1$ is still more preferably
halogen,
cyano, or
C1-C4 alkyl that may be substituted with halogen.
$R^1$ is further still more preferably halogen or C1-C4 alkyl.
$R^1$ is further still more preferably methyl.

In Formulas (I) and (I'), examples of the "C1-C10 alkyl" in the "substituted or unsubstituted C1-C10 alkyl" represented by R² include those mentioned above; preferably linear C1-C6 alkyl or branched C3-C8 alkyl; more preferably linear C1-C4 alkyl or branched C3-C8 alkyl; even more preferably linear C1-C4 alkyl or branched C3-C6 alkyl; and still more preferably branched C3-C6 alkyl.

The linear C1-C4 alkyl is preferably methyl, ethyl, or n-propyl; and more preferably methyl.

The branched C3-C8 alkyl is preferably isobutyl, isopropyl, sec-butyl, tert-butyl, tert-pentyl, 1,1,2,2,-tetramethylpropyl, 1,1,2,2,-tetramethylethyl, or 1,1-diethylmethyl; and more preferably isopropyl or tert-butyl.

In Formulas (I) and (I'), examples of the "substituent" in the "substituted or unsubstituted C1-C10 alkyl" represented by R² include those mentioned above. The substituent is preferably halogen, C3-C7 cycloalkyl that may be substituted with C1-C4 alkyl, phenyl, C1-C6 alkoxy, or one or more C3-C10 monocyclic or polycyclic unsaturated heterocyclic groups containing 1 to 3 identical or different heteroatoms selected from nitrogen, oxygen, and sulfur; more preferably halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom; and even more preferably fluorine, C3-C7 cycloalkyl that may be substituted with C1-C4 alkyl, phenyl, methoxy, or one or more C3-C6 monocyclic unsaturated heterocyclic groups containing one oxygen atom or one sulfur atom.

Specific examples include fluorine, cyclopropyl, cyclopropyl substituted with methyl, cyclobutyl, cyclopentyl, phenyl, methoxy, thienyl, etc.; more preferably fluorine, cyclopropyl, cyclobutyl, cyclopentyl, methoxy, and the following:

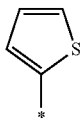

and even more preferably fluorine and cyclopropyl.

When the C1-C10 alkyl is substituted, the number of substituents is not particularly limited, but is preferably 1 to 3.

When the C1-C10 alkyl is substituted with "halogen," the number of substituents is preferably 1 to 3; when the C1-C10 alkyl is substituted with "C3-C7 cycloalkyl that may be substituted with C1-C4 alkyl," the number of substituents is preferably 1; when the C1-C10 alkyl is substituted with "phenyl," the number of substituents is preferably 1; when the C1-C10 alkyl is substituted with "C1-C6 alkoxy," the number of substituents is preferably 1; and when the C1-C10 alkyl is substituted with a "C3-C10 monocyclic or polycyclic unsaturated heterocyclic group containing 1 to 3 identical or different heteroatoms selected from nitrogen, oxygen, and sulfur," the number of substituents is preferably 1.

The "substituted or unsubstituted C1-C10 alkyl" represented by R² is preferably C1-C10 alkyl that may be substituted with halogen, C3-C7 cycloalkyl that may be substituted with C1-C4 alkyl, phenyl, C1-C6 alkoxy, or one or more C3-C10 monocyclic or polycyclic unsaturated heterocyclic groups containing 1 to 3 identical or different heteroatoms selected from nitrogen, oxygen, and sulfur; more preferably linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom; even more preferably linear C1-C4 alkyl that is substituted with fluorine or C3-C7 cycloalkyl that may be substituted with C1-C4 alkyl; or branched C3-C8 alkyl that may be substituted with fluorine, C3-C7 cycloalkyl, one or more C3-C6 monocyclic unsaturated heterocyclic groups containing one oxygen atom or one sulfur atom, phenyl, or C1-C4 alkoxy.

Specific examples include the following:

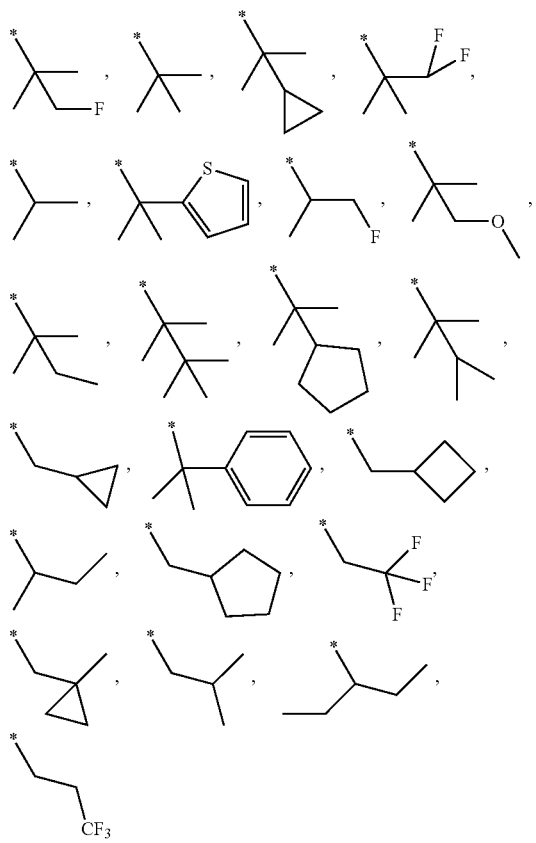

and the like.

The "substituted or unsubstituted C1-C10 alkyl" represented by R² is more preferably linear C1-C4 alkyl that is substituted with C3-C7 cycloalkyl, or branched C3-C6 alkyl that may be substituted with halogen, C3-C7 cycloalkyl, one or more C3-C6 monocyclic unsaturated heterocyclic groups containing one sulfur atom, or C1-C4 alkoxy; and even more preferably linear C1-C4 alkyl that is substituted with C3-C7 cycloalkyl, or branched C3-C6 alkyl that may be substituted with fluorine, C3-C7 cycloalkyl, one or more C3-C6 monocyclic unsaturated heterocyclic groups containing one sulfur atom, or C1-C4 alkoxy.

Specific examples include the following:

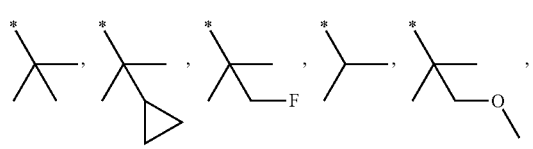

and the like.

The "substituted or unsubstituted C1-C10 alkyl" represented by $R^2$ is more preferably branched C3-C6 alkyl that may be substituted with halogen or C3-C5 cycloalkyl;

even more preferably branched C3-C6 alkyl that may be substituted with fluorine or C3-C5 cycloalkyl; and still more preferably isopropyl or tert-butyl that may be substituted with fluorine or cyclopropyl.

Specific examples include the following:

and the like.

In Formula (I), examples of the "C3-C7 cycloalkyl" in the "substituted or unsubstituted C3-C7 cycloalkyl" represented by $R^2$ include those mentioned above.

Specific examples include cyclopropyl, cyclobutyl, cyclopentyl, cyclohexyl, etc.; preferably C3-C5 cycloalkyl; more preferably C3-C4 cycloalkyl; and even more preferably cyclopropyl.

In Formula (I'), examples of the "C3-C4 cycloalkyl" in the "substituted or unsubstituted C3-C4 cycloalkyl" represented by $R^2$ include those mentioned above.

Specific examples include cyclopropyl, cyclobutyl, etc.; and preferably cyclopropyl.

In Formulas (I) and (I'), examples of the "substituent" in the "substituted or unsubstituted C3-C7 cycloalkyl" represented by $R^2$ include those mentioned above; and preferably halogen, C1-C4 alkyl, halogeno C1-C4 alkyl, and C3-C5 cycloalkyl.

Specific examples include fluorine, methyl, ethyl, fluoromethyl, difluoromethyl, cyclopropyl, etc.; and more preferably halogen, C1-C4 alkyl, and C3-C5 cycloalkyl.

Specific examples include fluorine, methyl, and cyclopropyl; and more preferably methyl.

When the above C3-C7 cycloalkyl or C3-C4 cycloalkyl is substituted, the number of substituents is not particularly limited, but is preferably 1 or 2.

When the C3-C7 cycloalkyl is substituted with "halogen," the number of substituents is preferably 1 or 2.

When the C3-C7 cycloalkyl is substituted with "C1-C4 alkyl," the number of substituents is preferably 1 or 2.

When the C3-C7 cycloalkyl is substituted with "halogeno C1-C4 alkyl," the number of substituents is preferably 1.

When the C3-C7 cycloalkyl is substituted with "C3-C5 cycloalkyl," the number of substituents is preferably 1.

In Formula (I), the "substituted or unsubstituted C3-C7 cycloalkyl" represented by $R^2$ is preferably C3-C7 cycloalkyl that may be substituted with halogen, C1-C4 alkyl, halogeno C1-C4 alkyl, or C3-C5 cycloalkyl.

Specific examples include the following:

and the like.

The "substituted or unsubstituted C3-C7 cycloalkyl" represented by $R^2$ is more preferably C3-C7 cycloalkyl that may be substituted with halogen, C1-C4 alkyl, or C3-C5 cycloalkyl; and even more preferably C3-C7 cycloalkyl that may be substituted with fluorine, C1-C4 alkyl, or C3-C5 cycloalkyl.

Specific examples include the following:

and the like.

The "substituted or unsubstituted C3-C7 cycloalkyl" represented by $R^2$ is more preferably C3-C5 cycloalkyl that may be substituted with C1-C4 alkyl;

even more preferably C3-C5 cycloalkyl that may be substituted with methyl;

still more preferably cyclopropyl that may be substituted with methyl; and further still more preferably the following:

[structure]

In Formula (I'), the "substituted or unsubstituted C3-C4 cycloalkyl" represented by $R^2$ is preferably C3-C4 cycloalkyl that may be substituted with halogen, C1-C4 alkyl, halogeno C1-C4 alkyl, or C3-C5 cycloalkyl.

Specific examples include the following:

[structures]

and the like.

The "substituted or unsubstituted C3-C4 cycloalkyl" represented by $R^2$ is more preferably C3-C4 cycloalkyl that may be substituted with halogen, C1-C4 alkyl, or C3-C5 cycloalkyl; and even more preferably C3-C4 cycloalkyl that may be substituted with fluorine, C1-C4 alkyl, or C3-C5 cycloalkyl.

Specific examples include the following:

[structures]

and the like.

The "substituted or unsubstituted C3-C4 cycloalkyl" represented by $R^2$ is more preferably C3-C4 cycloalkyl that may be substituted with C1-C4 alkyl, even more preferably C3-C4 cycloalkyl that may be substituted with methyl, still more preferably cyclopropyl that may be substituted with methyl, and further still more preferably the following:

[structure]

In Formulas (I) and (I'), examples of the "C2-C6 alkenyl" in the "substituted or unsubstituted C2-C6 alkenyl" represented by $R^2$ include those mentioned above, preferably C2-C4 alkenyl, and more preferably isopropenyl.

In Formulas (I) and (I'), examples of the "substituent" in the "substituted or unsubstituted C2-C6 alkenyl" represented by $R^2$ include those mentioned above, preferably halogen, and more preferably fluorine.

When the C2-C6 alkenyl is substituted, the number of substituents is not particularly limited, but is preferably 1 to 3. When the substituent is halogen, the number of substituents is preferably 1.

In Formulas (I) and (I'), the "substituted or unsubstituted C2-C6 alkenyl" represented by $R^2$ is preferably C2-C6 alkenyl that may be substituted with halogen;

more preferably C2-C6 alkenyl that may be substituted with fluorine; and even more preferably the following:

[structure]

In Formulas (I) and (I'), examples of the "C3-C7 cycloalkenyl" and "C3-C4 cycloalkenyl" in the "substituted or unsubstituted C3-C7 cycloalkenyl" and "substituted or unsubstituted C3-C4 cycloalkenyl" represented by $R^2$ include those mentioned above, preferably C3-C4 cycloalkenyl, and more preferably cyclobutenyl.

In Formulas (I) and (I'), examples of the "substituent" in the "substituted or unsubstituted C3-C7 cycloalkenyl" and "substituted or unsubstituted C3-C4 cycloalkenyl" represented by $R^2$ include those mentioned above, preferably halogen, and more preferably fluorine.

When the C3-C7 cycloalkenyl or C3-C4 cycloalkenyl is substituted, the number of substituents is not particularly limited, but is preferably 1 to 3. When the substituent is halogen, the number of substituents is preferably 1.

In Formula (I), the "substituted or unsubstituted C3-C7 cycloalkenyl" represented by $R^2$ is preferably C3-C7 cycloalkenyl that may be substituted with halogen, and more preferably C3-C4 cycloalkenyl that may be substituted with halogen.

In Formula (I'), the "substituted or unsubstituted C3-C4 cycloalkenyl" represented by $R^2$ is preferably C3-C4 cycloalkenyl that may be substituted with halogen.

In Formulas (I) and (I'), examples of the "C4-C12 bridged cycloalkyl" in the "substituted or unsubstituted C4-C12 bridged cycloalkyl" represented by $R^2$ include those mentioned above;

preferably bicyclo[1.1.1]pentan-1-yl, bicyclo[2.2.1]heptan-2-yl, adamantan-2-yl, and bicyclo[3.1.1]heptan-3-yl;

more preferably bicyclo[1.1.1]pentan-1-yl, bicyclo[2.2.1]heptan-2-yl, and adamantan-2-yl;

even more preferably bicyclo[1.1.1]pentan-1-yl and bicyclo[2.2.1]heptan-2-yl; and still more preferably bicyclo[2.2.1]heptan-2-yl.

In Formulas (I) and (I'), examples of the "substituent" in the "substituted or unsubstituted C4-C12 bridged cycloalkyl" represented by $R^2$ include those mentioned above, preferably C1-C4 alkyl, and more preferably methyl.

When the C4-C12 bridged cycloalkyl is substituted, the number of substituents is not particularly limited, but is preferably 1 to 3. When the substituent is C1-C4 alkyl, the number of substituents is preferably 1 to 3, and more preferably 3.

In Formulas (I) and (I'), the "substituted or unsubstituted C4-C12 bridged cycloalkyl" represented by $R^2$ is preferably C4-C12 bridged cycloalkyl that may be substituted with C1-C4 alkyl; and more preferably C4-C12 bridged cycloalkyl that may be substituted with methyl and is selected from bicyclo[1.1.1]pentan-1-yl, bicyclo[2.2.1]heptan-2-yl, adamantan-2-yl, and bicyclo[3.1.1]heptan-3-yl.

Specific examples include bicyclo[1.1.1]pentan-1-yl, bicyclo[2.2.1]heptan-2-yl, adamantan-2-yl, 2,6,6-trimethyl-bicyclo[3.1.1]heptan-3-yl, etc.

The "substituted or unsubstituted C4-C12 bridged cycloalkyl" represented by $R^2$ is more preferably C4-C12 bridged cycloalkyl;

even more preferably bicyclo[1.1.1]pentan-1-yl or bicyclo[2.2.1]heptan-2-yl; and still more preferably bicyclo[2.2.1]heptan-2-yl.

In Formulas (I) and (I'), examples of the "C6-C14 aromatic hydrocarbon" in the "substituted or unsubstituted C6-C14 aromatic hydrocarbon" represented by $R^2$ include those mentioned above, and preferably phenyl.

Examples of the "substituent" in the "substituted or unsubstituted C6-C14 aromatic hydrocarbon" represented by $R^2$ include those mentioned above.

The "substituted or unsubstituted C6-C14 aromatic hydrocarbon" represented by $R^2$ is preferably phenyl.

In Formulas (I) and (I'), the "C3-C10 monocyclic or polycyclic saturated or unsaturated heterocyclic group containing 1 to 3 identical or different heteroatoms selected from nitrogen, oxygen, and sulfur" in the "substituted or unsubstituted C3-C10 monocyclic or polycyclic saturated or unsaturated heterocyclic group containing 1 to 3 identical or different heteroatoms selected from nitrogen, oxygen, and sulfur" represented by $R^2$ is preferably a C3-C6 monocyclic unsaturated heterocyclic group containing one nitrogen atom, one oxygen atom, or one sulfur atom;

more preferably a C4-C5 monocyclic unsaturated heterocyclic group containing one nitrogen atom, one oxygen atom, or one sulfur atom; and even more preferably thienyl or furanyl.

Examples of the "substituent" in the "substituted or unsubstituted C3-C10 monocyclic or polycyclic saturated or unsaturated heterocyclic group containing 1 to 3 identical or different heteroatoms selected from nitrogen, oxygen, and sulfur" represented by $R^2$ include those mentioned above.

The "substituted or unsubstituted C3-C10 monocyclic or polycyclic saturated or unsaturated heterocyclic group containing 1 to 3 identical or different heteroatoms selected from nitrogen, oxygen, and sulfur" represented by $R^2$ is preferably a C3-C6 monocyclic unsaturated heterocyclic group containing one nitrogen atom, one oxygen atom, or one sulfur atom;

more preferably a C4-C5 monocyclic unsaturated heterocyclic group containing one nitrogen atom, one oxygen atom, or one sulfur atom; and even more preferably thienyl or furanyl.

$R^2$ in Formula (I) is preferably,
substituted or unsubstituted C1-C10 alkyl,
substituted or unsubstituted C3-C7 cycloalkyl,
substituted or unsubstituted C2-C6 alkenyl, or
substituted or unsubstituted C4-C12 bridged cycloalkyl.

$R^2$ is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C7 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl that may be substituted with C1-C4 alkyl.

$R^2$ is even more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C7 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl.

$R^2$ is still more preferably
linear C1-C4 alkyl that is substituted with C3-C7 cycloalkyl;
branched C3-C6 alkyl that may be substituted with halogen, C3-C7 cycloalkyl, one or more C3-C6 monocyclic unsaturated heterocyclic groups containing one sulfur atom, or C1-C4 alkoxy;
C3-C7 cycloalkyl that may be substituted with halogen, C1-C4 alkyl, or C3-C5 cycloalkyl;
C2-C6 alkenyl that may be substituted with halogen; or
C4-C12 bridged cycloalkyl selected from bicyclo[1.1.1]pentan-1-yl and bicyclo[2.2.1]heptan-2-yl.

$R^2$ is further still more preferably
branched C3-C6 alkyl that may be substituted with halogen or C3-C5 cycloalkyl;
C3-C5 cycloalkyl that may be substituted with C1-C4 alkyl, or bicyclo[2.2.1]heptan-2-yl.

$R^2$ is further still more preferably
isopropyl or tert-butyl that may be substituted with fluorine or cyclopropyl, or
cyclopropyl that may be substituted with methyl.

Moreover, $R^2$ in Formula (I') is preferably
substituted or unsubstituted C1-C10 alkyl,
substituted or unsubstituted C3-C4 cycloalkyl,
substituted or unsubstituted C2-C6 alkenyl, or
substituted or unsubstituted C4-C12 bridged cycloalkyl.

$R^2$ is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C4 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl that may be substituted with C1-C4 alkyl.

$R^2$ is even more preferably linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C4 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl.

$R^2$ is still more preferably
linear C1-C4 alkyl that is substituted with C3-C7 cycloalkyl;
branched C3-C6 alkyl that may be substituted with halogen, C3-C7 cycloalkyl, one or more C3-C6 monocyclic unsaturated heterocyclic groups containing one sulfur atom, or C1-C4 alkoxy;

C3-C4 cycloalkyl that may be substituted with halogen, C1-C4 alkyl, or C3-C5 cycloalkyl;
C2-C6 alkenyl that may be substituted with halogen; or
C4-C12 bridged cycloalkyl selected from bicyclo[1.1.1]pentan-1-yl and bicyclo[2.2.1]heptan-2-yl.

$R^2$ is further still more preferably
branched C3-C6 alkyl that may be substituted with halogen or C3-C5 cycloalkyl;
C3-C4 cycloalkyl that may be substituted with C1-C4 alkyl; or bicyclo[2.2.1]heptan-2-yl.

$R^2$ is further still more preferably
isopropyl or tert-butyl that may be substituted with fluorine or cyclopropyl, or
cyclopropyl that may be substituted with methyl.

In Formulas (I) and (I'), X is N or $CR^3$, and preferably $CR^3$.

In Formulas (I) and (I'), examples of the "halogen" represented by $R^3$ include those mentioned above, and preferably bromine and chlorine.

In Formulas (I) and (I'), examples of the "C1-C6 alkyl" in the "substituted or unsubstituted C1-C6 alkyl" represented by $R^3$ include those mentioned above, preferably C1-C4 alkyl, and more preferably methyl.

Examples of the "substituent" in the "substituted or unsubstituted C1-C6 alkyl" represented by $R^3$ include those mentioned above.

The "substituted or unsubstituted C1-C6 alkyl" represented by $R^3$ is preferably C1-C6 alkyl, more preferably C1-C4 alkyl, and even more preferably methyl.

In Formulas (I) and (I'), examples of the "C2-C6 alkenyl" in the "substituted or unsubstituted C2-C6 alkenyl" represented by $R^3$ include those mentioned above, and preferably vinyl and isopropenyl.

Examples of the "substituent" in the "substituted or unsubstituted C2-C6 alkenyl" represented by $R^3$ include those mentioned above.

In Formulas (I) and (I'), the "substituted or unsubstituted C2-C6 alkenyl" represented by $R^3$ is preferably vinyl or isopropenyl.

Examples of the "C2-C6 alkynyl" in the "substituted or unsubstituted C2-C6 alkynyl" represented by $R^3$ include those mentioned above, preferably C2-C4 alkynyl, and more preferably ethynyl or propynyl.

The number of triple bonds in the "C2-C6 alkynyl" is preferably 1, and the triple bond is preferably positioned between a carbon atom bonded to a 7H-pyrrolo[2,3-d]pyrimidine skeleton and a carbon atom adjacent to the carbon atom.

Examples of the "substituent" in the "substituted or unsubstituted C2-C6 alkynyl" represented by $R^3$ include those mentioned above; and preferably
C1-C6 alkyl that may be substituted with hydroxy,
C3-C7 cycloalkyl that may be substituted with hydroxy,
one or more C3-C10 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur.

Specific examples include
hydroxyisopropyl,
hydroxycyclopentyl,
hydroxycyclobutyl,
morpholino,
tetrahydropyranyl,
pyrazolyl that may be substituted with methyl, imidazo[1,2-b]pyridazinyl,
imidazolyl that may be substituted with methyl, and pyridinyl.

The "substituent" is more preferably
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur.

The "substituent" is even more preferably
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C6 monocyclic unsaturated heterocyclic groups that may be substituted with C1-C4 alkyl and contains 1 to 3 identical or different heteroatoms selected from nitrogen, oxygen, and sulfur.

The "substituent" is still more preferably
C1-C4 alkyl that may be substituted with hydroxy,
C3-C5 cycloalkyl that may be substituted with hydroxy,
one or more C3-C6 monocyclic saturated heterocyclic groups containing 1 to 3 identical or different heteroatoms selected from nitrogen and oxygen, or
one or more C3-C6 monocyclic unsaturated heterocyclic groups that may be substituted with methyl and contains 1 to 3 nitrogen atoms.

The "substituent" is further still more preferably
isopropyl that may be substituted with hydroxy,
C3-C5 cycloalkyl that may be substituted with hydroxy,
one or more C4-C5 monocyclic saturated heterocyclic groups containing 1 to 3 identical or different heteroatoms selected from nitrogen and oxygen, or
one or more C3-C6 monocyclic unsaturated heterocyclic groups that may be substituted with methyl and contains 1 to 3 nitrogen atoms.

The "substituted or unsubstituted C2-C6 alkynyl" represented by $R^3$ is preferably C2-C4 alkynyl that may be substituted with
C1-C6 alkyl that may be substituted with hydroxy,
C3-C7 cycloalkyl that may be substituted with hydroxy,
one or more C3-C10 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur.

Specific examples include the following:

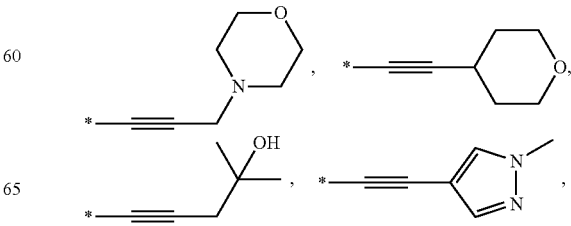

-continued

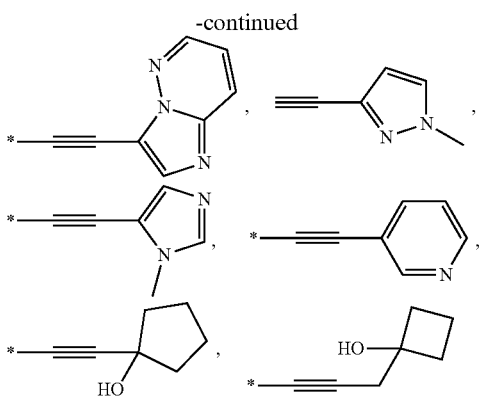

The "substituted or unsubstituted C2-C6 alkynyl" represented by R³ is more preferably C2-C4 alkynyl that may be substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur.

The "substituted or unsubstituted C2-C6 alkynyl" represented by R³ is even more preferably C2-C4 alkynyl that is substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C6 monocyclic unsaturated heterocyclic groups that may be substituted with C1-C4 alkyl and contains 1 to 3 identical or different heteroatoms selected from nitrogen, oxygen, and sulfur.

The "substituted or unsubstituted C2-C6 alkynyl" represented by R³ is still more preferably ethynyl or propynyl that is substituted with
C1-C4 alkyl that may be substituted with hydroxy,
C3-C5 cycloalkyl that may be substituted with hydroxy,
one or more C3-C6 monocyclic saturated heterocyclic groups containing 1 to 3 identical or different heteroatoms selected from nitrogen and oxygen, or
one or more C3-C6 monocyclic unsaturated heterocyclic groups that may be substituted with methyl and contains 1 to 3 nitrogen atoms.

The "substituted or unsubstituted C2-C6 alkynyl" represented by R³ is further still more preferably ethynyl or propynyl that is substituted with
isopropyl that may be substituted with hydroxy,
C3-C5 cycloalkyl that may be substituted with hydroxy,
one or more C4-C5 monocyclic saturated heterocyclic groups containing 1 to 3 identical or different heteroatoms selected from nitrogen and oxygen, or
one or more C3-C6 monocyclic unsaturated heterocyclic groups that may be substituted with methyl and contains 1 to 3 nitrogen atoms.

Examples of the "C1-C6 alkoxy" in the "substituted or unsubstituted C1-C6 alkoxy" represented by R³ include those mentioned above, preferably C1-C4 alkoxy, and more preferably methoxy.

Examples of the "substituent" in the "substituted or unsubstituted C1-C6 alkoxy" represented by R³ include those mentioned above;
preferably one or more C3-C10 monocyclic saturated heterocyclic groups containing 1 to 3 identical or different heteroatoms selected from nitrogen, oxygen, and sulfur; and
more preferably one or more C3-C6 monocyclic saturated heterocyclic groups containing one oxygen atom.

The "substituted or unsubstituted C1-C6 alkoxy" represented by R³ is C1-C4 alkoxy that may be substituted with one or more C3-C10 monocyclic saturated heterocyclic groups containing 1 to 3 identical or different heteroatoms selected from nitrogen, oxygen, and sulfur, or
C1-C4 alkoxy that may be substituted with one or more C3-C6 monocyclic saturated heterocyclic groups containing one oxygen atom;
more preferably C1-C4 alkoxy; and
even more preferably methoxy.

In Formulas (I) and (I'), examples of the "substituent" in the "substituted or unsubstituted amino" represented by R³ include those mentioned above.

In Formulas (I) and (I'), the "C6-C14 aromatic hydrocarbon" in the "substituted or unsubstituted C6-C14 aromatic hydrocarbon" represented by R³ include those mentioned above, and preferably phenyl.

Examples of the "substituent" in the "substituted or unsubstituted C6-C14 aromatic hydrocarbon" represented by R³ include those mentioned above.

In Formulas (I) and (I'), the "substituted or unsubstituted C6-C14 aromatic hydrocarbon" represented by R³ is preferably phenyl.

In Formulas (I) and (I'), the "C3-C10 monocyclic or polycyclic saturated or unsaturated heterocyclic group containing 1 to 3 identical or different heteroatoms selected from nitrogen, oxygen, and sulfur" in the "substituted or unsubstituted C3-C10 monocyclic or polycyclic saturated or unsaturated heterocyclic group containing 1 to 3 identical or different heteroatoms selected from nitrogen, oxygen, and sulfur" represented by R³ is preferably a C3-C6 monocyclic unsaturated heterocyclic group containing one oxygen atom or one sulfur atom, and more preferably thienyl or furanyl.

Examples of the "substituent" in the "substituted or unsubstituted C3-C10 monocyclic or polycyclic saturated or unsaturated heterocyclic group containing 1 to 3 identical or different heteroatoms selected from nitrogen, oxygen, and sulfur" represented by R³ include those mentioned above.

The "substituted or unsubstituted C3-C10 monocyclic or polycyclic saturated or unsaturated heterocyclic group containing 1 to 3 identical or different heteroatoms selected from nitrogen, oxygen, and sulfur" represented by R³ is preferably a C3-C6 monocyclic unsaturated heterocyclic group containing one oxygen atom or one sulfur atom, and more preferably thienyl or furanyl.

R³ is preferably
hydrogen,
halogen,
substituted or unsubstituted C1-C6 alkyl,
substituted or unsubstituted C2-C6 alkenyl, or
substituted or unsubstituted C1-C6 alkoxy.

R³ is more preferably
hydrogen;
halogen;
C1-C6 alkyl;

C2-C4 alkynyl that may be substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
C1-C4 alkoxy that may be substituted with one or more C3-C6 monocyclic saturated heterocyclic groups containing 1 to 3 identical or different heteroatoms selected from nitrogen, oxygen, and sulfur.

$R^3$ is even more preferably
hydrogen;
halogen;
C1-C4 alkyl;
C2-C4 alkynyl that may be substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
C1-C4 alkoxy.

$R^3$ is still more preferably
hydrogen; or
C2-C4 alkynyl that is substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C6 monocyclic unsaturated heterocyclic groups that may be substituted with C1-C4 alkyl and contains 1 to 3 identical or different heteroatoms selected from nitrogen, oxygen, and sulfur.

$R^3$ is further still more preferably
hydrogen; or
ethynyl or propynyl that is substituted with
C1-C4 alkyl that may be substituted with hydroxy,
C3-C5 cycloalkyl that may be substituted with hydroxy,
one or more C3-C6 monocyclic saturated heterocyclic groups containing 1 to 3 identical or different heteroatoms selected from nitrogen and oxygen, or
one or more C3-C6 monocyclic unsaturated heterocyclic groups that may be substituted with methyl and contains 1 to 3 nitrogen atoms.

$R^3$ is further still more preferably hydrogen.

In Formulas (I) and (I'), n is an integer of 0 to 3, preferably 0 to 2, more preferably 1 or 2, and even more preferably 1.

When n is 2 or 3, $R^1$ may be identical or different from each other, and is preferably identical.

In Formulas (I) and (I'), the bonding position between the amide structure and the pyrazolyl group is preferably as shown in Formulas (II) and (II') below.

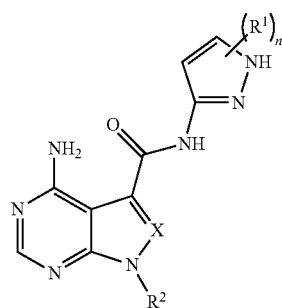

(II)

(II')

Moreover, when n is 1, the bonding position between the substituent $R^1$ and the pyrazolyl group is preferably as shown in Formulas (VIII) and (VIII') below.

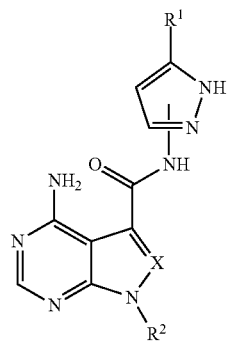

(VIII)

(VIII')

When n is 1, the bonding position between the substituent $R^1$ and the pyrazolyl group is more preferably as shown in Formulas (IX) and (IX') below:

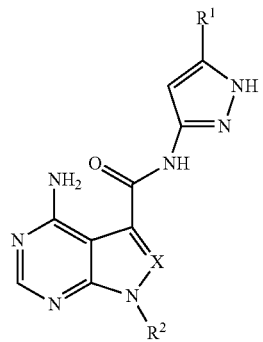

(IX)

(IX')

[1] The present invention provides a compound represented by Formula (I) below or a salt thereof:

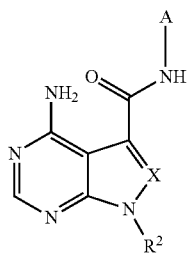

(I)

wherein A is pyrazolyl substituted with n-number of $R^1$;
$R^1$ is
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
$R^2$ is
substituted or unsubstituted C1-C10 alkyl,
substituted or unsubstituted C3-C7 cycloalkyl,
substituted or unsubstituted C2-C6 alkenyl,
substituted or unsubstituted C3-C7 cycloalkenyl,
substituted or unsubstituted C4-C12 bridged cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
X is
N or
$CR^3$, wherein $R^3$ is
  hydrogen,
  halogen,
  cyano,
  substituted or unsubstituted C1-C6 alkyl,
  substituted or unsubstituted C2-C6 alkenyl,
  substituted or unsubstituted C2-C6 alkynyl,
  substituted or unsubstituted C1-C6 alkoxy,
  substituted or unsubstituted amino,
  substituted or unsubstituted C6-C14 aromatic hydrocarbon, or
  a substituted or unsubstituted C3-C10 monocyclic or polycyclic unsaturated heterocyclic group containing 1 to 3 identical or different heteroatoms selected from nitrogen, oxygen, and sulfur; and
n is an integer of 0 to 3,
wherein when n is 2 or 3, $R^1$ may be identical or different from each other.

[2] In Formula (I),
A is preferably pyrazolyl substituted with n-number of $R^1$;
$R^1$ is preferably
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;

$R^2$ is preferably
substituted or unsubstituted C1-C10 alkyl,
substituted or unsubstituted C3-C7 cycloalkyl,
substituted or unsubstituted C2-C6 alkenyl, or
substituted or unsubstituted C4-C12 bridged cycloalkyl;
X is preferably
N or
$CR^3$, wherein $R^3$ is
  hydrogen,
  halogen,
  substituted or unsubstituted C1-C6 alkyl,
  substituted or unsubstituted C2-C6 alkynyl, or
  substituted or unsubstituted C1-C6 alkoxy; and
n is preferably an integer of 1 to 3,
wherein when n is 2 or 3, $R^1$ may be identical or different from each other.

[3] In Formula (I),
A is more preferably pyrazolyl substituted with n-number of $R^1$;
$R^1$ is more preferably
halogen;
cyano;
C1-C6 alkyl that may be substituted with halogen or C1-C4 alkoxy;
C3-C7 cycloalkyl;
phenyl; or
a C3-C6 monocyclic unsaturated heterocyclic group containing one oxygen atom or one sulfur atom;
$R^2$ is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C7 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl that may be substituted with C1-C4 alkyl;
X is more preferably
N or
$CR^3$, wherein $R^3$ is
  hydrogen;
  halogen;
  C1-C6 alkyl;
  C2-C4 alkynyl that may be substituted with
  C1-C6 alkyl that may be substituted with hydroxy, C3-C7 cycloalkyl that may be substituted with hydroxy,
  one or more C3-C6 monocyclic saturated heterocyclic groups containing 1 to 3 identical or different heteroatoms selected from nitrogen, oxygen, and sulfur, or
  one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
  C1-C4 alkoxy that may be substituted with one or more C3-C6 monocyclic saturated heterocyclic groups containing 1 to 3 identical or different heteroatoms selected from nitrogen, oxygen, and sulfur; and
n is more preferably 1 or 2,
wherein when n is 2, $R^1$ may be identical or different from each other.

In another embodiment of the present invention, a compound of Formula (I) wherein pyrazolyl is bonded to an amide structure at 3-position is preferable. Moreover, a preferred embodiment of the compound of Formula (I)

wherein pyrazolyl is bonded to an amide structure at 3-position in the present invention is

[4] a compound represented by Formula (II) below or a salt thereof:

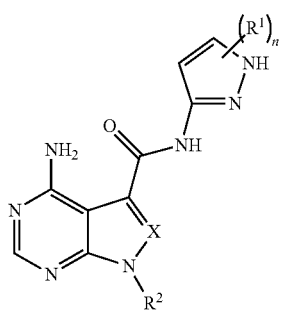

wherein R¹ is
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
R² is
substituted or unsubstituted C1-C10 alkyl,
substituted or unsubstituted C3-C7 cycloalkyl,
substituted or unsubstituted C2-C6 alkenyl, or
substituted or unsubstituted C4-C12 bridged cycloalkyl;
X is
N or
CR³, wherein R³ is
  hydrogen,
  halogen,
  substituted or unsubstituted C1-C6 alkyl,
  substituted or unsubstituted C2-C6 alkenyl, or
  substituted or unsubstituted C1-C6 alkoxy; and
n is an integer of 1 to 3,
wherein when n is 2 or 3, R¹ may be identical or different from each other.

In the present invention, the compound represented by Formula (II) above is also referred to simply as Compound (II).

[5] In Formula (II),
R¹ is more preferably
halogen;
cyano;
C1-C6 alkyl that may be substituted with halogen or C1-C4 alkoxy;
C3-C7 cycloalkyl;
phenyl; or
a C3-C6 monocyclic unsaturated heterocyclic group containing one oxygen atom or one sulfur atom;
R² is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C7 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl that may be substituted with C1-C4 alkyl;
X is more preferably
N or
CR³, wherein R³ is
  hydrogen;
  halogen;
  C1-C6 alkyl;
  C2-C4 alkynyl that may be substituted with
  C1-C6 alkyl that may be substituted with hydroxy,
  C3-C7 cycloalkyl that may be substituted with hydroxy,
  one or more C3-C6 monocyclic saturated heterocyclic groups containing 1 to 3 identical or different heteroatoms selected from nitrogen, oxygen, and sulfur, or
  one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
  C1-C4 alkoxy that may be substituted with one or more C3-C6 monocyclic saturated heterocyclic groups containing 1 to 3 identical or different heteroatoms selected from nitrogen, oxygen, and sulfur; and
n is more preferably 1 or 2,
wherein when n is 2, R¹ may be identical or different from each other.

[6] In Formula (II),
R¹ is more preferably
halogen;
cyano;
C1-C6 alkyl that may be substituted with halogen;
C3-C7 cycloalkyl;
phenyl; or
a C3-C6 monocyclic unsaturated heterocyclic group containing one oxygen atom or one sulfur atom;
R² is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C7 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl;
X is more preferably
N or
CR³, wherein R³ is
  hydrogen;
  halogen;
  C1-C4 alkyl;
  C2-C4 alkynyl that may be substituted with
  C1-C6 alkyl that may be substituted with hydroxy,
  C3-C7 cycloalkyl that may be substituted with hydroxy,
  one or more C3-C6 monocyclic saturated heterocyclic groups containing 1 to 3 identical or different heteroatoms selected from nitrogen, oxygen, and sulfur, or
  one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
  C1-C4 alkoxy; and
n is more preferably 1 or 2,
wherein when n is 2, R¹ may be identical or different from each other.

[7] In Formula (II),
R¹ is more preferably
halogen,
cyano, or
C1-C4 alkyl that may be substituted with halogen;
R² is more preferably
linear C1-C4 alkyl that is substituted with C3-C7 cycloalkyl;
branched C3-C6 alkyl that may be substituted with halogen, C3-C7 cycloalkyl, one or more C3-C6 monocyclic unsaturated heterocyclic groups containing one sulfur atom, or C1-C4 alkoxy;
C3-C7 cycloalkyl that may be substituted with halogen, C1-C4 alkyl, or C3-C5 cycloalkyl;
C2-C6 alkenyl that may be substituted with halogen; or
C4-C12 bridged cycloalkyl selected from bicyclo[1.1.1]pentan-1-yl and bicyclo[2.2.1]heptan-2-yl;
X is more preferably
N or
CR³, wherein R³ is
hydrogen; or
C2-C4 alkynyl that is substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C6 monocyclic unsaturated heterocyclic groups that may be substituted with C1-C4 alkyl and contains 1 to 3 identical or different heteroatoms selected from nitrogen, oxygen, and sulfur; and
n is more preferably an integer of 1.

Preferred in another embodiment of the present invention is

[8] a compound represented by Formula (IX) below or a salt thereof:

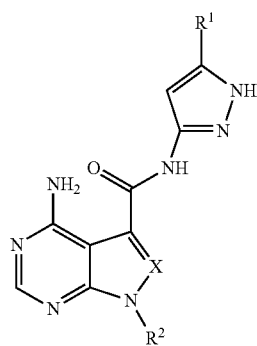

(IX)

wherein R¹ is
halogen;
cyano;
C1-C6 alkyl that may be substituted with halogen;
C3-C7 cycloalkyl;
phenyl; or
a C3-C6 monocyclic unsaturated heterocyclic group containing one oxygen atom or one sulfur atom;
R² is
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C7 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl;
X is
N or
CR³, wherein R³ is
hydrogen;
halogen;
C1-C4 alkyl;
C2-C4 alkynyl that may be substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
C1-C4 alkoxy.

In the present invention, the compound represented by Formula (IX) above is also referred to simply as Compound (IX).

[9] In Formula (IX),
R¹ is more preferably
halogen,
cyano, or
C1-C4 alkyl that may be substituted with halogen;
R² is more preferably
linear C1-C4 alkyl that is substituted with C3-C7 cycloalkyl;
branched C3-C6 alkyl that may be substituted with halogen, C3-C7 cycloalkyl, one or more C3-C6 monocyclic unsaturated heterocyclic groups containing one sulfur atom, or C1-C4 alkoxy;
C3-C7 cycloalkyl that may be substituted with halogen, C1-C4 alkyl, or C3-C5 cycloalkyl;
C2-C6 alkenyl that may be substituted with halogen; or
C4-C12 bridged cycloalkyl selected from bicyclo[1.1.1]pentan-1-yl and bicyclo[2.2.1]heptan-2-yl; and
X is more preferably
N or
CR³, wherein R³ is
hydrogen; or
C2-C4 alkynyl that may be substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C6 monocyclic unsaturated heterocyclic groups that may be substituted with C1-C4 alkyl and contains 1 to 3 identical or different heteroatoms selected from nitrogen, oxygen, and sulfur.

[10] In Formula (IX),
R¹ is more preferably
bromine,
cyano, or
C1-C4 alkyl that may be substituted with fluorine;
R² is more preferably
linear C1-C4 alkyl that is substituted with C3-C7 cycloalkyl;
branched C3-C6 alkyl that may be substituted with fluorine, C3-C7 cycloalkyl, one or more C3-C6 monocyclic unsaturated heterocyclic groups containing one sulfur atom, or C1-C4 alkoxy;

C3-C7 cycloalkyl that may be substituted with fluorine, C1-C4 alkyl, or C3-C5 cycloalkyl;
C2-C6 alkenyl that may be substituted with fluorine; or
C4-C12 bridged cycloalkyl selected from bicyclo[1.1.1]pentan-1-yl and bicyclo[2.2.1]heptan-2-yl; and
X is more preferably
N or
$CR^3$, wherein $R^3$ is
  hydrogen; or
  C2-C4 alkynyl that is substituted with
    C1-C6 alkyl that may be substituted with hydroxy,
    C3-C7 cycloalkyl that may be substituted with hydroxy,
    one or more C3-C6 monocyclic saturated heterocyclic groups containing 1 to 3 identical or different heteroatoms selected from nitrogen, oxygen, and sulfur, or
    one or more C3-C6 monocyclic unsaturated heterocyclic groups that may be substituted with C1-C4 alkyl and contains 1 to 3 identical or different heteroatoms selected from nitrogen, oxygen, and sulfur.

Moreover, in another embodiment of the present invention,

[11] in Formula (IX),
$R^1$ is more preferably halogen or C1-C4 alkyl;
$R^2$ is more preferably
branched C3-C6 alkyl that may be substituted with halogen or C3-C5 cycloalkyl,
C3-C5 cycloalkyl that may be substituted with C1-C4 alkyl, or bicyclo[2.2.1]heptan-2-yl; and
X is more preferably
N or
$CR^3$, wherein $R^3$ is
  hydrogen; or
  ethynyl or propynyl that is substituted with
    C1-C4 alkyl that may be substituted with hydroxy,
    C3-C5 cycloalkyl that may be substituted with hydroxy,
    one or more C3-C6 monocyclic saturated heterocyclic groups containing 1 to 3 identical or different heteroatoms selected from nitrogen and oxygen, or
    one or more C3-C6 monocyclic unsaturated heterocyclic groups that may be substituted with methyl and contains 1 to 3 nitrogen atoms.

[12] In Formula (IX),
$R^1$ is more preferably bromine or methyl;
$R^2$ is more preferably
branched C3-C6 alkyl that may be substituted with fluorine or C3-C5 cycloalkyl, or
C3-C5 cycloalkyl that may be substituted with methyl; and
X is more preferably
N or
$CR^3$, wherein $R^3$ is hydrogen.

[13] In Formula (IX),
$R^1$ is more preferably methyl;
$R^2$ is more preferably
isopropyl or tert-butyl that may be substituted with fluorine or cyclopropyl, or
cyclopropyl that may be substituted with methyl; and
X is more preferably
N or
$CR^3$, wherein $R^3$ is hydrogen.

Moreover,

[14] in Formulas (I), (II), and (IX) of the present invention, when X is N,
$R^1$ is preferably
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur; and
$R^2$ is preferably
substituted or unsubstituted C1-C10 alkyl,
substituted or unsubstituted C3-C7 cycloalkyl,
substituted or unsubstituted C2-C6 alkenyl, or
substituted or unsubstituted C4-C12 bridged cycloalkyl.

Moreover,

[15] in Formulas (I), (II), and (IX) of the present invention, when X is $CR^3$ ($R^3$ is as defined above),
$R^1$ is preferably
halogen,
substituted or unsubstituted C1-C6 alkyl, or
a substituted or unsubstituted C3-C10 monocyclic or polycyclic saturated or unsaturated heterocyclic group containing 1 to 3 identical or different heteroatoms selected from nitrogen, oxygen, and sulfur; and
$R^2$ is preferably
substituted or unsubstituted C1-C10 alkyl,
substituted or unsubstituted C3-C7 cycloalkyl, or
substituted or unsubstituted C4-C12 bridged cycloalkyl.

Specific examples of the compound of the present invention include, but are not limited to, compounds produced in the Examples described later.

Specific preferred examples of Compound (I) are as follows:

[16]
(1) 4-amino-1-cyclopentyl-N-(5-ethyl-1H-pyrazol-3-yl)-1H-pyrazolo[3,4-d]pyrimidine-3-carboxamide (example compound 1);
(2) 4-amino-1-cyclopentyl-N-(5-(furan-2-yl)-1H-pyrazol-3-yl)-1H-pyrazolo[3,4-d]pyrimidine-3-carboxamide (example compound 2);
(3) 4-amino-1-cyclopentyl-N-(5-(furan-3-yl)-1H-pyrazol-3-yl)-1H-pyrazolo[3,4-d]pyrimidine-3-carboxamide (example compound 3);
(4) 4-amino-1-cyclopentyl-N-(5-(thiophen-2-yl)-1H-pyrazol-3-yl)-1H-pyrazolo[3,4-d]pyrimidine-3-carboxamide (example compound 4);
(5) 4-amino-1-cyclopentyl-N-(5-phenyl-1H-pyrazol-3-yl)-1H-pyrazolo[3,4-d]pyrimidine-3-carboxamide (example compound 5);
(6) 4-amino-1-cyclopentyl-N-(5-cyclopentyl-1H-pyrazol-3-yl)-1H-pyrazolo[3,4-d]pyrimidine-3-carboxamide (example compound 6);
(7) 4-amino-1-cyclopentyl-N-(5-cyclopropyl-1H-pyrazol-3-yl)-1H-pyrazolo[3,4-d]pyrimidine-3-carboxamide (example compound 7);
(8) 4-amino-1-cyclopentyl-N-(3-propyl-1H-pyrazol-5-yl)-1H-pyrazolo[3,4-d]pyrimidine-3-carboxamide (example compound 8);
(9) 4-amino-1-cyclopentyl-N-(1,3-dimethyl-1H-pyrazol-5-yl)-1H-pyrazolo[3,4-d]pyrimidine-3-carboxamide (example compound 9);
(10) 4-amino-1-cyclopentyl-N-(5-isopropyl-1H-pyrazol-3-yl)-1H-pyrazolo[3,4-d]pyrimidine-3-carboxamide (example compound 10);
(11) 4-amino-1-cyclobutyl-N-(5-methyl-1H-pyrazol-3-yl)-1H-pyrazolo[3,4-d]pyrimidine-3-carboxamide (example compound 11);
(12) 4-amino-N-(5-methyl-1H-pyrazol-3-yl)-1-((1-methylcyclopropyl)methyl)-1H-pyrazolo[3,4-d]pyrimidine-3-carboxamide (example compound 12);

(13) 4-amino-N-(5-methyl-1H-pyrazol-3-yl)-1-(2,2,2-trifluoroethyl)-1H-pyrazolo[3,4-d]pyrimidine-3-carboxamide (example compound 13);
(14) 4-amino-N-(5-methyl-1H-pyrazol-3-yl)-1-(3,3,3-trifluoropropyl)-1H-pyrazolo[3,4-d]pyrimidine-3-carboxamide (example compound 14);
(15) 4-amino-1-(sec-butyl)-N-(5-methyl-1H-pyrazol-3-yl)-1H-pyrazolo[3,4-d]pyrimidine-3-carboxamide (example compound 15);
(16) 4-amino-1-(cyclobutylmethyl)-N-(5-methyl-1H-pyrazol-3-yl)-1H-pyrazolo[3,4-d]pyrimidine-3-carboxamide (example compound 16);
(17) 4-amino-N-(5-bromo-1H-pyrazol-3-yl)-1-(cyclobutylmethyl)-1H-pyrazolo[3,4-d]pyrimidine-3-carboxamide (example compound 17);
(18) 4-amino-1-(cyclopropylmethyl)-N-(5-methyl-1H-pyrazol-3-yl)-1H-pyrazolo[3,4-d]pyrimidine-3-carboxamide (example compound 18);
(19) 4-amino-1-(cyclopentylmethyl)-N-(5-methyl-1H-pyrazol-3-yl)-1H-pyrazolo[3,4-d]pyrimidine-3-carboxamide (example compound 19);
(20) 4-amino-N-(5-bromo-1H-pyrazol-3-yl)-1-(cyclopentylmethyl)-1H-pyrazolo[3,4-d]pyrimidine-3-carboxamide (example compound 20);
(21) 4-amino-1-isopropyl-N-(5-(trifluoromethyl)-1H-pyrazol-3-yl)-1H-pyrazolo[3,4-d]pyrimidine-3-carboxamide (example compound 21);
(22) 4-amino-N-(5-bromo-1H-pyrazol-3-yl)-1-isopropyl-1H-pyrazolo[3,4-d]pyrimidine-3-carboxamide (example compound 22);
(23) 4-amino-N-(5-methyl-1H-pyrazol-3-yl)-1-((1R,2R)-2-methylcyclohexyl)-1H-pyrazolo[3,4-d]pyrimidine-3-carboxamide (example compound 23);
(24) 4-amino-1-(4,4-dimethylcyclohexyl)-N-(5-methyl-1H-pyrazol-3-yl)-1H-pyrazolo[3,4-d]pyrimidine-3-carboxamide (example compound 24);
(25) 4-amino-N-(5-bromo-1H-pyrazol-3-yl)-1-(4,4-dimethylcyclohexyl)-1H-pyrazolo[3,4-d]pyrimidine-3-carboxamide (example compound 25);
(26) 4-amino-1-(3,3-dimethylcyclobutyl)-N-(5-methyl-1H-pyrazol-3-yl)-1H-pyrazolo[3,4-d]pyrimidine-3-carboxamide (example compound 26);
(27) 4-amino-1-(bicyclo[2.2.1]heptan-2-yl)-N-(5-methyl-1H-pyrazol-3-yl)-1H-pyrazolo[3,4-d]pyrimidine-3-carboxamide (example compound 27);
(28) 4-amino-1-(bicyclo[2.2.1]heptan-2-yl)-N-(5-bromo-1H-pyrazol-3-yl)-1H-pyrazolo[3,4-d]pyrimidine-3-carboxamide (example compound 28);
(29) 1-(adamantan-2-yl)-4-amino-N-(5-methyl-1H-pyrazol-3-yl)-1H-pyrazolo[3,4-d]pyrimidine-3-carboxamide (example compound 29);
(30) 4-amino-N-(5-methyl-1H-pyrazol-3-yl)-1-((2S,3R)-2,6,6-trimethylbicyclo[3.1.1]heptan-3-yl)-1H-pyrazolo[3,4-d]pyrimidine-3-carboxamide (example compound 30);
(31) 4-amino-1-(3-fluoroprop-1-en-2-yl)-N-(5-methyl-1H-pyrazol-3-yl)-1H-pyrazolo[3,4-d]pyrimidine-3-carboxamide (example compound 31);
(32) 4-amino-N-(5-bromo-1H-pyrazol-3-yl)-1-cyclohexyl-1H-pyrazolo[3,4-d]pyrimidine-3-carboxamide (example compound 32);
(33) 4-amino-1-cyclohexyl-N-(5-(difluoromethyl)-1H-pyrazol-3-yl)-1H-pyrazolo[3,4-d]pyrimidine-3-carboxamide (example compound 33);
(34) 4-amino-1-(tert-butyl)-N-(5-methyl-1H-pyrazol-3-yl)-1H-pyrazolo[3,4-d]pyrimidine-3-carboxamide (example compound 34);
(35) 4-amino-N-(5-bromo-1H-pyrazol-3-yl)-1-(tert-butyl)-1H-pyrazolo[3,4-d]pyrimidine-3-carboxamide (example compound 35);
(36) 4-amino-1-(tert-butyl)-N-(5-(trifluoromethyl)-1H-pyrazol-3-yl)-1H-pyrazolo[3,4-d]pyrimidine-3-carboxamide (example compound 36);
(37) 4-amino-1-(tert-butyl)-N-(5-(furan-2-yl)-1H-pyrazol-3-yl)-1H-pyrazolo[3,4-d]pyrimidine-3-carboxamide (example compound 37);
(38) 4-amino-1-(tert-butyl)-N-(5-cyano-1H-pyrazol-3-yl)-1H-pyrazolo[3,4-d]pyrimidine-3-carboxamide (example compound 38);
(39) 4-amino-1-(tert-butyl)-N-(5-ethyl-1H-pyrazol-3-yl)-1H-pyrazolo[3,4-d]pyrimidine-3-carboxamide (example compound 39);
(40) 4-amino-1-(tert-butyl)-N-(5-isopropyl-1H-pyrazol-3-yl)-1H-pyrazolo[3,4-d]pyrimidine-3-carboxamide (example compound 40);
(41) 4-amino-1-(tert-butyl)-N-(5-cyclopropyl-1H-pyrazol-3-yl)-1H-pyrazolo[3,4-d]pyrimidine-3-carboxamide (example compound 41);
(42) 4-amino-1-(tert-butyl)-N-(5-cyclobutyl-1H-pyrazol-3-yl)-1H-pyrazolo[3,4-d]pyrimidine-3-carboxamide (example compound 42);
(43) 4-amino-1-(4,4-difluorocyclohexyl)-N-(5-methyl-1H-pyrazol-3-yl)-1H-pyrazolo[3,4-d]pyrimidine-3-carboxamide (example compound 43);
(44) 4-amino-N-(5-bromo-1H-pyrazol-3-yl)-1-(4,4-difluorocyclohexyl)-1H-pyrazolo[3,4-d]pyrimidine-3-carboxamide (example compound 44);
(45) 4-amino-7-isopropyl-N-(5-methyl-1H-pyrazol-3-yl)-7H-pyrrolo[2,3-d]pyrimidine-5-carboxamide (example compound 45);
(46) 4-amino-7-(1-fluoropropan-2-yl)-N-(5-methyl-1H-pyrazol-3-yl)-7H-pyrrolo[2,3-d]pyrimidine-5-carboxamide (example compound 46);
(47) 4-amino-7-(4,4-dimethylcyclohexyl)-N-(5-methyl-1H-pyrazol-3-yl)-7H-pyrrolo[2,3-d]pyrimidine-5-carboxamide (example compound 47);
(48) 4-amino-7-(tert-butyl)-N-(5-methyl-1H-pyrazol-3-yl)-7H-pyrrolo[2,3-d]pyrimidine-5-carboxamide (example compound 48);
(49) 4-amino-7-(tert-butyl)-N-(5-(furan-2-yl)-1H-pyrazol-3-yl)-7H-pyrrolo[2,3-d]pyrimidine-5-carboxamide (example compound 49);
(50) 4-amino-7-(1-fluoro-2-methylpropan-2-yl)-N-(5-methyl-1H-pyrazol-3-yl)-7H-pyrrolo[2,3-d]pyrimidine-5-carboxamide (example compound 50);
(51) 4-amino-N-(5-methyl-1H-pyrazol-3-yl)-7-(1-methylcyclopropyl)-7H-pyrrolo[2,3-d]pyrimidine-5-carboxamide (example compound 51);
(52) 4-amino-7-(2-cyclopropylpropan-2-yl)-N-(5-methyl-1H-pyrazol-3-yl)-7H-pyrrolo[2,3-d]pyrimidine-5-carboxamide (example compound 52);
(53) 4-amino-7-(1-methoxy-2-methylpropan-2-yl)-N-(5-methyl-1H-pyrazol-3-yl)-7H-pyrrolo[2,3-d]pyrimidine-5-carboxamide (example compound 53);
(54) 4-amino-7-(1-(fluoromethyl)cyclopropyl)-N-(5-methyl-1H-pyrazol-3-yl)-7H-pyrrolo[2,3-d]pyrimidine-5-carboxamide (example compound 54);
(55) 4-amino-7-(1-(difluoromethyl)cyclopropyl)-N-(5-methyl-1H-pyrazol-3-yl)-7H-pyrrolo[2,3-d]pyrimidine-5-carboxamide (example compound 55);
(56) 4-amino-N-(5-methyl-1H-pyrazol-3-yl)-7-(2-(thiophen-2-yl)propan-2-yl)-7H-pyrrolo[2,3-d]pyrimidine-5-carboxamide (example compound 56);

(57) 4-amino-7-(3,3-difluorocyclopentyl)-N-(5-methyl-1H-pyrazol-3-yl)-7H-pyrrolo[2,3-d]pyrimidine-5-carboxamide (example compound 57);
(58) 4-amino-7-(bicyclo[1.1.1]pentan-1-yl)-N-(5-methyl-1H-pyrazol-3-yl)-7H-pyrrolo[2,3-d]pyrimidine-5-carboxamide (example compound 58);
(59) 4-amino-N-(5-methyl-1H-pyrazol-3-yl)-7-(1-methylcyclopentyl)-7H-pyrrolo[2,3-d]pyrimidine-5-carboxamide (example compound 59);
(60) 4-amino-N-(5-methyl-1H-pyrazol-3-yl)-7-(2-phenylpropan-2-yl)-7H-pyrrolo[2,3-d]pyrimidine-5-carboxamide (example compound 60);
(61) 4-amino-N-(5-methyl-1H-pyrazol-3-yl)-7-(2,3,3-trimethylbutan-2-yl)-7H-pyrrolo[2,3-d]pyrimidine-5-carboxamide (example compound 61);
(62) 4-amino-7-(2,3-dimethylbutan-2-yl)-N-(5-methyl-1H-pyrazol-3-yl)-7H-pyrrolo[2,3-d]pyrimidine-5-carboxamide (example compound 62);
(63) 4-amino-N-(5-bromo-1H-pyrazol-3-yl)-7-(tert-butyl)-7H-pyrrolo[2,3-d]pyrimidine-5-carboxamide (example compound 63);
(64) 4-amino-7-(tert-butyl)-N-(5-(methoxymethyl)-1H-pyrazol-3-yl)-7H-pyrrolo[2,3-d]pyrimidine-5-carboxamide (example compound 64);
(65) 4-amino-N-(5-bromo-1H-pyrazol-3-yl)-7-isopropyl-7H-pyrrolo[2,3-d]pyrimidine-5-carboxamide (example compound 65);
(66) 4-amino-N-(5-bromo-1H-pyrazol-3-yl)-7-(1-fluoro-2-methylpropan-2-yl)-7H-pyrrolo[2,3-d]pyrimidine-5-carboxamide (example compound 66);
(67) 4-amino-N-(5-bromo-1H-pyrazol-3-yl)-7-(1-methylcyclopropyl)-7H-pyrrolo[2,3-d]pyrimidine-5-carboxamide (example compound 67);
(68) 4-amino-N-(5-methyl-1H-pyrazol-3-yl)-7-(1-methylcyclobutyl)-7H-pyrrolo[2,3-d]pyrimidine-5-carboxamide (example compound 68);
(69) 4-amino-7-cyclobutyl-N-(5-methyl-1H-pyrazol-3-yl)-7H-pyrrolo[2,3-d]pyrimidine-5-carboxamide (example compound 69);
(70) 4-amino-N-(5-methyl-1H-pyrazol-3-yl)-7-(tert-pentyl)-7H-pyrrolo[2,3-d]pyrimidine-5-carboxamide (example compound 70);
(71) 4-amino-7-(bicyclo[2.2.1]heptan-2-yl)-N-(5-methyl-1H-pyrazol-3-yl)-7H-pyrrolo[2,3-d]pyrimidine-5-carboxamide (example compound 71);
(72) 4-amino-7-cyclopentyl-N-(5-methyl-1H-pyrazol-3-yl)-7H-pyrrolo[2,3-d]pyrimidine-5-carboxamide (example compound 72);
(73) 4-amino-7-(tert-butyl)-6-methyl-N-(3-methyl-1H-pyrazol-5-yl)-7H-pyrrolo[2,3-d]pyrimidine-5-carboxamide (example compound 73);
(74) 7-([1,1'-bi(cyclopropan)]-1-yl)-4-amino-N-(5-methyl-1H-pyrazol-3-yl)-7H-pyrrolo[2,3-d]pyrimidine-5-carboxamide (example compound 74);
(75) 4-amino-6-chloro-N-(5-methyl-1H-pyrazol-3-yl)-7-(1-methylcyclopropyl)-7H-pyrrolo[2,3-d]pyrimidine-5-carboxamide (example compound 75);
(76) 4-amino-6-bromo-N-(5-methyl-1H-pyrazol-3-yl)-7-(1-methylcyclopropyl)-7H-pyrrolo[2,3-d]pyrimidine-5-carboxamide (example compound 76);
(77) 4-amino-6-methoxy-N-(5-methyl-1H-pyrazol-3-yl)-7-(1-methylcyclopropyl)-7H-pyrrolo[2,3-d]pyrimidine-5-carboxamide (example compound 77);
(78) 4-amino-6-chloro-7-(1-fluoro-2-methylpropan-2-yl)-N-(5-methyl-1H-pyrazol-3-yl)-7H-pyrrolo[2,3-d]pyrimidine-5-carboxamide (example compound 78);
(79) 4-amino-6-(3-hydroxy-3-methyl-1-butyn-1-yl)-N-(5-methyl-1H-pyrazol-3-yl)-7-(1-methylcyclopropyl)-7H-pyrrolo[2,3-d]pyrimidine-5-carboxamide (example compound 79);
(80) 4-amino-N-(5-methyl-1H-pyrazol-3-yl)-7-(1-methylcyclopropyl)-6-(pyridin-3-ylethynyl)-7H-pyrrolo[2,3-d]pyrimidine-5-carboxamide (example compound 80);
(81) 4-amino-6-((1-hydroxycyclopentyl)ethynyl)-N-(5-methyl-1H-pyrazol-3-yl)-7-(1-methylcyclopropyl)-7H-pyrrolo[2,3-d]pyrimidine-5-carboxamide (example compound 81);
(82) 4-amino-6-((1-methyl-1H-pyrazol-4-yl)ethynyl)-N-(5-methyl-1H-pyrazol-3-yl)-7-(1-methylcyclopropyl)-7H-pyrrolo[2,3-d]pyrimidine-5-carboxamide (example compound 82);
(83) 4-amino-6-((1-methyl-1H-imidazol-5-yl)ethynyl)-N-(5-methyl-1H-pyrazol-3-yl)-7-(1-methylcyclopropyl)-7H-pyrrolo[2,3-d]pyrimidine-5-carboxamide (example compound 83);
(84) 4-amino-N-(5-methyl-1H-pyrazol-3-yl)-7-(1-methylcyclopropyl)-6-(3-morpholino-1-propyn-1-yl)-7H-pyrrolo[2,3-d]pyrimidine-5-carboxamide (example compound 84);
(85) 4-amino-6-(3-(1-hydroxycyclobutyl)-1-propyne)-N-(5-methyl-1H-pyrazol-3-yl)-7-(1-methylcyclopropyl)-7H-pyrrolo[2,3-d]pyrimidine-5-carboxamide (example compound 85);
(86) 4-amino-N-(5-methyl-1H-pyrazol-3-yl)-7-(1-methylcyclopropyl)-6-((tetrahydro-2H-pyran-4-yl)ethynyl)-7H-pyrrolo[2,3-d]pyrimidine-5-carboxamide (example compound 86);
(87) 4-amino-N-(5-methyl-1H-pyrazol-3-yl)-6-((1-methyl-1H-pyrazol-3-yl)ethynyl)-7-(1-methylcyclopropyl)-7H-pyrrolo[2,3-d]pyrimidine-5-carboxamide (example compound 87);
(88) 4-amino-6-(imidazo[1,2-b]pyridazin-3-ylethynyl)-N-(5-methyl-1H-pyrazol-3-yl)-7-(1-methylcyclopropyl)-7H-pyrrolo[2,3-d]pyrimidine-5-carboxamide (example compound 88);
(89) 4-amino-6-ethoxy-N-(5-methyl-1H-pyrazol-3-yl)-7-(1-methylcyclopropyl)-7H-pyrrolo[2,3-d]pyrimidine-5-carboxamide (example compound 89); and
(90) (R)-4-amino-N-(5-methyl-1H-pyrazol-3-yl)-7-(1-methylcyclopropyl)-6-((tetrahydrofuran-2-yl)methoxy)-7H-pyrrolo[2,3-d]pyrimidine-5-carboxamide (example compound 90).

More preferred examples of Compound (I) are as follows:
[17]
(27) 4-amino-1-(bicyclo[2.2.1]heptan-2-yl)-N-(5-methyl-1H-pyrazol-3-yl)-1H-pyrazolo[3,4-d]pyrimidine-3-carboxamide (example compound 27);
(34) 4-amino-1-(tert-butyl)-N-(5-methyl-1H-pyrazol-3-yl)-1H-pyrazolo[3,4-d]pyrimidine-3-carboxamide (example compound 34);
(45) 4-amino-7-isopropyl-N-(5-methyl-1H-pyrazol-3-yl)-7H-pyrrolo[2,3-d]pyrimidine-5-carboxamide (example compound 45);
(48) 4-amino-7-(tert-butyl)-N-(5-methyl-1H-pyrazol-3-yl)-7H-pyrrolo[2,3-d]pyrimidine-5-carboxamide (example compound 48);
(50) 4-amino-7-(1-fluoro-2-methylpropan-2-yl)-N-(5-methyl-1H-pyrazol-3-yl)-7H-pyrrolo[2,3-d]pyrimidine-5-carboxamide (example compound 50);
(51) 4-amino-N-(5-methyl-1H-pyrazol-3-yl)-7-(1-methylcyclopropyl)-7H-pyrrolo[2,3-d]pyrimidine-5-carboxamide (example compound 51);

(52) 4-amino-7-(2-cyclopropylpropan-2-yl)-N-(5-methyl-1H-pyrazol-3-yl)-7H-pyrrolo[2,3-d]pyrimidine-5-carboxamide (example compound 52);
(65) 4-amino-N-(5-bromo-1H-pyrazol-3-yl)-7-isopropyl-7H-pyrrolo[2,3-d]pyrimidine-5-carboxamide (example compound 65);
(68) 4-amino-N-(5-methyl-1H-pyrazol-3-yl)-7-(1-methylcyclobutyl)-7H-pyrrolo[2,3-d]pyrimidine-5-carboxamide (example compound 68);
(71) 4-amino-7-(bicyclo[2.2.1]heptan-2-yl)-N-(5-methyl-1H-pyrazol-3-yl)-7H-pyrrolo[2,3-d]pyrimidine-5-carboxamide (example compound 71);
(72) 4-amino-7-cyclopentyl-N-(5-methyl-1H-pyrazol-3-yl)-7H-pyrrolo[2,3-d]pyrimidine-5-carboxamide (example compound 72);
(79) 4-amino-6-(3-hydroxy-3-methyl-1-butyn-1-yl)-N-(5-methyl-1H-pyrazol-3-yl)-7-(1-methylcyclopropyl)-7H-pyrrolo[2,3-d]pyrimidine-5-carboxamide (example compound 79);
(80) 4-amino-N-(5-methyl-1H-pyrazol-3-yl)-7-(1-methylcyclopropyl)-6-(pyridin-3-ylethynyl)-7H-pyrrolo[2,3-d]pyrimidine-5-carboxamide (example compound 80);
(81) 4-amino-6-((1-hydroxycyclopentyl)ethynyl)-N-(5-methyl-1H-pyrazol-3-yl)-7-(1-methylcyclopropyl)-7H-pyrrolo[2,3-d]pyrimidine-5-carboxamide (example compound 81);
(82) 4-amino-6-((1-methyl-1H-pyrazol-4-yl)ethynyl)-N-(5-methyl-1H-pyrazol-3-yl)-7-(1-methylcyclopropyl)-7H-pyrrolo[2,3-d]pyrimidine-5-carboxamide (example compound 82);
(83) 4-amino-6-((1-methyl-1H-imidazol-5-yl)ethynyl)-N-(5-methyl-1H-pyrazol-3-yl)-7-(1-methylcyclopropyl)-7H-pyrrolo[2,3-d]pyrimidine-5-carboxamide (example compound 83);
(84) 4-amino-N-(5-methyl-1H-pyrazol-3-yl)-7-(1-methylcyclopropyl)-6-(3-morpholino-1-propyn-1-yl)-7H-pyrrolo[2,3-d]pyrimidine-5-carboxamide (example compound 84); and
(85) 4-amino-6-(3-(1-hydroxycyclobutyl)-1-propyne)-N-(5-methyl-1H-pyrazol-3-yl)-7-(1-methylcyclopropyl)-7H-pyrrolo[2,3-d]pyrimidine-5-carboxamide (example compound 85).

Even more preferred examples of Compound (I) are as follows:

[18]
(34) 4-amino-1-(tert-butyl)-N-(5-methyl-1H-pyrazol-3-yl)-1H-pyrazolo[3,4-d]pyrimidine-3-carboxamide (example compound 34);
(48) 4-amino-7-(tert-butyl)-N-(5-methyl-1H-pyrazol-3-yl)-7H-pyrrolo[2,3-d]pyrimidine-5-carboxamide (example compound 48);
(50) 4-amino-7-(1-fluoro-2-methylpropan-2-yl)-N-(5-methyl-1H-pyrazol-3-yl)-7H-pyrrolo[2,3-d]pyrimidine-5-carboxamide (example compound 50);
(51) 4-amino-N-(5-methyl-1H-pyrazol-3-yl)-7-(1-methylcyclopropyl)-7H-pyrrolo[2,3-d]pyrimidine-5-carboxamide (example compound 51); and
(52) 4-amino-7-(2-cyclopropylpropan-2-yl)-N-(5-methyl-1H-pyrazol-3-yl)-7H-pyrrolo[2,3-d]pyrimidine-5-carboxamide (example compound 52).

Moreover, the present invention provides a RET inhibitor comprising the compound or a salt thereof according to any one of [1] to [18] as an active ingredient.

Moreover, the present invention provides a pharmaceutical composition comprising the compound or a salt thereof according to any one of [1] to [18].

Moreover, the present invention provides a pharmaceutical composition comprising the compound or a salt thereof according to any one of [1] to [18], wherein the pharmaceutical composition prevents or treats a disease that can be treated by RET inhibition.

Moreover, the present invention provides an antitumor agent comprising the compound or a salt thereof according to any one of [1] to [18].

Moreover, the present invention provides an antitumor agent comprising the compound or a salt thereof according to any one of [1] to [18], wherein the antitumor agent treats a malignant tumor with enhanced activation of RET.

Moreover, the present invention provides the compound or a salt thereof according to any one of [1] to [18] for use in prevention or treatment of a malignant tumor.

Moreover, the present invention provides the compound or a salt thereof according to any one of [1] to [18] for use in prevention or treatment of a malignant tumor, wherein the malignant tumor is a malignant tumor with enhanced activation of RET.

Moreover, the present invention provides use of the compound or a salt thereof according to any one of [1] to [18] for producing an antitumor agent.

Moreover, the present invention provides use of the compound or a salt thereof according to any one of [1] to [18] for producing an antitumor agent, wherein the antitumor agent is an antitumor agent for treating a malignant tumor with enhanced activation of RET.

Moreover, the present invention provides use of the compound or a salt thereof according to any one of [1] to [18] for producing a RET inhibitor.

Moreover, the present invention provides a method for preventing or treating a malignant tumor, the method comprising administering the compound or a salt thereof according to any one of [1] to [18] to a mammal.

Moreover, the present invention provides a method for preventing or treating a malignant tumor, the method comprising administering the compound or a salt thereof according to any one of [1] to [18] to a mammal, wherein the malignant tumor is a malignant tumor with enhanced activation of RET.

Moreover, the present invention provides a method of inhibiting RET comprising administering the compound or a salt thereof according to any one of [1] to [18] to a mammal.

Moreover, the present invention provides

[19] a compound represented by Formula (I') below or a salt thereof:

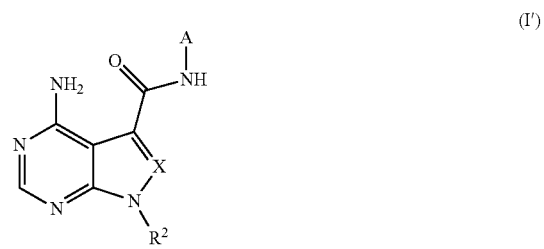

wherein A is pyrazolyl substituted with n-number of $R^1$;
$R^1$ is
halogen,
cyano,
substituted or unsubstituted C1-C6 alkyl,
substituted or unsubstituted C3-C7 cycloalkyl, substituted or unsubstituted C6-C14 aromatic hydrocarbon, or a substituted or unsubstituted C3-C10 monocyclic or polycyclic saturated or unsaturated heterocyclic group containing 1 to 3 identical or different heteroatoms selected from nitrogen, oxygen, and sulfur;

$R^2$ is substituted or unsubstituted C1-C10 alkyl,
substituted or unsubstituted C3-C4 cycloalkyl,
substituted or unsubstituted C2-C6 alkenyl,
substituted or unsubstituted C3-C4 cycloalkenyl,
substituted or unsubstituted C4-C12 bridged cycloalkyl,
substituted or unsubstituted C6-C14 aromatic hydrocarbon, or a substituted or unsubstituted C3-C10 monocyclic or polycyclic saturated or unsaturated heterocyclic group containing 1 to 3 identical or different heteroatoms selected from nitrogen, oxygen, and sulfur;

X is
N or
$CR^3$, wherein $R^3$ is
  hydrogen,
  halogen,
  cyano,
  substituted or unsubstituted C1-C6 alkyl,
  substituted or unsubstituted C2-C6 alkenyl,
  substituted or unsubstituted C2-C6 alkynyl,
  substituted or unsubstituted C1-C6 alkoxy,
  substituted or unsubstituted amino,
  substituted or unsubstituted C6-C14 aromatic hydrocarbon, or
  a substituted or unsubstituted C3-C10 monocyclic or polycyclic unsaturated heterocyclic group containing 1 to 3 identical or different heteroatoms selected from nitrogen, oxygen, and sulfur; and n is an integer of 0 to 3, wherein when n is 2 or 3, $R^1$ may be identical or different from each other.

[20] In Formula (I'),
A is preferably pyrazolyl substituted with n-number of $R^1$;
$R^1$ is preferably
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
$R^2$ is preferably
substituted or unsubstituted C1-C10 alkyl,
substituted or unsubstituted C3-C4 cycloalkyl,
substituted or unsubstituted C2-C6 alkenyl, or
substituted or unsubstituted C4-C12 bridged cycloalkyl,
X is preferably
N or
$CR^3$, wherein $R^3$ is
  hydrogen,
  halogen,
  substituted or unsubstituted C1-C6 alkyl,
  substituted or unsubstituted C2-C6 alkenyl, or
  substituted or unsubstituted C1-C6 alkoxy; and
n is preferably an integer of 1 to 3,
wherein when n is 2 or 3, $R^1$ may be identical or different from each other.

[21] In Formula (I'),
A is pyrazolyl substituted with n-number of $R^1$;
$R^1$ is more preferably
halogen;
cyano;
C1-C6 alkyl that may be substituted with halogen or C1-C4 alkoxy;
C3-C7 cycloalkyl;
phenyl; or
a C3-C6 monocyclic unsaturated heterocyclic group containing one oxygen atom or one sulfur atom;
$R^2$ is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C4 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl that may be substituted with C1-C4 alkyl;
X is more preferably
N or
$CR^3$, wherein $R^3$ is
  hydrogen;
  halogen;
  C1-C6 alkyl;
  C2-C4 alkynyl that may be substituted with
  C1-C6 alkyl that may be substituted with hydroxy,
  C3-C7 cycloalkyl that may be substituted with hydroxy,
  one or more C3-C6 monocyclic saturated heterocyclic groups containing 1 to 3 identical or different heteroatoms selected from nitrogen, oxygen, and sulfur, or
  one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
  C1-C4 alkoxy that may be substituted with one or more C3-C6 monocyclic saturated heterocyclic groups containing 1 to 3 identical or different heteroatoms selected from nitrogen, oxygen, and sulfur; and n is more preferably 1 or 2, wherein when n is 2, $R^1$ may be identical or different from each other.

In another embodiment of the present invention, a compound of Formula (I') wherein pyrazolyl is bonded to an amide structure at 3-position is preferable. Moreover, a preferred embodiment of the compound of Formula (I') wherein pyrazolyl is bonded to an amide structure at 3-position in present invention is

[22] a compound represented by Formula (II') below or a salt thereof:

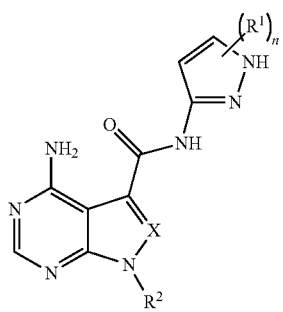

(II')

wherein $R^1$ is
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur;
$R^2$ is
substituted or unsubstituted C1-C10 alkyl,
substituted or unsubstituted C3-C4 cycloalkyl,
substituted or unsubstituted C2-C6 alkenyl, or
substituted or unsubstituted C4-C12 bridged cycloalkyl;
X is
N or
$CR^3$, wherein $R^3$ is
hydrogen,
halogen,
substituted or unsubstituted C1-C6 alkyl,
substituted or unsubstituted C2-C6 alkynyl, or
substituted or unsubstituted C1-C6 alkoxy; and
n is an integer of 1 to 3,
wherein when n is 2 or 3, $R^1$ may be identical or different from each other.

In the present invention, the compound represented by Formula (II') above is also referred to simply as Compound (II').

[23] In Formula (II'),
$R^1$ is more preferably
halogen;
cyano;
C1-C6 alkyl that may be substituted with halogen or C1-C4 alkoxy;
C3-C7 cycloalkyl;
phenyl; or
a C3-C6 monocyclic unsaturated heterocyclic group containing one oxygen atom or one sulfur atom;
$R^2$ is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C4 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl that may be substituted with C1-C4 alkyl;
X is more preferably
N or
$CR^3$, wherein $R^3$ is
hydrogen;
halogen;
C1-C6 alkyl;
C2-C4 alkynyl that may be substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
C1-C4 alkoxy that may be substituted with one or more C3-C6 monocyclic saturated heterocyclic groups containing 1 to 3 identical or different heteroatoms selected from nitrogen, oxygen, and sulfur; and
n is more preferably 1 or 2,
wherein when n is 2, $R^1$ may be identical or different from each other.

[24] In Formula (II'),
$R^1$ is more preferably
halogen;
cyano;
C1-C6 alkyl that may be substituted with halogen;
C3-C7 cycloalkyl;
phenyl; or
a C3-C6 monocyclic unsaturated heterocyclic group containing one oxygen atom or one sulfur atom;
$R^2$ is more preferably
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C4 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl; and
X is more preferably
N or
$CR^3$, wherein $R^3$ is
hydrogen;
halogen;
C1-C4 alkyl,
C2-C4 alkynyl that may be substituted with
C1-C6 alkyl that may be substituted with hydroxy;
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
C1-C4 alkoxy; and
n is more preferably 1 or 2,
wherein when n is 2, $R^1$ may be identical or different from each other.

[25] In Formula (II'),
$R^1$ is more preferably
halogen,
cyano, or
C1-C4 alkyl that may be substituted with halogen;
$R^2$ is more preferably
linear C1-C4 alkyl that is substituted with C3-C7 cycloalkyl;
branched C3-C6 alkyl that may be substituted with halogen, C3-C7 cycloalkyl, one or more C3-C6 monocyclic unsaturated heterocyclic groups containing one sulfur atom, or C1-C4 alkoxy;
C3-C4 cycloalkyl that may be substituted with halogen, C1-C4 alkyl, or C3-C5 cycloalkyl;
C2-C6 alkenyl that may be substituted with halogen; or
C4-C12 bridged cycloalkyl selected from bicyclo[1.1.1]pentan-1-yl and bicyclo[2.2.1]heptan-2-yl;
X is more preferably
N or
CR$^3$, wherein R$^3$ is
    hydrogen; or
    C2-C4 alkynyl that is substituted with
    C1-C6 alkyl that may be substituted with hydroxy,
    C3-C7 cycloalkyl that may be substituted with hydroxy,
    one or more C3-C6 monocyclic saturated heterocyclic groups containing 1 to 3 identical or different heteroatoms selected from nitrogen, oxygen, and sulfur, or
    one or more C3-C6 monocyclic unsaturated heterocyclic groups that may be substituted with C1-C4 alkyl and contains 1 to 3 identical or different heteroatoms selected from nitrogen, oxygen, and sulfur; and
n is more preferably an integer of 1.

Preferred in another embodiment of the present invention is

[26] a compound represented by Formula (IX') below or a salt thereof:

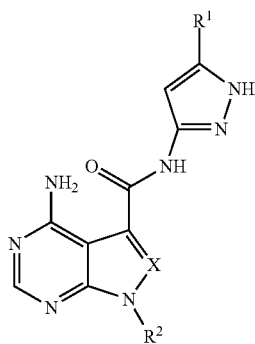

(IX')

wherein R$^1$ is
halogen;
cyano;
C1-C6 alkyl that may be substituted with halogen;
C3-C7 cycloalkyl;
phenyl; or
a C3-C6 monocyclic unsaturated heterocyclic group containing one oxygen atom or one sulfur atom;
R$^2$ is
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C4 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl; and
X is
N or
CR$^3$, wherein R$^3$ is
    hydrogen;
    halogen;
    C1-C4 alkyl;
    C2-C4 alkynyl that may be substituted with
    C1-C6 alkyl that may be substituted with hydroxy,
    C3-C7 cycloalkyl that may be substituted with hydroxy,
    one or more C3-C6 monocyclic saturated heterocyclic groups containing 1 to 3 identical or different heteroatoms selected from nitrogen, oxygen, and sulfur, or
    one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
    C1-C4 alkoxy.

In the present invention, the compound represented by Formula (IX') above is also referred to simply as Compound (IX').

[27] In Formula (IX'),
R$^1$ is more preferably
halogen,
cyano, or
C1-C4 alkyl that may be substituted with halogen;
R$^2$ is more preferably
linear C1-C4 alkyl that is substituted with C3-C7 cycloalkyl;
branched C3-C6 alkyl that may be substituted with halogen,
C3-C7 cycloalkyl, one or more C3-C6 monocyclic unsaturated heterocyclic groups containing one sulfur atom, or C1-C4 alkoxy;
C3-C4 cycloalkyl that may be substituted with halogen, C1-C4 alkyl, or C3-C5 cycloalkyl;
C2-C6 alkenyl that may be substituted with halogen; or
C4-C12 bridged cycloalkyl selected from bicyclo[1.1.1]pentan-1-yl and bicyclo[2.2.1]heptan-2-yl; and
X is more preferably
N or
CR$^3$, wherein R$^3$ is
    hydrogen; or
    C2-C4 alkynyl that is substituted with
    C1-C6 alkyl that may be substituted with hydroxy,
    C3-C7 cycloalkyl that may be substituted with hydroxy,
    one or more C3-C6 monocyclic saturated heterocyclic groups containing 1 to 3 identical or different heteroatoms selected from nitrogen, oxygen, and sulfur, or
    one or more C3-C6 monocyclic unsaturated heterocyclic groups that may be substituted with C1-C4 alkyl and contains 1 to 3 identical or different heteroatoms selected from nitrogen, oxygen, and sulfur.

[28] In Formula (IX'),
R$^1$ is more preferably
bromine,
cyano, or
C1-C4 alkyl that may be substituted with fluorine;
R$^2$ is more preferably
linear C1-C4 alkyl that is substituted with C3-C7 cycloalkyl;
branched C3-C6 alkyl that may be substituted with fluorine,
C3-C7 cycloalkyl, one or more C3-C6 monocyclic unsaturated heterocyclic groups containing one sulfur atom, or C1-C4 alkoxy;
C3-C4 cycloalkyl that may be substituted with fluorine, C1-C4 alkyl, or C3-C5 cycloalkyl;
C2-C6 alkenyl that may be substituted with fluorine; or
C4-C12 bridged cycloalkyl selected from bicyclo[1.1.1]pentan-1-yl and bicyclo[2.2.1]heptan-2-yl; and
X is more preferably
N or
CR$^3$, wherein R$^3$ is
    hydrogen; or
    C2-C4 alkynyl that is substituted with
    C1-C6 alkyl that may be substituted with hydroxy, C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C6 monocyclic unsaturated heterocyclic groups that may be substituted with C1-C4 alkyl and contains 1 to 3 identical or different heteroatoms selected from nitrogen, oxygen, and sulfur.

Moreover, in another embodiment of the present invention,

[29] in Formula (IX'),
$R^1$ is more preferably halogen or C1-C4 alkyl;
$R^2$ is more preferably
branched C3-C6 alkyl that may be substituted with halogen or C3-C5 cycloalkyl,
C3-C4 cycloalkyl that may be substituted with C1-C4 alkyl, or bicyclo[2.2.1]heptan-2-yl; and
X is more preferably
N or
$CR^3$, wherein $R^3$ is
hydrogen; or
ethynyl or propynyl that is substituted with
C1-C4 alkyl that may be substituted with hydroxy,
C3-C5 cycloalkyl that may be substituted with hydroxy,
one or more C3-C6 monocyclic saturated heterocyclic groups containing 1 to 3 identical or different heteroatoms selected from nitrogen and oxygen, or
one or more C3-C6 monocyclic unsaturated heterocyclic groups that may be substituted with methyl and contains 1 to 3 nitrogen atoms.

[30] In Formula (IX'),
$R^1$ is more preferably bromine or methyl;
$R^2$ is more preferably
branched C3-C6 alkyl that may be substituted with fluorine or C3-C5 cycloalkyl, or
C3-C4 cycloalkyl that may be substituted with methyl; and
X is more preferably
N or
$CR^3$, wherein $R^3$ is hydrogen.

[31] In Formula (IX'),
$R^1$ is more preferably methyl;
$R^2$ is more preferably
isopropyl or tert-butyl that may be substituted with fluorine or cyclopropyl, or
cyclopropyl that may be substituted with methyl; and
X is more preferably
N or
$CR^3$, wherein $R^3$ is hydrogen.

Moreover,

[32] in Formulas (I'), (II'), and (IX') of the present invention, when X is N,
$R^1$ is preferably
halogen,
cyano,
substituted or unsubstituted C1-C6 alkyl,
substituted or unsubstituted C3-C7 cycloalkyl,
substituted or unsubstituted C6-C14 aromatic hydrocarbon, or
a substituted or unsubstituted C3-C10 monocyclic or polycyclic saturated or unsaturated heterocyclic group containing 1 to 3 identical or different heteroatoms selected from nitrogen, oxygen, and sulfur; and
$R^2$ is preferably
substituted or unsubstituted C1-C10 alkyl,
substituted or unsubstituted C3-C4 cycloalkyl,
substituted or unsubstituted C2-C6 alkenyl, or
substituted or unsubstituted C4-C12 bridged cycloalkyl.

Moreover,

[33] in Formulas (I'), (II'), and (IX') of the present invention, when X is $CR^3$ ($R^3$ is as defined above),
$R^1$ is preferably
halogen,
substituted or unsubstituted C1-C6 alkyl, or
a substituted or unsubstituted C3-C10 monocyclic or polycyclic saturated or unsaturated heterocyclic group containing 1 to 3 identical or different heteroatoms selected from nitrogen, oxygen, and sulfur; and
$R^2$ is preferably
substituted or unsubstituted C1-C10 alkyl,
substituted or unsubstituted C3-C4 cycloalkyl, or
substituted or unsubstituted C4-C12 bridged cycloalkyl.

Specific examples of the compound of the present invention include, but are not limited to, compounds produced in the Examples described later.

Specific preferred examples of Compound (I') are as follows:

[34]
(11) 4-amino-1-cyclobutyl-N-(5-methyl-1H-pyrazol-3-yl)-1H-pyrazolo[3,4-d]pyrimidine-3-carboxamide (example compound 11);
(12) 4-amino-N-(5-methyl-1H-pyrazol-3-yl)-1-((1-methylcyclopropyl)methyl)-1H-pyrazolo[3,4-d]pyrimidine-3-carboxamide (example compound 12);
(13) 4-amino-N-(5-methyl-1H-pyrazol-3-yl)-1-(2,2,2-trifluoroethyl)-1H-pyrazolo[3,4-d]pyrimidine-3-carboxamide (example compound 13);
(14) 4-amino-N-(5-methyl-1H-pyrazol-3-yl)-1-(3,3,3-trifluoropropyl)-1H-pyrazolo[3,4-d]pyrimidine-3-carboxamide (example compound 14);
(15) 4-amino-1-(sec-butyl)-N-(5-methyl-1H-pyrazol-3-yl)-1H-pyrazolo[3,4-d]pyrimidine-3-carboxamide (example compound 15);
(16) 4-amino-1-(cyclobutylmethyl)-N-(5-methyl-1H-pyrazol-3-yl)-1H-pyrazolo[3,4-d]pyrimidine-3-carboxamide (example compound 16);
(17) 4-amino-N-(5-bromo-1H-pyrazol-3-yl)-1-(cyclobutylmethyl)-1H-pyrazolo[3,4-d]pyrimidine-3-carboxamide (example compound 17);
(18) 4-amino-1-(cyclopropylmethyl)-N-(5-methyl-1H-pyrazol-3-yl)-1H-pyrazolo[3,4-d]pyrimidine-3-carboxamide (example compound 18);
(19) 4-amino-1-(cyclopentylmethyl)-N-(5-methyl-1H-pyrazol-3-yl)-1H-pyrazolo[3,4-d]pyrimidine-3-carboxamide (example compound 19);
(20) 4-amino-N-(5-bromo-1H-pyrazol-3-yl)-1-(cyclopentylmethyl)-1H-pyrazolo[3,4-d]pyrimidine-3-carboxamide (example compound 20);
(21) 4-amino-1-isopropyl-N-(5-(trifluoromethyl)-1H-pyrazol-3-yl)-1H-pyrazolo[3,4-d]pyrimidine-3-carboxamide (example compound 21);
(22) 4-amino-N-(5-bromo-1H-pyrazol-3-yl)-1-isopropyl-1H-pyrazolo[3,4-d]pyrimidine-3-carboxamide (example compound 22);
(26) 4-amino-1-(3,3-dimethylcyclobutyl)-N-(5-methyl-1H-pyrazol-3-yl)-1H-pyrazolo[3,4-d]pyrimidine-3-carboxamide (example compound 26);
(27) 4-amino-1-(bicyclo[2.2.1]heptan-2-yl)-N-(5-methyl-1H-pyrazol-3-yl)-1H-pyrazolo[3,4-d]pyrimidine-3-carboxamide (example compound 27);
(28) 4-amino-1-(bicyclo[2.2.1]heptan-2-yl)-N-(5-bromo-1H-pyrazol-3-yl)-1H-pyrazolo[3,4-d]pyrimidine-3-carboxamide (example compound 28);

(29) 1-(adamantan-2-yl)-4-amino-N-(5-methyl-1H-pyrazol-3-yl)-1H-pyrazolo[3,4-d]pyrimidine-3-carboxamide (example compound 29);

(30) 4-amino-N-(5-methyl-1H-pyrazol-3-yl)-1-((2S,3R)-2,6,6-trimethylbicyclo[3.1.1]heptan-3-yl)-1H-pyrazolo[3,4-d]pyrimidine-3-carboxamide (example compound 30);

(31) 4-amino-1-(3-fluoroprop-1-en-2-yl)-N-(5-methyl-1H-pyrazol-3-yl)-1H-pyrazolo[3,4-d]pyrimidine-3-carboxamide (example compound 31);

(34) 4-amino-1-(tert-butyl)-N-(5-methyl-1H-pyrazol-3-yl)-1H-pyrazolo[3,4-d]pyrimidine-3-carboxamide (example compound 34);

(35) 4-amino-N-(5-bromo-1H-pyrazol-3-yl)-1-(tert-butyl)-1H-pyrazolo[3,4-d]pyrimidine-3-carboxamide (example compound 35);

(36) 4-amino-1-(tert-butyl)-N-(5-(trifluoromethyl)-1H-pyrazol-3-yl)-1H-pyrazolo[3,4-d]pyrimidine-3-carboxamide (example compound 36);

(37) 4-amino-1-(tert-butyl)-N-(5-(furan-2-yl)-1H-pyrazol-3-yl)-1H-pyrazolo[3,4-d]pyrimidine-3-carboxamide (example compound 37);

(38) 4-amino-1-(tert-butyl)-N-(5-cyano-1H-pyrazol-3-yl)-1H-pyrazolo[3,4-d]pyrimidine-3-carboxamide (example compound 38);

(39) 4-amino-1-(tert-butyl)-N-(5-ethyl-1H-pyrazol-3-yl)-1H-pyrazolo[3,4-d]pyrimidine-3-carboxamide (example compound 39);

(40) 4-amino-1-(tert-butyl)-N-(5-isopropyl-1H-pyrazol-3-yl)-1H-pyrazolo[3,4-d]pyrimidine-3-carboxamide (example compound 40);

(41) 4-amino-1-(tert-butyl)-N-(5-cyclopropyl-1H-pyrazol-3-yl)-1H-pyrazolo[3,4-d]pyrimidine-3-carboxamide (example compound 41);

(42) 4-amino-1-(tert-butyl)-N-(5-cyclobutyl-1H-pyrazol-3-yl)-1H-pyrazolo[3,4-d]pyrimidine-3-carboxamide (example compound 42);

(45) 4-amino-7-isopropyl-N-(5-methyl-1H-pyrazol-3-yl)-7H-pyrrolo[2,3-d]pyrimidine-5-carboxamide (example compound 45);

(46) 4-amino-7-(1-fluoropropan-2-yl)-N-(5-methyl-1H-pyrazol-3-yl)-7H-pyrrolo[2,3-d]pyrimidine-5-carboxamide (example compound 46);

(48) 4-amino-7-(tert-butyl)-N-(5-methyl-1H-pyrazol-3-yl)-7H-pyrrolo[2,3-d]pyrimidine-5-carboxamide (example compound 48);

(49) 4-amino-7-(tert-butyl)-N-(5-(furan-2-yl)-1H-pyrazol-3-yl)-7H-pyrrolo[2,3-d]pyrimidine-5-carboxamide (example compound 49);

(50) 4-amino-7-(1-fluoro-2-methylpropan-2-yl)-N-(5-methyl-1H-pyrazol-3-yl)-7H-pyrrolo[2,3-d]pyrimidine-5-carboxamide (example compound 50);

(51) 4-amino-N-(5-methyl-1H-pyrazol-3-yl)-7-(1-methylcyclopropyl)-7H-pyrrolo[2,3-d]pyrimidine-5-carboxamide (example compound 51);

(52) 4-amino-7-(2-cyclopropylpropan-2-yl)-N-(5-methyl-1H-pyrazol-3-yl)-7H-pyrrolo[2,3-d]pyrimidine-5-carboxamide (example compound 52);

(53) 4-amino-7-(1-methoxy-2-methylpropan-2-yl)-N-(5-methyl-1H-pyrazol-3-yl)-7H-pyrrolo[2,3-d]pyrimidine-5-carboxamide (example compound 53);

(54) 4-amino-7-(1-(fluoromethyl)cyclopropyl)-N-(5-methyl-1H-pyrazol-3-yl)-7H-pyrrolo[2,3-d]pyrimidine-5-carboxamide (example compound 54);

(55) 4-amino-7-(1-(difluoromethyl)cyclopropyl)-N-(5-methyl-1H-pyrazol-3-yl)-7H-pyrrolo[2,3-d]pyrimidine-5-carboxamide (example compound 55);

(56) 4-amino-N-(5-methyl-1H-pyrazol-3-yl)-7-(2-(thiophen-2-yl)propan-2-yl)-7H-pyrrolo[2,3-d]pyrimidine-5-carboxamide (example compound 56);

(58) 4-amino-7-(bicyclo[1.1.1]pentan-1-yl)-N-(5-methyl-1H-pyrazol-3-yl)-7H-pyrrolo[2,3-d]pyrimidine-5-carboxamide (example compound 58);

(60) 4-amino-N-(5-methyl-1H-pyrazol-3-yl)-7-(2-phenylpropan-2-yl))-7H-pyrrolo[2,3-d]pyrimidine-5-carboxamide (example compound 60);

(61) 4-amino-N-(5-methyl-1H-pyrazol-3-yl)-7-(2,3,3-trimethylbutan-2-yl)-7H-pyrrolo[2,3-d]pyrimidine-5-carboxamide (example compound 61);

(62) 4-amino-7-(2,3-dimethylbutan-2-yl)-N-(5-methyl-1H-pyrazol-3-yl)-7H-pyrrolo[2,3-d]pyrimidine-5-carboxamide (example compound 62);

(63) 4-amino-N-(5-bromo-1H-pyrazol-3-yl)-7-(tert-butyl)-7H-pyrrolo[2,3-d]pyrimidine-5-carboxamide (example compound 63);

(64) 4-amino-7-(tert-butyl)-N-(5-(methoxymethyl)-1H-pyrazol-3-yl)-7H-pyrrolo[2,3-d]pyrimidine-5-carboxamide (example compound 64);

(65) 4-amino-N-(5-bromo-1H-pyrazol-3-yl)-7-isopropyl-7H-pyrrolo[2,3-d]pyrimidine-5-carboxamide (example compound 65);

(66) 4-amino-N-(5-bromo-1H-pyrazol-3-yl)-7-(1-fluoro-2-methylpropan-2-yl)-7H-pyrrolo[2,3-d]pyrimidine-5-carboxamide (example compound 66);

(67) 4-amino-N-(5-bromo-1H-pyrazol-3-yl)-7-(1-methylcyclopropyl)-7H-pyrrolo[2,3-d]pyrimidine-5-carboxamide (example compound 67);

(68) 4-amino-N-(5-methyl-1H-pyrazol-3-yl)-7-(1-methylcyclobutyl)-7H-pyrrolo[2,3-d]pyrimidine-5-carboxamide (example compound 68);

(69) 4-amino-7-cyclobutyl-N-(5-methyl-1H-pyrazol-3-yl)-7H-pyrrolo[2,3-d]pyrimidine-5-carboxamide (example compound 69);

(70) 4-amino-N-(5-methyl-1H-pyrazol-3-yl)-7-(tert-pentyl)-7H-pyrrolo[2,3-d]pyrimidine-5-carboxamide (example compound 70);

(71) 4-amino-7-(bicyclo[2.2.1]heptan-2-yl)-N-(5-methyl-1H-pyrazol-3-yl)-7H-pyrrolo[2,3-d]pyrimidine-5-carboxamide (example compound 71);

(73) 4-amino-7-(tert-butyl)-6-methyl-N-(3-methyl-1H-pyrazol-5-yl)-7H-pyrrolo[2,3-d]pyrimidine-5-carboxamide (example compound 73);

(74) 7-([1,1'-bi(cyclopropan)]-1-yl)-4-amino-N-(5-methyl-1H-pyrazol-3-yl)-7H-pyrrolo[2,3-d]pyrimidine-5-carboxamide (example compound 74);

(75) 4-amino-6-chloro-N-(5-methyl-1H-pyrazol-3-yl)-7-(1-methylcyclopropyl)-7H-pyrrolo[2,3-d]pyrimidine-5-carboxamide (example compound 75);

(76) 4-amino-6-bromo-N-(5-methyl-1H-pyrazol-3-yl)-7-(1-methylcyclopropyl)-7H-pyrrolo[2,3-d]pyrimidine-5-carboxamide (example compound 76);

(77) 4-amino-6-methoxy-N-(5-methyl-1H-pyrazol-3-yl)-7-(1-methylcyclopropyl)-7H-pyrrolo[2,3-d]pyrimidine-5-carboxamide (example compound 77);

(78) 4-amino-6-chloro-7-(1-fluoro-2-methylpropan-2-yl)-N-(5-methyl-1H-pyrazol-3-yl)-7H-pyrrolo[2,3-d]pyrimidine-5-carboxamide (example compound 78);

(79) 4-amino-6-(3-hydroxy-3-methyl-1-butyn-1-yl)-N-(5-methyl-1H-pyrazol-3-yl)-7-(1-methylcyclopropyl)-7H-pyrrolo[2,3-d]pyrimidine-5-carboxamide (example compound 79);

(80) 4-amino-N-(5-methyl-1H-pyrazol-3-yl)-7-(1-methylcyclopropyl)-6-(pyridin-3-ylethynyl)-7H-pyrrolo[2,3-d]pyrimidine-5-carboxamide (example compound 80);

(81) 4-amino-6-((1-hydroxycyclopentyl)ethynyl)-N-(5-methyl-1H-pyrazol-3-yl)-7-(1-methylcyclopropyl)-7H-pyrrolo[2,3-d]pyrimidine-5-carboxamide (example compound 81);

(82) 4-amino-6-((1-methyl-1H-pyrazol-4-yl)ethynyl)-N-(5-methyl-1H-pyrazol-3-yl)-7-(1-methylcyclopropyl)-7H-pyrrolo[2,3-d]pyrimidine-5-carboxamide (example compound 82);

(83) 4-amino-6-((1-methyl-1H-imidazol-5-yl)ethynyl)-N-(5-methyl-1H-pyrazol-3-yl)-7-(1-methylcyclopropyl)-7H-pyrrolo[2,3-d]pyrimidine-5-carboxamide (example compound 83);

(84) 4-amino-N-(5-methyl-1H-pyrazol-3-yl)-7-(1-methylcyclopropyl)-6-(3-morpholino-1-propyn-1-yl)-7H-pyrrolo[2,3-d]pyrimidine-5-carboxamide (example compound 84);

(85) 4-amino-6-(3-(1-hydroxycyclobutyl)-1-propyne)-N-(5-methyl-1H-pyrazol-3-yl)-7-(1-methylcyclopropyl)-7H-pyrrolo[2,3-d]pyrimidine-5-carboxamide (example compound 85);

(86) 4-amino-N-(5-methyl-1H-pyrazol-3-yl)-7-(1-methylcyclopropyl)-6-((tetrahydro-2H-pyran-4-yl)ethynyl)-7H-pyrrolo[2,3-d]pyrimidine-5-carboxamide (example compound 86);

(87) 4-amino-N-(5-methyl-1H-pyrazol-3-yl)-6-((1-methyl-1H-pyrazol-3-yl)ethynyl)-7-(1-methylcyclopropyl)-7H-pyrrolo[2,3-d]pyrimidine-5-carboxamide (example compound 87);

(88) 4-amino-6-(imidazo[1,2-b]pyridazin-3-ylethynyl)-N-(5-methyl-1H-pyrazol-3-yl)-7-(1-methylcyclopropyl)-7H-pyrrolo[2,3-d]pyrimidine-5-carboxamide (example compound 88);

(89) 4-amino-6-ethoxy-N-(5-methyl-1H-pyrazol-3-yl)-7-(1-methylcyclopropyl)-7H-pyrrolo[2,3-d]pyrimidine-5-carboxamide (example compound 89); and

(90) (R)-4-amino-N-(5-methyl-1H-pyrazol-3-yl)-7-(1-methylcyclopropyl)-6-((tetrahydrofuran-2-yl)methoxy)-7H-pyrrolo[2,3-d]pyrimidine-5-carboxamide (example compound 90).

More preferred examples of Compound (I') are as follows:
[35]

(27) 4-amino-1-(bicyclo[2.2.1]heptan-2-yl)-N-(5-methyl-1H-pyrazol-3-yl)-1H-pyrazolo[3,4-d]pyrimidine-3-carboxamide (example compound 27);

(34) 4-amino-1-(tert-butyl)-N-(5-methyl-1H-pyrazol-3-yl)-1H-pyrazolo[3,4-d]pyrimidine-3-carboxamide (example compound 34);

(45) 4-amino-7-isopropyl-N-(5-methyl-1H-pyrazol-3-yl)-7H-pyrrolo[2,3-d]pyrimidine-5-carboxamide (example compound 45);

(48) 4-amino-7-(tert-butyl)-N-(5-methyl-1H-pyrazol-3-yl)-7H-pyrrolo[2,3-d]pyrimidine-5-carboxamide (example compound 48);

(50) 4-amino-7-(1-fluoro-2-methylpropan-2-yl)-N-(5-methyl-1H-pyrazol-3-yl)-7H-pyrrolo[2,3-d]pyrimidine-5-carboxamide (example compound 50);

(51) 4-amino-N-(5-methyl-1H-pyrazol-3-yl)-7-(1-methylcyclopropyl)-7H-pyrrolo[2,3-d]pyrimidine-5-carboxamide (example compound 51);

(52) 4-amino-7-(2-cyclopropylpropan-2-yl)-N-(5-methyl-1H-pyrazol-3-yl)-7H-pyrrolo[2,3-d]pyrimidine-5-carboxamide (example compound 52);

(65) 4-amino-N-(5-bromo-1H-pyrazol-3-yl)-7-isopropyl-7H-pyrrolo[2,3-d]pyrimidine-5-carboxamide (example compound 65);

(68) 4-amino-N-(5-methyl-1H-pyrazol-3-yl)-7-(1-methylcyclobutyl)-7H-pyrrolo[2,3-d]pyrimidine-5-carboxamide (example compound 68);

(71) 4-amino-7-(bicyclo[2.2.1]heptan-2-yl)-N-(5-methyl-1H-pyrazol-3-yl)-7H-pyrrolo[2,3-d]pyrimidine-5-carboxamide (example compound 71);

(79) 4-amino-6-(3-hydroxy-3-methyl-1-butyn-1-yl)-N-(5-methyl-1H-pyrazol-3-yl)-7-(1-methylcyclopropyl)-7H-pyrrolo[2,3-d]pyrimidine-5-carboxamide (example compound 79);

(80) 4-amino-N-(5-methyl-1H-pyrazol-3-yl)-7-(1-methylcyclopropyl)-6-(pyridin-3-ylethynyl)-7H-pyrrolo[2,3-d]pyrimidine-5-carboxamide (example compound 80);

(81) 4-amino-6-((1-hydroxycyclopentyl)ethynyl)-N-(5-methyl-1H-pyrazol-3-yl)-7-(1-methylcyclopropyl)-7H-pyrrolo[2,3-d]pyrimidine-5-carboxamide (example compound 81);

(82) 4-amino-6-((1-methyl-1H-pyrazol-4-yl)ethynyl)-N-(5-methyl-1H-pyrazol-3-yl)-7-(1-methylcyclopropyl)-7H-pyrrolo[2,3-d]pyrimidine-5-carboxamide (example compound 82);

(83) 4-amino-6-((1-methyl-1H-imidazol-5-yl)ethynyl)-N-(5-methyl-1H-pyrazol-3-yl)-7-(1-methylcyclopropyl)-7H-pyrrolo[2,3-d]pyrimidine-5-carboxamide (example compound 83);

(84) 4-amino-N-(5-methyl-1H-pyrazol-3-yl)-7-(1-methylcyclopropyl)-6-(3-morpholino-1-propyn-1-yl)-7H-pyrrolo[2,3-d]pyrimidine-5-carboxamide (example compound 84); and

(85) 4-amino-6-(3-(1-hydroxycyclobutyl)-1-propyne)-N-(5-methyl-1H-pyrazol-3-yl)-7-(1-methylcyclopropyl)-7H-pyrrolo[2,3-d]pyrimidine-5-carboxamide (example compound 85).

Even more preferred examples of Compound (I') are as follows:
[36]

(34) 4-amino-1-(tert-butyl)-N-(5-methyl-1H-pyrazol-3-yl)-1H-pyrazolo[3,4-d]pyrimidine-3-carboxamide (example compound 34);

(48) 4-amino-7-(tert-butyl)-N-(5-methyl-1H-pyrazol-3-yl)-7H-pyrrolo[2,3-d]pyrimidine-5-carboxamide (example compound 48);

(50) 4-amino-7-(1-fluoro-2-methylpropan-2-yl)-N-(5-methyl-1H-pyrazol-3-yl)-7H-pyrrolo[2,3-d]pyrimidine-5-carboxamide (example compound 50);

(51) 4-amino-N-(5-methyl-1H-pyrazol-3-yl)-7-(1-methylcyclopropyl)-7H-pyrrolo[2,3-d]pyrimidine-5-carboxamide (example compound 51); and

(52) 4-amino-7-(2-cyclopropylpropan-2-yl)-N-(5-methyl-1H-pyrazol-3-yl)-7H-pyrrolo[2,3-d]pyrimidine-5-carboxamide (example compound 52).

Moreover, the present invention provides a RET inhibitor comprising the compound or a salt thereof according to any one of [19] to [36] as an active ingredient.

Moreover, the present invention provides a pharmaceutical composition comprising the compound or a salt thereof according to any one of [19] to [36].

Moreover, the present invention provides a pharmaceutical composition comprising the compound or a salt thereof according to any one of [19] to [36], wherein the pharmaceutical composition prevents or treats a disease that can be treated by RET inhibition.

Moreover, the present invention provides an antitumor agent comprising the compound or a salt thereof according to any one of [19] to [36].

Moreover, the present invention provides an antitumor agent comprising the compound or a salt thereof according to any one of [19] to [36], wherein the antitumor agent treats a malignant tumor with enhanced activation of RET.

Moreover, the present invention provides the compound or a salt thereof according to any one of [19] to [36] for use in prevention or treatment of a malignant tumor.

Moreover, the present invention provides the compound or a salt thereof according to any one of [19] to [36] for use in prevention or treatment of a malignant tumor, wherein the malignant tumor is a malignant tumor with enhanced activation of RET.

Moreover, the present invention provides use of the compound or a salt thereof according to any one of [19] to [36] for producing an antitumor agent.

Moreover, the present invention provides use of the compound or a salt thereof according to any one of [19] to [36] for producing an antitumor agent, wherein the antitumor agent is an antitumor agent for treating a malignant tumor with enhanced activation of RET.

Moreover, the present invention provides use of the compound or a salt thereof according to any one of [19] to [36] for producing a RET inhibitor.

Moreover, the present invention provides a method for preventing or treating a malignant tumor, the method comprising administering the compound or a salt thereof according to any one of [19] to [36] to a mammal.

Moreover, the present invention provides a method for preventing or treating a malignant tumor, the method comprising administering the compound or a salt thereof according to any one of [19] to [36] to a mammal, wherein the malignant tumor is a malignant tumor with enhanced activation of RET.

Moreover, the present invention provides a method of inhibiting RET comprising administering the compound or a salt thereof according to any one of [19] to [36] to a mammal.

Next, the method for producing the compound of the present invention is described.

Compound (I) of the present invention may be produced, for example, through the production methods below or the methods described in the Examples. Compound (I') of the present invention may also be produced by the same method for producing Compound (I). However, the method for producing Compounds (I) and (I') is not limited to these reaction examples.

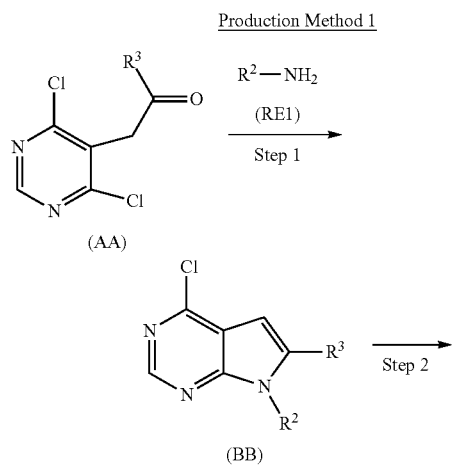

Production Method 1

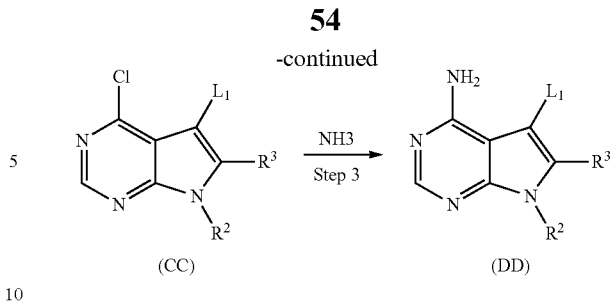

wherein $L_1$ is a leaving group, and $R^2$ and $R^3$ are as defined above.

Step 1

This step synthesizes a compound represented by Formula (BB) from a compound represented by Formula (AA).

Step 1 is performed using an amino compound represented by Formula (RE1) or a salt thereof in an amount of 0.5 to 5 moles, preferably 0.9 to 1.5 moles, per mole of the compound represented by Formula (AA).

Examples of bases include inorganic bases, such as sodium hydrogen carbonate, sodium carbonate, potassium carbonate, cesium carbonate, cesium hydroxide, sodium hydride, and potassium hydride; and organic amines, such as trimethylamine, triethylamine, tripropylamine, diisopropylethylamine, N-methylmorpholine, pyridine, 4-(N,N-dimethylamino)pyridine, lutidine, and collidine. The amount of the base used is 1 to 100 moles, preferably 1 to 10 moles, per mole of the compound represented by Formula (AA). The amino compound can be obtained from commercial suppliers, or can be produced through a known method. Moreover, the reaction can be promoted by adding an acid during the reaction, if necessary. Examples of acids include formic acid, acetic acid, hydrochloric acid, phosphoric acid, and the like. The amount of the acid used is 1 to 100 moles, preferably 1 to 5 moles, per mole of the compound represented by Formula (AA).

As the solvent used in the reaction, any solvent that does not adversely affect the reaction can be used. Examples of the solvent include alcohols (e.g., methanol and ethanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethylsulfoxide, and hexamethylphosphoramide), water, and mixtures thereof.

The reaction time ranges from 0.1 to 100 hours, preferably 0.5 to 48 hours. The reaction temperature ranges from 0 to 120° C., preferably 50 to 120° C.

The thus-obtained compound represented by Formula (BB) can be subjected to the subsequent step after, or without, isolation and purification by known separation and purification means, such as concentration, vacuum concentration, crystallization, solvent extraction, reprecipitation, and chromatography.

Step 2

This step synthesizes a compound represented by Formula (CC) from the compound represented by Formula (BB).

Step 2 is performed using a halogenating reagent in an amount of 1 to 10 moles, preferably 1 to 5 moles, per mole of the compound represented by Formula (BB).

Examples of halogenating reagents include N-iodosuccinimide, N-bromosuccinimide, N-chlorosuccinimide, iodine, bromine, and the like. The reaction solvent is not particularly limited, and any solvent that does not adversely affect the reaction can be used. Examples of the solvent include toluene, benzene, tetrahydrofuran, 1,4-dioxane, dimethylformamide, dimethylacetamide, N-methylpyrrolidinone, dimethylsulfoxide, and mixtures thereof.

Examples of the leaving group represented by $L_1$ include chlorine, bromine, iodine, and the like.

The reaction temperature generally ranges from −78 to 200° C., preferably 0 to 50° C. The reaction time generally ranges from 5 minutes to 6 days, preferably 10 minutes to 3 days.

The thus-obtained compound represented by Formula (CC) can be subjected to the subsequent step after, or without, isolation and purification by known separation and purification means, such as concentration, vacuum concentration, crystallization, solvent extraction, reprecipitation, and chromatography.

Step 3

This step produces a compound represented by Formula (DD) by reacting the compound represented by Formula (CC) with ammonia or a salt thereof. The amount of ammonia or a salt thereof used in this step is generally an equimolar to excessive molar amount per mole of the compound represented by Formula (CC).

The reaction solvent is not particularly limited, and any solvent that does not adversely affect the reaction can be used. Examples of the solvent include water, methanol, ethanol, isopropanol, tert-butyl alcohol, tetrahydrofuran, 1,4-dioxane, dimethylformamide, N-methylpyrrolidone, 1,2-dimethoxyethane, dimethylsulfoxide, and mixtures thereof.

The reaction temperature generally ranges from 0 to 200° C., preferably room temperature to 150° C. The reaction time generally ranges from 5 minutes to 7 days, preferably 30 minutes to 48 hours.

The thus-obtained compound represented by Formula (DD) can be subjected to the subsequent step after, or without, isolation and purification by known separation and purification means, such as concentration, vacuum concentration, crystallization, solvent extraction, reprecipitation, and chromatography.

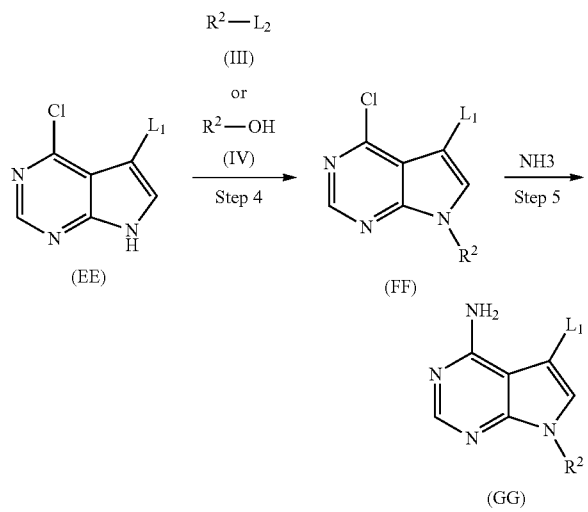

wherein $L_1$ and $L_2$ are each a leaving group, and $R^2$ is as defined above.

Step 4

This step produces a compound represented by Formula (FF) using a compound represented by Formula (EE) and a compound represented by Formula (III) or (IV).

When the compound represented by Formula (III) is used as an alkylating reagent, the compound represented by Formula (FF) can be produced in the presence of a base. In Formula (III), $L_2$ is a leaving group such as chlorine, bromine, iodine, methanesulfonic acid ester, or p-toluenesulfonic acid ester; and can be obtained from commercial suppliers, or can be produced through a known method. The amount of the compound represented by Formula (III) used is 1 to 10 moles, preferably 1 to 5 moles, per mole of the compound represented by Formula (EE).

Examples of bases include inorganic bases, such as sodium hydrogen carbonate, sodium carbonate, potassium carbonate, cesium carbonate, cesium hydroxide, sodium hydride, and potassium hydride; and organic amines, such as trimethylamine, triethylamine, tripropylamine, diisopropylethylamine, N-methylmorpholine, pyridine, 4-(N,N-dimethylamino)pyridine, lutidine, and collidine. The amount of the base used is 1 to 100 moles, preferably 2 to 10 moles, per mole of the compound represented by Formula (EE).

Examples of the solvent include N,N-dimethylformamide, N,N-dimethylacetamide, dimethylsulfoxide, tetrahydrofuran, 1,4-dioxane, N-methylpyrrolidin-2-one, acetonitrile, and the like. These solvents may be used alone or in a mixture.

The reaction time ranges from 0.1 to 100 hours, preferably 0.5 to 24 hours. The reaction temperature ranges from 0° C. to the boiling temperature of the solvent, preferably 0 to 100° C.

When the compound of Formula (IV) is used as an alkylating reagent, the compound represented by Formula (FF) can be produced through a Mitsunobu reaction. This step can generally be performed by a known method, for example, the method disclosed in Chemical Reviews, Vol. 109, p. 2551 (2009). For example, this step can be performed in the presence of a Mitsunobu reagent and a phosphine reagent in a solvent that does not adversely affect the reaction. This step is generally performed using the compound represented by Formula (IV) in an amount of 1 to 10 moles, preferably 1 to 5 moles, per mole of the compound represented by Formula (EE).

Examples of Mitsunobu reagents include diethyl azodicarboxylate, diisopropyl azodicarboxylate, and the like. The amount of the Mitsunobu reagent used is 1 to 10 moles, preferably 1 to 5 moles, per mole of the compound represented by Formula (EE).

Examples of phosphine reagents include triphenylphosphine and tributylphosphine. The amount of the phosphine reagent used is 1 to 10 moles, preferably 1 to 5 moles, per mole of the compound represented by Formula (EE).

The reaction solvent is not particularly limited, and any solvent that does not adversely affect the reaction can be used. Examples of the solvent include toluene, benzene, tetrahydrofuran, 1,4-dioxane, dimethylformamide, dimethylacetamide, N-methylpyrrolidinone, dimethylsulfoxide, and mixtures thereof.

The reaction temperature generally ranges from −78 to 200° C., preferably 0 to 50° C. The reaction time generally ranges from 5 minutes to 3 days, preferably 10 minutes to 10 hours.

The thus-obtained compound represented by Formula (FF) can be subjected to the subsequent step after, or without, isolation and purification by known separation and purification means, such as concentration, vacuum concentration, crystallization, solvent extraction, reprecipitation, and chromatography.

Step 5

This step produces a compound represented by Formula (GG) by reacting the compound represented by Formula (FF) with ammonia or a salt thereof. The amount of ammonia or a salt thereof used in this step is generally an equimolar to excessive molar amount per mole of the compound represented by Formula (FF).

The reaction solvent is not particularly limited, and any solvent that does not adversely affect the reaction can be used. Examples of the solvent include water, methanol, ethanol, isopropanol, tert-butyl alcohol, tetrahydrofuran, 1,4-dioxane, dimethylformamide, 1,2-dimethoxyethane, N-methylpyrrolidone, dimethylsulfoxide, and mixtures thereof.

The reaction temperature generally ranges from 0 to 200° C., preferably room temperature to 150° C. The reaction time generally ranges from 5 minutes to 7 days, preferably 30 minutes to 24 hours.

The thus-obtained compound represented by Formula (GG) can be subjected to the subsequent step after, or without, isolation and purification by known separation and purification means, such as concentration, vacuum concentration, crystallization, solvent extraction, reprecipitation, and chromatography.

Production Method 3

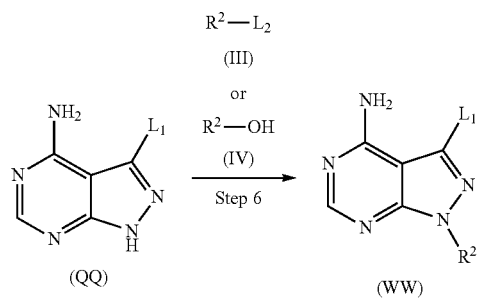

wherein $L_1$ and $L_2$ are each a leaving group, and $R^2$ is as defined above.

Step 6

This step produces a compound represented by Formula (WW) using a compound represented by Formula (QQ) and a compound represented by Formula (III) or (IV).

When the compound represented by Formula (III) is used as an alkylating reagent, the compound represented by Formula (WW) can be produced in the presence of a base. In Formula (III), $L_2$ is a leaving group such as chlorine, bromine, iodine, methanesulfonic acid ester, or p-toluenesulfonic acid ester; and can be obtained from commercial suppliers, or can be produced through a known method. The amount of the compound represented by Formula (III) used is 1 to 10 moles, preferably 1 to 5 moles, per mole of the compound represented by Formula (QQ).

Examples of bases include inorganic bases, such as sodium hydrogen carbonate, sodium carbonate, potassium carbonate, cesium carbonate, cesium hydroxide, sodium hydride, and potassium hydride; and organic amines, such as trimethylamine, triethylamine, tripropylamine, diisopropylethylamine, N-methylmorpholine, pyridine, 4-(N,N-dimethylamino)pyridine, lutidine, and collidine. The amount of the base used is 1 to 100 moles, preferably 2 to 10 moles, per mole of the compound represented by Formula (QQ). Examples of the solvent include N,N-dimethylformamide, N,N-dimethylacetamide, dimethylsulfoxide, tetrahydrofuran, 1,4-dioxane, N-methylpyrrolidin-2-one, acetonitrile, and the like. These solvents may be used alone or in a mixture.

The reaction time ranges from 0.1 to 100 hours, preferably 0.5 to 24 hours. The reaction temperature ranges from 0° C. to the boiling temperature of the solvent, preferably 0 to 100° C.

When the compound of Formula (IV) is used as an alkylating reagent, the compound represented by Formula (WW) can be produced through a Mitsunobu reaction. This step can generally be performed by a known method, for example, the method disclosed in Chemical Reviews, Vol. 109, p. 2551 (2009). For example, this step can be performed in the presence of a Mitsunobu reagent and a phosphine reagent in a solvent that does not adversely affect the reaction. This step is generally performed using the compound represented by Formula (IV) in an amount of 1 to 10 moles, preferably 1 to 5 moles, per mole of the compound represented by Formula (QQ).

Examples of Mitsunobu reagents include diethyl azodicarboxylate, diisopropyl azodicarboxylate, and the like. The amount of the Mitsunobu reagent used is 1 to 10 moles, preferably 1 to 5 moles, per mole of the compound represented by Formula (QQ). Examples of phosphine reagents include triphenylphosphine and tributylphosphine. The amount of the phosphine reagent used is 1 to 10 moles, preferably 1 to 5 moles, per mole of the compound represented by Formula (QQ).

The reaction solvent is not particularly limited, and any solvent that does not adversely affect the reaction can be used. Examples of the solvent include toluene, benzene, tetrahydrofuran, 1,4-dioxane, dimethylformamide, dimethylacetamide, N-methylpyrrolidinone, dimethylsulfoxide, and mixtures thereof.

The reaction temperature generally ranges from −78 to 200° C., preferably 0 to 50° C. The reaction time generally ranges from 5 minutes to 3 days, preferably 10 minutes to 10 hours.

The thus-obtained compound represented by Formula (WW) can be subjected to the subsequent step after, or without, isolation and purification by known separation and purification means, such as concentration, vacuum concentration, crystallization, solvent extraction, reprecipitation, and chromatography.

Production Method 4

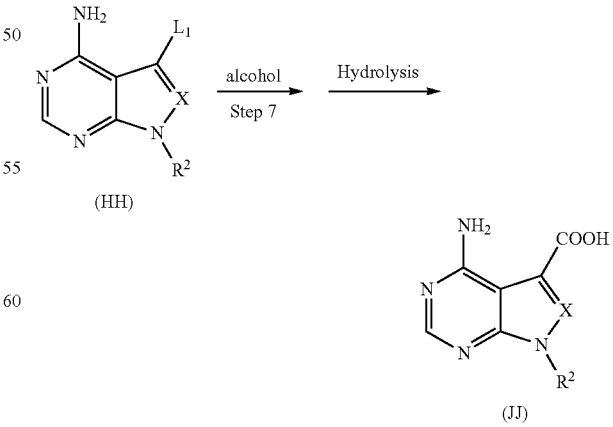

wherein $L_1$ is a leaving group, and $R^2$ and X are as defined above.

Step 7

This step produces a compound represented by Formula (JJ) by reacting a compound represented by Formula (HH) in a carbon monoxide atmosphere in the presence of an alcohol using, for example, a transition metal and optionally a base in a solvent that does not adversely affect the reaction.

The compound represented by Formula (HH) can be produced by steps 1 to 3, steps 4 and 5, or step 6 of the production method of the present application.

In this step, the pressure of carbon monoxide is generally 1 atm to 10 atms, preferably 1 atm to 7 atms.

The amount of the alcohol compound used is 1 to an excessive molar amount, preferably 1 to 200 moles, per mole of the compound represented by Formula (HH). Examples of alcohol compounds include methanol, ethanol, propanol, isopropyl alcohol, diethylaminoethanol, isobutanol, 4-(2-hydroxyethyl)morpholine, 3-morpholinopropanol, diethylaminopropanol, and the like.

Examples of transition metal catalysts usable in this step include palladium catalysts (e.g., palladium acetate, tris (benzylideneacetone)dipalladium, bis(triphenylphosphine) palladium(II) dichloride, 1,1-bis(diphenylphosphino)ferrocene-palladium(II) dichloride-dichloromethane complex, carbon-supported palladium, etc.). As necessary, a ligand (e.g., triphenylphosphine, xantphos, tri-tert-butylphosphine, etc.) is added. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (HH). The amount of the ligand used is generally 0.000 1 to 4 moles, preferably 0.01 to 2 moles, per mole of the compound represented by Formula (HH).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, and sodium hydride. The amount of the base used is generally 0.1 to 50 moles, preferably 1 to 20 moles, per mole of the compound represented by Formula (HH).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof. The reaction time ranges from 0.1 to 100 hours, preferably 0.5 to 24 hours. The reaction temperature is 0° C. to 200° C., preferably 0 to 150° C.

When a mixture of an ester form corresponding to the alcohol used and a carboxylic acid compound (JJ) is obtained after this reaction, a hydrolysis reaction can be performed to convert the mixture into a compound represented by Formula (JJ). Hydrolysis is performed using a base. Examples of bases include organic bases, such as diethylamine, diisopropylamine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, lithium hydroxide, and calcium hydroxide.

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof.

The reaction time ranges from 0.1 to 100 hours, preferably 0.5 to 24 hours. The reaction temperature ranges from 0° C. to the boiling temperature of the solvent, preferably 0 to 150° C.

The thus-obtained compound represented by Formula (JJ) can be subjected to the subsequent step after, or without, isolation and purification by known separation and purification means, such as concentration, vacuum concentration, crystallization, solvent extraction, reprecipitation, and chromatography.

Production Method 5

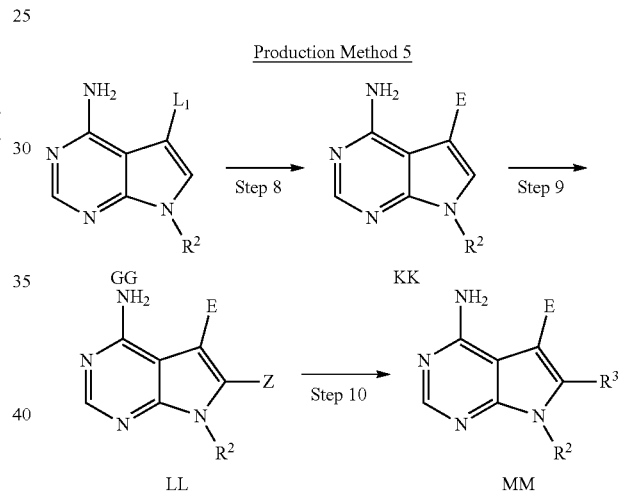

wherein $L_1$ is a leaving group; E is ester, cyano, or carboxylic acid equivalent, such as carboxamide; Z is halogen; and $R^2$ and $R^3$ are as defined above.

Step 8 This step produces an ester derivative or cyano derivative represented by Formula (KK) by reacting the compound represented by Formula (GG), in a carbon monoxide atmosphere in the presence of an alcohol, or using a cyano compound, such as copper cyanide or zinc cyanide, using, for example, a transition metal catalyst and optionally a base in a solvent that does not adversely affect the reaction.

The compound represented by Formula (GG) can be produced by steps 1 to 3, steps 4 and 5 of the production method of the present application.

In the production of the ester derivative, the pressure of carbon monoxide is generally 1 atm to 10 atms, preferably 1 atm to 7 atms. The amount of the alcohol compound used as a reaction agent is 1 to an excessive molar amount, preferably 1 to 200 moles, per mole of the compound represented by Formula (GG). Examples of alcohol compounds include methanol, ethanol, propanol, isopropyl alcohol, diethylaminoethanol, isobutanol, 4-(2-hydroxyethyl) morpholine, 3-morpholinopropanol, diethylaminopropanol, and the like.

In the production of the cyano derivative, examples of the cyano compound used as a reaction agent include copper cyanide, zinc cyanide, tri-n-butylcyanotin, and the like. The amount of the cyano compound used as an agent is generally 1 to 100 moles, preferably 1 to 10 moles, per mole of the compound represented by Formula (GG).

Examples of transition metal catalysts usable in this step for both the production of the ester derivative and the production of the cyano derivative include palladium catalysts (e.g., palladium acetate, tetrakis triphenylphosphine palladium, tris(benzylideneacetone)dipalladium, bis(triphenylphosphine)palladium(II) dichloride, 1,1-bis(diphenylphosphino)ferrocene-palladium(II) dichloride-dichloromethane complex, carbon-supported palladium, etc.). As necessary, a ligand (e.g., triphenylphosphine, xantphos, tri-tert-butylphosphine, etc.) is added. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (GG). The amount of the ligand used is generally 0.000 1 to 4 moles, preferably 0.01 to 2 moles, per mole of the compound represented by Formula (GG).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, and sodium hydride. The amount of the base used is generally 0.1 to 50 moles, preferably 1 to 20 moles, per mole of the compound represented by Formula (GG).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof. The reaction time ranges from 0.1 to 100 hours, preferably 0.5 to 24 hours. The reaction temperature is 0° C. to 200° C., preferably 0 to 150° C. The thus-obtained compound represented by Formula (KK) can be subjected to the subsequent step after, or without, isolation and purification by known separation and purification means, such as concentration, vacuum concentration, crystallization, solvent extraction, reprecipitation, and chromatography.

Step 9

This step produces a halogen compound (LL) by treating the compound represented by Formula (KK) with a halogenating agent.

This step is generally performed using a halogenated reagent in an amount of 1 to 10 moles, preferably 1 to 5 moles, per mole of the compound represented by Formula (KK).

Examples of halogenating reagents include 1-chloromethyl-4-fluoro-1,4-diazoniabicyclo[2.2.2]octane bis(tetrafluoroborate), N-iodosuccinimide, N-bromosuccinimide, N-chlorosuccinimide, iodine, bromine, and the like. The reaction solvent is not particularly limited, and any solvent that does not adversely affect the reaction can be used. Examples of the solvent include dichloromethane, chloroform, toluene, benzene, tetrahydrofuran, 1,4-dioxane, dimethylformamide, dimethylacetamide, N-methylpyrrolidinone, dimethylsulfoxide, and mixtures thereof.

Examples of the halogen represented by Z include fluorine, chlorine, bromine, iodine, and the like.

The reaction temperature generally ranges from −78 to 200° C., preferably 0 to 50° C. The reaction time generally ranges from 5 minutes to 6 days, preferably 10 minutes to 3 days.

The thus-obtained compound represented by Formula (LL) can be subjected to the subsequent step after, or without, isolation and purification by known separation and purification means, such as concentration, vacuum concentration, crystallization, solvent extraction, reprecipitation, and chromatography.

Moreover, E can be converted to another E, as required, by a known method, such as hydrolysis or solvolysis. For example, cyano can be converted to carboxamide by hydrolysis, and cyano or carboxamide can be converted to ester by solvolysis.

Step 10

This step produces a compound represented by Formula (MM) by subjecting the compound represented by Formula (LL) to a coupling reaction with a borate derivative, boric acid derivative, tin derivative, acetylene derivative, or alkoxide derivative that has $R^3$ using, for example, a transition metal and optionally a base in a solvent that does not adversely affect the reaction.

The amount of the borate derivative, boric acid derivative, tin derivative, acetylene derivative, or alkoxide derivative that has $R^3$ used is 1 to 100 moles, preferably 1 to 20 moles. Examples of transition metal catalysts usable in this step include palladium catalysts (e.g., palladium acetate, tetrakis triphenylphosphine palladium, tris(benzylideneacetone)dipalladium, bis(triphenylphosphine)palladium(II) dichloride, 1,1-bis(diphenylphosphino)ferrocene-palladium(II) dichloride-dichloromethane complex, etc.). As necessary, a ligand (e.g., triphenylphosphine, xantphos, 2-dicyclohexylphosphino-2',4',6'-triisopropylbiphenyl, 2-dicyclohexylphosphino-2',6'-dimethoxybiphenyl, tricyclohexylphosphine, tri-tert-butylphosphine, etc.) is added. Examples of copper catalysts include copper iodide, copper bromide, and copper chloride. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (LL). Transition metal catalysts can be used in combination, as necessary. The amount of the ligand used is generally 0.000 1 to 4 moles, preferably 0.01 to 2 moles, per mole of the compound represented by Formula (LL).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, potassium phosphate, sodium hydroxide, and sodium hydride. The amount of the base used is generally 0.1 to 50 moles, preferably 1 to 20 moles, per mole of the compound represented by Formula (LL).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol, ethanol, and ethylene glycol), aprotic polar solvents (e.g., dimethylformamide, dimethylacetamide, N-methylpyrrolidinone, dimethylsulfoxide, and hexamethylphosphoramide), water, and mixtures thereof.

The reaction time ranges from 0.1 to 100 hours, preferably 0.5 to 24 hours. The reaction temperature ranges from 0° C. to the boiling temperature of the solvent, preferably 0 to 160° C. Moreover, the reaction can be performed while appropriately protecting the compound represented by Formula (LL) with a protecting group, such as Boc (tert-butoxycarbonyl), and then the protecting group can be removed.

The thus-obtained compound represented by Formula (MM) can be subjected to the subsequent step after, or without, isolation and purification by known separation and purification means, such as concentration, vacuum concentration, crystallization, solvent extraction, reprecipitation, and chromatography.

Production Method 6

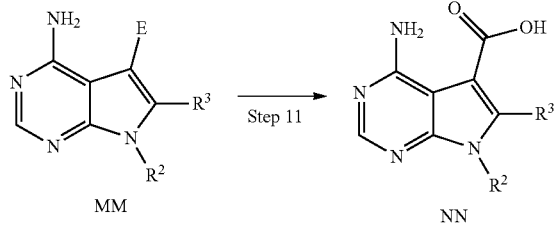

wherein E, $R^2$, and $R^3$ are as defined above.
Step 11

This step produces a carboxylic acid compound represented by Formula (NN) by hydrolyzing the compound represented by Formula (MM).

Hydrolysis is performed using a base or an acid. Examples of bases include organic bases, such as diethylamine, diisopropylamine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, potassium hydroxide, lithium hydroxide, and calcium hydroxide. Examples of acids include hydrochloric acid, sulfuric acid, phosphoric acid, and the like.

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol, ethanol, and ethylene glycol), aprotic polar solvents (e.g., dimethylformamide, dimethylacetamide, N-methylpyrrolidinone, dimethylsulfoxide, and hexamethylphosphoramide), water, and mixtures thereof.

The reaction time ranges from 0.1 to 100 hours, preferably 0.5 to 24 hours. The reaction temperature ranges from 0° C. to the boiling temperature of the solvent, preferably 0 to 160° C.

The thus-obtained compound represented by Formula (NN) can be subjected to the subsequent step after, or without, isolation and purification by known separation and purification means, such as concentration, vacuum concentration, crystallization, solvent extraction, reprecipitation, and chromatography.

Production Method 7

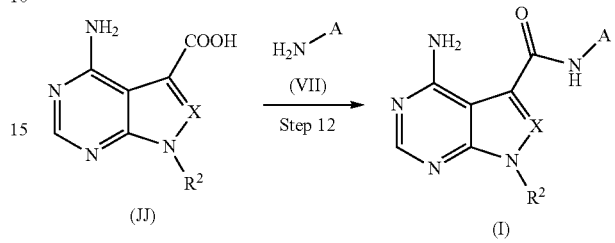

wherein A, $R^2$, and X are as defined above.
Step 12

This step produces a compound represented by Formula (I) by performing an amidation reaction using the compound represented by Formula (JJ) and a compound represented by Formula (VII). This step is performed in the presence of an appropriate condensing agent or activating agent as an amidation reagent, using the compound of Formula (VII) in an amount of 0.5 to 10 moles, preferably 1 to 3 moles, per mole of the compound represented by Formula (JJ).

The reaction solvent is not particularly limited, and any solvent that does not adversely affect the reaction can be used. Examples of the solvent include isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethylsulfoxide, acetonitrile, and mixtures thereof.

The reaction temperature generally ranges from −78 to 200° C., preferably 0 to 100° C. The reaction time generally ranges from 5 minutes to 7 days, preferably 5 minutes to 3 days, more preferably 5 minutes to 1 day.

Examples of condensing agents and activating agents include diphenylphosphoryl azide, N,N'-dicyclohexylcarbodiimide, benzotriazol-1-yloxy-trisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, combination of 1-ethyl-3-(3-dimethylaminopropyl)carbodiimide and 1-hydroxybenzotriazole, 2-chloro-1,3-dimethylimidazolinium chloride, (dimethylamino)-N,N-dimethyl(3H-[1,2,3]triazolo[4,5-b]pyridin-3-yloxy)methaniminium hexafluorophosphate, 1,1-carbonyldiimidazole, N-hydroxysuccinic acid imide, and the like.

Further, a base may be added during the above reaction as necessary. Examples of bases include organic bases, such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, diazabicycloundecene, diazabicyclononene, and butyllithium; and inorganic bases, such as sodium hydrogen carbonate, sodium carbonate, potassium carbonate, cesium carbonate, sodium hydroxide, and sodium hydride. The amount of the base added is 1 to 100 moles, preferably 1 to 10 moles, per mole of the compound represented by Formula (JJ).

After completion of the reaction, a base, such as a sodium hydroxide solution, can be added to perform a post-treatment.

The thus-obtained compound represented by Formula (I) can be isolated and purified by known separation and purification means, such as concentration, vacuum concentration, crystallization, solvent extraction, reprecipitation, and chromatography.

Production Method 8

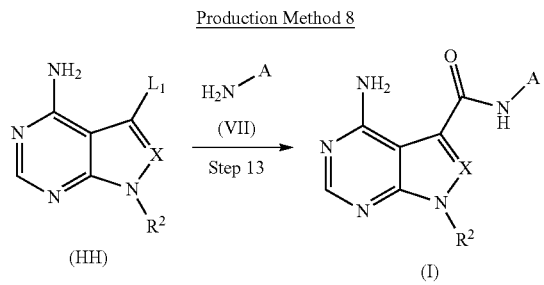

wherein $L_1$ is a leaving group, and A, $R^2$, and X are as defined above.

Step 13

This step produces a compound represented by Formula (I) by reacting the compound represented by Formula (HH) in the presence of Compound (VII) in a carbon monoxide atmosphere using, for example, a transition metal and optionally a base in a solvent that does not adversely affect the reaction.

In this step, the pressure of carbon monoxide is 1 atm to 10 atms, preferably 1 atm to 7 atms.

Examples of transition metal catalysts usable in this step include palladium catalysts (e.g., palladium acetate, tris(dibenzylideneacetone)dipalladium, bis(triphenylphosphine)palladium(II) dichloride, 1,1-bis(diphenylphosphino)ferrocene-palladium(II) dichloride-dichloromethane complex, carbon-supported palladium, etc.). As necessary, a ligand (e.g., triphenylphosphine, xantphos, tri-tert-butylphosphine, etc.) is added. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (HH). The amount of the ligand used is generally 0.000 1 to 4 moles, preferably 0.01 to 2 moles, per mole of the compound represented by Formula (HH).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, 1,8-diazabicyclo[5.4.0]undec-7-ene, potassium hexamethyldisilazide, and butyllithium; and inorganic bases, such as sodium hydrogen carbonate, sodium carbonate, potassium carbonate, cesium carbonate, sodium hydroxide, and sodium hydride. The amount of the base used is generally 0.1 to 50 moles, preferably 1 to 20 moles, per mole of the compound represented by Formula (HH).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof. The reaction time ranges from 0.1 to 100 hours, preferably 0.5 to 24 hours. The reaction temperature is 0° C. to 250° C., preferably 0 to 200° C.

The thus-obtained compound represented by Formula (I) can be isolated and purified by known separation and purification means, such as concentration, vacuum concentration, crystallization, solvent extraction, reprecipitation, and chromatography.

Production Method 9

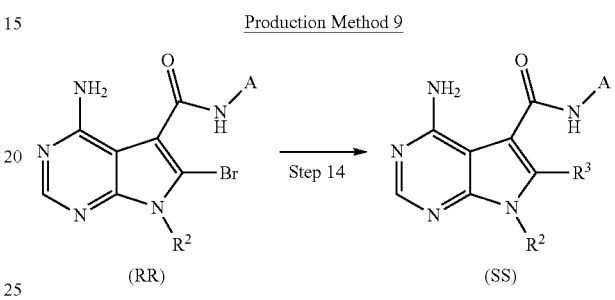

wherein A, $R^2$, and $R^3$ are as defined above.

This step produces a compound represented by Formula (SS) by subjecting a compound represented by Formula (RR) to a coupling reaction with a borate derivative, boric acid derivative, tin derivative, or acetylene derivative that has $R^3$ using, for example, a transition metal and optionally a base in a solvent that does not adversely affect the reaction.

The amount of the borate derivative, boric acid derivative, tin derivative, or acetylene derivative that has $R^3$ used is 1 to 100 moles, preferably 1 to 20 moles. Examples of transition metal catalysts usable in this step include palladium catalysts (e.g., palladium acetate, tetrakis triphenylphosphine palladium, tris(benzylideneacetone)dipalladium, bis(triphenylphosphine)palladium(II) dichloride, 1,1-bis(diphenylphosphino)ferrocene-palladium(II) dichloride-dichloromethane complex, etc.). As necessary, a ligand (e.g., triphenylphosphine, xantphos, 2-dicyclohexylphosphino-2', 4',6'-triisopropylbiphenyl, 2-dicyclohexylphosphino-2',6'-dimethoxybiphenyl, tricyclohexylphosphine, tri-tert-butylphosphine, etc.) is added. Examples of copper catalysts include copper iodide, copper bromide, and copper chloride. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (RR). Transition metal catalysts can be used in combination, as necessary. The amount of the ligand used is generally 0.000 1 to 4 moles, preferably 0.01 to 2 moles, per mole of the compound represented by Formula (RR).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, potassium phosphate, sodium hydroxide, and sodium hydride. The amount of the base used is generally 0.1 to 50 moles, preferably 1 to 20 moles, per mole of the compound represented by Formula (RR).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol, ethanol, and ethylene glycol), aprotic polar solvents (e.g., dimethylformamide, dimethylacetamide, N-methylpyrrolidinone, dimethylsulfoxide, and hexamethylphosphoramide), water, and mixtures thereof.

The reaction time ranges from 0.1 to 100 hours, preferably 0.5 to 24 hours. The reaction temperature ranges from 0° C. to the boiling temperature of the solvent, preferably 0 to 160° C.

The thus-obtained compound represented by Formula (SS) can be isolated and purified by known separation and purification means, such as concentration, vacuum concentration, crystallization, solvent extraction, reprecipitation, and chromatography.

When the compound of the present invention has isomers, such as optical isomers, stereoisomers, regioisomers, and rotational isomers, mixtures of any of the isomers are included within the scope of the compound of the present invention. For example, when the compound of the present invention has optical isomers, the optical isomer separated from a racemic mixture is also included within the scope of the compound of the present invention. Each of such isomers can be obtained as a single compound by known synthesis and separation means (e.g., concentration, solvent extraction, column chromatography, recrystallization, etc.).

The compound or a salt thereof of the present invention may be in the form of crystals. Single crystals and polymorphic mixtures are included within the scope of the compound or a salt thereof of the present invention. Such crystals can be produced by crystallization according to a crystallization method known per se in the art. The compound or a salt thereof of the present invention may be a solvate (e.g., a hydrate) or a non-solvate. Any of such forms are included within the scope of the compound or a salt thereof of the present invention. Compounds labeled with an isotope (e.g., $^{2}$H, $^{3}$H, $^{13}$C, $^{14}$C, $^{35}$S, $^{125}$I, etc.) are also included within the scope of the compound or a salt thereof of the present invention.

A prodrug of the compound or a salt thereof of the present invention refers to a compound that can be converted to the compound or a salt thereof of the present invention through a reaction with an enzyme, gastric acid, or the like, under physiological conditions in vivo, i.e., a compound that can be converted to the compound or a salt thereof of the present invention by enzymatic oxidation, reduction, hydrolysis, or the like; or a compound that can be converted to the compound or a salt thereof of the present invention by hydrolysis with gastric acid or the like. Further, the prodrug of the compound or a salt thereof of the present invention may be compounds that can be converted to the compound or a salt thereof of the present invention under physiological conditions, such as those described in "Iyakuhin no Kaihatsu [Development of Pharmaceuticals]," Vol. 7, Molecular Design, published in 1990 by Hirokawa Shoten Co., pp. 163-198.

The salt of the compound of the present invention refers to a common salt used in the field of organic chemistry. Examples of such salts include base addition salts to a carboxyl group when the compound has a carboxyl group, and acid addition salts to an amino or basic heterocyclic group when the compound has an amino or basic heterocyclic group.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochloride, sulfate, nitrate, phosphate, and perchlorate; organic acid salts such as acetate, formate, maleate, fumarate, tartrate, citrate, ascorbate, and trifluoroacetate; and sulfonates such as methanesulfonate, isethionate, benzenesulfonate, and p-toluenesulfonate.

The compound or a salt thereof of the present invention has superior RET inhibitory activity and is useful as an antitumor agent. Preferable antitumor agents are antitumor agents for treating malignant tumors with enhanced activation of RET. The compound or a salt thereof of the present invention has excellent RET selectivity and has the advantage that there are few side effects caused by inhibition of other kinases.

In the present specification, "RET" means RET (rearranged during transfection) tyrosine kinase, and includes human RET and non-human mammal RET, preferably human RET. Further, the term "RET" includes isoforms.

Moreover, due to their excellent RET inhibitory activity, the compound or a salt thereof of the present invention is useful as a pharmaceutical preparation for preventing and treating RET-related diseases. Examples of the "RET-related diseases" include diseases whose incidence can be reduced, and whose symptom can be remitted, relieved, and/or completely cured by deleting, suppressing, and/or inhibiting the function of RET. The "RET-related diseases" are preferably diseases that can be treated by RET inhibition. Examples of such diseases include, but not limited to, malignant tumors, etc. Examples of the malignant tumor include those with enhanced activation of RET. The malignant tumor with enhanced activation of RET refers a malignant tumor with enhanced activation of RET due to the translocation, mutation (including point mutation and gene fusion mutation), and overexpression (including states in which the number of copies of the RET gene increases, the messenger RNA of RET is overexpressed, the number of RET proteins increases, and the RET proteins are constantly activated) of the RET gene.

The type of malignant tumor to be treated by the compound or a salt thereof of the present invention is not particularly limited. Examples of malignant tumors include epithelial cancers (respiratory system cancers, digestive system cancers, reproductive system cancers, secretion system cancers, etc.), sarcomas, hematopoietic tumors, central nervous system tumors, and peripheral nerve tumors.

Specific examples of the type of cancer include head and neck cancer, thyroid cancer, esophagus cancer, gastric cancer, duodenal cancer, liver cancer, biliary tract cancer (gallbladder, cholangiocarcinoma, etc.), pancreas cancer, colorectal cancer (colon cancer, rectal cancer, etc.), lung cancer (non-small cell lung cancer, small cell lung cancer, mesothelioma, etc.), breast cancer, ovarian cancer, uterine cancer (cervical cancer, endometrial cancer, etc.), renal cancer, renal pelvis-ureteral cancer, bladder cancer, prostate cancer, testicular tumor, leukemia, malignant lymphoma, multiple myeloma, osteosarcoma, soft-tissue sarcoma, skin cancer, brain tumor, adrenal tumor, neuroblastoma, and the like.

The target cancer is preferably lung cancer (non-small cell lung cancer, small cell lung cancer, mesothelioma, etc.), colorectal cancer (colon cancer, rectal cancer, etc.), thyroid cancer, breast cancer, brain tumor, and leukemia; more preferably non-small cell lung cancer and thyroid cancer; and more preferably non-small cell lung cancer and thyroid cancer with enhanced activation of RET. The meaning of the phrase "enhanced activation of RET" is as defined above.

The pharmaceutical composition comprising the compound or a salt thereof of the present invention is preferably a pharmaceutical composition for preventing or treating diseases that can be treated by RET inhibition. Preferable pharmaceutical compositions are antitumor agents. When the compound or a salt thereof of the present invention is used as a pharmaceutical preparation, a pharmaceutical carrier can be added, if required, thereby forming a suitable dosage form according to prevention and treatment purposes. Examples of the dosage form include oral preparations, injections, suppositories, ointments, patches, and the like. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or coating agent in solid preparations; or as a solvent, solubilizing agent, suspending agent, isotonizing agent, pH adjuster/buffer, or soothing agent in liquid preparations. Moreover, pharmaceutical preparation additives, such as antiseptics, antioxidants, colorants, sweeteners, and stabilizers, may also be used, if required.

Examples of excipients include lactose, sucrose, D-mannitol, starch, crystalline cellulose, calcium silicate, and the like.

Examples of binders include hydroxypropyl cellulose, methyl cellulose, polyvinylpyrrolidone, candy powder, hypromellose, and the like.

Examples of disintegrants include sodium starch glycolate, carmellose calcium, croscarmellose sodium, crospovidone, low-substituted hydroxy propyl cellulose, partially pregelatinized starch, and the like.

Examples of lubricants include talc, magnesium stearate, sucrose fatty acid ester, stearic acid, sodium stearyl fumarate, and the like.

Examples of coating agents include ethyl cellulose, aminoalkyl methacrylate copolymer RS, hypromellose, sucrose, and the like.

Examples of solvents include water, propylene glycol, physiological saline, and the like.

Examples of solubilizing agents include polyethylene glycol, ethanol, α-cyclodextrin, macrogol 400, polysorbate 80, and the like.

Examples of suspending agents include carrageenan, crystalline cellulose/carmellose sodium, polyoxyethylene hydrogenated castor oil, and the like.

Examples of isotonizing agents include sodium chloride, glycerin, potassium chloride, and the like.

Examples of pH adjusters/buffers include sodium citrate, hydrochloric acid, lactic acid, phosphoric acid, sodium dihydrogen phosphate, and the like.

Examples of soothing agents include procaine hydrochloride, lidocaine, and the like.

Examples of antiseptics include ethyl parahydroxybenzoate, cresol, benzalkonium chloride, and the like.

Examples of antioxidants include sodium sulfite, ascorbic acid, natural vitamin E, and the like.

Examples of colorants include titanium oxide, iron sesquioxide, Food Blue No. 1, copper chlorophyll, and the like.

Examples of sweeteners include aspartame, saccharin, sucralose, l-menthol, mint flavor, and the like.

Examples of stabilizers include sodium pyrosulfite, disodium edetate, erythorbic acid, magnesium oxide, dibutylhydroxytoluene, and the like.

When a solid preparation for oral administration is prepared, an excipient, optionally an excipient, a binder, a disintegrator, a lubricant, a colorant, a sweetener, and the like, may be added to the compound of the present invention; and the resulting mixture may be formulated into tablets, coated tablets, granules, powders, capsules, etc., according to an ordinary method.

When an injection is prepared, a pH adjuster, a buffer, a stabilizer, an isotonizing agent, a local anesthetic, and the like may be added to the compound of the present invention; and the resulting mixture may be formulated into subcutaneous, intramuscular, and intravenous injections according to an ordinary method.

The amount of the compound of the present invention to be incorporated in each of such dosage unit forms depends on the condition of the patient to whom the compound is administered, the dosage form, etc. In general, in the case of an oral agent, an injection, and a suppository, the amount of the compound of the present invention is preferably 0.05 to 1000 mg, 0.01 to 500 mg, and 1 to 1000 mg, respectively, per dosage unit form.

The daily dose of the medicine in such a dosage form depends on the condition, body weight, age, gender, etc., of the patient, and cannot be generalized. For example, the daily dose of the compound of the present invention for an adult (body weight: 50 kg) may be generally 0.05 to 5000 mg, and preferably 0.1 to 1000 mg; and is preferably administered in one dose, or in two to three divided doses, per day.

In the present invention, examples of mammals to which Compound (I) or a salt thereof is administered include humans, monkeys, mice, rats, rabbits, dogs, cats, cows, horses, pigs, sheep, and the like.

EXAMPLES

The following describes the present invention in more detail with reference to Examples. However, the present invention is not limited to the Examples.

Commercially available reagents were used in the Examples, unless otherwise specified. For silica gel column chromatography, the following columns were used: Purif-Pack (registered trademark) SI produced by Moritex Corp., KP-Sil (registered trademark) silica prepacked column produced by Biotage, HP-Sphere (registered trademark) silica prepacked column produced by Biotage, or HP-Sil (registered trademark) silica prepacked column produced by Biotage. For basic silica gel column chromatography, a Purif-Pack (registered trademark) NH produced by Moritex Corp. or KP-NH (registered trademark) prepacked column produced by Biotage was used. For preparative thin-layer chromatography, Kieselgel TM 60F 254, Art. 5744 produced by Merck or an $NH_2$ Silica Gel 60F254 Plate produced by Wako was used. NMR spectra were measured by using an AL400 (400 MHz; produced by JEOL), Mercury 400 (400 MHz; produced by Agilent Technologies, Inc.) model spectrometer, or Inova 400 (400 MHz; produced by Agilent Technologies, Inc.) model spectrometer equipped with an OMNMR probe (Protasis). The measurement was carried out using tetramethylsilane as an internal standard when tetramethylsilane was contained in a deuterated solvent;

otherwise, an NMR solvent was used as an internal standard. All the δ values are shown in ppm. Microwave reaction was performed using an Initiator produced by Biotage.

LCMS spectra were measured using an Acquity SQD (quadrupole) produced by Waters Corporation under the following conditions.
Column: Acquity UPLC (trade mark) BEH C18, 2.1×50 mm, 1.7 μm (produced by Waters Corporation)
MS detection: ESI positive
UV detection: 254 and 210 nm
Column flow rate: 0.5 mL/min
Mobile phase: Water/acetonitrile (0.1% formic acid)
Injection volume: 1 μL gradient

| Time (min) | Water | Acetonitrile |
|---|---|---|
| 0 | 95 | 5 |
| 0.1 | 95 | 5 |
| 2.1 | 5 | 95 |
| 3.0 | STOP | |

Preparative reversed-phase HPLC purification was performed using a preparative separation system available from Gilson, Inc.
Column: CombiPrep Pro C18, 50×30 mmI.D., S-5 μm (produced by YMC)
UV detection: 254 nm
Column flow rate: 40 mL/min
Mobile phase: Water/acetonitrile (0.1% formic acid)
Injection volume: 0.1 to 1 mL The following are the abbreviations used and the meaning of each.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
brs: broad singlet
CDI: carbonyldiimidazole
DMSO-$d_6$: deuterated dimethyl sulfoxide
CDCl$_3$: deuterated chloroform
CD$_3$OD: deuterated methanol
THF: tetrahydrofuran
DMF: N,N-dimethylformamide
DMA: N,N-dimethylacetamide
NMP: 1-methyl-2-pyrrolidinone
DMSO: dimethyl sulfoxide
HATU: (dimethylamino)-N,N-dimethyl(3H-[1,2,3]triazolo[4,5-b]pyridin-3-yloxy)methane iminium hexafluorophosphate
DIAD: diisopropyl azodicarboxylate
DIPEA: diisopropylethylamine
DME: 1,2-dimethoxyethane Reference Example 1: Synthesis of 4-amino-1-cyclopentyl-1H-pyrazolo[3,4-d]pyrimidine-3-carboxylic acid Step 1: Synthesis of 1-cyclopentyl-3-iodo-1H-pyrazolo[3,4-d]pyrimidin-4-amine A suspension of 3.0 g of 3-iodo-1H-pyrazolo[3,4-d]pyrimidin-4-amine synthesized in accordance with the procedure described in International Publication No. WO2007/126841, 3.4 g of iodocyclopentane, and 4.8 g of potassium carbonate in 30 mL of DMF was heated to 80° C. and stirred for 18 hours. After the resulting mixture was cooled to room temperature, 200 mL of water was added thereto, followed by filtration of the formed solid. The solid was washed with water and dried, thereby obtaining 3.7 g of the title compound as a yellow solid.
Physical Properties: m/z[M+H]$^+$ 330.1.

Step 2: Synthesis of 4-amino-1-cyclopentyl-1H-pyrazolo[3,4-d]pyrimidine-3-carboxylic acid 21 g of 1-cyclopentyl-3-iodo-1H-pyrazolo[3,4-d]pyrimidin-4-amine obtained in step 1, 42 ml of 2-diethylaminoethanol, and 2.24 g of Pd(PPh$_3$)$_2$Cl$_2$ were dissolved in 120 ml of NMP, and the inside of the system was replaced with carbon monoxide, followed by heating to 120° C. After stirring for 2 hours, the resulting mixture was cooled to room temperature, and 50 ml of methanol was added thereto. 19 ml of a 5N aqueous sodium hydroxide solution was further added thereto and stirred for 30 minutes. After addition of water, the aqueous layer was washed with ethyl acetate, and the washed aqueous layer was adjusted with hydrochloric acid to a pH of 3. The precipitated solid was collected by filtration, washed with water, and dried, thereby obtaining 9.8 g of the title compound as a pale yellow solid.
Physical Properties: m/z[M+H]$^+$ 248.3.

Reference Example 2: Synthesis of 4-amino-1-(4,4-dimethylcyclohexyl)-1H-pyrazolo[3,4-d]pyrimidine-3-carboxylic acid Step 1: Synthesis of 1-(4,4-dimethylcyclohexyl)-3-iodo-1H-pyrazolo[3,4-d]pyrimidin-4-amine 6.08 mL of diisopropyl azodicarboxylate was added to a solution of 4 g of 3-iodo-1H-pyrazolo[3,4-d]pyrimidin-4-amine, 5.89 g of 4,4-dimethylcyclohexanol, and 8.0 g of triphenylphosphine in 30 mL of THF at room temperature, followed by stirring overnight. After concentration, the residue was purified by silica gel chromatography (hexane->hexane/ethyl acetate=1/1), thereby obtaining 3.9 g of the title compound as a white solid.
Physical Properties: m/z[M+H]$^+$ 373.1.

Step 2: Synthesis of 4-amino-1-(4,4-dimethylcyclohexyl)-1H-pyrazolo[3,4-d]pyrimidine-3-carboxylic acid 3.14 g of 1-(4,4-dimethylcyclohexyl)-3-iodo-1H-pyrazolo[3,4-d]pyrimidin-4-amine obtained in step 1, 5.61 mL of 2-diethylaminoethanol, and 297 mg of Pd(PPh$_3$)$_2$Cl$_2$ were dissolved in 15 mL of NMP, and the inside of the system was replaced with carbon monoxide, followed by heating to 120° C. After stirring for 2 hours, the resulting mixture was cooled to room temperature, and 15 mL of methanol was added thereto. 6.9 mL of a 5N aqueous sodium hydroxide solution was further added thereto and stirred for 30 minutes. After addition of water, the aqueous layer was washed with ethyl acetate, and the washed aqueous layer was adjusted with hydrochloric acid to a pH of 3. The precipitated solid was collected by filtration, washed with water, and dried, thereby obtaining 2.2 g of the title compound as a pale yellow solid.
Physical Properties: m/z[M+H]$^+$ 290.3.

Reference Example 3: Synthesis of 4-amino-1-(tert-butyl)-1H-pyrazolo[3,4-d]pyrimidine-3-carboxylic acid Step 1: Synthesis of methyl 4-amino-1-(tert-butyl)-1H-pyrazolo[3,4-d]pyrimidine-3-carboxylate 3.33 g of triethylamine and 1.35 g of a 1,1'-bis(diphenylphosphino)ferrocene-palladium(II) dichloride-dichloromethane complex were added to a suspension of 4.45 g of 3-bromo-1-(tert-butyl)-1H-pyrazolo[3,4-d]pyrimidin-4-amine in 45 mL of methanol. The mixture was stirred in a carbon monoxide atmosphere in an autoclave at 0.5 MPa and at 100° C. for 3 hours. After cooling, the mixture was dissolved in chloroform, washed with water, and dried over anhydrous sodium sulfate. The dried mixture was then filtered and concentrated. The obtained residue was purified by silica gel column chromatography (hexane-ethyl acetate), and the obtained solid was suspended and washed with hexane-ethyl acetate. After filtration, the solid was dried at 70° C. under reduced pressure, thereby obtaining 2.37 g of the title compound as a pale orange solid.
Physical Properties: m/z[M+H]$^+$ 250.1.

Step 2: Synthesis of 4-amino-1-(tert-butyl)-1H-pyrazolo[3,4-d] pyrimidine-3-carboxylic acid 2.23 g of methyl 4-amino-1-(tert-butyl)-1H-pyrazolo[3,4-d]pyrimidine-3-carboxylate obtained in step 1 of Reference Example 3 was suspended in 33 mL of methanol, and 3.58 mL of a 5M aqueous sodium hydroxide solution was added thereto. The mixture was heated under reflux with stirring for 30 minutes. After cooling, the reaction solution was neutralized with a 5M hydrochloric acid aqueous solution and diluted with water to collect the precipitated solid by filtration. The obtained solid was dried at 60° C. under reduced pressure, thereby obtaining 2.05 g of the title compound as a colorless solid.
Physical Properties: m/z[M+H]$^+$ 236.3.

Reference Example 4: Synthesis of 4-amino-1-(4,4-difluorocyclohexyl)-1H-pyrazolo[3,4-d]pyrimidine-3-carboxylic acid Step 1: Synthesis of 1-(4,4-difluorocyclohexyl)-3-iodo-1H-pyrazolo[3,4-d]pyrimidin-4-amine 1.6 mL of diisopropyl azodicarboxylate was added to a solution of 1.6 g of 3-iodo-1H-pyrazolo[3,4-d]pyrimidin-4-amine, 1.0 g of 4,4-difluorocyclohexanol, and 2.1 g of triphenylphosphine in 50 mL of THF at room temperature, followed by stirring overnight. After concentration, the mixture was suspended and washed with methanol and filtered. The obtained solid was dried at 60° C. under reduced pressure, thereby obtaining 1.5 g of the title compound as a colorless solid.
Physical Properties: m/z[M+H]$^+$ 380.2.

Step 2: Synthesis of methyl 4-amino-1-(4,4-difluorocyclohexyl)-1H-pyrazolo[3,4-d]pyrimidine-3-carboxylate A mixture solution of 1.5 g of 1-(4,4-difluorocyclohexyl)-3-iodo-1H-pyrazolo[3,4-d]pyrimidin-4-amine obtained in step 1 of Reference Example 4, 330 mg of a 1,1'-bis(diphenylphosphino)ferrocene-palladium(II) dichloride-dichloromethane complex, and 3 mL of N,N-diisopropylethylamine in 30 mL of methanol was stirred in a carbon monoxide atmosphere in an autoclave at 0.45 MPa and at 100° C. for 2 hours. After cooling, the mixture was concentrated and purified by silica gel column chromatography (hexane-ethyl acetate). After concentration, the obtained crude product was re-purified by basic silica gel chromatography (hexane-ethyl acetate), and the obtained solid was suspended and washed with hexane-ethyl acetate, followed by filtration and drying under reduced pressure, thereby obtaining 650 mg of the title compound as a colorless solid.
Physical Properties: m/z[M+H]$^+$ 312.1.

Step 3: Synthesis of 4-amino-1-(4,4-difluorocyclohexyl)-1H-pyrazolo[3,4-d]pyrimidine-3-carboxylic acid According to the synthesis procedure of step 2 in Reference Example 3, using 653 mg of methyl-4-amino-1-(4,4-difluorocyclohexyl)-1H-pyrazolo[3,4-d]pyrimidine-3-carboxylate obtained in step 2 above, instead of methyl 4-amino-1-(tert-butyl)-1H-pyrazolo[3,4-d]pyrimidine-3-carboxylate used in step 2 of Reference Example 3, 605 mg of the title compound was obtained as a colorless solid.
Physical Properties: m/z[M+H]$^+$ 298.1.

Reference Example 5: Synthesis of tert-butyl 5-amino-3-methyl-1H-pyrazole-1-carboxylate 75 g of 5-methyl-1H-pyrazol-3-amine was dissolved in 800 mL of dichloromethane, and 750 mL of a 5N NaOH aqueous solution was added thereto. 184.5 g of di-tert-butyl dicarbonate was added to the solution, and the mixture was stirred at room temperature for 3 days. Water was added to the solution, followed by extraction with chloroform. The organic layer was washed with water and dried over anhydrous magnesium sulfate. The organic solution was concentrated under reduced pressure, and the obtained solid was washed with hexane, thereby obtaining 68 g of the title compound as a white solid.
Physical Properties: m/z[M+H]$^+$ 198.1
NMR (DMSO-d6) δ ppm 1.51 (s, 9H), 1.98 (s, 3H), 5.13 (s, 1H), 6.23 (s, 2H).

Reference Example 6: Synthesis of 4-amino-7-isopropyl-7H-pyrrolo[2,3-d]pyrimidine-5-carboxylic acid Step 1: Synthesis of 4-chloro-5-iodo-7-isopropyl-7H-pyrrolo[2,3-d]pyrimidine 5.79 mL of DIAD was added to a solution of 4.0 g of 4-chloro-5-iodo-7H-pyrrolo[2,3-d]pyrimidine, 2.58 g of propan-2-ol, and 7.51 g of triphenylphosphine in 30 mL of tetrahydrofuran. The reaction solution was stirred for 18 hours. The reaction solution was concentrated, and the obtained residue was purified by silica gel chromatography (hexane->hexane/ethyl acetate=1/1), thereby obtaining 4.0 g of the title compound as a pale yellow solid.
Physical Properties: m/z[M+H]$^+$ 322.0.

Step 2: Synthesis of 5-iodo-7-isopropyl-7H-pyrrolo[2,3-d]pyrimidin-4-amine 30 mL of 1,2-dimethoxyethane and 30 mL of 28% ammonia water were added to 3 g of 4-chloro-5-iodo-7-isopropyl-7H-pyrrolo[2,3-d]pyrimidine obtained in step 1 above, and the mixture was stirred in a stainless pressure-resistant tube at 115° C. for 18 hours. 300 mL of water was added to the reaction solution, and the obtained solid was washed with water, thereby obtaining 2.0 g of the title compound as a white solid.

Physical Properties: m/z[M+H]$^+$ 303.1.

Step 3: Synthesis of 4-amino-7-isopropyl-7H-pyrrolo[2,3-d]pyrimidine-5-carboxylic acid 3.8 g of 5-iodo-7-isopropyl-7H-pyrrolo[2,3-d]pyrimidin-4-amine obtained in step 2 above, 8.3 mL of 2-diethylamino ethanol, and 0.44 g of Pd(PPh$_3$)$_2$Cl$_2$ were dissolved in 10 mL of NMP, and the inside of the system was replaced with carbon monoxide, followed by heating to 120° C. After stirring for 2 hours, the reaction mixture was cooled to room temperature, and 7 mL of methanol was added thereto. 3.5 mL of a 5N aqueous sodium hydroxide solution was further added, and the mixture was stirred for 30 minutes. After addition of water, the aqueous layer was washed with ethyl acetate and adjusted with hydrochloric acid to a pH of 3, followed by filtration of the precipitated solid. The obtained solid was washed with water and dried, thereby obtaining 0.670 g of the title compound as a pale yellow solid.

Physical Properties: m/z[M+H]$^+$ 221.2.

Reference Example 7: Synthesis of 4-amino-7-(tert-butyl)-7H-pyrrolo[2,3-d]pyrimidine-5-carboxylic acid

Step 1: Synthesis of 7-(tert-butyl)-4-chloro-7H-pyrrolo[2,3-d]pyrimidine

A mixture solution of 29.3 g of 2-(4,6-dichloropyrimidin-5-yl)acetaldehyde, 13.4 g of tert-butylamine, and 29.7 g of N,N-diisopropylethylamine in 200 mL of ethanol was stirred with heating under reflux for 2 hours. After cooling, the reaction mixture was concentrated. The residue was diluted with ethyl acetate, washed with water and subsequently with a saturated aqueous sodium chloride solution. The obtained organic layer was dried over anhydrous sodium sulfate, filtered, and concentrated. The obtained residue was purified by silica gel chromatography, thereby obtaining 21.5 g of the title compound as a colorless solid.

Physical Properties: m/z[M+H]$^+$ 210.0.

Step 2: Synthesis of 7-(tert-butyl)-4-chloro-5-iodo-7H-pyrrolo[2,3-d]pyrimidine 46.7 g of N-iodosuccinimide was added to a solution of 36 g of 7-(tert-butyl)-4-chloro-7H-pyrrolo[2,3-d]pyrimidine obtained in step 1 in 360 mL of DMF, and the mixture was stirred at room temperature for 3 days. The mixture was diluted with ethyl acetate and washed with water 3 times, followed by washing with a saturated aqueous sodium chloride solution. The obtained organic layer was dried over anhydrous sodium sulfate, filtered, and concentrated. The obtained solid was suspended and washed with hexane-ethyl acetate, and filtered, followed by drying under reduced pressure, thereby obtaining 45.5 g of the title compound as a pale orange solid.

Physical Properties: m/z[M+H]$^+$ 335.9.

Step 3: Synthesis of 7-(tert-butyl)-5-iodo-7H-pyrrolo[2,3-d]pyrimidin-4-amine A suspension of 52 g of 7-(tert-butyl)-4-chloro-5-iodo-7H-pyrrolo[2,3-d]pyrimidine obtained in step 2 in 180 mL of THF and 180 mL of 28% ammonia water was stirred at 120° C. for 14 hours in an autoclave. After cooling, the mixture was diluted with water to collect the precipitated solid by filtration, followed by drying at 60° C. under reduced pressure, thereby obtaining 52 g of the title compound as a colorless solid.

Physical Properties: m/z[M+H]$^+$ 317.3.

Step 4: Synthesis of methyl 4-amino-7-(tert-butyl)-7H-pyrrolo[2,3-d]pyrimidine-5-carboxylate A suspension of 15 g of 7-(tert-butyl)-5-iodo-7H-pyrrolo[2,3-d]pyrimidin-4-amine obtained in step 3, 1.94 g of a 1,1'-bis(diphenylphosphino)ferrocene-palladium(II) dichloride-dichloromethane complex, and 13.2 mL of triethylamine in 150 mL of methanol was stirred in a carbon monoxide atmosphere in an autoclave at 100° C. and 0.45 MPa for 1.5 hours. After cooling, the reaction solution was concentrated and purified by silica gel chromatography (hexane-ethyl acetate). The obtained solid was suspended and washed with hexane-ethyl acetate, filtrated, and dried under reduced pressure, thereby obtaining 9.70 g of the title compound as a dark red solid.

Physical Properties: m/z[M+H]$^+$ 249.3.

Step 5: 4-amino-7-(tert-butyl)-7H-pyrrolo[2,3-d]pyrimidine-5-carboxylic acid 23.4 mL of a 5M aqueous sodium hydroxide solution was added to a suspension of 9.70 g of methyl 4-amino-7-(tert-butyl)-7H-pyrrolo[2,3-d]pyrimidine-5-carboxylate obtained in step 4 in 97 mL of methanol. The mixture was stirred with heating under reflux for 2 hours. After cooling, the mixture was neutralized with a 5M hydrochloric acid aqueous solution to precipitate a brown solid. After dilution with water, the solid was filtered and dried at 60° C. under reduced pressure, thereby obtaining 8.0 g of the title compound as a brown solid.

Physical Properties: m/z[M+H]$^+$ 235.2.

Reference Example 8: Synthesis of 7-(tert-butyl)-5-iodo-6-methyl-7H-pyrrolo[2,3-d]pyrimidin-4-amine

Step 1: Synthesis of 1-(4,6-dichloropyrimidin-5-yl)propan-2-ol 1 g of 2-(4,6-dichloropyrimidin-5-yl)acetaldehyde was dissolved in 20 mL of THF, and the reactor was cooled to −78° C. 4.36 mL of a methylmagnesium bromide diethyl ether solution (3 mol/L) was slowly added dropwise thereto. At the same temperature, the mixture was stirred for 1 hour, and a saturated aqueous ammonium chloride solution was slowly added thereto to terminate the reaction. The reaction mixture was stirred at room temperature for 10 minutes and placed in a separatory funnel, followed by extraction with ethyl acetate. The organic layer was washed with a saturated aqueous sodium chloride solution, and then dried over sodium sulfate to remove the solvent. The residue was purified by basic silica gel chromatography (hexane/ethyl acetate=1/0->3/1), thereby obtaining 446 mg of the title compound as a colorless oil.

Physical Properties: m/z[M+H]$^+$ 207.0.

Step 2: Synthesis of 1-(4,6-dichloropyrimidin-5-yl)propan-2-one 246 mg of 1-(4,6-dichloropyrimidin-5-yl)propan-2-ol obtained in step 1 was dissolved in 2.5 mL of dichloromethane, and 1.0 g of a Dess-Martin reagent was added thereto, followed by stirring at room temperature for 1 hour. A 10% sodium thiosulfate aqueous solution and saturated sodium bicarbonate water were added to the reaction solution, and the mixture was further stirred for 30 minutes. The reaction mixture was extracted with chloroform, and the organic layer was washed with water and a saturated aqueous sodium chloride solution, followed by addition of sodium sulfate for drying. After removal of the solvent, the residue was purified by silica gel chromatography (hexane/ethyl acetate=1/0->3/1), thereby obtaining 198 mg of the title compound as a yellow solid.
Physical Properties: m/z[M+H]$^+$ 205.0.

Step 3: Synthesis of 1-(4-(tert-butylamino)-6-chloropyrimidin-5-yl)propan-2-one 198 mg of 1-(4,6-dichloropyrimidin-5-yl)propan-2-one obtained in step 2, 122 μL of tert-butylamine, and 252 μL of diisopropylethylamine were dissolved in 2 mL of ethanol, and the solution was stirred at 90° C. overnight.
After the reaction mixture was concentrated, the residue was purified by silica gel chromatography (hexane/ethyl acetate=1/0->3/1), thereby obtaining 64 mg of the title compound as a colorless oil.
Physical Properties: m/z[M+H]$^+$ 242.1.

Step 4: Synthesis of 7-(tert-butyl)-4-chloro-6-methyl-7H-pyrrolo[2,3-d]pyrimidine 64 mg of 1-(4-(tert-butylamino)-6-chloropyrimidin-5-yl)propan-2-one obtained in step 3 and 42 μL of acetic acid were dissolved in 5.5 mL of ethanol, and the solution was reacted in a microwave reactor at 120° C. for 1 hour. After removal of the solvent, the residue was purified by silica gel chromatography (hexane/ethyl acetate=1/0->4/1), thereby obtaining 54 mg of the title compound as a colorless oil.
Physical Properties: m/z[M+H]$^+$ 224.1.

Step 5: Synthesis of 7-(tert-butyl)-4-chloro-5-iodo-6-methyl-7H-pyrrolo[2,3-d]pyrimidine 7-(tert-butyl)-4-chloro-6-methyl-7H-pyrrolo[2,3-d]pyrimidine obtained in step 4 was dissolved in 1.5 mL of DMF. 64 mg of N-iodosuccinimide was added thereto, and the mixture was stirred at room temperature overnight. A 10% aqueous sodium thiosulfate solution was added to the reaction solution to terminate the reaction, and the reaction solution was extracted with ethyl acetate. The organic layer was washed with water and a saturated aqueous sodium chloride solution, and dried over sodium sulfate, followed by removal of the solvent. The residue was purified by silica gel chromatography (hexane/ethyl acetate=1/0->4/1), thereby obtaining 69 mg of the title compound as a white solid.
Physical Properties: m/z[M+H]$^+$ 349.9.

Step 6: 7-(tert-butyl)-5-iodo-6-methyl-7H-pyrrolo[2,3-d]pyrimidin-4-amine 60 mg of 7-(tert-butyl)-4-chloro-5-iodo-6-methyl-7H-pyrrolo[2,3-d]pyrimidine obtained in step 5 was reacted with 600 μL of DME and 600 μL of ammonia water in a pressure-resistant tube at 115° C. for 12 hours. After air cooling, water was added to the reaction mixture. The obtained white solid was filtered and dried, thereby obtaining 45 mg of the title compound.
Physical Properties: m/z[M+H]$^+$ 331.0.

Example 1: Synthesis of 4-amino-1-cyclopentyl-N-(5-ethyl-1H-pyrazol-3-yl)-1H-pyrazolo[3,4-d]pyrimidine-3-carboxamide 30 mg of 4-amino-1-cyclopentyl-1H-pyrazolo[3,4-d]pyrimidine-3-carboxylic acid obtained in step 2 of Reference Example 1, 16 mg of 5-ethyl-1H-pyrazol-3-amine, and 55 mg of HATU were dissolved in 1 mL of DMF, and 62 μL of diisopropylethylamine was added thereto. The mixture was stirred at room temperature for 18 hours, and water was added to the reaction solution, followed by extraction with chloroform. The organic layer was washed with water, and dried over anhydrous magnesium sulfate, followed by concentration of the organic solution under reduced pressure. The residue was purified by silica gel chromatography (chloroform->chloroform/methanol=10/1), thereby obtaining 29 mg of the title compound as a white solid.

Example 2: Synthesis of 4-amino-1-cyclopentyl-N-(5-(furan-2-yl)-1H-pyrazol-3-yl)-1H-pyrazolo[3,4-d]pyrimidine-3-carboxamide According to the synthesis procedure of Example 1, using 5-(furan-2-yl)-1H-pyrazol-3-amine instead of 5-ethyl-1H-pyrazol-3-amine, the title compound (55%) was obtained as a brownish solid.

Example 3: Synthesis of 4-amino-1-cyclopentyl-N-(5-(furan-3-yl)-1H-pyrazol-3-yl)-1H-pyrazolo[3,4-d]pyrimidine-3-carboxamide According to the synthesis procedure of Example 1, using 5-(furan-3-yl)-1H-pyrazol-3-amine instead of 5-ethyl-1H-pyrazol-3-amine, the title compound (76%) was obtained as a brownish solid.

Example 4: Synthesis of 4-amino-1-cyclopentyl-N-(5-(thiophen-2-yl)-1H-pyrazol-3-yl)-1H-pyrazolo[3,4-d]pyrimidine-3-carboxamide According to the synthesis procedure of Example 1, using 5-(thiophen-2-yl)-1H-pyrazol-3-amine instead of 5-ethyl-1H-pyrazol-3-amine, the title compound (60%) was obtained as a brownish solid.

Example 5: Synthesis of 4-amino-1-cyclopentyl-N-(5-phenyl-1H-pyrazol-3-yl)-1H-pyrazolo[3,4-d]pyrimidine-3-carboxamide According to the synthesis procedure of Example 1, using 5-phenyl-1H-pyrazol-3-amine instead of 5-ethyl-1H-pyrazol-3-amine, the title compound (77%) was obtained as a brownish solid.

Example 6: Synthesis of 4-amino-1-cyclopentyl-N-(5-cyclopentyl-1H-pyrazol-3-yl)-1H-pyrazolo[3,4-d]pyrimidine-3-carboxamide According to the synthesis procedure of Example 1, using 5-cyclopentyl-1H-pyrazol-3-amine instead of 5-ethyl-1H-pyrazol-3-amine, the title compound (63%) was obtained as a brownish solid.

Example 7: Synthesis of 4-amino-1-cyclopentyl-N-(5-cyclopropyl-1H-pyrazol-3-yl)-1H-pyrazolo[3,4-d]pyrimidine-3-carboxamide According to the synthesis procedure of Example 1, using 5-cyclopropyl-1H-pyrazol-3-amine instead of 5-ethyl-1H-pyrazol-3-amine, the title compound (68%) was obtained as a brownish solid.

Example 8: Synthesis of 4-amino-1-cyclopentyl-N-(3-propyl-1H-pyrazol-5-yl)-1H-pyrazolo[3,4-d]pyrimidine-3-carboxamide According to the synthesis procedure of Example 1, using 5-propyl-1H-pyrazol-3-amine instead of 5-ethyl-1H-pyrazol-3-amine, the title compound (70%) was obtained as a brownish solid.

Example 9: Synthesis of 4-amino-1-cyclopentyl-N-(1,3-dimethyl-1H-pyrazol-5-yl)-1H-pyrazolo[3,4-d]pyrimidine-3-carboxamide According to the synthesis procedure of Example 1, using 1,3-dimethyl-1H-pyrazol-5-amine instead of 5-ethyl-1H-pyrazol-3-amine, the title compound (28%) was obtained as a white solid.

Example 10: Synthesis of 4-amino-1-cyclopentyl-N-(5-isopropyl-1H-pyrazol-3-yl)-1H-pyrazolo[3,4-d]pyrimidine-3-carboxamide According to the synthesis procedure of Example 1, using 5-isopropyl-1H-pyrazol-3-amine instead of 5-ethyl-1H-pyrazol-3-amine, the title compound (89%) was obtained as a brownish solid.

Example 11: Synthesis of 4-amino-1-cyclobutyl-N-(5-methyl-1H-pyrazol-3-yl)-1H-pyrazolo[3,4-d]pyrimidine-3-carboxamide According to the synthesis procedures of steps 1 and 2 in Reference Example 1, using bromocyclobutane instead of iodocyclopentane, 4-amino-1-cyclobutyl-1H-pyrazolo[3,4-d]pyrimidine-3-carboxylic acid was obtained as a brownish solid. According to the procedure of Example 1, using 4-amino-1-cyclobutyl-1H-pyrazolo[3,4-d]pyrimidine-3-carboxylic acid instead of 4-amino-1-cyclopentyl-1H-pyrazolo[3,4-d]pyrimidine-3-carboxylic acid, and using 5-methyl-1H-pyrazol-3-amine instead of 5-ethyl-1H-pyrazol-3-amine, the title compound (50%) was obtained as a brownish solid.

Example 12: Synthesis of 4-amino-N-(5-methyl-1H-pyrazol-3-yl)-1-((1-methylcyclopropyl)methyl)-1H-pyrazolo[3,4-d]pyrimidine-3-carboxamide According to the synthesis procedures of steps 1 and 2 in Reference Example 1, using (1-methylcyclopropyl)methyl methanesulfonate instead of iodocyclopentane, 4-amino-7-((1-methylcyclopropyl)methyl)-7H-pyrazolo[3,4-d]pyrimidine-5-carboxylic acid was obtained as a brownish solid. According to the procedure of Example 1, using 4-amino-7-((1-methylcyclopropyl)methyl)-7H-pyrazolo[3,4-d]pyrimidine-5-carboxylic acid instead of 4-amino-1-cyclopentyl-1H-pyrazolo[3,4-d]pyrimidine-3-carboxylic acid and using 5-methyl-1H-pyrazol-3-amine instead of 5-ethyl-1H-pyrazol-3-amine, the title compound (38%) was obtained as a brownish solid.

Example 13: Synthesis of 4-amino-N-(5-methyl-1H-pyrazol-3-yl)-1-(2,2,2-trifluoroethyl)-1H-pyrazolo[3,4-d]pyrimidine-3-carboxamide According to the synthesis procedures of steps 1 and 2 in Reference Example 1, using 2,2,2-trifluoroethyl methanesulfonate instead of iodocyclopentane, 4-amino-1-(2,2,2-trifluoroethyl)-1H-pyrazolo[3,4-d]pyrimidine-3-carboxylic acid was obtained as a brownish solid. According to the procedure of Example 1, using 4-amino-1-(2,2,2-trifluoroethyl)-1H-pyrazolo[3,4-d]pyrimidine-3-carboxylic acid instead of 4-amino-1-cyclopentyl-1H-pyrazolo[3,4-d]pyrimidine-3-carboxylic acid, and using 5-methyl-1H-pyrazol-3-amine instead of 5-ethyl-1H-pyrazol-3-amine, the title compound (51%) was obtained as a white solid.

Example 14: Synthesis of 4-amino-N-(5-methyl-1H-pyrazol-3-yl)-1-(3,3,3-trifluoropropyl)-1H-pyrazolo[3,4-d]pyrimidine-3-carboxamide According to the synthesis procedures of steps 1 and 2 in Reference Example 1, using 3-bromo-1,1,1-trifluoropropane instead of iodocyclopentane, 4-amino-1-(3,3,3-trifluoropropyl)-1H-pyrazolo[3,4-d]pyrimidine-3-carboxylic acid was obtained as a white solid. According to the procedure of Example 1, using 4-amino-1-(3,3,3-trifluoropropyl)-1H-pyrazolo[3,4-d]pyrimidine-3-carboxylic acid instead of 4-amino-1-cyclopentyl-1H-pyrazolo[3,4-d]pyrimidine-3-carboxylic acid, and using 5-methyl-1H-pyrazol-3-amine instead of 5-ethyl-1H-pyrazol-3-amine, the title compound (84%) was obtained as a white solid.

Example 15: Synthesis of 4-amino-1-(sec-butyl)-N-(5-methyl-1H-pyrazol-3-yl)-1H-pyrazolo[3,4-d]pyrimidine-3-carboxamide According to the synthesis procedures of steps 1 and 2 in Reference Example 1, using 2-bromobutane instead of iodocyclopentane, 4-amino-7-(sec-butyl)-7H-pyrazolo[2,3-d]pyrimidine-5-carboxylic acid was obtained as a white solid. According to the procedure of Example 1, using 4-amino-7-(sec-butyl)-7H-pyrazolo[2,3-d]pyrimidine-5-carboxylic acid instead of 4-amino-1-cyclopentyl-1H-pyrazolo[3,4-d]pyrimidine-3-carboxylic acid, and using 5-methyl-1H-pyrazol-3-amine instead of 5-ethyl-1H-pyrazol-3-amine, the title compound (62%) was obtained as a brownish solid.

Example 16: Synthesis of 4-amino-1-(cyclobutylmethyl)-N-(5-methyl-1H-pyrazol-3-yl)-1H-pyrazolo[3,4-d]pyrimidine-3-carboxamide According to the synthesis procedures of steps 1 and 2 in Reference Example 1, using (bromomethyl)cyclobutane instead of iodocyclopentane, 4-amino-1-(cyclobutylmethyl)-1H-pyrazolo[3,4-d]pyrimidine-3-carboxylic acid was obtained as a white solid. According to the procedure of Example 1, using 4-amino-1-(cyclobutylmethyl)-1H-pyrazolo[3,4-d]pyrimidine-3-carboxylic acid instead of 4-amino-1-cyclopentyl-1H-pyrazolo[3,4-d]pyrimidine-3-carboxylic acid, and using 5-methyl-1H-pyrazol-3-amine instead of 5-ethyl-1H-pyrazol-3-amine, the title compound was obtained as a brownish solid (63%).

Example 17: Synthesis of 4-amino-N-(5-bromo-1H-pyrazol-3-yl)-1-(cyclobutylmethyl)-1H-pyrazolo[3,4-d]pyrimidine-3-carboxamide According to the synthesis procedures of steps 1 and 2 in Reference Example 1, using (bromomethyl)cyclobutane instead of iodocyclopentane, 4-amino-1-(cyclobutylmethyl)-1H-pyrazolo[3,4-d]pyrimidine-3-carboxylic acid was obtained as a white solid. According to the procedure of Example 1, using 5-bromo-1H-pyrazol-3-amine instead of 5-ethyl-1H-pyrazol-3-amine, and using 4-amino-1-(cyclobutylmethyl)-1H-pyrazolo[3,4-d]pyrimidine-3-carboxylic acid instead of 4-amino-1-cyclopentyl-1H-pyrazolo[3,4-d]pyrimidine-3-carboxylic acid, the title compound was obtained as a brownish solid (42%).

Example 18: Synthesis of 4-amino-1-(cyclopropylmethyl)-N-(5-methyl-1H-pyrazol-3-yl)-1H-pyrazolo[3,4-d]pyrimidine-3-carboxamide According to the synthesis procedures of steps 1 and 2 in Reference Example 1, using (bromomethyl)cyclopropane instead of iodocyclopentane, 4-amino-1-(cyclopropylmethyl)-1H-pyrazolo[3,4-d]pyrimidine-3-carboxylic acid was obtained as a white solid. According to the procedure of Example 1, using 4-amino-1-(cyclopropylmethyl)-1H-pyrazolo[3,4-d]pyrimidine-3-carboxylic acid instead of 4-amino-1-cyclopentyl-1H-pyrazolo[3,4-d]pyrimidine-3-carboxylic acid, and using 5-methyl-1H-pyrazol-3-amine instead of 5-ethyl-1H-pyrazol-3-amine, the title compound was obtained as a brownish solid (71%).

Example 19: Synthesis of 4-amino-1-(cyclopentylmethyl)-N-(5-methyl-1H-pyrazol-3-yl)-1H-pyrazolo[3,4-d]pyrimidine-3-carboxamide According to the synthesis procedures of steps 1 and 2 in Reference Example 1, using (bromomethyl)cyclopentane instead of iodocyclopentane, 4-amino-1-(cyclopentylmethyl)-1H-pyrazolo[3,4-d]pyrimidine-3-carboxylic acid was obtained as a brownish solid. According to the procedure of Example 1, using 4-amino-1-(cyclopentylmethyl)-1H-pyrazolo[3,4-d]pyrimidine-3-carboxylic acid instead of 4-amino-1-cyclopentyl-1H-pyrazolo [3,4-d]pyrimidine-3-carboxylic acid, and using 5-methyl-1H-pyrazol-3-amine instead of 5-ethyl-1H-pyrazol-3-amine, the title compound (53%) was obtained as a white solid.

Example 20: Synthesis of 4-amino-N-(5-bromo-1H-pyrazol-3-yl)-1-(cyclopentylmethyl)-1H-pyrazolo[3,4-d]pyrimidine-3-carboxamide According to the synthesis procedures of steps 1 and 2 in Reference Example 1, using (bromomethyl)cyclopentane instead of iodocyclopentane, 4-amino-1-(cyclopentylmethyl)-1H-pyrazolo[3,4-d]pyrimidine-3-carboxylic acid was obtained as a brownish solid. According to the procedure of Example 1, using 5-bromo-1H-pyrazol-3-amine instead of 5-ethyl-1H-pyrazol-3-amine, and using 4-amino-1-(cyclopentylmethyl)-1H-pyrazolo[3,4-d]pyrimidine-3-carboxylic acid instead of 4-amino-1-cyclopentyl-1H-pyrazolo[3,4-d]pyrimidine-3-carboxylic acid, the title compound (61%) was obtained as a brownish solid.

Example 21: Synthesis of 4-amino-1-isopropyl-N-(5-(trifluoromethyl)-1H-pyrazol-3-yl)-1H-pyrazolo[3,4-d]pyrimidine-3-carboxamide According to the synthesis procedures of steps 1 and 2 in Reference Example 1, using 2-bromopropane instead of iodocyclopentane, 4-amino-1-isopropyl-1H-pyrazolo[3,4-d]pyrimidine-3-carboxylic acid was obtained as a white solid. According to the procedure of Example 1, using 5-(trifluoromethyl)-1H-pyrazol-3-amine instead of 5-ethyl-1H-pyrazol-3-amine, and using 4-amino-1-isopropyl-1H-pyrazolo[3,4-d]pyrimidine-3-carboxylic acid instead of 4-amino-1-cyclopentyl-1H-pyrazolo[3,4-d]pyrimidine-3-carboxylic acid, the title compound (22%) was obtained as a brownish solid.

Example 22: Synthesis of 4-amino-N-(5-bromo-1H-pyrazol-3-yl)-1-isopropyl-1H-pyrazolo[3,4-d]pyrimidine-3-carboxamide According to the synthesis procedures of steps 1 and 2 in Reference Example 1, using 2-bromopropane instead of iodocyclopentane, 4-amino-1-isopropyl-1H-pyrazolo[3,4-d]pyrimidine-3-carboxylic acid was obtained as a white solid. According to the procedure of Example 1, using 5-bromo-1H-pyrazol-3-amine instead of 5-ethyl-1H-pyrazol-3-amine, and using 4-amino-1-isopropyl-1H-pyrazolo[3,4-d]pyrimidine-3-carboxylic acid instead of 4-amino-1-cyclopentyl-1H-pyrazolo[3,4-d]pyrimidine-3-carboxylic acid, the title compound (50%) was obtained as a brownish solid.

Example 23: Synthesis of 4-amino-N-(5-methyl-1H-pyrazol-3-yl)-1-((1R,2R)-2-methylcyclohexyl)-1H-pyrazolo[3,4-d]pyrimidine-3-carboxamide According to the synthesis procedures of steps 1 and 2 in Reference Example 1, using [(1S,2R)-2-methylcyclohexyl]methanesulfonate instead of iodocyclopentane, 4-amino-1-((1R, 2R)-2-methylcyclohexyl)-1H-pyrazolo[3,4-d]pyrimidine-3-carboxylic acid was obtained as a brownish solid. According to the procedure of Example 1, using 4-amino-1-((1R, 2R)-2-methylcyclohexyl)-1H-pyrazolo[3,4-d]pyrimidine-3-carboxylic acid instead of 4-amino-1-cyclopentyl-1H-pyrazolo[3,4-d]pyrimidine-3-carboxylic acid and using 5-methyl-1H-pyrazol-3-amine instead of 5-ethyl-1H-pyrazol-3-amine, the title compound (35%) was obtained as a white solid.

Example 24: Synthesis of 4-amino-1-(4,4-dimethylcyclohexyl)-N-(5-methyl-1H-pyrazol-3-yl)-1H-pyrazolo[3,4-d]pyrimidine-3-carboxamide 35 mg of 4-amino-1-(4,4-dimethylcyclohexyl)-1H-pyrazolo[3,4-d]pyrimidine-3-carboxylic acid obtained in step 2 in Reference Example 2, 14 mg of 5-methyl-1H-pyrazol-3-amine, and 55 mg of HATU were dissolved in 1 mL of DMF, and 63 μL of diisopropylethylamine was added thereto. After stirring at room temperature for 18 hours, water was added to the reaction solution, followed by extraction with chloroform. The organic layer was washed with water and dried over anhydrous magnesium sulfate, followed by concentration of the organic solution under reduced pressure. The residue was purified by silica gel chromatography (chloroform->chloroform/methanol=10/1), thereby obtaining 27 mg of the title compound as a white solid.

Example 25: Synthesis of 4-amino-N-(5-bromo-1H-pyrazol-3-yl)-1-(4,4-dimethylcyclohexyl)-1H-pyrazolo[3,4-d]pyrimidine-3-carboxamide According to the procedure of Example 24, using 5-bromo-1H-pyrazol-3-amine instead of 5-methyl-1H-pyrazol-3-amine, the title compound (53%) was obtained as a brownish solid.

Example 26: Synthesis of 4-amino-1-(3,3-dimethyl-cyclobutyl)-N-(5-methyl-1H-pyrazol-3-yl)-1H-pyrazolo[3,4-d]pyrimidine-3-carboxamide According to the synthesis procedures of steps 1 and 2 in Reference Example 2, using 3,3-dimethylcyclobutanol instead of 4,4-dimethylcyclohexanol, 4-amino-1-(3,3-dimethylcyclobutyl)-1H-pyrazolo[3,4-d]pyrimidine-3-carboxylic acid was obtained as a white solid. According to the procedure of Example 24, using 4-amino-1-(3,3-dimethylcyclobutyl)-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid, the title compound (47%) was obtained as a brownish solid.

Example 27: Synthesis of 4-amino-1-(bicyclo[2.2.1]heptan-2-yl)-N-(5-methyl-1H-pyrazol-3-yl)-1H-pyrazolo[3,4-d]pyrimidine-3-carboxamide According to the synthesis procedures of steps 1 and 2 in Reference Example 2, using bicyclo[2.2.1]heptan-2-ol instead of 4,4-dimethylcyclohexanol, 4-amino-1-(bicyclo[2.2.1]heptane)-1H-pyrazolo[3,4-d]pyrimidine-3-carboxylic acid was obtained as a brownish solid. According to the procedure of Example 24, using 4-amino-1-(bicyclo[2.2.1]heptane)-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid, the title compound (57%) was obtained as a brownish solid.

Example 28: Synthesis of 4-amino-1-(bicyclo[2.2.1]heptan-2-yl)-N-(5-bromo-1H-pyrazol-3-yl)-1H-pyrazolo[3,4-d]pyrimidine-3-carboxamide According to the synthesis procedures of steps 1 and 2 in Reference Example 2, using bicyclo[2.2.1]heptan-2-ol instead of 4,4-dimethylcyclohexanol, 4-amino-1-(bicyclo[2.2.1]heptane)-1H-pyrazolo[3,4-d]pyrimidine-3-carboxylic acid was obtained as a brownish solid. According to the procedure of Example 24, using 4-amino-1-(bicyclo[2.2.1]heptane)-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid, and using 3-bromo-1H-pyrazol-5-amine instead of 5-methyl-1H-pyrazol-3-amine, the title compound (61%) was obtained as a brownish solid.

Example 29: Synthesis of 1-(adamantan-2-yl)-4-amino-N-(5-methyl-1H-pyrazol-3-yl)-1H-pyrazolo[3,4-d]pyrimidine-3-carboxamide According to the synthesis procedures of steps 1 and 2 in Reference Example 2, using adamantan-2-ol instead of 4,4-dimethylcyclohexanol, 1-(adamantan-2-yl)-4-amino-N-(5-methyl-1H-pyrazol-3-yl)-1H-pyrazolo[3,4-d]pyrimidine-3-carboxylic acid was obtained as a brownish solid. According to the procedure of Example 24, using 1-(adamantan-2-yl)-4-amino-N-(5-methyl-1H-pyrazol-3-yl)-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid, the title compound (69%) was obtained as a brownish solid.

Example 30: Synthesis of 4-amino-N-(5-methyl-1H-pyrazol-3-yl)-1-((2S,3R)-2,6,6-trimethylbicyclo[3.1.1]heptan-3-yl)-1H-pyrazolo[3,4-d]pyrimidine-3-carboxamide According to the synthesis procedures of steps 1 and 2 in Reference Example 2, using (2S,3S)-2,6,6-trimethylnorpinan-3-ol instead of 4,4-dimethylcyclohexanol, 4-amino-1-((2S,3R)-2,6,6-trimethylbicyclo[3.1.1]heptan-3-yl)-1H-pyrazolo[3,4-d]pyrimidine-3-carboxylic acid was obtained as a brownish solid. According to the procedure of Example 24, using 4-amino-1-((2S,3R)-2,6,6-trimethylbicyclo[3.1.1]heptan-3-yl)-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid, the title compound (61%) was obtained as a brownish solid.

Example 31: Synthesis of 4-amino-1-(3-fluoroprop-1-en-2-yl)-N-(5-methyl-1H-pyrazol-3-yl)-1H-pyrazolo[3,4-d]pyrimidine-3-carboxamide According to the synthesis procedures of steps 1 and 2 in Reference Example 2, using 1,3-difluoropropan-2-ol instead of 4,4-dimethylcyclohexanol, 4-amino-1-(3-fluoroprop-1-en-2-yl)-1H-pyrazolo[3,4-d]pyrimidine-3-carboxylic acid was obtained as a brownish solid. According to the procedure of Example 24, using 4-amino-1-(3-fluoroprop-1-en-2-yl)-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid, the title compound (65%) was obtained as a brownish solid.

Example 32: Synthesis of 4-amino-N-(5-bromo-1H-pyrazol-3-yl)-1-cyclohexyl-1H-pyrazolo[3,4-d]pyrimidine-3-carboxamide According to the synthesis procedures of steps 1 and 2 in Reference Example 2, using cyclohexanol instead of 4,4-dimethylcyclohexanol, 4-amino-1-cyclohexyl-1H-pyrazolo[3,4-d]pyrimidine-3-carboxylic acid was obtained as a brownish solid. According to the procedure of Example 24, using 4-amino-1-cyclohexyl-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid and using 3-bromo-1H-pyrazol-5-amine instead of 5-methyl-1H-pyrazol-3-amine, the title compound (23%) was obtained as a brownish solid.

Example 33: Synthesis of 4-amino-1-cyclohexyl-N-(5-(difluoromethyl)-1H-pyrazol-3-yl)-1H-pyrazolo[3,4-d]pyrimidine-3-carboxamide According to the synthesis procedures of steps 1 and 2 in Reference Example 2, using cyclohexanol instead of 4,4-dimethylcyclohexanol, 4-amino-1-cyclohexyl-1H-pyrazolo[3,4-d]pyrimidine-3-carboxylic acid was obtained as a brownish solid. According to the procedure of Example 24, using 4-amino-1-cyclohexyl-1H-pyrazolo[3,4-d]pyrimidine-3-carboxylic acid instead of 4-amino-1-(4,4-dimethylcyclohexyl)-1H-pyrazolo[3,4-d]pyrimidine-3-carboxylic acid, and using 5-(difluoromethyl)-1H-pyrazol-3-amine instead of 5-methyl-1H-pyrazol-3-amine, the title compound (41%) was obtained as a brownish solid.

Example 34: Synthesis of 4-amino-1-(tert-butyl)-N-(5-methyl-1H-pyrazol-3-yl)-1H-pyrazolo[3,4-d]pyrimidine-3-carboxamide 429 mg of HATU was added to a suspension of 177 mg of 4-amino-1-(tert-butyl)-1H-pyrazolo[3,4-d]pyrimidine-3-carboxylic acid obtained in step 2 of Reference Example 3, 109 mg of 5-methyl-1H-pyrazol-3-amine, and 0.393 mL of N,N-diisopropylethylamine in 4 mL of DMF, and the mixture was stirred at room temperature overnight. 100 μL of a 5M aqueous sodium hydroxide solution was added to the reaction solution, and stirred for 1 hour. Thereafter, the mixture was neutralized with a 5M hydrochloric acid aqueous solution. After extraction with chloroform, the extract was dried over anhydrous sodium sulfate, filtered, and concentrated. The obtained residue was suspended and washed with methanol, filtered, and dried at 60° C. under reduced pressure, thereby obtaining 97 mg of the title compound as a colorless solid.

Example 35: Synthesis of 4-amino-N-(5-bromo-1H-pyrazol-3-yl)-1-(tert-butyl)-1H-pyrazolo[3,4-d]pyrimidine-3-carboxamide According to the procedure of Example 34, using 3-bromo-1H-pyrazol-5-amine instead of 5-methyl-1H-pyrazol-3-amine, the title compound was obtained as a pale brownish solid (25%).

Example 36: Synthesis of 4-amino-1-(tert-butyl)-N-(5-(trifluoromethyl)-1H-pyrazol-3-yl)-1H-pyrazolo[3,4-d]pyrimidine-3-carboxamide According to the procedure of Example 34, using 5-(trifluoromethyl)-1H-pyrazol-3-amine instead of 5-methyl-1H-pyrazol-3-amine, the title compound (72%) was obtained as a pale brownish solid.

Example 37: Synthesis of 4-amino-1-(tert-butyl)-N-(5-(furan-2-yl)-1H-pyrazol-3-yl)-1H-pyrazolo[3,4-d]pyrimidine-3-carboxamide According to the procedure of Example 34, using 3-(furan-2-yl)-1H-pyrazol-5-amine instead of 5-methyl-1H-pyrazol-3-amine, the title compound (32%) was obtained as a pale brownish solid.

Example 38: Synthesis of 4-amino-1-(tert-butyl)-N-(5-cyano-1H-pyrazol-3-yl)-1H-pyrazolo[3,4-d]pyrimidine-3-carboxamide According to the procedure of Example 34, using 5-amino-1H-pyrazole-3-carbonitrile instead of 5-methyl-1H-pyrazol-3-amine, the title compound (22%) was obtained as a brownish solid.

Example 39: Synthesis of 4-amino-1-(tert-butyl)-N-(5-ethyl-1H-pyrazol-3-yl)-1H-pyrazolo[3,4-d]pyrimidine-3-carboxamide According to the synthesis procedure of Example 34, using 3-ethyl-1H-pyrazol-5-amine instead of 5-methyl-1H-pyrazol-3-amine, followed by purification with preparative reversed-phase HPLC, the title compound (55%) was obtained as a brownish solid.

Example 40: Synthesis of 4-amino-1-(tert-butyl)-N-(5-isopropyl-1H-pyrazol-3-yl)-1H-pyrazolo[3,4-d]pyrimidine-3-carboxamide According to the synthesis procedure of Example 34, using 3-isopropyl-1H-pyrazol-5-amine instead of 5-methyl-1H-pyrazol-3-amine, followed by purification with preparative reversed-phase HPLC, the title compound (81%) was obtained as a brownish solid.

Example 41: Synthesis of 4-amino-1-(tert-butyl)-N-(5-cyclopropyl-1H-pyrazol-3-yl)-1H-pyrazolo[3,4-d]pyrimidine-3-carboxamide According to the synthesis procedure of Example 34, using 3-cyclopropyl-1H-pyrazol-5-amine instead of 5-methyl-1H-pyrazol-3-amine, followed by purification with preparative reversed-phase HPLC, the title compound (69%) was obtained as a brownish solid.

Example 42: Synthesis of 4-amino-1-(tert-butyl)-N-(5-cyclobutyl-1H-pyrazol-3-yl)-1H-pyrazolo[3,4-d]pyrimidine-3-carboxamide According to the procedure of Example 34, using 3-cyclobutyl-1H-pyrazol-5-amine instead of 5-methyl-1H-pyrazol-3-amine, followed by purification with preparative reversed-phase HPLC, the title compound (33%) was obtained as a brownish solid.

Example 43: Synthesis of 4-amino-1-(4,4-difluorocyclohexyl)-N-(5-methyl-1H-pyrazol-3-yl)-1H-pyrazolo[3,4-d]pyrimidine-3-carboxamide According to the synthesis procedure of Example 34, using 4-amino-1-(4,4-difluorocyclohexyl)-1H-pyrazolo[3,4-d]pyrimidine-3-carboxylic acid obtained in step 3 of Reference Example 4 instead of 4-amino-1-(tert-butyl)-1H-pyrazolo[3,4-d]pyrimidine-3-carboxylic acid of Example 34, the title compound (21%) was obtained as a colorless solid.

Example 44: Synthesis of 4-amino-N-(5-bromo-1H-pyrazol-3-yl)-1-(4,4-difluorocyclohexyl)-1H-pyrazolo[3,4-d]pyrimidine-3-carboxamide According to the synthesis procedure of Example 34, using 4-amino-1-(4,4-difluorocyclohexyl)-1H-pyrazolo[3,4-d]pyrimidine-3-carboxylic acid obtained in step 3 of Reference Example 4 instead of 4-amino-1-(tert-butyl)-1H-pyrazolo[3,4-d]pyrimidine-3-carboxylic acid of Example 34, and using 3-bromo-1H-pyrazol-5-amine instead of 5-methyl-1H-pyrazol-3-amine, the title compound (33%) was obtained as a colorless solid.

Example 45: Synthesis of 4-amino-7-isopropyl-N-(5-methyl-1H-pyrazol-3-yl)-7H-pyrrolo[2,3-d]pyrimidine-5-carboxamide 121 mg of 5-iodo-7-isopropyl-7H-pyrrolo[2,3-d]pyrimidin-4-amine obtained in step 2 of Reference Example 6, 197 mg of tert-butyl 5-amino-3-methyl-1H-pyrazole-1-carboxylate obtained in Reference Example 5, and 120 μL of 1,8-diazabicyclo[5.4.0]undec-7-ene were dissolved in 2 mL of DMA. 33 mg of 1,1'-bis(diphenylphosphino)ferrocenepalladium(II) dichloride-dichloromethane was further added thereto, and the mixture was stirred in a carbon monoxide atmosphere at 110° C. for 4 hours. The residue obtained by concentrating the reaction mixture was purified by silica gel chromatography (hexane/ethyl acetate=1/1->ethyl acetate/methanol=10/1), thereby obtaining 52 mg of the title compound as a pale brown solid.

Example 46: Synthesis of 4-amino-7-(1-fluoropropan-2-yl)-N-(5-methyl-1H-pyrazol-3-yl)-7H-pyrrolo[2,3-d]pyrimidine-5-carboxamide According to the synthesis procedures of steps 1 and 2 in Reference Example 6, using 1-fluoropropan-2-ol instead of propan-2-ol, 7-(1-fluoropropan-2-yl)-5-iodo-7H-pyrrolo[2,3-d]pyrimidin-4-amine was obtained as a white solid. According to the procedure of Example 45, using 7-(1-fluoropropan-2-yl)-5-iodo-7H-pyrrolo[2,3-d]pyrimidin-4-amine instead of 5-iodo-7-isopropyl-7H-pyrrolo[2,3-d]pyrimidin-4-amine, the title compound was obtained as a brownish solid (90%).

Example 47: Synthesis of 4-amino-7-(4,4-dimethylcyclohexyl)-N-(5-methyl-1H-pyrazol-3-yl)-7H-pyrrolo[2,3-d]pyrimidine-5-carboxamide According to the synthesis procedures of steps 1 and 2 in Reference Example 6, using 4,4-dimethylcyclohexanol instead of propan-2-ol, 7-(4,4-dimethylcyclohexyl)-5-iodo-7H-pyrrolo[2,3-d]pyrimidin-4-amine was obtained as a yellow solid. According to the procedure of Example 45, using 7-(4,4-dimethylcyclohexyl)-5-iodo-7H-pyrrolo[2,3-d]pyrimidin-4-amine instead of 5-iodo-7-isopropyl-7H-pyrrolo[2,3-d]pyrimidin-4-amine, the title compound (31%) was obtained as a brownish solid.

Example 48: Synthesis of 4-amino-7-(tert-butyl)-N-(5-methyl-1H-pyrazol-3-yl)-7H-pyrrolo[2,3-d]pyrimidine-5-carboxamide A solution of 6.0 g of 7-(tert-butyl)-5-iodo-7H-pyrrolo[2,3-d]pyrimidin-4-amine obtained in step 3 of Reference Example 7, 7.48 g of tert-butyl 5-amino-3-methyl-pyrazole-1-carboxylate obtained in Reference Example 5, 5.67 mL of 1,8-diazabicyclo[5.4.0]undec-7-ene, and 1.55 g of a 1,1'-bis(diphenylphosphino)ferrocene-palladium(II) dichloride-dichloromethane complex in 200 mL of DMA was stirred in a carbon monoxide atmosphere at 100° C. for 3 hours. The reaction solution was concentrated and then purified by silica gel chromatography (hexane-ethyl acetate-methanol), followed by purification by basic silica gel chromatography, thereby obtaining 3.24 g of the title compound as a brownish solid.

Example 49: Synthesis of 4-amino-7-(tert-butyl)-N-(5-(furan-2-yl)-1H-pyrazol-3-yl)-7H-pyrrolo[2,3-d]pyrimidine-5-carboxamide According to the procedure of Example 48, using 5-(furan-2-yl)-1H-pyrazol-3-amine instead of tert-butyl 5-amino-3-methyl-pyrazole-1-carboxylate used in Example 48, the title compound (42%) was obtained as a pale brownish solid.

Example 50: Synthesis of 4-amino-7-(1-fluoro-2-methylpropan-2-yl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using 1-fluoro-2-methylpropane-2-amine hydrochloride instead of tert-butylamine, 7-(1-fluoro-2-methylpropan-2-yl)-5-iodo-7H-pyrrolo[2,3-d]pyrimidin-4-amine was obtained as a white solid. According to the procedure of Example 48, using 7-(1-fluoro-2-methylpropan-2-yl)-5-iodo-7H-pyrrolo[2,3-d]pyrimidin-4-amine instead of 7-(tert-butyl)-5-iodo-7H-pyrrolo[2,3-d]pyrimidin-4-amine, the title compound (70%) was obtained as a brownish solid.

Example 51: Synthesis of 4-amino-N-(5-methyl-1H-pyrazol-3-yl)-7-(1-methylcyclopropyl)-7H-pyrrolo[2,3-d]pyrimidine-5-carboxamide According to the synthesis procedures of steps 1, 2, and 3 in Reference Example 7, using 1-methylcyclopropane amine hydrochloride instead of tert-butylamine, 5-iodo-7-(1-methylcyclopropyl)-7H-pyrrolo[2,3-d]pyrimidin-4-amine was obtained as a white solid. According to the procedure of Example 48, using 5-iodo-7-(1-methylcyclopropyl)-7H-pyrrolo[2,3-d]pyrimidin-4-amine instead of 7-(tert-butyl)-5-iodo-7H-pyrrolo[2,3-d]pyrimidin-4-amine, the title compound (37%) was obtained as a brownish solid.

Example 52: Synthesis of 4-amino-7-(2-cyclopropylpropan-2-yl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using 2-cyclopropylpropane-2-amine hydrochloride instead of tert-butylamine, 7-(2-cyclopropylpropan-2-yl)-5-iodo-7H-pyrrolo[2,3-d]pyrimidin-4-amine was obtained as a white solid. According to the procedure of Example 48, using 7-(2-cyclopropylpropan-2-yl)-5-iodo-7H-pyrrolo[2,3-d]pyrimidin-4-amine instead of 7-(tert-butyl)-5-iodo-7H-pyrrolo[2,3-d]pyrimidin-4-amine, the title compound (60%) was obtained as a brownish solid.

Example 53: Synthesis of 4-amino-7-(1-methoxy-2-methylpropan-2-yl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using 2-methoxy-2-methylpropan-2-amine instead of tert-butylamine, 5-iodo-7-(1-methoxy-2-methylpropan-2-yl)-7H-pyrrolo[2,3-d]pyrimidin-4-amine was obtained as a white solid. According to the procedure of Example 48, using 5-iodo-7-(1-methoxy-2-methylpropan-2-yl)-7H-pyrrolo[2,3-d]pyrimidin-4-amine instead of 7-(tert-butyl)-5-iodo-7H-pyrrolo[2,3-d]pyrimidin-4-amine, the title compound (50%) was obtained as a brownish solid.

Example 54: Synthesis of 4-amino-7-(1-(fluoromethyl)cyclopropyl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using 1-(fluoromethyl)cyclopropane amine hydrochloride instead of tert-butylamine, 7-(1-(fluoromethyl)cyclopropyl)-5-iodo-7H-pyrrolo[2,3-d]pyrimidin-4-amine was obtained as a white solid. According to the procedure of Example 48, using 7-(1-(fluoromethyl)cyclopropyl)-5-iodo-7H-pyrrolo[2,3-d]pyrimidin-4-amine instead of 7-(tert-butyl)-5-iodo-7H-pyrrolo[2,3-d]pyrimidin-4-amine, the title compound (60%) was obtained as a brownish solid.

Example 55: Synthesis of 4-amino-7-(1-(difluoromethyl)cyclopropyl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using 1-(difluoromethyl)cyclopropane amine hydrochloride instead of tert-butylamine, 7-(1-(difluoromethyl)cyclopropyl)-5-iodo-7H-pyrrolo[2,3-d]pyrimidin-4-amine was obtained as a yellow solid.

According to the procedure of Example 48, using 7-(1-(difluoromethyl)cyclopropyl)-5-iodo-7H-pyrrolo[2,3-d]pyrimidin-4-amine instead of 7-(tert-butyl)-5-iodo-7H-pyrrolo[2,3-d]pyrimidin-4-amine, the title compound (40%) was obtained as a brownish solid.

Example 56: Synthesis of 4-amino-N-(5-methyl-1H-pyrazol-3-yl)-7-(2-(thiophen-2-yl)propan-2-yl)-7H-pyrrolo[2,3-d]pyrimidine-5-carboxamide According to the synthesis procedures of steps 1, 2, and 3 in Reference Example 7, using 2-(thiophen-2-yl)propan-2-amine instead of tert-butylamine, 5-iodo-7-(2-(thiophen-2-yl)propan-2-yl)-7H-pyrrolo[2,3-d]pyrimidin-4-amine was obtained as a yellow solid. According to the procedure of Example 48, using 5-iodo-7-(2-(thiophen-2-yl)propan-2-yl)-7H-pyrrolo[2,3-d]pyrimidin-4-amine instead of 7-(tert-butyl)-5-iodo-7H-pyrrolo[2,3-d]pyrimidin-4-amine, the title compound (70%) was obtained as a brownish solid.

Example 57: Synthesis of 4-amino-7-(3,3-difluorocyclopentyl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using 3,3-difluorocyclopentane amine hydrochloride instead of tert-butylamine, 7-(3,3-difluorocyclopentyl)-5-iodo-7H-pyrrolo[2,3-d]pyrimidin-4-amine was obtained as a yellow solid. According to the procedure of Example 48, using 7-(3,3-difluorocyclopentyl)-5-iodo-7H-pyrrolo[2,3-d]pyrimidin-4-amine instead of 7-(tert-butyl)-5-iodo-7H-pyrrolo[2,3-d]pyrimidin-4-amine, the title compound (50%) was obtained as a brownish solid.

Example 58: Synthesis of 4-amino-7-(bicyclo[1.1.1]pentan-1-yl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using bicyclo[1.1.1]pentane-1-amine hydrochloride instead of tert-butylamine, 7-(bicyclo[1.1.1]pentan-1-yl)-4-chloro-5-iodo-7H-pyrrolo[2,3-d]pyrimidine was obtained. According to the procedure of Example 48, using 7-(bicyclo[1.1.1]pentan-1-yl)-4-chloro-5-iodo-7H-pyrrolo[2,3-d]pyrimidine instead of 7-(tert-butyl)-5-iodo-7H-pyrrolo[2,3-d]pyrimidin-4-amine, the title compound (36%) was obtained as a colorless solid.

Example 59: Synthesis of 4-amino-N-(5-methyl-1H-pyrazol-3-yl)-7-(1-methylcyclopentyl)-7H-pyrrolo[2,3-d]pyrimidine-5-carboxamide According to the synthesis procedures of steps 1, 2, and 3 in Reference Example 7, using 1-methylcyclopentane amine hydrochloride instead of tert-butylamine, 5-iodo-7-(1-methylcyclopentyl)-7H-pyrrolo[2,3-d]pyrimidin-4-amine was obtained as a white solid. According to the procedure of Example 48, using 5-iodo-7-(1-methylcyclopentyl)-7H-pyrrolo[2,3-d]pyrimidin-4-amine instead of 7-(tert-butyl)-5-iodo-7H-pyrrolo[2,3-d]pyrimidin-4-amine, the title compound (20%) was obtained as a brownish solid.

Example 60: Synthesis of 4-amino-N-(5-methyl-1H-pyrazol-3-yl)-7-(2-phenylpropan-2-yl)-7H-pyrrolo[2,3-d]pyrimidine-5-carboxamide According to the synthesis procedures of steps 1, 2, and 3 in Reference Example 7, using 2-phenylpropan-2-amine instead of tert-butylamine, 5-iodo-7-(2-phenylpropan-2-yl)-7H-pyrrolo[2,3-d]pyrimidin-4-amine was obtained as a yellow solid. According to the procedure of Example 48, using 5-iodo-7-(2-phenylpropan-2-yl)-7H-pyrrolo[2,3-d]pyrimidin-4-amine instead of 7-(tert-butyl)-5-iodo-7H-pyrrolo[2,3-d]pyrimidin-4-amine, the title compound (41%) was obtained as a brownish solid.

Example 61: Synthesis of 4-amino-N-(5-methyl-1H-pyrazol-3-yl)-7-(2,3,3-trimethylbutan-2-yl)-7H-pyrrolo[2,3-d]pyrimidine-5-carboxamide According to the synthesis procedures of steps 1, 2, and 3 in Reference Example 7, using 2,3,3-trimethylbutan-2-amine instead of tert-butylamine, 5-iodo-7-(2,3,3-trimethylbutan-2-yl)-7H-pyrrolo[2,3-d]pyrimidin-4-amine was obtained as a white solid. According to the procedure of Example 48, using 5-iodo-7-(2,3,3-trimethylbutan-2-yl)-7H-pyrrolo[2,3-d]pyrimidin-4-amine instead of 7-(tert-butyl)-5-iodo-7H-pyrrolo[2,3-d]pyrimidin-4-amine, the title compound (60%) was obtained as a brownish solid.

Example 62: Synthesis of 4-amino-7-(2,3-dimethylbutan-2-yl)-N-(5-methyl-1H-pyrazol-3-yl)-7H-pyrrolo[2,3-d]pyrimidine-5-carboxamide According to the synthesis procedures of steps 1, 2, and 3 in Reference Example 7, using 2,3-dimethylbutane-2-amine hydrochloride instead of tert-butylamine, 7-(2,3-dimethylbutan-2-yl)-5-iodo-7H-pyrrolo[2,3-d]pyrimidin-4-amine was obtained as a white solid. According to the procedure of Example 48, using 7-(2,3-dimethylbutan-2-yl)-5-iodo-7H-pyrrolo[2,3-d]pyrimidin-4-amine instead of 7-(tert-butyl)-5-iodo-7H-pyrrolo[2,3-d]pyrimidin-4-amine, the title compound (50%) was obtained as a brownish solid.

Example 63: Synthesis of 4-amino-N-(5-bromo-1H-pyrazol-3-yl)-7-(tert-butyl)-7H-pyrrolo[2,3-d]pyrimidine-5-carboxamide 40 mg of 4-amino-7-(tert-butyl)-7H-pyrrolo[2,3-d]pyrimidine-5-carboxylic acid obtained in step 5 of Reference Example 7 was suspended in 2 mL of DMF, and 33 mg of 3-bromo-1H-pyrazol-5-amine, 89 µL of diisopropylethylamine, and 78 mg of HATU were added thereto, followed by stirring at room temperature overnight. 2 ml, of an aqueous sodium hydroxide solution (1 mol/L) was added to the reaction mixture, and the mixture was stirred at room temperature for 1 hour. Thereafter, the reaction mixture was partitioned between ethyl acetate and water. The organic layer was washed with water and a saturated aqueous sodium chloride solution, and dried over sodium sulfate. After concentration, the residue was purified by silica gel chromatography (ethyl acetate/methanol=1/0->10/1), thereby obtaining 6.5 mg of the title compound as a white solid.

Example 64: Synthesis of 4-amino-7-(tert-butyl)-N-(5-(methoxymethyl)-1H-pyrazol-3-yl)-7H-pyrrolo[2,3-d]pyrimidine-5-carboxamide According to the procedure of Example 63, using 5-(methoxymethyl)-1H-pyrazol-3-amine instead of 3-bromo-1H-pyrazol-5-amine, the title compound (24%) was obtained as a white solid.

Example 65: Synthesis of 4-amino-N-(5-bromo-1H-pyrazol-3-yl)-7-isopropyl-7H-pyrrolo[2,3-d]pyrimidine-5-carboxamide According to the procedure of Example 63, using 4-amino-7-isopropyl-7H-pyrrolo[2,3-d]pyrimidine-5-carboxylic acid obtained in step 3 of Reference Example 6 instead of 4-amino-7-(tert-butyl)-7H-pyrrolo[2,3-d]pyrimidine-5-carboxylic acid, the title compound (20%) was obtained as a brownish solid.

Example 66: Synthesis of 4-amino-N-(5-bromo-1H-pyrazol-3-yl)-7-(1-fluoro-2-methylpropan-2-yl)-7H-pyrrolo[2,3-d]pyrimidine-5-carboxamide According to the procedure of step 3 in Reference Example 6, using 7-(1-fluoro-2-methylpropan-2-yl)-5-iodo-7H-pyrrolo[2,3-d]pyrimidin-4-amine used in Example 50 instead of 7-(tert-butyl)-5-iodo-7H-pyrrolo[2,3-d]pyrimidin-4-amine, 4-amino-7-(1-fluoro-2-methylpropan-2-yl)-7H-pyrrolo[2,3-d]pyrimidine-5-carboxylic acid was obtained. According to the procedure of Example 63, using 4-amino-7-(1-fluoro-2-methylpropan-2-yl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (29%) was obtained as a white solid.

Example 67: Synthesis of 4-amino-N-(5-bromo-1H-pyrazol-3-yl)-7-(1-methylcyclopropyl)-7H-pyrrolo[2,3-d]pyrimidine-5-carboxamide According to the procedure of step 3 in Reference Example 6, using 5-iodo-7-(1-methylcyclopropyl)-7H-pyrrolo[2,3-d]pyrimidin-4-amine used in Example 51 instead of 7-(tert-butyl)-5-iodo-7H-pyrrolo[2,3-d]pyrimidin-4-amine, 4-amino-7-(1-methylcyclopropyl)-7H-pyrrolo[2,3-d]pyrimidine-5-carboxylic acid was obtained. According to the procedure of Example 63, using 4-amino-7-(1-methylcyclopropyl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (19%) was obtained as a white solid.

Example 68: Synthesis of 4-amino-N-(5-methyl-1H-pyrazol-3-yl)-7-(1-methylcyclobutyl)-7H-pyrrolo[2,3-d]pyrimidine-5-carboxamide According to the synthesis procedures of steps 1 to 5 in Reference Example 7, using 1-methylcyclobutane-amine hydrochloride instead of tert-butylamine, 4-amino-7-(methyl cyclobutyl)-7H-pyrrolo[2,3-d]pyrimidine-5-carboxylic acid was obtained as a white solid. According to the procedure of Example 63, using 4-amino-7-(methyl cyclobutyl)-7H-pyrrolo[2,3-d]pyrimidine-5-carboxylic acid instead of 4-amino-7-(tert-butyl)-7H-pyrrolo[2,3-d]pyrimidine-5-carboxylic acid, and using 5-methyl-1H-pyrazol-3-amine instead of 3-bromo-1H-pyrazol-5-amine, the title compound (15%) was obtained as a brownish solid.

Example 69: Synthesis of 4-amino-7-cyclobutyl-N-(5-methyl-1H-pyrazol-3-yl)-7H-pyrrolo[2,3-d]pyrimidine-5-carboxamide According to the synthesis procedures of steps 1 to 5 in Reference Example 7, using cyclobutane amine instead of tert-butylamine, 4-amino-7-cyclobutyl-7H-pyrrolo[2,3-d]pyrimidine-5-carboxylic acid was obtained. According to the procedure of Example 63, using 4-amino-7-cyclobutyl-7H-pyrrolo[2,3-d]pyrimidine-5-carboxylic acid instead of 4-amino-7-(tert-butyl)-7H-pyrrolo[2,3-d]pyrimidine-5-carboxylic acid, and using 5-methyl-1H-pyrazol-3-amine instead of 3-bromo-1H-pyrazol-5-amine, the title compound (8%) was obtained as a brownish solid.

Example 70: Synthesis of 4-amino-N-(5-methyl-1H-pyrazol-3-yl)-7-(tert-pentyl)-7H-pyrrolo[2,3-d]pyrimidine-5-carboxamide According to the synthesis procedures of steps 1 to 5 in Reference Example 7, using 2-methylbutan-2-amine instead of tert-butylamine, 4-amino-7-(tert-pentyl)-7H-pyrrolo[2,3-d]pyrimidine-5-carboxylic acid was obtained as a white solid. According to the procedure of Example 63, using 4-amino-7-(tert-pentyl)-7H-pyrrolo[2,3-d]pyrimidine-5-carboxylic acid instead of 4-amino-7-(tert-butyl)-7H-pyrrolo[2,3-d]pyrimidine-5-carboxylic acid, and using 5-methyl-1H-pyrazol-3-amine instead of 3-bromo-1H-pyrazol-5-amine, the title compound (16%) was obtained as a brownish solid.

Example 71: Synthesis of 4-amino-7-(bicyclo[2.2.1]heptan-2-yl)-N-(5-methyl-1H-pyrazol-3-yl)-7H-pyrrolo[2,3-d]pyrimidine-5-carboxamide According to the synthesis procedures of steps 1 to 5 in Reference Example 7, using bicyclo[2.2.1]heptan-2-amine instead of tert-butylamine, 4-amino-7-(bicyclo[2.2.1]heptan-2-yl)-7H-pyrrolo[2,3-d]pyrimidine-5-carboxylic acid was obtained as a white solid. According to the procedure of Example 63, using 4-amino-7-(bicyclo[2.2.1]heptan-2-yl)-7H-pyrrolo[2,3-d]pyrimidine-5-carboxylic acid instead of 4-amino-7-(tert-butyl)-7H-pyrrolo[2,3-d]pyrimidine-5-carboxylic acid, and using 5-methyl-1H-pyrazol-3-amine instead of 3-bromo-1H-pyrazol-5-amine, the title compound (8%) was obtained as a brownish solid.

Example 72: Synthesis of 4-amino-7-cyclopentyl-N-(5-methyl-1H-pyrazol-3-yl)-7H-pyrrolo[2,3-d]pyrimidine-5-carboxamide According to the synthesis procedures of steps 1 to 3 in Reference Example 6, using cyclopentanol instead of propan-2-ol, 4-amino-7-cyclopentyl-7H-pyrrolo[2,3-d]pyrimidine-5-carboxylic acid was obtained as a white solid. According to the procedure of Example 63, using 4-amino-7-cyclopentyl-7H-pyrrolo[2,3-d]pyrimidine-5-carboxylic acid instead of 4-amino-7-(tert-butyl)-7H-pyrrolo[2,3-d]pyrimidine-5-carboxylic acid, and using 5-methyl-1H-pyrazol-3-amine instead of 3-bromo-1H-pyrazol-5-amine, the title compound (15%) was obtained as a white solid.

Example 73: Synthesis of 4-amino-7-(tert-butyl)-6-methyl-N-(3-methyl-1H-pyrazol-5-yl)-7H-pyrrolo[2,3-d]pyrimidine-5-carboxamide According to the procedure of Example 48, using 7-(tert-butyl)-5-iodo-6-methyl-7H-pyrrolo[2,3-d]pyrimidin-4-amine obtained in step 6 of Reference Example 8 instead of 7-(tert-butyl)-5-iodo-7H-pyrrolo[2,3-d]pyrimidin-4-amine to perform a reaction, the title compound (6.7%) was obtained as a white solid.

Example 74: Synthesis of 7-([1,1'-bi(cyclopropan)]-1-yl)-4-amino-N-(5-methyl-1H-pyrazol-3-yl)-7H-pyrrolo[2,3-d]pyrimidine-5-carboxamide According to the synthesis procedures of steps 1, 2, and 3 in Reference Example 7, using 1-cyclopropyl cyclopropane amine hydrochloride instead of tert-butylamine, 7-([1,1'-bi(cyclopropan)]-1-yl)-5-iodo-7H-pyrrolo[2,3-d]pyrimidin-4-amine was obtained as a brownish solid. According to the procedure of Example 48, using 7-([1,1'-bi(cyclopropan)]-1-yl)-5-iodo-7H-pyrrolo[2,3-d]pyrimidin-4-amine instead of 7-(tert-butyl)-5-iodo-7H-pyrrolo[2,3-d]pyrimidin-4-amine, the title compound (59%) was obtained as a brownish solid.

Example 75: Synthesis of 4-amino-6-chloro-N-(5-methyl-1H-pyrazol-3-yl)-7-(1-methylcyclopropyl)-7H-pyrrolo[2,3-d]pyrimidine-5-carboxamide Step 1: Synthesis of methyl 4-amino-7-(1-methylcyclopropyl)-7H-pyrrolo[2,3-d]pyrimidine-5-carboxylate 12.1 g of triethylamine and 2.25 g of a [1,1'-bis(diphenylphosphino)ferrocene]palladium(II) dichloride dichloromethane complex were added to a suspension of 18.85 g of 5-iodo-7-(1-methylcyclopropyl)-7H-pyrrolo[2,3-d]pyrimidin-4-amine obtained as an intermediate in Example 51 in 180 mL of methanol. The mixture was stirred in a carbon monoxide atmosphere in an autoclave at 0.5 MPa and at 100° C. for 1.5 hours. After cooling, the solvent was removed, and the residue was dissolved in 300 mL of chloroform. 20 g of Celite was added thereto, followed by stirring at room temperature for 1 hour. The insoluble matter was removed by filtration, and the filtrate was washed with water and a saturated aqueous sodium chloride solution, dried over anhydrous magnesium sulfate, and filtered, followed by concentration. The obtained residue was purified by silica gel column chromatography (chloroform/methanol=100/1->20/1), and the solvent was removed. The obtained solid was suspended and washed with ethyl acetate, thereby obtaining 11.6 g of the title compound.

Step 2: Synthesis of methyl 4-amino-6-chloro-7-(1-methylcyclopropyl)-7H-pyrrolo[2,3-d]pyrimidine-5-carboxylate 1.71 g of methyl 4-amino-7-(1-methylcyclopropyl)-7H-pyrrolo[2,3-d]pyrimidine-5-carboxylate obtained in step 1 was dissolved in 17 mL of DMF, and 1.39 g of N-chlorosuccinimide was added thereto, followed by stirring at 50° C. for 2 hours. 80 mL of a 10% sodium thiosulfate aqueous solution and 120 mL of water were added to the reaction solution, and the mixture was stirred with ice cooling for 3 hours, followed by stirring at room temperature overnight. The precipitate was collected by filtration and washed with water, thereby obtaining 1.13 g of the title compound.

Step 3: Synthesis of 4-amino-6-chloro-7-(1-methylcyclopropyl)-7H-pyrrolo[2,3-d]pyrimidine-5-carboxylic acid 272 mg of methyl 4-amino-6-chloro-7-(1-methylcyclopropyl)-7H-pyrrolo[2,3-d]pyrimidine-5-carboxylate obtained in step 2 was dissolved in 2.7 mL of THF and 2.7 mL of methanol, and 1.45 mL of a lithium hydroxide aqueous solution (4 mol/L) was added thereto, followed by stirring at room temperature overnight. 20 mL of water and a 2N hydrochloric acid aqueous solution were added to the reaction solution to acidify the solution, thereby obtaining a precipitate. The organic solvent was removed, and the residue was stirred with ice cooling for 1 hour, followed by filtration, thereby obtaining 248 mg of the title compound.

Step 4: Synthesis of 4-amino-6-chloro-N-(5-methyl-1H-pyrazol-3-yl)-7-(1-methylcyclopropyl)-7H-pyrrolo[2,3-d]pyrimidine-5-carboxamide 2.5 mL of DMF was added to 48 mg of 4-amino-6-chloro-7-(1-methylcyclopropyl)-7H-pyrrolo[2,3-d]pyrimidine-5-carboxylic acid obtained in step 3, and 33 mg of 1-hydroxybenztriazole and 38 mg of 1-(3-dimethylaminopropyl)-3-ethyl carbodiimide hydrochloride were further added thereto, followed by stirring at room temperature for 1.5 hours. 106 mg of tert-butyl 5-amino-3-methyl-1H-pyrazole-1-carboxylate synthesized in Reference Example 5 was added to the reaction solution, and the mixture was cooled to 0° C. Thereafter, 0.45 mL of a lithium hexamethyldisilazide solution (1M THF) was added thereto, followed by stirring at 0° C. for 30 minutes. 5 mL of a 1N aqueous sodium hydroxide solution was added to the reaction solution, and the mixture was stirred at room temperature for 1 hour. The reaction solution was partitioned between ethyl acetate and water. The organic layer was washed with water three times and washed with a saturated aqueous sodium chloride solution, followed by drying over anhydrous sodium sulfate. After filtration, the resulting solution was concentrated. The residue was purified by silica gel column (ethyl acetate/methanol=1/0->8/1), thereby obtaining 15 mg of the title compound.

Example 76: Synthesis of 4-amino-6-bromo-N-(5-methyl-1H-pyrazol-3-yl)-7-(1-methylcyclopropyl)-7H-pyrrolo[2,3-d]pyrimidine-5-carboxamide Step 1: Synthesis of methyl 4-amino-6-bromo-7-(1-methylcyclopropyl)-7H-pyrrolo[2,3-d]pyrimidine-5-carboxylate 2.3 g of methyl 4-amino-7-(1-methylcyclopropyl)-7H-pyrrolo[2,3-d]pyrimidine-5-carboxylate obtained in step 1 of Example 75 was dissolved in 47 mL of chloroform, and 3.3 g of N-bromosuccinimide was added thereto, followed by stirring at room temperature for 3 days. The reaction solution was partitioned between chloroform and a 10% sodium thiosulfate aqueous solution. The organic layer was washed with water and a saturated aqueous sodium chloride solution, and dried over anhydrous sodium sulfate. After filtration, the filtrate was concentrated. Methanol and water were added to the residue to form a suspension, and methanol was removed. The residue was stirred at 0° C. for 1 hour, and the solid was collected by filtration, thereby obtaining 2.50 g of the title compound.

Step 2: Synthesis of 4-amino-6-bromo-7-(1-methylcyclopropyl)-7H-pyrrolo[2,3-d]pyrimidine-5-carboxylic acid According to the procedure of step 3 in Example 75, using 1.10 g of methyl 4-amino-6-bromo-7-(1-methylcyclopropyl)-7H-pyrrolo[2,3-d]pyrimidine-5-carboxylate obtained in step 1, the title compound (97%) was obtained.

Step 3: Synthesis of 4-amino-6-bromo-N-(5-methyl-1H-pyrazol-3-yl)-7-(1-methylcyclopropyl)-7H-pyrrolo[2,3-d]pyrimidine-5-carboxamide According to the procedure of step 4 in Example 75, using 238 mg of 4-amino-6-bromo-7-(1-methylcyclopropyl)-7H- pyrrolo[2,3-d]pyrimidine-5-carboxylic acid obtained in step 2, the title compound (26%) was obtained.

Example 77: Synthesis of 4-amino-6-methoxy-N-(5-methyl-1H-pyrazol-3-yl)-7-(1-methylcyclopropyl)-7H-pyrrolo[2,3-d]pyrimidine-5-carboxamide Step 1: Synthesis of 4-amino-6-methoxy-7-(1-methylcyclopropyl)-7H-pyrrolo[2,3-d]pyrimidine-5-carboxylic acid 560 mg of methyl 4-amino-6-chloro-7-(1-methylcyclopropyl)-7H-pyrrolo[2,3-d]pyrimidine-5-carboxylate obtained in step 2 of Example 75 was suspended in 10 mL of THF, and 121 mg of 4-dimethylamino pyridine and 1.52 g of di-tert-butyl dicarbonate were added to the suspension with stirring. The mixture was stirred at 50° C. for 1 hour. After cooling, the reaction solution was concentrated, and partitioned between ethyl acetate and water. The organic layer was washed with water and a saturated aqueous sodium chloride solution. Anhydrous sodium sulfate was added, and the mixture was filtered, and concentrated. 10 mL of methanol was added to the residue, and 1 mL of sodium methoxide (methanol solution of about 5 mol/L) was added thereto with stirring, followed by stirring at 50° C. for 1 hour. After cooling, the mixture was concentrated, and the residue was partitioned between chloroform and saturated ammonium chloride. The organic layer was washed with water and a saturated aqueous sodium chloride solution. Anhydrous sodium sulfate was added, and the mixture was filtered and concentrated. 1 ml of dichloromethane and 2 mL of trifluoroacetic acid were added to the residue, and the mixture was stirred at room temperature for 1 hour. After concentration, the residue was partitioned between chloroform and a saturated aqueous sodium bicarbonate solution. The organic layer was washed with water and a saturated aqueous sodium chloride solution. Anhydrous sodium sulfate was added, and the mixture was filtered and concentrated. The residue was dissolved in 20 mL of methanol, and 2.3 mL of an aqueous sodium hydroxide solution (4 mol/L) was added thereto, and the mixture was stirred at 50° C. for 1 hour, followed by further stirring at 80° C. for 1 hour. After cooling, 20 mL of water and a 2N hydrochloric acid aqueous solution were added to the reaction solution to acidify the solution, thereby obtaining a precipitate. After the organic solvent was removed, the residue was stirred with ice cooling for 1 hour and filtered, thereby obtaining 417 mg of the title compound.

Step 2: Synthesis of 4-amino-6-methoxy-N-(5-methyl-1H-pyrazol-3-yl)-7-(1-methylcyclopropyl)-7H-pyrrolo[2,3-d]pyrimidine-5-carboxamide According to the procedure of step 4 in Example 75, using 30 mg of 4-amino-6-methoxy-7-(1-methylcyclopropyl)-7H-pyrrolo[2,3-d]pyrimidine-5-carboxylic acid obtained in step 1, the title compound (36%) was obtained.

Example 78: Synthesis of 4-amino-6-chloro-7-(1-fluoro-2-methylpropan-2-yl)-N-(5-methyl-1H-pyrazol-3-yl)-7H-pyrrolo[2,3-d]pyrimidine-5-carboxamide According to the procedure of step 4 in Example 75, using 30 mg of 4-amino-6-chloro-7-(1-fluoro-2-methylpropan-2-yl)-7H-pyrrolo[2,3-d]pyrimidine-5-carboxylic acid that was synthesized using 7-(1-fluoro-2-methylpropan-2-yl)-5-iodo-7H-pyrrolo[2,3-d]pyrimidin-4-amine obtained as an intermediate in Example 50 in accordance with the procedures of steps 1 to 3 in Example 75, the title compound (16%) was obtained.

Example 79: Synthesis of 4-amino-6-(3-hydroxy-3-methyl-1-butyn-1-yl)-N-(5-methyl-1H-pyrazol-3-yl)-7-(1-methylcyclopropyl)-7H-pyrrolo[2,3-d]pyrimidine-5-carboxamide 35 mg of 4-amino-6-bromo-N-(5-methyl-1H-pyrazol-3-yl)-7-(1-methylcyclopropyl)-7H-pyrrolo[2,3-d]pyrimidine-5-carboxamide obtained in Example 76 was dissolved in 1 mL of DMF. 1.7 mg of copper iodide, 87 µL of 2-methyl-3-butyn-1-ol, 31 µL of triethylamine, and 10 mg of tetrakis triphenylphosphine palladium were added thereto and degassed, followed by stirring at 100° C. for 2 hours. The reaction solution was partitioned between chloroform and water. The organic layer was washed with a saturated aqueous sodium chloride solution, dried over anhydrous sodium sulfate, and filtered, followed by concentration. The residue was purified by silica gel column (ethyl acetate/methanol=1/0->4/1), thereby obtaining 14 mg of the title compound.

Example 80: Synthesis of 4-amino-N-(5-methyl-1H-pyrazol-3-yl)-7-(1-methylcyclopropyl)-6-(pyridin-3-ylethynyl)-7H-pyrrolo[2,3-d]pyrimidine-5-carboxamide According to the procedure of Example 79, using 3-ethynylpyridine instead of 2-methyl-3-butyn-1-ol, the title compound (72%) was obtained.

Example 81: Synthesis of 4-amino-6-((1-hydroxycyclopentyl)ethynyl)-N-(5-methyl-1H-pyrazol-3-yl)-7-(1-methylcyclopropyl)-7H-pyrrolo[2,3-d]pyrimidine-5-carboxamide According to the procedure of Example 79, using 1-ethynylcyclopentan-1-ol instead of 2-methyl-3-butyn-1-ol, the title compound (18%) was obtained.

Example 82: Synthesis of 4-amino-6-((1-methyl-1H-pyrazol-4-yl)ethynyl)-N-(5-methyl-1H-pyrazol-3-yl)-7-(1-methylcyclopropyl)-7H-pyrrolo[2,3-d]pyrimidine-5-carboxamide According to the procedure of Example 79, using 4-ethynyl-1-methyl-1H-pyrazole instead of 2-methyl-3-butyn-1-ol, the title compound (43%) was obtained.

Example 83: Synthesis of 4-amino-6-((1-methyl-1H-imidazol-5-yl)ethynyl)-N-(5-methyl-1H-pyrazol-3-yl)-7-(1-methylcyclopropyl)-7H-pyrrolo[2,3-d]pyrimidine-5-carboxamide According to the procedure of Example 79, using 5-ethynyl-1-methyl-1H-imidazole instead of 2-methyl-3-butyn-1-ol, the title compound (57%) was obtained.

Example 84: Synthesis of 4-amino-N-(5-methyl-1H-pyrazol-3-yl)-7-(1-methylcyclopropyl)-6-(3-morpholino-1-propyn-1-yl)-7H-pyrrolo[2,3-d]pyrimidine-5-carboxamide According to the procedure of Example 79, using 4-(2-propyn-1-yl)morpholine instead of 2-methyl-3-butyn-1-ol, the title compound (39%) was obtained.

Example 85: Synthesis of 4-amino-6-(3-(1-hydroxy-cyclobutyl)-1-propyne)-N-(5-methyl-1H-pyrazol-3-yl)-7-(1-methylcyclopropyl)-7H-pyrrolo[2,3-d]pyrimidine-5-carboxamide According to the procedure of Example 79, using 1-(2-propyn-1-yl)cyclobutan-1-ol instead of 2-methyl-3-butyn-1-ol, the title compound (58%) was obtained.

Example 86: Synthesis of 4-amino-N-(5-methyl-1H-pyrazol-3-yl)-7-(1-methylcyclopropyl)-6-((tetrahydro-2H-pyran-4-yl)ethynyl)-7H-pyrrolo[2,3-d]pyrimidine-5-carboxamide According to the procedure of Example 79, using 4-ethynyltetrahydro-2H-pyrane instead of 2-methyl-3-butyn-1-ol, the title compound (56%) was obtained.

Example 87: Synthesis of 4-amino-N-(5-methyl-1H-pyrazol-3-yl)-6-((1-methyl-1H-pyrazol-3-yl)ethynyl)-7-(1-methylcyclopropyl)-7H-pyrrolo[2,3-d]pyrimidine-5-carboxamide According to the procedure of Example 79, using 3-ethynyl-1-methyl-pyrazole instead of 2-methyl-3-butyn-1-ol, the title compound (28%) was obtained.

Example 88: Synthesis of 4-amino-6-(imidazo[1,2-b]pyridazin-3-ylethynyl)-N-(5-methyl-1H-pyrazol-3-yl)-7-(1-methylcyclopropyl)-7H-pyrrolo[2,3-d]pyrimidine-5-carboxamide According to the procedure of Example 79, using 1-ethynylimidazo[1,2-b]pyridazine instead of 2-methyl-3-butyn-1-ol, the title compound (19%) was obtained.

Example 89: Synthesis of 4-amino-6-ethoxy-N-(5-methyl-1H-pyrazol-3-yl)-7-(1-methylcyclopropyl)-7H-pyrrolo[2,3-d]pyrimidine-5-carboxamide

Step 1: Synthesis of 4-amino-6-ethoxy-7-(1-methylcyclopropyl)-7H-pyrrolo[2,3-d]pyrimidine-5-carboxylic acid 630 mg of methyl 4-amino-6-bromo-7-(1-methylcyclopropyl)-7H-pyrrolo[2,3-d]pyrimidine-5-carboxylate obtained in step 1 of Example 76 was suspended in 10 mL of THF. 119 mg of 4-dimethylamino pyridine and 1.27 g of di-tert-butyl dicarbonate were added thereto with stirring, and the solution was stirred at 50° C. for 1 hour. After cooling, the reaction solution was concentrated, and partitioned between ethyl acetate and water. The organic layer was washed with water and a saturated aqueous sodium chloride solution. Anhydrous sodium sulfate was added thereto, and the mixture was filtered and concentrated. 15 mL of ethanol was added to the residue, and 2.28 mL of sodium ethoxide (28% ethanol solution) was also added with stirring, followed by stirring at room temperature overnight. The reaction solution was neutralized with a 2N hydrochloric acid aqueous solution, and then concentrated. The residue was partitioned between chloroform and water. The organic layer was washed with a saturated aqueous sodium chloride solution, and anhydrous sodium sulfate was added thereto. After filtration, the resulting solution was concentrated. 3 mL of dichloromethane and 6 mL of trifluoroacetic acid were added to the residue, and the mixture was stirred at room temperature for 1.5 hours. After concentration, the residue was partitioned between chloroform and a saturated aqueous sodium bicarbonate solution. The organic layer was washed with water and a saturated aqueous sodium chloride solution, and anhydrous sodium sulfate was added thereto, followed by filtration and concentration. The residue was dissolved in 20 mL of methanol, and 3.88 mL of an aqueous sodium hydroxide solution (4 mol/L) was added thereto, followed by stirring at 60° C. for 3 hours. After cooling, 50 mL of water and a 2N hydrochloric acid aqueous solution were added to the reaction solution to acidify the solution, thereby obtaining a precipitate. The organic solvent was removed, and the residue was stirred with ice cooling for 1 hour, followed by filtration, thereby obtaining 432 mg of the title compound.

Step 2: Synthesis of 4-amino-6-ethoxy-N-(5-methyl-1H-pyrazol-3-yl)-7-(1-methylcyclopropyl)-7H-pyrrolo[2,3-d]pyrimidine-5-carboxamide 1.2 mL of DMF was added to 67 mg of 4-amino-6-ethoxy-7-(1-methylcyclopropyl)-7H-pyrrolo[2,3-d]pyrimidine-5-carboxylic acid obtained in step 1, and 41 mg of 1-hydroxybenzotriazole and 51 mg of 1-(3-dimethylaminopropyl)-3-ethyl carbodiimide hydrochloride were further added thereto, followed by stirring at room temperature for 2 hours. 143 mg of tert-butyl 5-amino-3-methyl-1H-pyrazole-1-carboxylate synthesized in Reference Example 5 was added to the reaction solution, and 0.60 mL of a sodium tert-butoxide solution (2M THF) was added thereto at room temperature. After stirring for 30 minutes, 5 mL of a 1N aqueous sodium hydroxide solution was added to the reaction solution, followed by stirring at room temperature for 1 hour. The reaction solution was partitioned between ethyl acetate and water, and the organic layer was washed with water three times, and washed with a saturated aqueous sodium chloride solution. After drying over anhydrous sodium sulfate, the resulting solution was filtered and concentrated. The residue was purified by silica gel column (ethyl acetate/methanol=1/0->5/1), thereby obtaining 33 mg of the title compound.

Example 90: Synthesis of (R)-4-amino-N-(5-methyl-1H-pyrazol-3-yl)-7-(1-methylcyclopropyl)-6-((tetrahydrofuran-2-yl)methoxy)-7H-pyrrolo[2,3-d]pyrimidine-5-carboxamide

Step 1: Synthesis of methyl 4-(bis(tert-butoxycarbonyl)amino)-6-chloro-7-(1-methylcyclopropyl)-7H-pyrrolo[2,3-d]pyrimidine-5-carboxylate 351 mg of methyl 4-amino-6-chloro-7-(1-methylcyclopropyl)-7H-pyrrolo[2,3-d]pyrimidine-5-carboxylate obtained in step 2 of Example 75 was suspended in 6.3 mL of THF, and 76 mg of 4-dimethylamino pyridine and 818 mg of di-tert-butyl dicarbonate were added thereto with stirring. The solution was then stirred at 60° C. for 1 hour. After cooling, the reaction solution was concentrated, and the residue was purified by silica gel column (hexane/ethyl acetate=4/1->2/3), thereby obtaining 523 mg of the title compound.

Step 2: Synthesis of (R)-methyl 4-(bis(tert-butoxycarbonyl)amino)-7-(1-methylcyclopropyl)-6-((tetrahydrofuran-2-yl)methoxy)-7H-pyrrolo[2,3-d]pyrimidine-5-carboxylate 86 µL of (R)-(−)-tetrahydrofurfuryl alcohol was added to a suspension of 35 mg of sodium hydride (60%) in 1 mL of DMF with ice cooling, and the mixture was stirred at room temperature for 30 minutes. A solution of 212 mg of methyl 4-(bis(tert-butoxycarbonyl)amino)-6-chloro-7-(1-methylcyclopropyl)-7H-pyrrolo[2,3-d]pyrimidine-5-carboxylate obtained in step 1 in 1 mL of DMF was added to this solution, and the mixture was stirred at room temperature for 1.5 hours. The reaction solution was partitioned between chloroform and water, and the organic layer was washed with a saturated aqueous sodium chloride solution. Anhydrous sodium sulfate was added thereto, and the mixture was filtered, and then concentrated. The residue was purified by silica gel column (hexane/ethyl acetate=4/1->2/3), thereby obtaining 141 mg of the title compound.

Step 3: Synthesis of (R)-4-amino-7-(1-methylcyclopropyl)-6-((tetrahydrofuran-2-yl)methoxy)-7H-pyrrolo[2,3-d]pyrimidine-5-carboxylic acid 1.5 mL of chloroform and 2 mL of trifluoroacetic acid were added to 141 mg of (R)-methyl 4-(bis(tert-butoxycarbonyl)amino)-7-(1-methylcyclopropyl)-6-((tetrahydrofuran-2-yl)methoxy)-7H-pyrrolo[2,3-d]pyrimidine-5-carboxylate obtained in step 2, and the mixture was stirred at room temperature for 1.5 hours. After concentration, 2 mL of methanol and 2 mL of tetrahydrofuran were added to the residue, and 1.29 mL of an aqueous sodium hydroxide solution (4 mol/L) was further added thereto, followed by stirring at 60° C. for 3 hours. After cooling, 10 mL of water, and a 2N hydrochloric acid aqueous solution were added to the reaction solution to acidify the solution, thereby obtaining a precipitate. After the organic solvent was removed, the residue was stirred with ice cooling for 1 hour, followed by filtration, thereby obtaining 52 mg of the title compound.

Step 4: Synthesis of (R)-4-amino-N-(5-methyl-1H-pyrazol-3-yl)-7-(1-methylcyclopropyl)-6-((tetrahydrofuran-2-yl)methoxy)-7H-pyrrolo[2,3-d]pyrimidine-5-carboxamide According to the procedure of step 2 in Example 89, using 52 mg of (R)-4-amino-7-(1-methylcyclopropyl)-6-((tetrahydrofuran-2-yl)methoxy)-7H-pyrrolo[2,3-d]pyrimidine-5-carboxylic acid obtained in step 1, the title compound (39%) was obtained.

Comparative Example 1: Synthesis of 4-amino-1-cyclopentyl-N-(4-fluoro-1H-indazol-3-yl)-1H-pyrazolo[3,4-d]pyrimidine-3-carboxamide According to the synthesis procedure of Example 1, using 4-fluoro-1H-indazol-3-amine instead of 5-ethyl-1H-pyrazol-3-amine, the title compound (48%) was obtained as a brownish solid.

Comparative Example 2: Synthesis of 4-amino-1-cyclobutyl-N-(4-methylthiazol-2-yl)-1H-pyrazolo[3,4-d]pyrimidine-3-carboxamide According to the synthesis procedures of steps 1 and 2 in Reference Example 1, using bromocyclobutane instead of iodocyclopentane, 4-amino-1-cyclobutyl-1H-pyrazolo[3,4-d]pyrimidine-3-carboxylic acid was obtained as a brownish solid. According to the synthesis procedure of Example 1, using 4-amino-1-cyclobutyl-1H-pyrazolo[3,4-d]pyrimidine-3-carboxylic acid instead of 4-amino-1-cyclopentyl-1H-pyrazolo[3,4-d]pyrimidine-3-carboxylic acid, and using 4-methylthiazol-2-amine instead of 5-ethyl-1H-pyrazol-3-amine, the title compound (83%) was obtained as a brownish solid.

Comparative Example 3: Synthesis of 4-amino-1-cyclobutyl-N-(4-methyl-1H-imidazol-2-yl)-1H-pyrazolo[3,4-d]pyrimidine-3-carboxamide According to the synthesis procedures of steps 1 and 2 in Reference Example 1, using bromocyclobutane instead of iodocyclopentane, 4-amino-1-cyclobutyl-1H-pyrazolo[2,3-d]pyrimidine-3-carboxylic acid was obtained as a brownish solid. According to the synthesis procedure of Example 1, using 4-amino-1-cyclobutyl-1H-pyrazolo[3,4-d]pyrimidine-3-carboxylic acid instead of 4-amino-1-cyclopentyl-1H-pyrazolo[3,4-d]pyrimidine-3-carboxylic acid, and using 4-methyl-1H-imidazol-2-amine instead of 5-ethyl-1H-pyrazol-3-amine, the title compound (58%) was obtained as a brownish solid.

Comparative Example 4: Synthesis of 1-(tert-butyl)-3-(p-tolyl)pyrazolo[3,4-d]pyrimidin-4-amine In accordance with the synthesis procedure described in Tetrahedron Letters, 52(44), 5761-5763; 2011, the title compound (30%) was obtained as a white solid.

Tables 1 to 14 show the formulae and physical properties of the compounds obtained in the Examples and Comparative Examples.

TABLE 1

| Comp. of Ex. | Formula | Physical Properties |
|---|---|---|
| 1 | 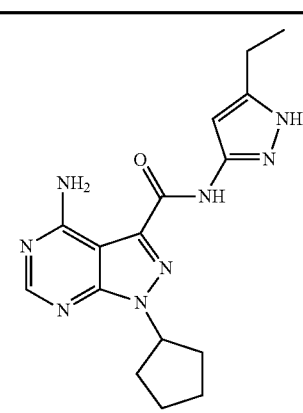 | m/z [M + H]+ 342.1<br>1H-NMR (400 MHz, DMSO-d6) δ ppm 1.20 (t, J = 7.6 Hz, 3H), 1.67-1.70 (m, 2H), 1.92-1.95 (m, 2H), 2.08-2.12 (m, 4H), 2.60 (q, J = 7.6 Hz, 2H), 5.22-5.25 (m, 1H), 6.42 (s, 1H), 8.23 (brs, 1H), 8.24 (s, 1H), 8.31 (brs, 1H), 10.37 (s, 1H), 12.31 (s, 1H). |

TABLE 1-continued
| Comp. of Ex. | Formula | Physical Properties |
|---|---|---|
| 2 | 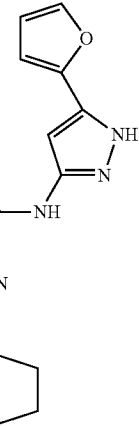 | m/z [M + H]+ 379.1<br>1H-NMR (400 MHz, DMSO-d6) δ ppm 1.68-1.71 (m, 2H), 1.90-2.00 (m, 2H), 2.09-2.12 (m, 4H), 5.21-5.28 (m, 1H), 6.63 (s, 1H), 6.88 (m, 1H), 6.91 (brs, 1H), 7.79 (s, 1H), 8.11 (brs, 1H), 8.25 (s, 1H), 8.48 (brs, 1H), 10.70 (s, 1H), 13.16 (s, 1H). |
| 3 | 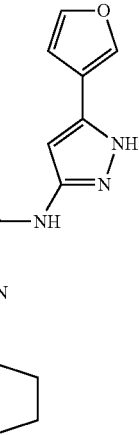 | m/z [M + H]+ 379.3<br>1H-NMR (400 MHz, DMSO-d6) δ ppm 1.68-1.71 (m, 2H), 1.93-1.97 (m, 2H), 2.09-2.14 (m, 4H), 5.23-5.26 (m, 1H), 6.91-6.93 (m, 2H), 7.77 (s, 1H), 8.11 (brs, 1H), 8.17 (s, 1H), 8.25 (s, 1H), 8.52 (brs, 1H), 10.61 (s, 1H), 12.90 (s, 1H). |
| 4 | 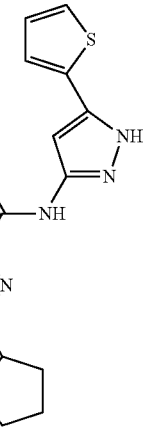 | m/z [M + H]+ 395.2<br>1H-NMR (400 MHz, DMSO-d6) δ ppm 1.69 (m, 2H), 1.90-2.00 (m, 2H), 2.11-2.13 (m, 4H), 5.21-5.29 (m, 1H), 6.85-6.87 (m, 1H), 7.14 (m, 1H), 7.50 (brs, 1H), 7.60 (brs, 1H), 8.12 (brs, 1H), 8.25 (s, 1H), 8.47 (brs, 1H), 10.69 (s, 1H), 13.15 (s, 1H). |

TABLE 1-continued
| Comp. of Ex. | Formula | Physical Properties |
|---|---|---|
| 5 | 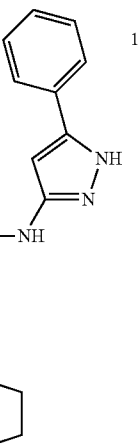 | m/z [M + H]+ 389.1<br>1H-NMR (400 MHz, DMSO-d6) δ ppm 1.68-1.71 (m, 2H), 1.94-1.99 (m, 2H), 2.10-2.13 (m, 4H), 5.23-5.27 (m, 1H), 7.07 (s, 1H), 7.34-7.38 (m, 1H), 7.44-7.48 (m, 2H), 7.78-7.80 (m, 2H), 8.12 (brs, 1H), 8.25 (s, 1H), 8.52 (brs, 1H), 10.63 (s, 1H), 13.12 (s, 1H). |
| 6 | 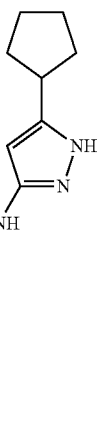 | m/z [M + H]+ 381.2<br>1H-NMR (400 MHz, DMSO-d6) δ ppm 1.55-1.72 (m, 8H), 1.91-2.03 (m, 4H), 2.07-2.12 (m, 4H), 3.00-3.04 (m, 1H), 5.21-5.25 (m, 1H), 6.41 (s, 1H), 8.08 (brs, 1H), 8.23 (s, 1H), 8.50 (brs, 1H), 10.38 (s, 1H), 12.32 (s, 1H). |
| 7 | 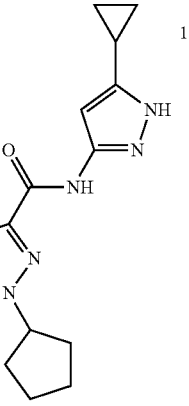 | m/z [M + H]+ 353.3<br>1H-NMR (400 MHz, DMSO-d6) δ ppm 0.69-0.72 (m, 2H), 0.91-0.93 (m, 2H), 1.65-1.70 (m, 2H), 1.88-1.96 (m, 3H), 2.07-2.12 (m, 4H), 5.21-5.23 (m, 1H), 6.29 (s, 1H), 8.08 (brs, 1H), 8.23 (s, 1H), 8.48 (brs, 1H), 10.36 (s, 1H), 12.33 (s, 1H). |
Note: In the tables and figures, "Comp." denotes compounds, and "Ex." denotes Examples.

TABLE 2
| 8 | 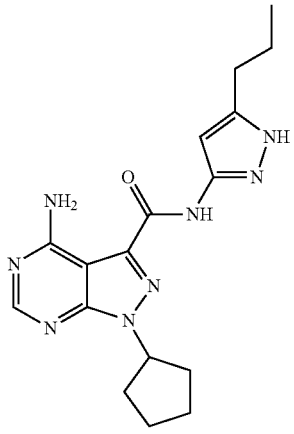 [SMILES: CCCc1cc(NC(=O)c2nn(C3CCCC3)c3ncnc(N)c23)n[nH]1] | m/z [M + H] + 355.4<br>1H-NMR (400 MHz, DMSO-d6) δ ppm 0.91 (t, J = 7.2 Hz, 3H), 1.57-1.64 (m, 2H), 1.66-1.88 (m, 2H), 1.91-1.98 (m, 2H), 2.07-2.12 (m, 4H), 2.56 (t, J = 7.6 Hz, 2H), 5.21-5.25 (m, 1H), 6.41 (s, 1H), 8.08 (brs, 1H), 8.24 (s, 1H), 8.50 (brs, 1H), 10.38 (s, 1H), 12.31 (s, 1H). |
| --- | --- | --- |
| 9 | 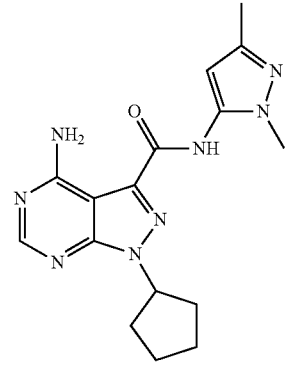 [SMILES: Cc1cc(NC(=O)c2nn(C3CCCC3)c3ncnc(N)c23)n(C)n1] | m/z [M + H] + 341.3<br>1H-NMR (400 MHz, DMSO-d6) δ ppm 1.64-1.71 (m, 2H), 1.89-1.98 (m, 2H), 2.06-2.09 (m, 4H), 2.13 (s, 3H), 3.60 (s, 3H), 5.04-5.26 (m, 1H), 6.03 (s, 1H), 8.09 (brs, 1H), 8.24 (s, 1H), 8.36 (brs, 1H), 10.49 (s, 1H). |
| 10 | 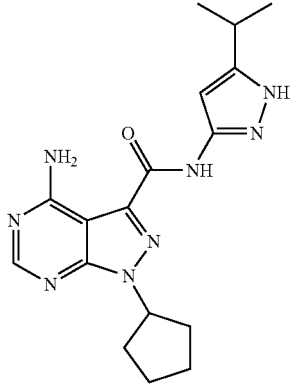 [SMILES: CC(C)c1cc(NC(=O)c2nn(C3CCCC3)c3ncnc(N)c23)n[nH]1] | m/z [M + H] + 355.2<br>1H-NMR (400 MHz, DMSO-d6) δ ppm 1.23 (d, J = 6.8 Hz, 6H), 1.65-1.70 (m, 2H), 1.90-1.97 (m, 2H), 2.08-2.12 (m, 4H), 2.92-2.95 (m, 1H), 5.21-5.25 (m, 1H), 6.42 (s, 1H), 8.08 (brs, 1H), 8.24 (s, 1H), 8.50 (brs, 1H), 10.37 (s, 1H), 12.31 (s, 1H). |
| 11 | 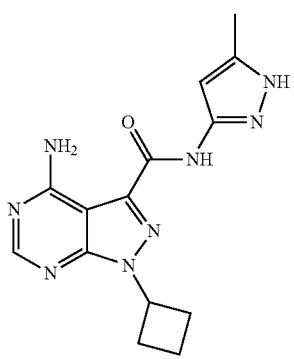 [SMILES: Cc1cc(NC(=O)c2nn(C3CCC3)c3ncnc(N)c23)n[nH]1] | m/z [M + H] + 313.3<br>1H-NMR (400 MHz, DMSO-d6) δ ppm 1.84-1.92 (m, 2H), 2.24 (s, 3H), 2.40-2.41 (m, 2H), 2.74-2.84 (m, 2H), 5.30-5.36 (m, 1H), 6.40 (s, 1H), 8.10 (brs, 1H), 8.23 (s, 1H), 8.49 (brs, 1H), 10.51 (brs, 1H), 12.29 (brs, 1H). |

TABLE 2-continued
| | | |
|---|---|---|
| 12 | 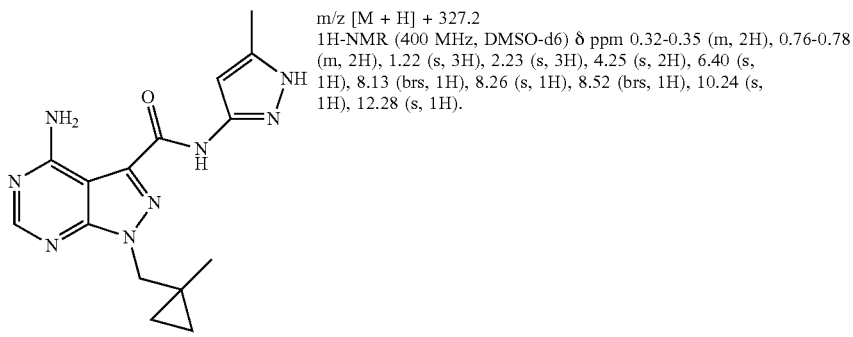 | m/z [M + H] + 327.2<br>1H-NMR (400 MHz, DMSO-d6) δ ppm 0.32-0.35 (m, 2H), 0.76-0.78 (m, 2H), 1.22 (s, 3H), 2.23 (s, 3H), 4.25 (s, 2H), 6.40 (s, 1H), 8.13 (brs, 1H), 8.26 (s, 1H), 8.52 (brs, 1H), 10.24 (s, 1H), 12.28 (s, 1H). |
| 13 | 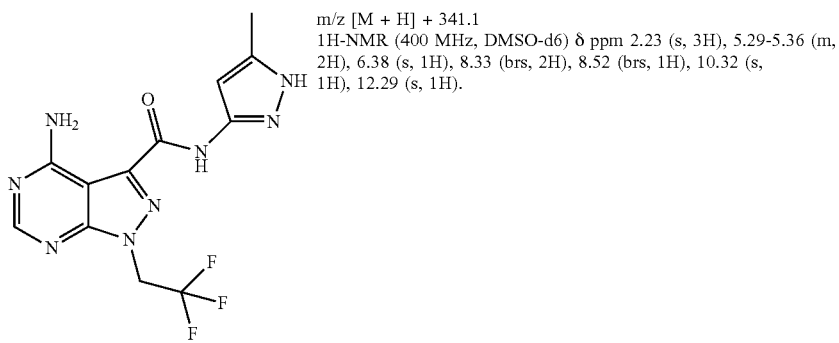 | m/z [M + H] + 341.1<br>1H-NMR (400 MHz, DMSO-d6) δ ppm 2.23 (s, 3H), 5.29-5.36 (m, 2H), 6.38 (s, 1H), 8.33 (brs, 2H), 8.52 (brs, 1H), 10.32 (s, 1H), 12.29 (s, 1H). |
| 14 | 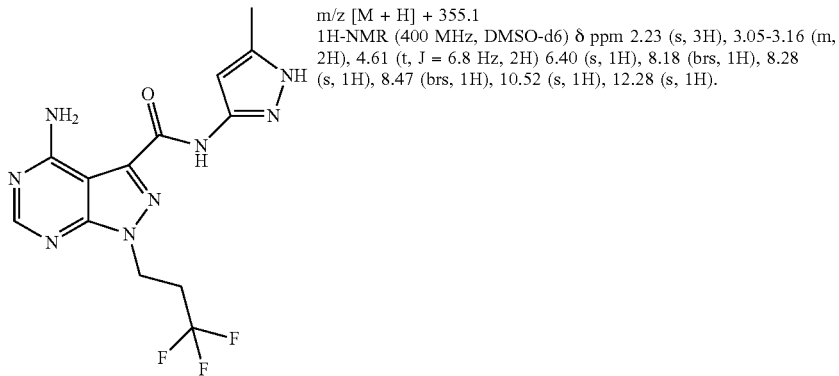 | m/z [M + H] + 355.1<br>1H-NMR (400 MHz, DMSO-d6) δ ppm 2.23 (s, 3H), 3.05-3.16 (m, 2H), 4.61 (t, J = 6.8 Hz, 2H) 6.40 (s, 1H), 8.18 (brs, 1H), 8.28 (s, 1H), 8.47 (brs, 1H), 10.52 (s, 1H), 12.28 (s, 1H). |
TABLE 3
| | | |
|---|---|---|
| 15 | 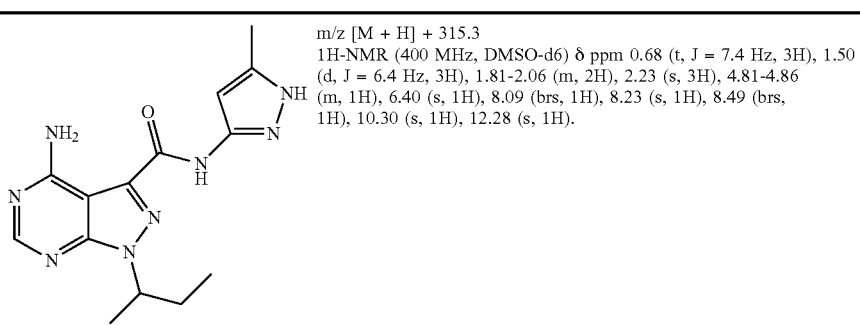 | m/z [M + H] + 315.3<br>1H-NMR (400 MHz, DMSO-d6) δ ppm 0.68 (t, J = 7.4 Hz, 3H), 1.50 (d, J = 6.4 Hz, 3H), 1.81-2.06 (m, 2H), 2.23 (s, 3H), 4.81-4.86 (m, 1H), 6.40 (s, 1H), 8.09 (brs, 1H), 8.23 (s, 1H), 8.49 (brs, 1H), 10.30 (s, 1H), 12.28 (s, 1H). |

TABLE 3-continued
| | | |
|---|---|---|
| 16 | 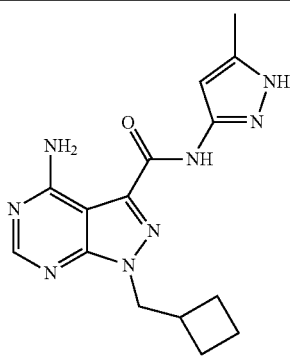 | m/z [M + H] + 327.2<br>1H-NMR (400 MHz, DMSO-d6) δ ppm 1.79-1.87 (m, 4H), 1.92-1.98 (m, 2H), 2.23 (s, 3H), 2.88-2.95 (m, 1H), 4.40 (d, J = 7.2 Hz, 2H), 6.37 (s, 1H), 8.12 (brs, 1H), 8.25 (s, 1H), 8.49 (brs, 1H), 10.24 (s, 1H), 12.26 (s, 1H). |
| 17 | 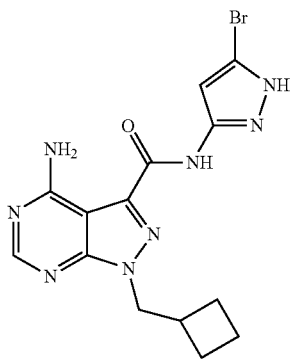 [SMILES: Nc1ncnc2c1c(C(=O)Nc1cc(Br)[nH]n1)nn2CC1CCC1] | m/z [M + H] + 392.9<br>1H-NMR (400 MHz, DMSO-d6) δ ppm 1.79-1.87 (m, 4H), 1.92-1.98 (m, 2H), 2.89-2.93 (m, 1H), 4.43 (d, J = 6.8 Hz, 2H), 6.36 (s, 1H), 8.22 (brs, 1H), 8.28 (s, 1H), 8.38 (brs, 1H), 11.45 (s, 1H), 12.81 (s, 1H). |
| 18 | 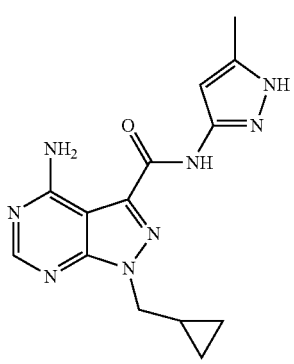 [SMILES: Cc1cc(NC(=O)c2nn(CC3CC3)c3ncnc(N)c23)n[nH]1] | m/z [M + H] + 313.7<br>1H-NMR (400 MHz, DMSO-d6) δ ppm 0.43-0.52 (m, 4H), 1.34-1.39 (m, 1H), 2.23 (s, 3H), 4.24 (d, J = 6.8 Hz, 2H), 6.38 (s, 1H), 8.13 (brs, 1H), 8.25 (s, 1H), 8.50 (brs, 1H), 10.28 (s, 1H), 12.26 (s, 1H). |
| 19 | 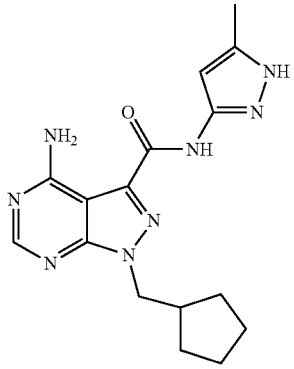 [SMILES: Cc1cc(NC(=O)c2nn(CC3CCCC3)c3ncnc(N)c23)n[nH]1] | m/z [M + H] + 341.1<br>1H-NMR (400 MHz, DMSO-d6) δ ppm 1.22-1.60 (m, 8H), 2.22 (s, 3H), 2.53-2.59 (m, 1H), 4.27-4.30 (m, 2H), 6.37 (s, 1H), 8.12 (brs, 1H), 8.25 (s, 1H), 8.50 (brs, 1H), 10.27 (s, 1H), 12.25 (s, 1H). |

TABLE 3-continued
| 20 | 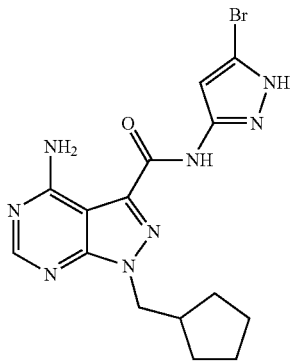 [SMILES: Nc1ncnc2c1c(C(=O)Nc1cc(Br)[nH]n1)nn2CC1CCCC1] | m/z [M + H] + 407.7<br>1H-NMR (400 MHz, DMSO-d6) δ ppm 1.21-1.61 (m, 8H), 2.53-2.58 (m, 1H), 4.31-4.33 (m, 2H), 6.36 (s, 1H), 8.21 (brs, 1H), 8.27 (s, 1H), 8.39 (brs, 1H), 11.46 (s, 1H), 12.81 (s, 1H). |
| --- | --- | --- |
| 21 | 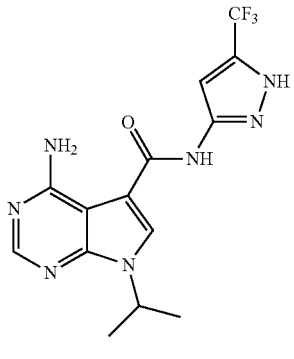 [SMILES: CC(C)n1cc(C(=O)Nc2cc(C(F)(F)F)[nH]n2)c2c(N)ncnc21] | m/z [M + H] + 356.3<br>1H-NMR (400 MHz, DMSO-d6) δ ppm 1.55 (d, J = 6.8 Hz, 6H), 5.09-5.13 (m, 1H), 6.67 (s, 1H), 8.20 (brs, 1H), 8.27 (s, 1H), 8.36 (brs, 1H), 11.39 (s, 1H), 13.40 (s, 1H). |
TABLE 4
| 22 | 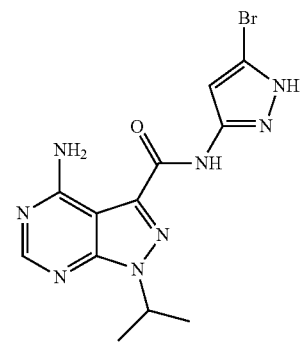 [SMILES: CC(C)n1nc(C(=O)Nc2cc(Br)[nH]n2)c2c(N)ncnc21] | m/z [M + H] + 366.9<br>1H-NMR (400 MHz, DMSO-d6) δ ppm 1.54 (d, J = 6.8 Hz, 6H), 5.07-5.12 (m, 1H), 6.38 (d, J = 1.6 Hz, 1H), 8.18 (brs, 1H), 8.26 (s, 1H), 8.37 (brs, 1H), 11.26 (s, 1H), 12.85 (s, 1H). |
| --- | --- | --- |
| 23 | 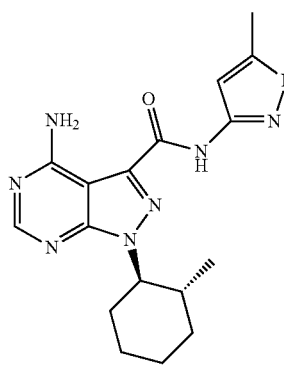 | m/z [M + H] + 355.4<br>1H-NMR (400 MHz, DMSO-d6) δ ppm 0.52 (d, J = 6.4 Hz, 3H), 1.15-1.47 (m, 4H), 1.70-1.73 (m, 1H), 1.82-1.84 (m, 3H), 1.20-2.08 (m, 1H), 2.23 (s, 3H), 4.31-4.37 (m, 1H), 6.39 (s, 1H), 8.11 (brs, 1H), 8.23 (s, 1H), 8.50 (brs, 1H), 10.34 (s, 1H), 12.27 (s, 1H). |

| | | |
|---|---|---|
| 24 | 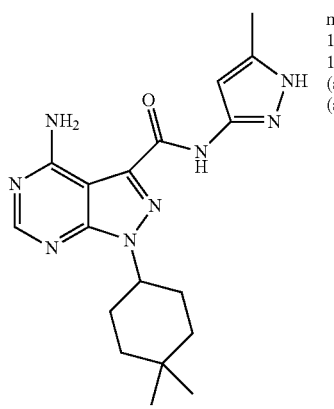 | m/z [M + H] + 369.3<br>1H-NMR (400 MHz, DMSO-d6) δ ppm 0.97 (s, 3H), 1.06 (s, 3H), 1.39-1.52 (m, 4H), 1.72-1.75 (m, 2H), 2.18-2.27 (m, 2H), 2.23 (s, 3H), 4.58-4.64 (m, 1H), 6.40 (s, 1H), 8.08 (brs, 1H), 8.23 (s, 1H), 8.52 (brs, 1H), 10.46 (s, 1H), 12.28 (s, 1H). |
| 25 | 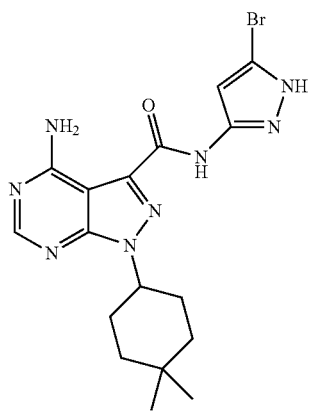 [SMILES: CC1(C)CCC(n2nc(C(=O)Nc3cc(Br)[nH]n3)c3c(N)ncnc32)CC1] | m/z [M + H] + 435.1<br>1H-NMR (400 MHz, DMSO-d6) δ ppm 0.97 (s, 3H), 1.05 (s, 3H), 1.40-1.53 (m, 4H), 1.76-1.79 (m, 2H), 2.19-2.28 (m, 2H), 4.62-4.63 (m, 1H), 6.38 (s, 1H), 8.18 (brs, 1H), 8.25 (s, 1H), 8.36 (brs, 1H), 11.21 (s, 1H), 12.89 (s, 1H). |
| 26 | 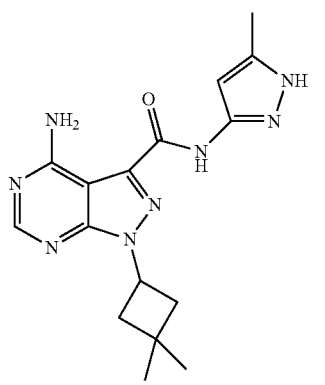 [SMILES: Cc1cc(NC(=O)c2nn(C3CC(C)(C)C3)c3ncnc(N)c23)n[nH]1] | m/z [M + H] + 341.3<br>1H-NMR (400 MHz, DMSO-d6) δ ppm 1.26 (s, 6H), 2.21-2.26 (m, 2H), 2.24 (s, 3H), 2.57-2.62 (m, 2H), 5.32-5.36 (m, 1H), 6.41 (s, 1H), 8.09 (brs, 1H), 8.22 (s, 1H), 8.51 (brs, 1H), 10.56 (s, 1H), 12.29 (s, 1H). |
| 27 | 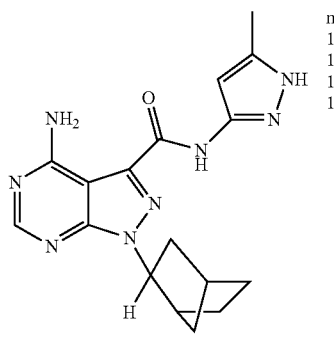 | m/z [M + H] + 353.4<br>1H-NMR (400 MHz, DMSO-d6) δ ppm 1.01-1.69 (m, 7H), 2.01 (m, 1H), 2.24 (s, 3H), 2.35 (m, 1H), 2.67 (brs, 1H), 5.08-5.10 (m, 1H), 6.40 (s, 1H), 8.08 (brs, 1H), 8.24 (s, 1H), 8.56 (brs, 1H), 10.47 (s, 1H), 12.29 (s, 1H). |

TABLE 4-continued
| 28 | 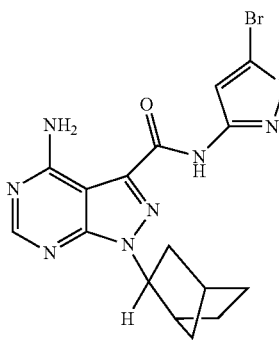 | m/z [M + H] + 417.3<br>1H-NMR (400 MHz, DMSO-d6) δ ppm 0.94-1.67 (m, 7H), 2.06 (m, 1H), 2.37 (m, 1H), 2.72 (brs, 1H), 5.80-5.12 (m, 1H), 6.40 (s, 1H), 8.18 (brs, 1H), 8.26 (s, 1H), 8.36 (brs, 1H), 11.01 (s, 1H), 12.95 (s, 1H). |
TABLE 5
| 29 | 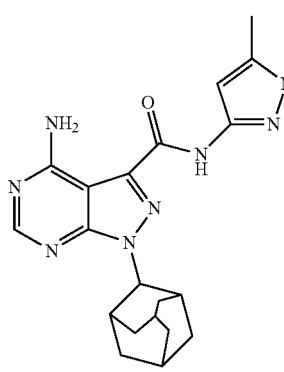 | m/z [M + H] + 393.2<br>1H-NMR (400 MHz, DMSO-d6) δ ppm 1.57-1.60 (m, 2H), 1.77 (brs, 2H), 1.91-1.98 (m, 6H), 2.24 (s, 3H), 2.33-2.36 (m, 2H), 2.60 (brs, 2H), 4.87 (s, 1H), 6.41 (s, 1H), 8.09 (brs, 1H), 8.22 (s, 1H), 8.54 (brs, 1H), 10.23 (s, 1H), 12.29 (s, 1H). |
| 30 | 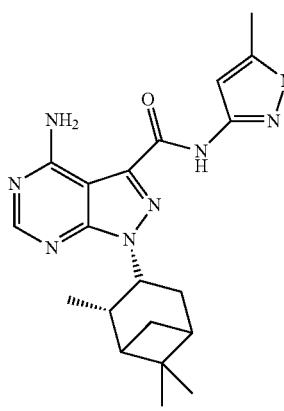 | m/z [M + H] + 395.4<br>1H-NMR (400 MHz, DMSO-d6) δ ppm 0.449 (d, J = 7.6 Hz, 3H), 1.24 (s, 3H), 1.30 (s, 3H), 1.54 (d, J = 7.6 Hz, 1H), 1.94-1.98 (m, 1H), 2.04-2.06 (m, 1H), 2.24 (s, 3H), 2.27-2.35 (m, 2H), 2.82-2.84 (m, 1H), 3.10-3.14 (m, 1H), 5.62-5.75 (m, 1H), 6.41 (s, 1H), 8.25 (brs, 1H), 8.26 (s, 1H), 8.50 (brs, 1H), 10.29 (s, 1H), 11.83 (s, 1H). |
| 31 | 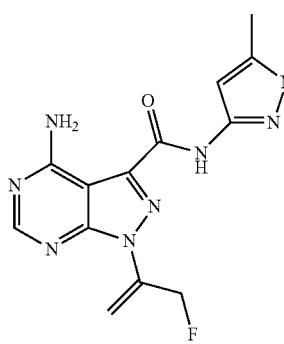 | m/z [M + H] + 317.1<br>1H-NMR (400 MHz, DMSO-d6) δ ppm 2.24 (s, 3H), 5.59 (brs, 1H), 5.61 (s, 1H), 5.72 (s, 1H), 6.42 (brs, 1H), 6.45 (brs, 1H), 8.29 (m, 1H), 8.34 (s, 1H), 8.68 (brs, 1H), 10.81 (s, 1H), 12.31 (s, 1H). |

TABLE 5-continued
| 32 | 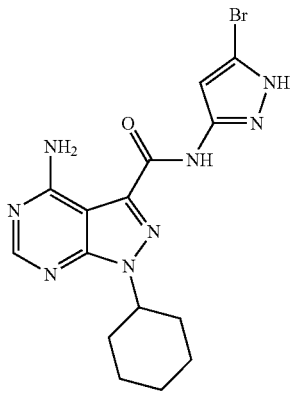 [SMILES: Nc1ncnc2c1c(C(=O)Nc1cc(Br)[nH]n1)nn2C1CCCCC1] | m/z [M + H] + 407.0<br>1H-NMR (400 MHz, DMSO-d6) δ ppm 1.23-2.10 (m, 10H), 4.69-4.71 (m, 1H), 6.38 (s, 1H), 8.19 (brs, 1H), 8.26 (s, 1H), 8.36 (brs, 1H), 11.25 (s, 1H), 12.84 (s, 1H). |
|---|---|---|
| 33 | 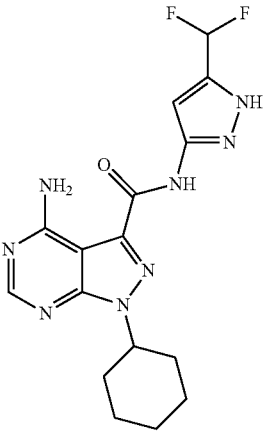 [SMILES: Nc1ncnc2c1c(C(=O)Nc1cc(C(F)F)[nH]n1)nn2C1CCCCC1] | m/z [M + H] + 377.3<br>1H-NMR (400 MHz, DMSO-d6) δ ppm 1.30-1.72 (m, 1H), 1.42-1.51 (m, 2H), 1.70-1.73 (m, 1H), 1.86-2.07 (m, 6H), 4.69-4.72 (m, 1H), 6.52 (s, 1H), 7.05-7.08 (m, 1H), 8.12 (brs, 1H), 8.24 (s, 1H), 8.40 (brs, 1H), 11.28 (s, 1H), 13.02 (s, 1H). |
| 34 | 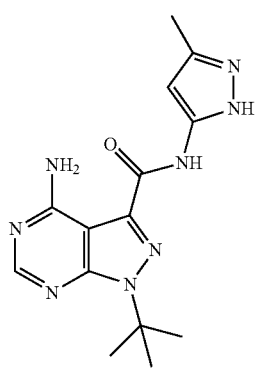 [SMILES: Cc1cc(NC(=O)c2nn(C(C)(C)C)c3ncnc(N)c23)[nH]n1] | m/z [M + H] + 315.1<br>1H-NMR (400 MHz, DMSO-d6) δ ppm 1.76 (s, 9H), 2.24 (s, 3H), 6.40 (s, 1H), 8.02 (brs, 1H), 8.23 (s, 1H), 8.57 (brs, 1H), 10.25 (s, 1H), 12.26 (s, 1H). |
| 35 | 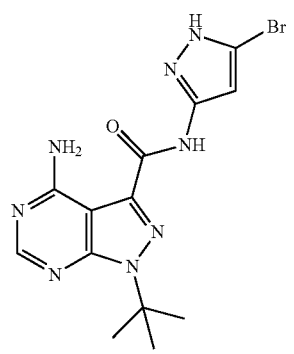 [SMILES: CC(C)(C)n1nc(C(=O)Nc2cc(Br)[nH]n2)c2c(N)ncnc21] | m/z [M + H] + 380.9<br>1H-NMR (400 MHz, DMSO-d6) δ ppm 1.77 (s, 9H), 6.39 (s, 1H), 8.15 (brs, 1H), 8.25 (m, 1H), 8.35 (brs, 1H), 11.00 (brs, 1H), 12.89 (brs, 1H). |

TABLE 6
| 36 | 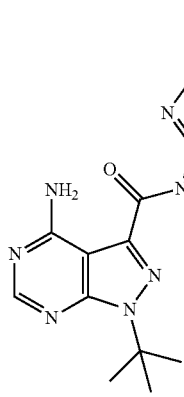 | m/z [M + H] + 369.4<br>1H-NMR (400 MHz, DMSO-d6) δ ppm 1.79 (s, 9H), 6.68 (brs, 1H), 8.12 (brs, 1H), 8.26 (s, 1H), 8.36 (brs, 1H), 11.13 (s, 1H), 13.44 (s, 1H). |
| --- | --- | --- |
| 37 | 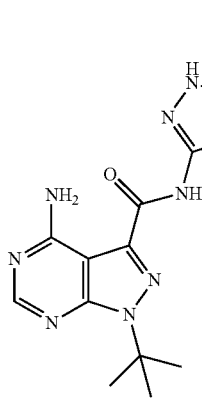 | m/z [M + H] + 367.1<br>1H-NMR (400 MHz, DMSO-d6) δ ppm 1.78 (s, 9H), 6.61-6.64 (m, 1H), 6.87-6.88 (m, 1H), 6.89-6.92 (m, 1H) 7.79 (s, 1H), 8.06 (brs, 1H), 8.24 (s, 1H), 8.55 (brs, 1H), 10.60 (s, 1H), 13.15 (s, 1H). |
| 38 | 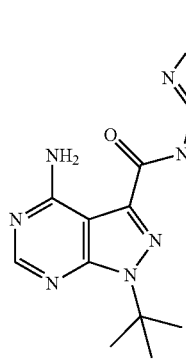 | mz [M + H] + 326.2<br>1H-NMR (400 MHz, DMSO-d6) δ ppm 1.75 (s, 9H), 6.91 (brs, 1H), 8.15 (brs, 1H), 8.29 (s, 1H), 8.36 (brs, H), 11.19 (brs, 1H), 13.85 (brs, 1H). |
| 39 | 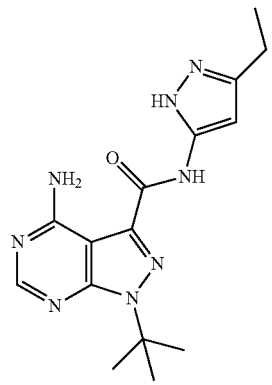 [SMILES: CCc1cc(NC(=O)c2nn(C(C)(C)C)c3ncnc(N)c23)[nH]n1] | m/z [M + H] + 329.3<br>1H-NMR (400 MHz, DMSO-d6) δ ppm 1.19 (t, J = 7.8 Hz, 3H), 1.74 (s, 9H), 2.59 (q, J = 7.8 Hz, 2H), 6.39 (s, 1H), 7.98 (brs, 1H), 8.23 (s, 1H), 8.64 (brs, 1H), 10.30 (brs, 1H), 12.27 (brs, 1H). |

| | | |
|---|---|---|
| 40 | 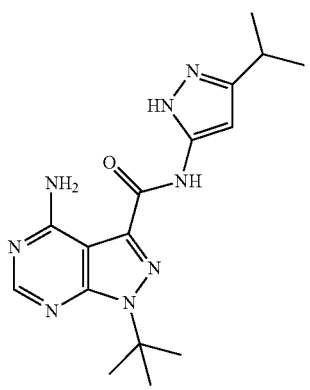 [SMILES: CC(C)c1cc(NC(=O)c2nn(C(C)(C)C)c3ncnc(N)c23)[nH]n1] | m./z [M + H] + 343.3<br>1H-NMR (400 MHz, DMSO-d6) δ ppm 1.21 (d, J = 7.0 Hz, 6H), 1.75 (s, 9H), 2.84-2.97 (m, 1H), 6.39 (s, 1H), 8.06 (brs, 1H), 8.23 (s, 1H), 8.62 (brs, 1H), 10.29 (brs, 1H), 12.31 (brs, 1H). |
| 41 | 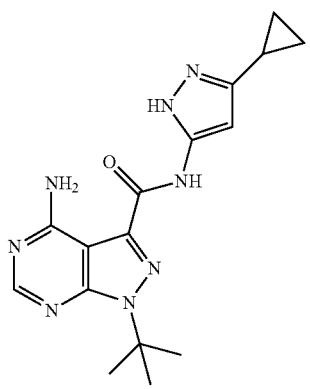 [SMILES: CC(C)(C)n1nc(C(=O)Nc2cc(C3CC3)n[nH]2)c2c(N)ncnc21] | m/z [M + H] + 341.2<br>1H NMR (400 MHz, DMSO d6) δ ppm 0.67-0.72 (m, 2H), 0.89-0.98 (m, 2H), 1.76 (s, 9H), 1.84-1.91 (m, 1H), 6.26 (s, 1H), 8.05 (brs, 1H), 8.22 (s, 1H), 8.59 (brs, 1H), 10.28 (brs, 1H), 12.34 (brs, 1H). |
| 42 | 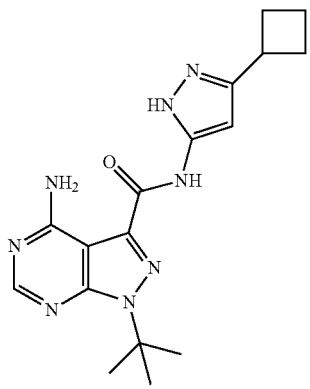 [SMILES: CC(C)(C)n1nc(C(=O)Nc2cc(C3CCC3)n[nH]2)c2c(N)ncnc21] | m/z [M + H] + 355.1<br>1H NMR (400 MHz, DMSO d6) δ ppm 1.74 (s, 9H), 1.77-1.98 (m, 2H), 2.08-2.17 (m, 2H), 2.21-2.32 (m, 2H), 3.44-3.52 (m, 1H), 6.45 (s, 1H), 8.06 (br s, 1H), 8.22 (s, 1H), 8.61 (br s, 1H), 10.30 (br s, 1H), 12.31 (br s, 1H). |

TABLE 7
| | | |
|---|---|---|
| 43 | 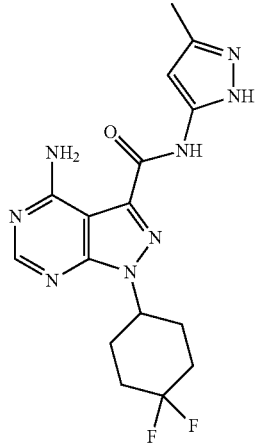 [SMILES: Cc1cc(NC(=O)c2nn(C3CCC(F)(F)CC3)c3ncnc(N)c23)[nH]n1] | m/z [M + H] + 377.0<br>1H-NMR (400 MHz, DMSO-d6) δ ppm 1.97-2.34 (m, 11H), 4.91-5.00 (m, 1H), 6.37 (s, 1H), 8.09 (brs, 1H), 8.23 (s, 1H), 8.49 (brs, 1H), 10.50 (brs, 1H), 12.25 (brs, 1H). |
| 44 | 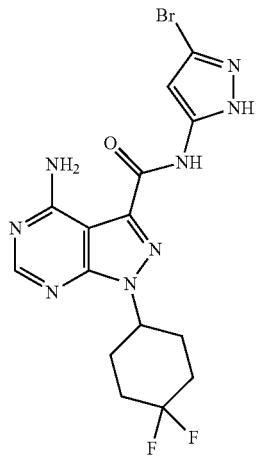 [SMILES: Nc1ncnc2c1c(C(=O)Nc1cc(Br)n[nH]1)nn2C1CCC(F)(F)CC1] | m/z [M + H] + 442.9<br>1H-NMR (400 MHz, DMSO-d6) δ ppm 2.01-2.30 (m, 8H), 4.96-4.99 (m, 1H), 6.36 (s, 1H), 8.07-8.22 (br m, 1 H), 8.24-8.26 (m, 1H), 8.34-8.37 (br m, 1H), 11.24 (s, 1H), 12.84 (s, 1H). |
| 45 | 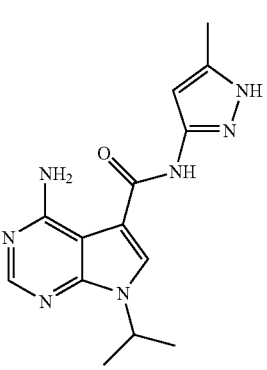 [SMILES: Cc1cc(NC(=O)c2cn(C(C)C)c3ncnc(N)c23)n[nH]1] | m/z [M + H] + 300.2<br>1H-NMR (400 MHz, DMSO-d6) δ ppm 1.43 (d, J = 6.4 Hz, 6H), 2.21 (s, 3H), 4.89-4.92 (m, 1H), 6.36 (s, 1H), 8.09 (s, 1H), 8.52 (s, 1H), 10.52 (s, 1H). |
| 46 | 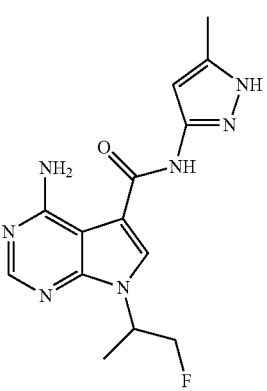 [SMILES: Cc1cc(NC(=O)c2cn(C(C)CF)c3ncnc(N)c23)n[nH]1] | m/z [M + H] + 318.1<br>1H-NMR (400 MHz, DMSO-d6) δ ppm 1.49 (d, J = 6.8 Hz, 3H), 2.21 (s, 3H), 4.62-4.77 (m, 2H), 5.06-5.15 (m, 1H), 6.37 (s, 1H), 8.10 (brs, 1H), 8.52 (s, 1H), 10.57 (s, 1H), 12.11 (s, 1H). |

TABLE 7-continued
| | | |
|---|---|---|
| 47 | 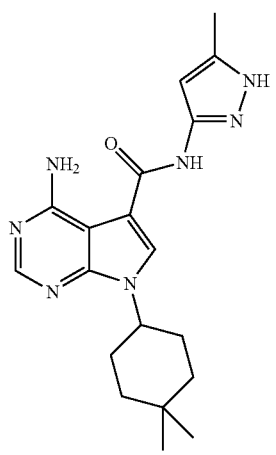 [SMILES: Cc1cc(NC(=O)c2cn(C3CCC(C)(C)CC3)c3ncnc(N)c23)n[nH]1] | m/z [M + H] + 368.3<br>1H-NMR (400 MHz, DMSO-d6) δ ppm 0.96 (s, 3H), 1.04 (s, 3H), 1.39-1.53 (m, 4H), 1.76-1.90 (m, 4H), 2.21 (s, 3H), 4.48-4.49 (m, 1H), 6.38 (s, 1H), 8.09 (s, 1H), 8.60 (s, 1H), 10.45 (s, 1H), 12.12 (s, 1H). |
| 48 | 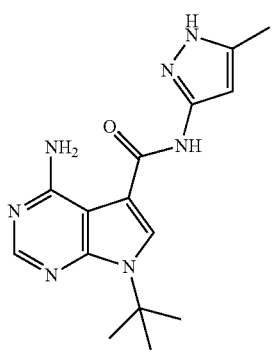 [SMILES: Cc1cc(NC(=O)c2cn(C(C)(C)C)c3ncnc(N)c23)n[nH]1] | m/z [M + H] + 314.1<br>1H-NMR (400 MHz, DMSO-d6) δ ppm 1.70 (s, 9H), 2.19 (s, 3H), 6.35 (d, J = 1.5 Hz, 1H), 8.07 (s, 1H), 8.47 (s, 1H), 10.59 (s, 1H), 12.07 (s, 1H). |
| 49 | 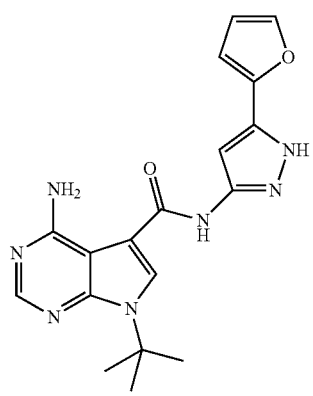 [SMILES: CC(C)(C)n1cc(C(=O)Nc2cc(-c3ccco3)[nH]n2)c2c(N)ncnc21] | m/z [M + H] + 366.2<br>1H-NMR (400 MHz, DMSO-d6) δ ppm 1.72 (s, 9H), 6.61 (s, 1H), 6.85-6.89 (m, 2H), 7.76 (s, 1H), 8.11 (s, 1H), 8.53 (s, 1H), 10.85 (s, 1H), 12.99 (s, 1H). |
TABLE 8
| | | |
|---|---|---|
| 50 | 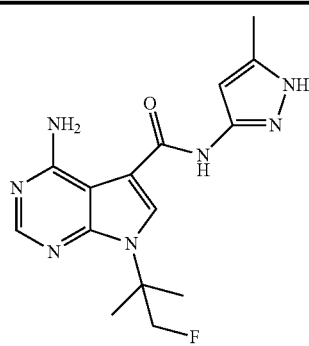 | m/z [M + H] + 332.2<br>1H-NMR 400 MHz, DMSO-d6) δ ppm 1.71 (s, 6H), 2.21 (s, 3H), 4.93 (s, 1H), 5.05 (s, 1H), 6.37 (s, 1H), 8.09 (s, 1H), 849 (s, 1H), 10.64 (s, 1H), 12.10 (s, 1H). |

TABLE 8-continued

| | | |
|---|---|---|
| 51 | [structure] | m/z [M + H] + 312.2
1H-NMR (400 MHz, DMSO-d6) δ ppm 0.97 (m, 2H), 1.13 (m, 2H), 1.54 (s, 3H), 2.21 (s, 3H), 6.36 (s, 1H), 8.11 (s, 1H), 8.37 (s, 1H), 10.50 (s, 1H), 12.09 (s, 1H). |
| 52 | [structure] | m/z [M + H] + 340.4
1H-NMR (400 MHz, DMSO-d6) δ ppm 0.49-0.56 (m, 4H), 1.62 (s, 6H), 1.81 (m, 1H), 2.23 (s, 3H), 6.39 (s, 1H), 8.09 (s, 1H), 8.56 (s, 1H), 10.65 (s, 1H), 12.10 (s, 1H). |
| 53 | [structure] | m/z [M + H] + 344.2
1H-NMR (400 MHz, DMSO-d6) δ ppm 1.67 (s, 6H), 2.67 (s, 3H), 3.12 (s, 3H), 3.91 (s, 2H), 6.36 (s, 1H), 8.07 (s, 1H), 8.42 (s, 1H), 10.63 (s, 1H), 12.10 (s, 1H). |
| 54 | [structure] | m/z [M + H] + 330.1
1H-NMR (400 MHz, DMSO-d6) δ ppm 1.28 (brs, 4H), 2.21 (s, 3H), 4.57 (s, 1H), 4.69 (s, 1H), 6.34 (s, 1H), 8.12 (s, 1H), 8.40 (s, 1H), 10.58 (s, 1H), 12.11 (s, 1H). |

TABLE 8-continued
| 55 | 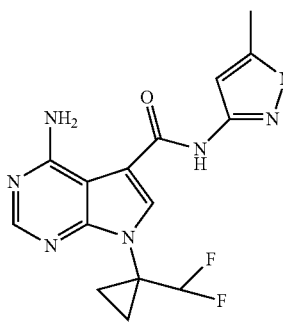 | m/z [M + H] + 348.1<br>1H-NMR (400 MHz, DMSO-d6) δ ppm 1.40-1.45 (m, 4H), 2.03 (s, 3H), 5.14 (s, 1H), 6.36 (s, 1H), 8.12 (s, 1H), 8.41 (s, 1H), 10.63 (s, 1H), 12.13 (s, 1H). |
|---|---|---|
| 56 | 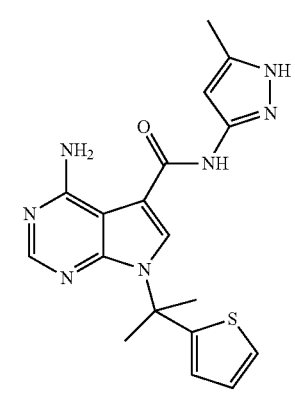 [SMILES: Cc1cc(NC(=O)c2cn(C(C)(C)c3cccs3)c3ncnc(N)c23)n[nH]1] | m/z [M + H] + 382.1<br>1H-NMR (400 MHz, DMSO-d6) δ ppm 2.17 (s, 6H), 2.22 (s, 3H), 6.38 (s, 1H), 6.90-6.91 (s, 2H), 7.32-7.33 (m, 1H), 7.96 (s, 1H), 8.59 (s, 1H), 10.70 (s, 1H), 12.12 (s, 1H). |
TABLE 9
| 57 | 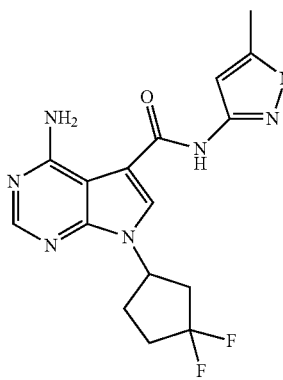 | m/z [M + H] + 362.2<br>1H-NMR (400 MHz, DMSO-d6) δ ppm 1.84-1.92 (m, 2H), 2.13-2.68 (m, 4H), 2.22 (s, 3H), 5.25-5.29 (m, 1H), 6.38 (s, 1H), 8.11 (s, 1H), 8.52 (s, 1H), 10.58 (s, 1H), 12.13 (s, 1H). |
|---|---|---|
| 58 | 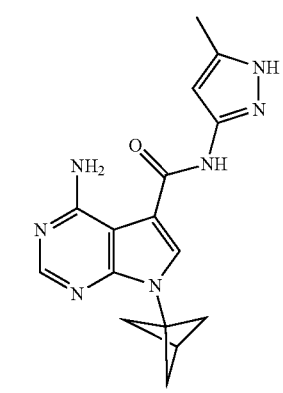 [SMILES: Cc1cc(NC(=O)c2cn(C34CC(C3)C4)c3ncnc(N)c23)n[nH]1] | m/z [M + H] + 324.1<br>1H-NMR (400 MHz, DMSO-d6) δ ppm 2.21 (s, 3H), 2.38 (brs, 6H), 2.68 (brs, 1H), 6.37 (brs, 1H), 8.09 (s, 1H), 8.40 (brs, 1H), 10.58 (brs, 1H), 12.10 (brs, 1H). |

| | | |
|---|---|---|
| 59 | 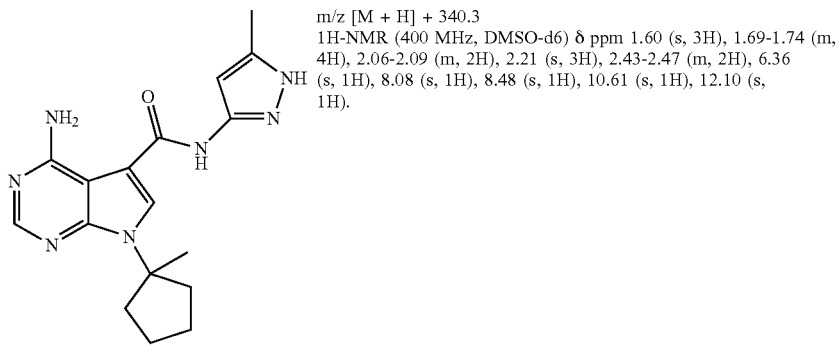 | m/z [M + H] + 340.3<br>1H-NMR (400 MHz, DMSO-d6) δ ppm 1.60 (s, 3H), 1.69-1.74 (m, 4H), 2.06-2.09 (m, 2H), 2.21 (s, 3H), 2.43-2.47 (m, 2H), 6.36 (s, 1H), 8.08 (s, 1H), 8.48 (s, 1H), 10.61 (s, 1H), 12.10 (s, 1H). |
| 60 | 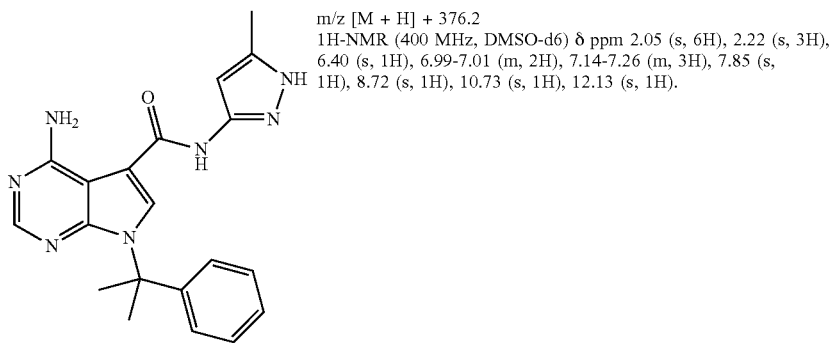 | m/z [M + H] + 376.2<br>1H-NMR (400 MHz, DMSO-d6) δ ppm 2.05 (s, 6H), 2.22 (s, 3H), 6.40 (s, 1H), 6.99-7.01 (m, 2H), 7.14-7.26 (m, 3H), 7.85 (s, 1H), 8.72 (s, 1H), 10.73 (s, 1H), 12.13 (s, 1H). |
| 61 | 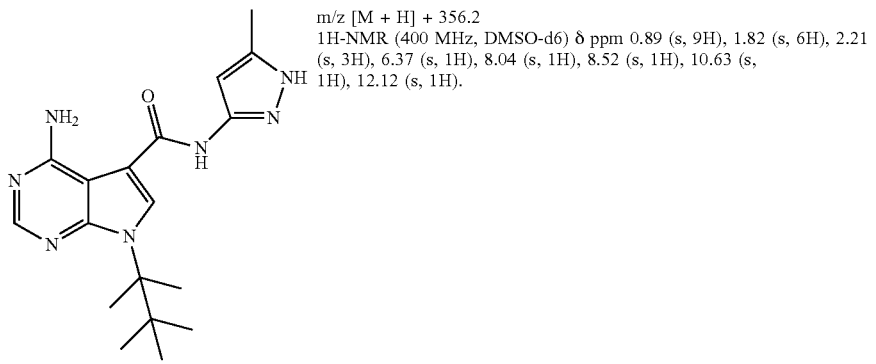 | m/z [M + H] + 356.2<br>1H-NMR (400 MHz, DMSO-d6) δ ppm 0.89 (s, 9H), 1.82 (s, 6H), 2.21 (s, 3H), 6.37 (s, 1H), 8.04 (s, 1H), 8.52 (s, 1H), 10.63 (s, 1H), 12.12 (s, 1H). |
| 62 | 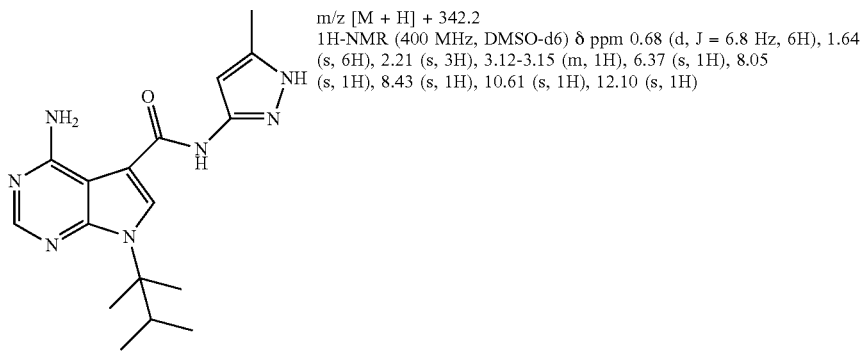 | m/z [M + H] + 342.2<br>1H-NMR (400 MHz, DMSO-d6) δ ppm 0.68 (d, J = 6.8 Hz, 6H), 1.64 (s, 6H), 2.21 (s, 3H), 3.12-3.15 (m, 1H), 6.37 (s, 1H), 8.05 (s, 1H), 8.43 (s, 1H), 10.61 (s, 1H), 12.10 (s, 1H) |

TABLE 9-continued

| | | |
|---|---|---|
| 63 | (structure: 4-amino-7-tert-butyl-pyrrolo[2,3-d]pyrimidine-5-carboxamide with N-(5-bromo-1H-pyrazol-3-yl)) | m/z [M + H] + 380.0<br>1H-NMR (400 MHz, DMSO-d6) δ ppm 1.74 (s, 9 H), 6.13 (s, 1 H), 8.14 (s, 1 H), 8.32 (s, 1H) 10.85-10.90 (m, 1 H), 12.98 (s, 1H). |

TABLE 10

| | | |
|---|---|---|
| 64 | (structure: 4-amino-7-tert-butyl-pyrrolo[2,3-d]pyrimidine-5-carboxamide with N-(5-(methoxymethyl)-1H-pyrazol-3-yl)) | m/z [M + H] + 344.2<br>1H-NMR (400 MHz, DMSO-d6) δ ppm 1.73 (s, 9 H) 3.27 (s, 3 H) 4.40 (s, 2 H) 6.58-6.61 (m, 1 H) 8.10 (s, 1 H) 8.51 (s, 1H), 10.73 (s, 1H), 12.49-12.52 (m, 1H). |
| 65 | (structure: 4-amino-7-isopropyl-pyrrolo[2,3-d]pyrimidine-5-carboxamide with N-(5-bromo-1H-pyrazol-3-yl)) | m/z [M + H] + 366.0<br>1H-NMR (400 MHz, DMSO-d6) δ ppm 1.45-1.47 (m, 6H), 4.92-4.95 (m, 1H), 6.13 (s, 1H), 7.94 (brs, 1H), 8.11 (s, 1H), 8.13 (s, 1H), 8.31 (s, 1H), 10.87 (s, 1H), 12.95 (s, 1H). |
| 66 | (structure: 4-amino-7-(1-fluoromethyl-1-methyl-ethyl)-pyrrolo[2,3-d]pyrimidine-5-carboxamide with N-(3-bromo-1H-pyrazol-5-yl)) | m/z [M + H] + 398.0<br>1H-NMR (400 MHz, DMSO-d6) δ ppm 1.74 (brs, 6H) 4.96 (brs, 1 H) 5.08 (brs, 1H) 6.14 (s, 1 H) 8.07-8.15 (m, 1 H), 8.31 (s, 1H), 10.91 (s, 1H), 12.99 (s, 1H). |
| 67 | (structure: 4-amino-7-(1-methylcyclopropyl)-pyrrolo[2,3-d]pyrimidine-5-carboxamide with N-(3-bromo-1H-pyrazol-5-yl)) | m/z [M + H] + 378.0<br>1H-NMR (400 MHz, DMSO-d6) δ ppm 0.96-1.06 (m, 2 H), 1.12-1.20 (m, 2 H), 1.55 (s, 3 H), 6.11-6.16 (m, 1 H), 8.11-8.18 (m, 1 H), 8.22-8.26 (m, 1 H), 10.74-10.95 (m, 1 H), 12.93 (brs, 1 H). |

TABLE 10-continued
| 68 | 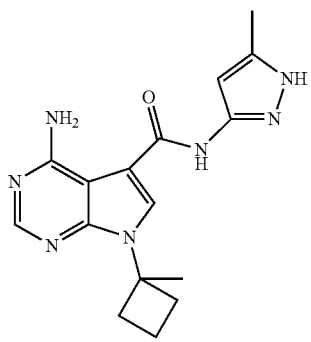 [SMILES: Cc1cc(NC(=O)c2cn(C3(C)CCC3)c3ncnc(N)c23)n[nH]1] | m/z [M + H] + 326.3<br>1H-NMR (400 MHz, DMSO-d6) δ ppm 1.65 (s, 3H), 1.86-1.89 (m, 1H), 1.98-2.03 (m, 1H), 2.31 (s, 3H), 2.31-2.36 (m, 2H), 2.62-2.67 (m, 2H), 6.37 (s, 1H), 8.06 (s, 1H), 8.38 (s, 1H), 10.58 (s, 1H), 12.10 (s, 1H). |
|---|---|---|
| 69 | 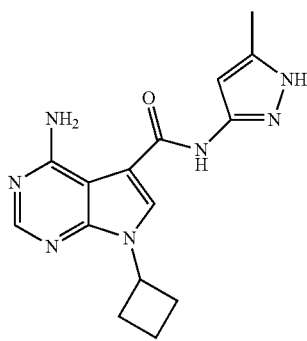 [SMILES: Cc1cc(NC(=O)c2cn(C3CCC3)c3ncnc(N)c23)n[nH]1] | m/z [M + H] + 312.2<br>1H-NMR (400 MHz, DMSO-d6) δ ppm 1.82-1.90 (m, 2H), 2.22 (s, 3H), 2.37-2.47 (m, 4H), 5.10-5.18 (m, 1H), 6.37 (s, 1H), 8.09 (s, 1H), 8.67 (s, 1H), 10.57 (s, 1H), 12.12 (s, 1H), |
| 70 | 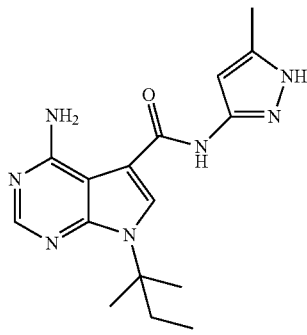 [SMILES: CCC(C)(C)n1cc(C(=O)Nc2cc(C)[nH]n2)c2c(N)ncnc21] | m/z [M + H] + 328.4<br>1H-NMR (400 MHz, DMSO-d6) δ ppm 0.53 (t, J = 7.4 Hz, 3H), 1.68 (s, 6H), 2.17-2.21 (m, 2H), 2.21 (s, 3H), 6.36 (s, 1H), 8.07 (s, 1H), 8.43 (s, 1H), 10.62 (s, 1H), 12.10 (s, 1H), |
TABLE 11
| 71 | 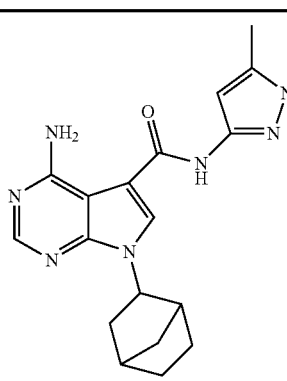 | m/z [M + H] + 352.4<br>1H-NMR (400 MHz, DMSO-d6) δ ppm 1.26-2.00 (m, 8H), 2.21 (s, 3H), 2.32 (m, 1H), 2.42 (m, 1H), 4.62 (m, 1H), 6.37 (s, 1H), 8.10 (s, 1H), 8.54 (s, 1H), 10.62 (s, 1H), 12.12 (s, 1H). |
|---|---|---|

TABLE 11-continued

| | | |
|---|---|---|
| 72 | [structure] | m/z [M + H] + 326.2<br>1H-NMR (400 MHz, DMSO-d6) δ ppm 1.68-1.72 (m, 2H), 1.79-1.90 (m, 4H), 2.12-2.17 (m, 2H), 2.21 (s, 3H), 5.06-5.09 (m, 1H), 6.37 (s, 1H), 8.09 (s, 1H), 8.46 (s, 1H), 10.58(s, 1H), 12.11 (s, 1H). |
| 73 | [structure] | m/z [M + H] + 328.1<br>1H-NMR (400 MHz, DMSO-d6) δ ppm 1.85 (s, 9 H), 2.22 (s, 3 H), 2.67 (s, 3 H), 6.40 (s, 1 H), 6.85 (s, 2 H), 8.08 (s, 1 H) 10.49 (s, 1 H), 12.11 (s, 1 H). |
| 74 | [structure] | m/z [M + H] + 338.3<br>1H-NMR (400 MHz, DMSO-d6) δ ppm 0.28-0.32 (m, 2H), 0.35-0.38 (m, 2H), 0.91-0.94 (m, 2H), 1.05-1.08 (m.2H), 1.51-1.53 (m, 1H), 2.21 (s, 3H), 6.36 (s, 1H), 8.11 (s, 1H), 8.34 (s, 1H), 10.55 (s, 1H), 12.10 (brs, 1H). |
| 75 | [structure] | m/z [M + H] + 346.0<br>1H-NMR (400 MHz, DMSO-d6) δ ppm 1.08-1.24 (m, 4H) 1.46 (s, 3H) 2.21 (s, 3H) 6.37 (s, 1H) 7.27 (s, 2H) 8.16 (s, 1H) 10.32 (s, 1H) 12.16 (s, 1H). |

TABLE 11-continued
| | | |
|---|---|---|
| 76 | 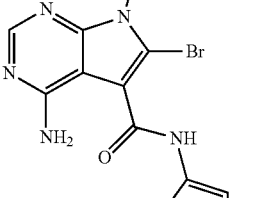 | m/z [M + H] + 392.0<br>1H NMR (400 MHz, DMSO-d6) δ ppm 1.10-1.32 (m, 4H) 1.46 (s, 3H) 2.21 (s, 3H) 6.38 (s, 1H) 7.18 (brs, 2H) 8.14 (s, 1H) 10.34 (s, 1H) 12.15 (brs, 1H). |
| 77 |  | m/z [M + H] + 342.2<br>1H-NMR (400 MHz, CHLOROFORM-d) δ ppm 1.09-1.15 (m, 2 H) 1.29-1.34 (m, 2 H) 1.70 (s, 3 H) 2.34 (s, 3 H) 4.26 (s, 3 H) 6.49-6.51 (m, 1 H) 8.34-8.36 (m.1 H) 9.16-9.19 (m, 1 H). |
TABLE 12
| | | |
|---|---|---|
| 78 | 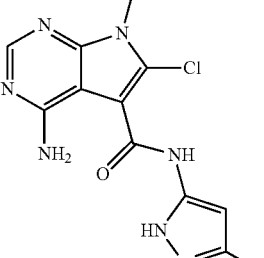 | m/z [M + H] + 366.1<br>1H-NMR (400 MHz, CHLOROFORM-d) δ ppm 1.97-2.02 (m, 6 H) 2.35 (s, 3 H) 5.15 (s, 1 H) 5.27 (s, 1 H) 6.57 (s, 1 H) 8.24 (s, 1 H) 8.98 (brs, 1 H). |
| 79 | 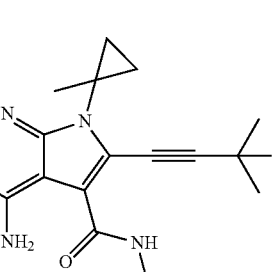 | m/z [M + H] + 394.1<br>1H NMR (400 MHz, DMSO-d6) δ ppm 1.03-1.11 (m, 2 H) 1.21-1.26 (m, 2 H) 1.49 (s, 3 H) 1.60 (s, 6 H) 2.21 (s, 3 H) 5.79 (br s, 1 H) 6.39 (br s, 1 H) 8.19 (s, 1 H) 9.89 (br s, 1 H) 12.24 (br s, 1 H). |

TABLE 12-continued
| | | |
|---|---|---|
| 80 | 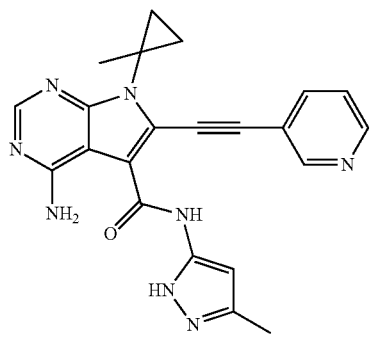 [SMILES: Cc1cc(NC(=O)c2c(C#Cc3cccnc3)n(C3(C)CC3)c3ncnc(N)c23)[nH]n1] | m/z [M + ] + 413.4<br>1H-NMR (400 MHz, DMSO-d6) δ ppm 1.17-1.25 (m, 2 H) 1.25-1.38 (m, 2 H) 1.55 (s, 3 H) 2.23 (s, 3 H) 6.44 (br s, 1 H) 7.52 (dd, J = 7.70, 4.77 Hz, 1 H) 8.14 (br dt, J = 7.97, 1.88 Hz, 1 H) 8.20 (s, 1 H) 8.66 (dd, J = 4.77, 1.47 Hz, 1 H) 8.96 (d, J = 1.10 Hz, 1 H) 10.32 (brs, 1 H) 12.34 (brs, 1 H). |
| 81 | 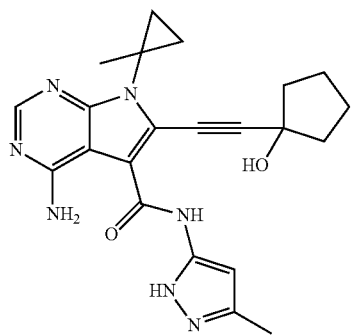 [SMILES: Cc1cc(NC(=O)c2c(C#CC3(O)CCCC3)n(C3(C)CC3)c3ncnc(N)c23)[nH]n1] | m/z [M + H] + 420.4<br>1H-NMR (400 MHz, DMSO-d6) δ ppm 0.99-1.16 (m, 2 H) 1.19-1.38 (m, 2 H) 1.50 (s, 3 H) 1.69-1.85 (m, 4 H) 1.92-2.07 (m, 2H) 2.07-2.17 (m, 2H) 2.22 (s, 3 H) 5.67 (s, 1 H) 6.41 (s, 1 H) 8.32 (s, 1 H) 9.91 (s, 1 H) 12.15-12.36 (m, 1 H). |
| 82 | 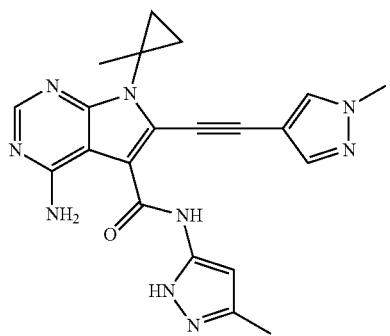 [SMILES: Cc1cc(NC(=O)c2c(C#Cc3cnn(C)c3)n(C3(C)CC3)c3ncnc(N)c23)[nH]n1] | m/z [M + H] + 416.2<br>1H NMR (400 MHz, DMSO-d6) δ ppm 1.09-1.14 (m, 2 H) 1.25-1.30 (m, 2 H) 1.50 (s, 3 H) 2.22 (s, 3 H) 3.89 (s, 3 H) 6.42 (s, 1 H) 7.94 (s, 1 H) 8.17 (s, 1 H) 8.30 (s, 1 H) 10.07 (s, 1 H) 12.22 (s, 1 H). |
| 83 | 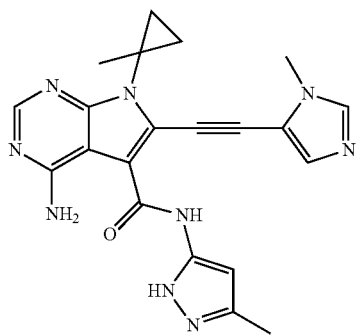 [SMILES: Cc1cc(NC(=O)c2c(C#Cc3cncn3C)n(C3(C)CC3)c3ncnc(N)c23)[nH]n1] | m/z [M + H] + 416.2<br>1H-NMR (400 MHz, DMSO-d6) δ ppm 1.10-1.17 (m, 2 H) 1.26-1.33 (m, 2 H) 1.54 (s, 3 H) 2.21 (s, 3 H) 3.75 (s, 3 H) 6.42 (s, 1 H) 7.60 (s, 1 H) 7.86 (s, 1 H) 8.19 (s, 1 H) 10.15 (s, 1 H) 12.21 (s, 1 H). |

TABLE 12-continued
| 84 | 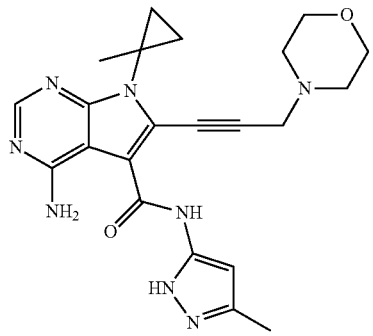 [SMILES: Cc1cc(NC(=O)c2c(C#CCN3CCOCC3)n(C3(C)CC3)c3ncnc(N)c23)[nH]n1] | m/z [M + H] + 435.2<br>1H-NMR (400 MHz, DMSO-d6) δ ppm 1.03-1.12 (m, 2 H) 1.22-1.28 (m, 2 H) 1.49 (s, 3 H) 2.21 (s, 3 H) 2.54-2.63 (m, 4 H) 3.54-3.61 (m, 4 H) 3.76 (s, 2 H) 6.38 (br s, 1 H) 8.17 (s, 1 H) 10.01 (br s, 1 H) 12.17 (br s, 1 H). |
TABLE 13
| 85 | 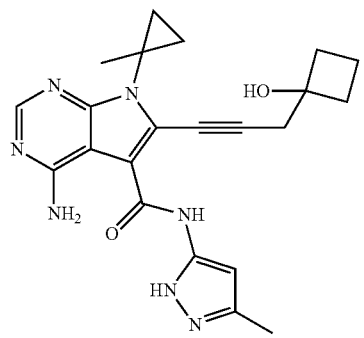 [SMILES: Cc1cc(NC(=O)c2c(C#CCC3(O)CCC3)n(C3(C)CC3)c3ncnc(N)c23)[nH]n1] | m/z [M + H] + 420.2<br>1H NMR (400 MHz, DMSO-d6) δ ppm 1.02-1.09 (m, 2 H) 1.20-1.26 (m, 2 H) 1.48 (s, 3 H) 1.50-1.72 (m, 2 H) 1.99-2.10 (m, 2 H) 2.10-2.19 (m, 2 H) 2.22 (s, 3 H) 2.93 (s, 2 H) 5.57 (s, 1 H) 6.39 (br s, 1 H) 8.15 (s, 1 H) 10.01 (s, 1 H) 12.23 (br s, 1 H). |
| 86 | 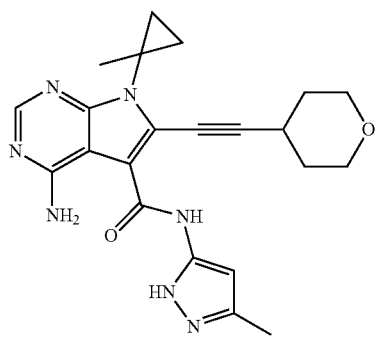 [SMILES: Cc1cc(NC(=O)c2c(C#CC3CCOCC3)n(C3(C)CC3)c3ncnc(N)c23)[nH]n1] | m/z [M + H] + 420.2<br>1H-NMR (400 MHz, CHLOROFORM-d) δ ppm 1.11 (s, 2 H) 1.36 (s, 2 H) 1.59 (s, 3 H) 1.93-2.03 (m, 2 H) 2.05-2.13 (m, 2 H) 2.34 (s, 3 H) 3.18 (dt, J = 8.89, 4.54 Hz, 1 H) 3.61 (ddd, J = 11.73, 8.80, 2.93 Hz, 2 H) 4.01 (dt, J = 12.10, 4.22 Hz, 2 H) 6.53 (br s, 1 H) 8.35 (s, 1 H) 9.79 (s, 1 H). |
| 87 | 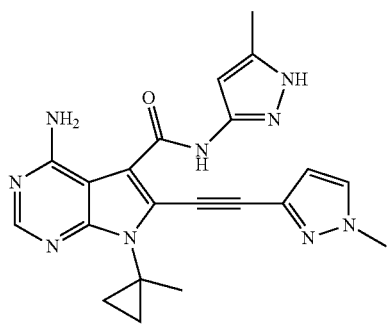 [SMILES: Cc1cc(NC(=O)c2c(C#Cc3ccn(C)n3)n(C3(C)CC3)c3ncnc(N)c23)n[nH]1] | m/z [M + H] + 416.2<br>1H-NMR (400 MHz, DMSO-d6) δ ppm: 1.08 (m, 2H), 1.29 (m, 2H), 1.52 (s, 3H), 2.22 (s, 3H), 3.91 (s, 3H), 6.42 (s, 1H), 6.81 (m, 1H), 7.86 (m, 1H), 8.14 (m, 1H), 10.13 (s, 1H). |

TABLE 13-continued
| 88 | 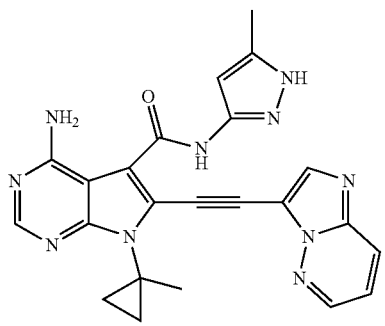 [SMILES: Cc1cc(NC(=O)c2c(C#Cc3cnc4cccnn34)n(C3(C)CC3)c3ncnc(N)c23)n[nH]1] | m/z [M + H] + 453.2<br>1H-NMR (400 MHz, DMSO-d6) δ ppm 1.16-1.19 (m, 2H), 1.34-1.37 (m, 2H), 1.57 (s, 3H), 2.23 (s, 3H).6.42 (s, 1H), 7.40-1.43 (m, 1H), 8.21 (s, 1H), 8.28-8.30 (m, 2H), 8.39 (m, 1H), 8.65-8.66 (m, 1H). |
|---|---|---|
| 89 | 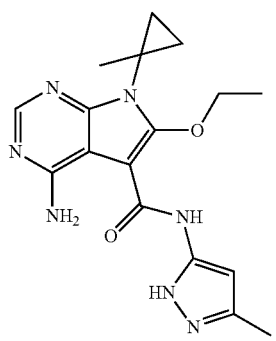 [SMILES: CCOc1c(C(=O)Nc2cc(C)n[nH]2)c2c(N)ncnc2n1C1(C)CC1] | m/z [M + H] + 356.2<br>1H-NMR (400 MHz, DMSO-d6) δ ppm 0.99-1.07 (m, 2 H) 1.14-1.21 (m, 2 H) 1.51 (t, J = 6.96 Hz, 3 H) 1.56 (s, 3 H) 2.20 (s, 3 H) 4.43 (q, J = 6.96 Hz, 2 H) 6.36 (s, 1 H) 8.12 (s, 1 H) 9.52 (s, 1 H) 12.09 (brs, 1 H). |
| 90 | 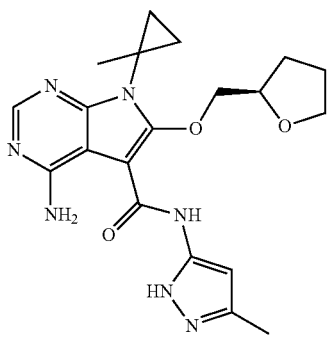 [SMILES: Cc1cc(NC(=O)c2c(OC[C@H]3CCCO3)n(C3(C)CC3)c3ncnc(N)c23)[nH]n1] | m/z [M + H] + 412.2<br>1H-NMR (400 MHz, DMSO-d6) δ ppm 1.01-1.07 (m, 2H) 1.13-1.20 (m, 2H) 1.59 (s, 3H) 1.72-1.94 (m, 3H) 1.99-2.09 (m, 1H) 2.18-2.22 (m, 3H) 3.64-3.71 (m, 1 H) 3.84-3.95 (m, 1 H) 4.24-4.35 (m, 2H) 4.44 (br d, J = 7.33 Hz, 1H) 6.32 (brs, 1H) 8.11 (s, 1H) 9.68 (brs, 1H) 12.06 (s, 1H). |
TABLE 14
| Compound 1 of Comparative Ex. | 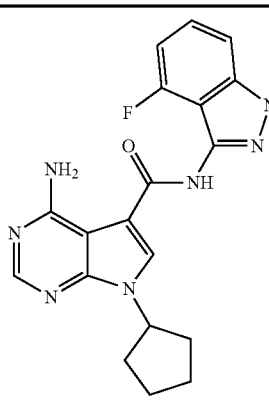 | m/z [M + H] + 381.2<br>1H-NMR (400 MHz, DMSO-d6) δ ppm 1.67-1.85 (m, 2H), 1.86-1.90 (m, 2H), 1.99-2.14 (m, 4H), 5.23-5.27 (m, 1H), 6.34 (brs, 2H), 7.18-7.22 (m, 1H), 7.58-7.65 (m, 2H).8.12-8.14 (m, 1H), 8.26 (s, (s, 1H). |
|---|---|---|

TABLE 14-continued

| | | |
|---|---|---|
| Compound 2 of Comparative Ex. | 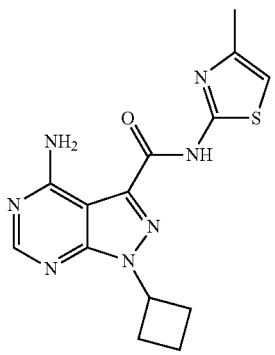 [SMILES: Cc1csc(NC(=O)c2nn(C3CCC3)c3ncnc(N)c23)n1] | m/z [M + H] + 331.3<br>1H-NMR (400 MHz, DMSO-d6) δ ppm 1.85-1.93 (n, 2H), 2.32 (s, 3H), 2.39-2.44 (m, 2H), 2.76-2.86 (m, 2H), 5.31-5.40 (m, 1H), 6.91 (s, 1H), 8.21 (brs, 2H), 8.30 (s, 1H), 12.64 (brs, 1H). |
| Compound 3 of Comparative Ex. | 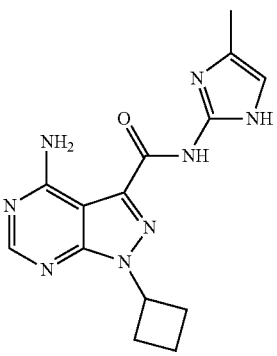 [SMILES: Cc1c[nH]c(NC(=O)c2nn(C3CCC3)c3ncnc(N)c23)n1] | m/z [M + H] + 313.3<br>1H-NMR (400 MHz, DMSO-d6) δ ppm 1.82-1.90 (m, 2H), 2.12 (s, 3H), 2.32-2.41 (m, 2H), 2.64-2.76 (n, 2H), 5.27-5.35 (m.1H), 6.60 (s, 1H), 7.89 (brs, 1H), 8.20 (s, 1H), 9.46 (brs, 1H). 11.99 (brs, 1H). |
| Compound 4 of Comparative Ex. | 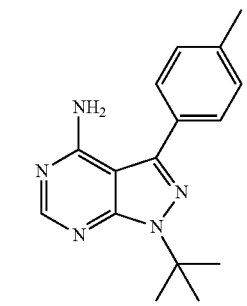 [SMILES: Cc1ccc(-c2nn(C(C)(C)C)c3ncnc(N)c23)cc1] | m/z [M + H] + 282.3<br>1H-NMR (400 MHz, CHLOROFORM-d) δ ppm 1.84 (s, 9H), 2.43 (s, 3H), 5.35 (brs, 2H), 7.33 (d, J = 7.8 Hz.2H), 7.58 (d, J = 7.8 Hz, 2H), 8.36 (s, 1H). |

Test Example 1: Measurement of RET Inhibitory Activity (In Vitro)

Regarding the conditions for measurement of in vitro inhibitory activity of compounds against RET kinase activity, the website of AnaSpec states that Srctide (GEEPLY-WSFPAKKK) corresponds to the substrate peptide for reaction to measure RET kinase activity. Thus, the amino acid sequence was partly modified and biotinylated to prepare biotinylated peptides (biotin-EEPLYWSFPAKKK). The purified recombinant human RET protein used in the test was purchased from Carna Biosciences, Inc.

To measure the inhibitory activity, first, the compounds of the present invention were individually diluted with dimethyl sulfoxide (DMSO) stepwise. Subsequently, RET protein, the substrate peptide (final concentration: 250 nM), magnesium chloride (final concentration: 10 mM), ATP (the final concentration: 10 μM), and a solution of the compound of the present invention in DMSO (final concentration of DMSO: 2.5%) were added to a buffer for kinase reaction (13.5 mM Tris, pH of 7.5, 2 mM dithiothreitol, 0.009% Tween-20). Each of the mixtures was incubated at 25° C. for 100 minutes to perform kinase reaction. EDTA was then added thereto to give a final concentration of 24 mM so that the reaction was terminated. A detection solution containing Eu-labeled antiphosphotyrosine antibody PT66 (PerkinElmer) and SureLight APC-SA (PerkinElmer) was added thereto, and each mixture was allowed to stand at room temperature for 2 hours or more. Finally, the intensity of fluorescence under the excitation light with a wavelength of 337 nm was measured with a PHERAstar FS (BMG Labtech) at the two wavelengths of 620 nm and 665 nm. The phosphorylation level was calculated from the ratio of the fluorescence intensity at the two wavelengths, and the compound concentration at which phosphorylation was inhibited by 50% was defined as the IC50 value (nM).

Table 15 shows IC50 (nM) of the RET (WT) inhibitory activity of the compounds of the Examples and compounds 1 to 3 of the Comparative Examples.

Vandetanib is known to have a high inhibitory activity against RET and exhibit a high antitumor effect (e.g., Carlomagno F. Cancer Res. 2002 Dec. 15; 62(24): 7284-90). The compounds of the present invention were found to exhibit in vitro RET inhibitory activity at an equivalent or higher level than Vandetanib.

Compounds 1 to 3 of Comparative Examples, which do not have a pyrazolyl group continuous with an amide group, respectively had an IC50 (nM) of 451, 752, and 486, exhibiting weak inhibitory activity. In contrast, the compounds of the present invention had an IC50 (nM) about 40 times, or more than 40 times, the IC50 (nM) of compounds 1 to 3 of Comparative Examples, revealing that the compounds of the present invention have a high RET inhibitory activity.

TABLE 15

| Compound of Examples | RET IC50(nM) |
|---|---|
| 1 | 1.94 |
| 2 | 6.66 |
| 4 | 6.94 |
| 5 | 7.79 |
| 7 | 8.5 |
| 8 | 3.3 |
| 10 | 10.2 |
| 11 | 1.73 |
| 12 | 8.24 |
| 13 | 6.52 |
| 15 | 4.6 |
| 16 | 4.96 |
| 17 | 4 |
| 18 | 3.2 |
| 20 | 5.83 |
| 21 | 2.03 |
| 22 | 1.07 |
| 24 | 2.2 |
| 25 | 2.27 |
| 26 | 1 |
| 27 | 0.43 |
| 28 | 0.4 |
| 29 | 0.61 |
| 31 | 1.97 |
| 32 | 1.86 |
| 33 | 1.86 |
| 34 | 0.29 |
| 35 | 0.15 |
| 36 | 1 |
| 37 | 5.13 |
| 38 | 1.48 |
| 39 | 1.53 |
| 41 | 10 |
| 44 | 4.58 |
| 45 | 0.788 |
| 46 | 0.48 |
| 47 | 0.59 |
| 48 | 0.21 |
| 49 | 10.33 |
| 50 | 0.2 |
| 51 | 0.17 |
| 52 | 0.16 |
| 53 | 0.76 |
| 54 | 0.23 |
| 55 | 0.36 |
| 56 | 0.279 |
| 57 | 1.47 |
| 58 | 0.27 |
| 59 | 0.51 |
| 60 | 3.51 |
| 61 | 0.83 |
| 62 | 2.27 |
| 63 | 0.15 |
| 65 | 0.23 |
| 66 | 0.15 |
| 67 | 0.15 |
| 68 | 0.337 |
| 69 | 0.46 |
| 70 | 0.79 |
| 71 | 0.4 |
| 72 | 0.266 |
| 73 | 0.32 |
| 74 | 0.61 |
| 75 | <0.15 |
| 76 | 0.14 |
| 77 | 1.35 |
| 78 | <0.15 |
| 79 | 0.07 |

TABLE 15-continued

| Compound of Examples | RET IC50(nM) |
|---|---|
| 80 | 0.09 |
| 81 | 0.04 |
| 82 | 0.15 |
| 83 | 0.17 |
| 84 | 0.1 |
| 85 | 0.1 |
| 86 | 0.15 |
| Compound 1 of Comparative Examples | 451 |
| Compound 2 of Comparative Examples | 752 |
| Compound 3 of Comparative Examples | 486 |

Test Example 2: RET Inhibitory Selectivity (In Vitro) Over Other Kinase Inhibitory Activity 1) RET Inhibitory Activity Measurement RET inhibitory activity was measured in the same manner as in Test Example 1.

2) SRC Inhibitory Activity Measurement

Regarding the conditions for measurement of in vitro inhibitory activity of compounds against SRC kinase activity, the price list of LabChip-series consumable reagents of PerkinElmer shows that FL-Peptide 4 corresponds to the substrate peptide for reaction to measure SRC kinase activity. Thus, FL-Peptide 4 was used as a substrate. The purified recombinant human SRC protein used in the test was purchased from Carna Biosciences, Inc.

To measure the inhibitory activity, first, the compounds of the present invention were individually diluted with dimethyl sulfoxide (DMSO) stepwise. Subsequently, SRC protein, FL-Peptide 4 (final concentration: 1.5 µM), magnesium chloride (final concentration: 10 mM), ATP (final concentration: 15 µM), and a solution of the compound of the present invention in DMSO (final concentration of DMSO: 5%) were added to a reaction buffer (100 mM HEPES, pH of 7.0, 1 mM dithiothreitol, 0.003% Brij35, 0.04% Tween-20) containing a phosphatase inhibitor cocktail (PhosSTOP, Roche) and a protease inhibitor cocktail (complete Mini, EDTA-free, Roche) at recommended concentrations. Each mixture was incubated at 30° C. for 90 minutes to perform kinase reaction. EDTA diluted with a separation buffer available from PerkinElmer (final concentration: 30 mM) was then added thereto to terminate the kinase reaction. Finally, non-phosphorylated substrate peptides (S) and phosphorylated peptides (P) were separated and detected by microchannel capillary electrophoresis using LabChip EZ Reader II (PerkinElmer). The phosphorylation level was calculated from the height of the peaks of S and P, and the compound concentration at which phosphorylation was inhibited by 50% was defined as IC50 value (nM).

3) LCK Inhibitory Activity Measurement

Regarding the conditions for measurement of in vitro inhibitory activity of compounds against LCK kinase activity, the website of AnaSpec states that Srctide (GEEPLYWSFPAKKK) corresponds to the substrate peptide for reaction to measure LCK kinase activity. Thus, the amino acid sequence was partly modified and biotinylated to prepare biotinylated peptides (biotin-EEPLYWSFPAKKK). The purified recombinant human LCK protein used in the test was purchased from Carna Biosciences, Inc.

To measure the inhibitory activity, first, the compounds of the present invention were individually diluted with dimethyl sulfoxide (DMSO) stepwise. Subsequently, LCK protein, the substrate peptides (final concentration: 250 nM), magnesium chloride (final concentration: 10 mM), ATP (final concentration: 50 µM), and a solution of the compound of the present invention in DMSO (final concentration of DMSO: 5%) were added to a buffer for kinase reaction (13.5 mM Tris, pH of 7.5, 2 mM dithiothreitol, 0.009% Tween-20). Each mixture was incubated at 25° C. for 60 minutes to perform kinase reaction. EDTA was then added thereto to give a final concentration of 40 mM so that the reaction was terminated. A detection solution containing Eu-labeled antiphosphotyrosine antibody PT66 (PerkinElmer) and SureLight APC-SA (PerkinElmer) was added thereto, and each mixture was allowed to stand at room temperature for 2 hours or more. Finally, the intensity of fluorescence under the excitation light with a wavelength of 337 nm was measured with a PHERAstar FS (BMG Labtech) at the two wavelengths of 620 nm and 665 nm. The phosphorylation level was calculated from the ratio of the fluorescence intensity at the two wavelengths, and the compound concentration at which phosphorylation was inhibited by 50% was defined as IC50 value (nM).

4) RET Inhibitory Selectivity

From the values obtained in sections 1) and 3) above, SRC inhibitory activity IC50 (nM)/RET inhibitory activity IC50 (nM) and LCK inhibitory activity IC50 (nM)/RET inhibitory activity IC50 (nM) were calculated, and the RET inhibitory selectivity of the tested compounds was examined.

TABLE 16

| Compound of Examples | SRC IC50(nM)/ RET IC50(nM) | LCK IC50(nM)/ RET IC50(nM) |
|---|---|---|
| 16 | 1387.7 | 282.5 |
| 20 | 1715.3 | 173.8 |
| 27 | 3737.2 | 932.6 |
| 31 | 1787.3 | 269.5 |
| 34 | 4296.6 | 1096.6 |
| 36 | 3210.0 | 346.0 |
| 38 | 1748.6 | 526.4 |
| 39 | 652.3 | 193.5 |
| 45 | 2659.9 | 413.7 |
| 47 | 1340.7 | 220.3 |
| 48 | 2890.5 | 633.3 |
| 50 | 4060.0 | 1280.0 |
| 51 | 7188.2 | 1882.4 |
| 52 | 3575.0 | 1131.3 |
| 53 | 1947.4 | 828.9 |
| 56 | 5896.1 | 2039.4 |
| 57 | 1381.0 | 341.5 |
| 58 | 1818.5 | 400.0 |
| 63 | 4446.7 | 906.7 |
| 65 | 6191.3 | 1160.9 |
| 67 | 3493.3 | 700.0 |
| 68 | 2151.3 | 400.6 |
| 71 | 3030.0 | 467.5 |
| 72 | 2725.6 | 469.9 |
| 74 | 3357.4 | 950.8 |
| 79 | 2171.4 | 1785.7 |
| 80 | 4677.8 | 1244.4 |
| 81 | 3275.0 | 2275.0 |
| 82 | 5306.7 | 1200.0 |
| 83 | 2329.4 | 852.9 |
| 84 | 4070.0 | 3730.0 |
| 85 | 1460.0 | 743.0 |
| 86 | 2846.7 | 1273.3 |
| Compound 4 of Comparative Examples | 15.3 | 15.1 |

As shown in Table 16, compound 4 of Comparative Examples exhibited about 15-fold higher inhibitory selectivity for RET over SRC or LCK.

In comparison, the compounds of the present invention exhibited several-hundred-fold to several-thousand-fold higher inhibitory selectivity for RET over SRC or LCK, revealing its excellent inhibitory selectivity for RET. The results also suggest that the compounds of the present invention have a low likelihood of involving side effects caused by inhibiting kinases other than RET.

Test Example 3: Evaluation of Cell Growth Inhibitory Effect on Tumor Cell Carrying RET Gene Defect (1)

An in vitro cell-killing test was performed on TT cells (a human thyroid cancer line carrying RET activating mutation (C634W)).

A suspension of TT cells in a 10% FBS-containing Ham's F12K (Kaighn's) medium (produced by Life Technologies Japan) was inoculated into each well of a 96-well flat-bottomed microplate in an amount of $5 \times 10^3$ (0.15 mL) for each well, and cultured in an incubator containing 5% carbon dioxide at 37° C. overnight (day 0). The compounds of the present invention were individually dissolved in dimethyl sulfoxide to give a concentration of 10 mM, and further diluted with a 10% FBS-containing RPMI1640 medium (produced by Wako Pure Chemical Industries, Ltd.) so that the compounds of the present invention respectively had a final concentration of 40, 12, 4, 1.2, 0.4, 0.12, 0.04, and 0.012 µM. The compounds of different concentrations were individually added to wells of the TT cell-containing culture plate described above in an amount of 0.05 mL for each well (day 1), and cultured in an incubator containing 5% carbon dioxide at 37° C. for 7 days. After culture (day 8), 0.1 mL of the medium was removed from each well, and 0.1 mL of a CellTiter Glo 2.0 reagent (Promega Corporation), which is an intracellular ATP luminescence detection reagent, was added thereto, followed by shaking for 1 minute. After shaking, each culture was allowed to stand at room temperature for 15 minutes, and the chemiluminescence was measured with a luminometer to use it as an index of the number of viable cells. The growth rate from day 1 of the compounds with different concentrations was calculated from the following equations, depending on the value of $T_{day\ 8}$ and $C_{day\ 1}$, to determine the concentration ($GI_{50}$ (µM)) of the tested compounds capable of suppressing cell growth by 50%.

$$T_{day\ 8} \geq C_{day\ 1}$$

Growth Rate (%)=$(T_{day\ 8} - C_{day\ 1})/(C_{day\ 8} - C_{day\ 1}) \times 100$       1)

T: The absorbance of the well to which a tested compound was added.
C: The absorbance of the well to which a tested compound was not added.
Day 1: The day on which a tested compound was added.
Day 8: The day on which evaluation was performed.

$$T_{day\ 8} < C_{day\ 1}$$

Growth Rate (%)=$(T_{day\ 8} - C_{day\ 1})/(C_{day\ 1}) \times 100$       2)

T: The absorbance of the well to which a tested compound was added.
C: The absorbance of the well to which a tested compound was not added.
Day 1: The day on which a tested compound was added.
Day 8: The day on which evaluation was performed.

Table 17 shows the results. The compounds of the present invention exhibited a higher growth inhibitory effect on TT cells than compound 4 of Comparative Examples or Vandetanib.

TABLE 17

| Compound of Examples | TT Cell GI50 (nM) |
|---|---|
| 22 | 73 |
| 26 | 72 |
| 27 | 53 |
| 28 | 25 |
| 29 | 79 |
| 34 | 49 |
| 35 | 23 |
| 45 | 76 |
| 46 | 47 |
| 48 | 21 |
| 50 | 21 |
| 51 | 31 |
| 52 | 10 |
| 53 | 65 |
| 54 | 32 |
| 55 | 26 |
| 56 | 45 |
| 58 | 24 |
| 59 | 37 |
| 63 | 14 |
| 65 | 32 |
| 66 | 20 |
| 67 | 8 |
| 68 | 27 |
| 69 | 48 |
| 70 | 82 |
| 71 | 57 |
| 72 | 30 |
| 73 | 64 |
| 74 | 59 |
| 75 | 27 |
| 76 | 27 |
| 78 | 76 |
| 79 | 6 |
| 80 | 7 |
| 81 | <3 |
| 82 | 23 |
| 83 | 14 |
| 84 | 16 |
| 85 | 6 |
| 86 | 24 |
| Compound 4 of Comparative Examples | 8774 |
| Vandetanib | 1143 |

Test Example 4: Evaluation of Cell Growth Inhibitory Effect on Tumor Cell Carrying RET Gene Defect (2)

An in vitro cell-killing test was performed on LC-2/ad cells (human lung adenocarcinoma line carrying CCDC6-RET fusion gene).

A suspension of LC-2/ad cells in a 10% FBS-containing RPMI1640 medium was inoculated into each well of a 96-well flat-bottomed microplate in an amount of $5 \times 10^3$ for each well (0.15 mL), and cultured in an incubator containing 5% carbon dioxide at 37° C. overnight (day 0). The compounds of the present invention were individually dissolved in dimethyl sulfoxide to give a concentration of 10 mM, and further diluted with a 10% FBS-containing RPMI1640 medium such that the compounds of the present invention respectively had a final concentration of 40, 12, 4, 1.2, 0.4, 0.12, 0.04, and 0.012 μM. The compounds of different concentrations were individually added to each well of the LC-2/ad cell-containing culture plate described above in an amount of 0.05 mL for each well (day 1), and cultured in an incubator containing 5% carbon dioxide at 37° C. for 7 days. After culture (day 8), 0.1 mL of the medium was removed from each well, and 0.1 mL of a CellTiter Glo 2.0 reagent (Promega Corporation), which is an intracellular ATP luminescence detection reagent, was added thereto, followed by shaking for 5 minutes. After shaking, each culture was allowed to stand at room temperature for 15 minutes, and the chemiluminescence was measured with a luminometer to use it as an index of the number of viable cells. The growth rate from day 1 of the compounds with different concentrations was calculated from the following equations, depending on the value of $T_{day\ 8}$ and $C_{day\ 1}$, to determine the concentration ($GI_{50}$ (μM)) of the tested compounds capable of suppressing cell growth by 50%.

$$T_{day\ 8} - C_{day\ 1}$$

$$\text{Growth Rate (\%)} = (T_{day\ 8} - C_{day\ 1})/(C_{day\ 8} - C_{day\ 1}) \times 100 \quad 1)$$

T: The absorbance of the well to which a tested compound was added.
C: The absorbance of the well to which a tested compound was not added.
Day 1: The day on which a tested compound was added.
Day 8: The day on which evaluation was performed.

$$T_{day\ 8} < C_{day\ 1}$$

$$\text{Growth Rate (\%)} = (T_{day\ 8} - C_{day\ 1})/(C_{day\ 1}) \times 100 \quad 2)$$

T: The absorbance of the well to which a tested compound was added.
C: The absorbance of the well to which a tested compound was not added.
Day 1: The day on which a tested compound was added.
Day 8: The day on which evaluation was performed.

Table 18 shows the results. The compounds of the present invention exhibited a higher growth inhibitory effect on LC-2/ad cells than compound 4 of Comparative Examples or Vandetanib.

TABLE 18

| Compound of Examples | LC-2/ad Cell GI50 (nM) |
|---|---|
| 27 | 246 |
| 34 | 364 |
| 35 | 340 |
| 46 | 353 |
| 47 | 285 |
| 48 | 179 |
| 50 | 176 |
| 51 | 153 |
| 52 | 242 |
| 53 | 341 |
| 54 | 128 |
| 55 | 238 |
| 56 | 185 |
| 58 | 171 |
| 59 | 203 |
| 62 | 358 |
| 63 | 254 |
| 66 | 209 |
| 67 | 332 |
| 68 | 210 |
| 70 | 229 |
| 71 | 328 |
| 72 | 252 |
| 73 | 148 |
| 74 | 337 |
| 75 | 121 |
| 76 | 141 |
| 77 | 218 |
| 79 | 300 |

TABLE 18-continued

| Compound of Examples | LC-2/ad Cell GI50 (nM) |
|---|---|
| 81 | 325 |
| 82 | 185 |
| 84 | 130 |
| 85 | 99 |
| 86 | 131 |
| Compound 4 of Comparative Examples Vandetanib | >10000 |
| | 1709 |

Test Example 5: Evaluation of Antitumor Effect on In Vivo Model Having TT (Human Thyroid Cancer Cell Line Carrying RET Activating Mutation) Cells Subcutaneously Implanted Human thyroid cancer cell lines (TT) were subcutaneously implanted into the right chest of 6- to 7-week-old BALB/cA Jcl-nu/nu male mice. About 3 weeks after the cell implantation, the length (mm) and the width (mm) of tumors found in mouse bodies were measured. After their tumor volume (tumor volume: TV) was calculated, the mice were divided into groups (n=5 or 6) so that the groups had a substantially equal mean TV. The day on which the mice were divided into groups was determined to be the "grouping day" (day 0 or 1).

Test solutions containing the compounds of the present invention were prepared at a dose of 100 mg/kg/day, and orally administered to the mice for consecutive 14 days (the first administration day is day 1). A control group was administered a solvent (0.5% HPMC/0.1N HCl).

Figure 2:
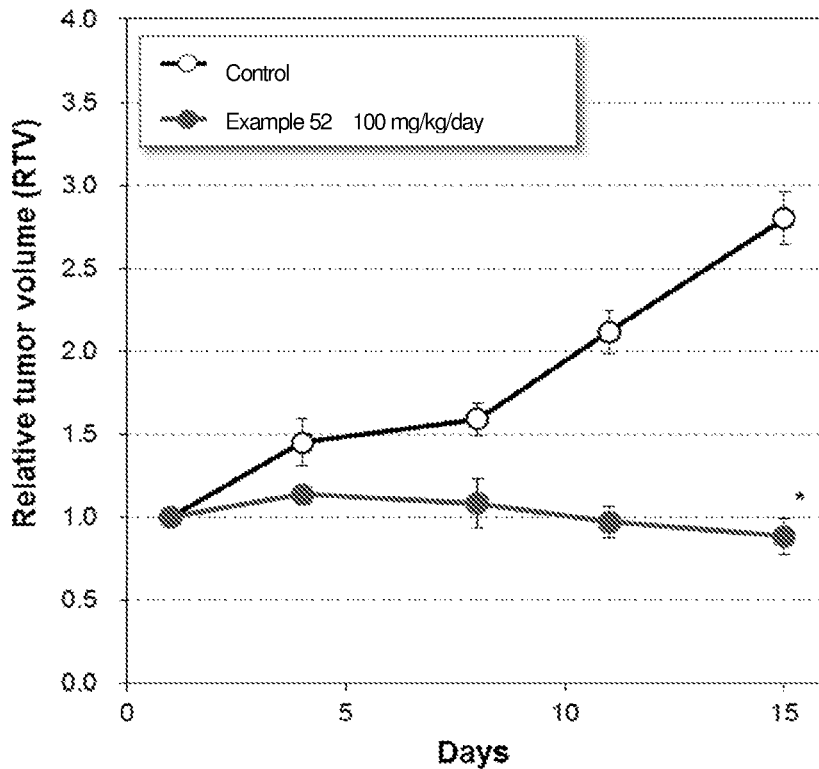
FIG. 2 illustrates changes in relative tumor volume during the test in Test Example 5

To determine the index of the antitumor effect, TV of each drug-administered group was measured on day 15, and the tumor volume on day 15 relative to the tumor volume on the grouping day (day 0 or 1) (relative tumor volume: RTV) and T/C (%) were calculated from the following equations to evaluate the antitumor effect. When a group administered any of the compounds of the present invention (test-solution-administered group) exhibited a statistically significantly smaller mean RTV (Dunnett's test or Student's t-test, $p<0.05$) than the mean RTV of the control group, an antitumor effect was determined to be present. FIGS. 1 and 2 and Tables 19 and 20 show the results. In the figures, the symbol "*" indicates a statistically significant difference.

TV (mm$^3$)=(length×width$^2$)/2

RTV=(TV on day 15)/(TV on day 0 or day 1)

T/C(%)=(the mean RTV of a test-solution-administered group)/(the mean RTV of the control group)×100

Figure 3:
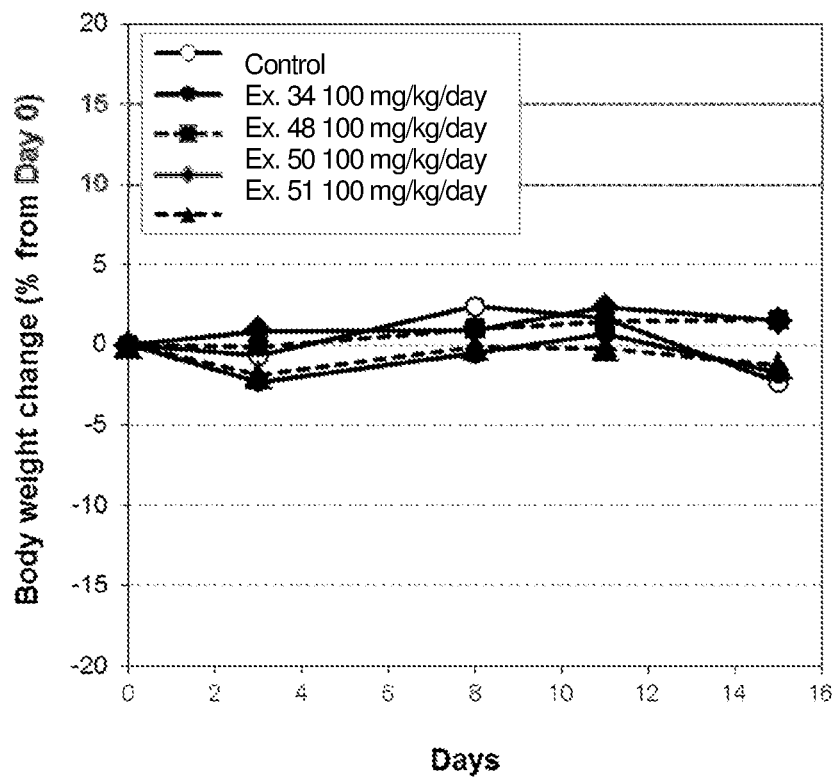
FIG. 3 illustrates changes in body weight during the test in Test Example 5.
Figure 4:
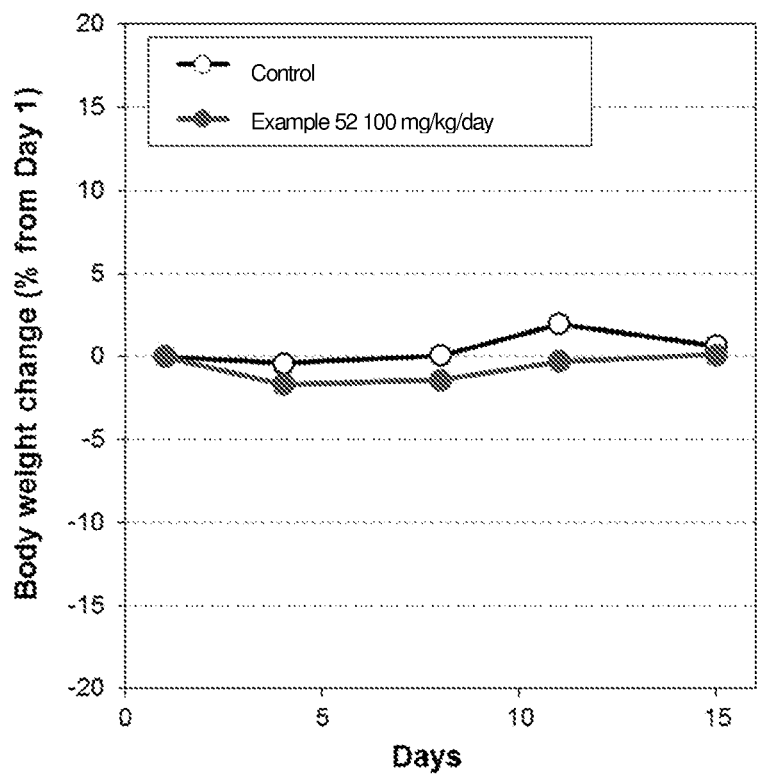
FIG. 4 illustrates changes in body weight during the test in Test Example 5.

To determine the index of the toxicity, the body weight (body weight: BW) of the mice was measured over time, and the mean body weight change (body weight change: BWC (%)) from the grouping day (day 0 or day 1) to day 15 was calculated from the following equation (n: the day on which the body weight was measured at 2 times/week, and the final measurement day is day 15 on which the final evaluation was performed). FIGS. 3 and 4 show the results.

BWC (%)=[(BW on day n)−(BW on day 0 or day 1)]/(BW on day 0 or day 1)×100

As is clear from FIGS. 1 and 2 and Tables 19 and 20, the compounds of the present invention exhibited a remarkable antitumor effect on human thyroid cancer lines TT carrying RET-activating mutation that were subcutaneously implanted into nude mice. As shown in FIGS. 3 and 4, toxicity, such as weight loss, was not observed.

TABLE 19

| Compound Name | Number of Animals | TV (mm$^3$) Day 0 Mean ± SE | TV (mm$^3$) Day 15 Mean ± SE | RTV Day 15 Mean ± SE | T/C (%) |
|---|---|---|---|---|---|
| Control | 5 | 139.61 ± 8.75 | 491.55 ± 36.88 | 3.53 ± 0.18 | 100 |
| Example 34 | 5 | 139.31 ± 9.14 | 205.51 ± 8.30 | 1.49 ± 0.09 | 42 |
| Example 48 | 5 | 138.44 ± 9.11 | 215.87 ± 25.61 | 1.55 ± 0.13 | 44 |
| Example 50 | 5 | 143.56 ± 9.24 | 253.41 ± 28.93 | 1.76 ± 0.16 | 50 |
| Example 51 | 5 | 134.36 ± 7.83 | 190.88 ± 15.75 | 1.42 ± 0.07 | 40 |

TABLE 20

| Compound Name | Number of Animals | TV (mm$^3$) Day 1 Mean ± SE | TV (mm$^3$) Day 15 Mean ± SE | RTV Day 15 Mean ± SE | T/C (%) |
|---|---|---|---|---|---|
| Control | 6 | 137.55 ± 14.64 | 381.97 ± 40.17 | 2.78 ± 0.16 | 100 |
| Example 52 | 6 | 140.33 ± 15.45 | 131.10 ± 31.12 | 0.89 ± 0.11 | 32 |

Test Example 6: Evaluation of Stability in Hepatic Microsome

Solutions of the tested compounds in DMSO/acetonitrile (the final concentration of each tested compound was 1 μM, the final concentration of DMSO was 0.01%, and the final concentration of acetonitrile was 1%) were individually added to a hepatic microsome mixture solution (mouse hepatic microsome with a final concentration of 0.25 mg/mL, a potassium phosphate buffer with a final concentration of 100 mM, and magnesium chloride with a final concentration of 3 mM), and each mixture was pre-incubated at 37° C. for 5 minutes. A NADPH-generating system (glucose-6-phosphate with a final concentration of 10 mM, oxidized nicotinamide adenine dinucleotide phosphate with a final concentration of 1 mM, and glucose-6-phosphate dehydrogenase with a final concentration of 1 unit/mL) was added to a portion of each mixture solution, and metabolic reaction was started. After incubation at 37° C. for 30 minutes, a double amount of ethanol was added thereto to terminate the reaction, thereby obtaining post-reaction samples. A double amount of ethanol was added to each of the remaining mixture solutions, and a NADPH-generating system was further added thereto, thereby obtaining pre-reaction samples. The pre-reaction samples and post-reaction samples were centrifuged at 2000×g, and their supernatant was filtered through a glass filter. Each filtrate was then introduced into LC-MS/MS, and MS/MS peaks of the tested compounds were detected. From the ratio of the post-reaction MS/MS peak to the pre-reaction MS/MS peak of the tested compounds, the percentage of the remaining tested compounds (remaining %) was calculated.

The results show that whereas compound 4 of Comparative Examples had a remaining percentage of 0% in any case, the compounds of the present invention or salts thereof described in the Examples had a high remaining percentage. This indicates that the compounds of the present invention or salts thereof are significantly more stable in mouse hepatic microsome than the compound of Comparative Examples.

Test Example 7: Evaluation of Oral Absorption

The compounds of the present invention were suspended or dissolved in 0.5% HPMC and 0.1N hydrochloric acid, and orally administered to BALB/cA mice. At a time point of 0.5, 1, 2, 4, and 6 hours after the oral administration, the blood of the mice was collected from their ocular fundus or facial vein, and centrifuged to obtain plasma. The concentration of the compounds in the obtained plasma was measured by LC-MS/MS, and oral absorption was evaluated.

The results reveal that the plasma concentration of the compounds of the present invention was sufficient, indicating excellent oral absorption.

The invention claimed is:
1. A method for treating a malignant tumor, comprising administering an effective amount of a compound represented by Formula (I) below or a salt thereof to a mammal in need thereof:

(I)

wherein A is pyrazolyl substituted with n-number of $R^1$;
$R^1$ is
  halogen,
  cyano,
  substituted or unsubstituted C1-C6 alkyl,
  substituted or unsubstituted C3-C7 cycloalkyl,
  substituted or unsubstituted C6-C14 aromatic hydrocarbon, or
  a substituted or unsubstituted C3-C10 monocyclic or polycyclic saturated or unsaturated heterocyclic group containing 1 to 3 identical or different heteroatoms selected from nitrogen, oxygen, and sulfur;
$R^2$ is
  substituted or unsubstituted C1-C10 alkyl,
  substituted or unsubstituted C3-C7 cycloalkyl,
  substituted or unsubstituted C2-C6 alkenyl,
  substituted or unsubstituted C3-C7 cycloalkenyl,
  substituted or unsubstituted C4-C12 bridged cycloalkyl, substituted or unsubstituted C6-C14 aromatic hydrocarbon, or
  a substituted or unsubstituted C3-C10 monocyclic or polycyclic saturated or unsaturated heterocyclic group containing 1 to 3 identical or different heteroatoms selected from nitrogen, oxygen, and sulfur;
X is
  $CR^3$, wherein $R^3$ is
    hydrogen,
    halogen,
    cyano,
    substituted or unsubstituted C1-C6 alkyl,
    substituted or unsubstituted C2-C6 alkenyl,
    substituted or unsubstituted C2-C6 alkynyl,
    substituted or unsubstituted C1-C6 alkoxy,
    substituted or unsubstituted amino,
    substituted or unsubstituted C6-C14 aromatic hydrocarbon, or
    a substituted or unsubstituted C3-C10 monocyclic or polycyclic unsaturated heterocyclic group containing 1 to 3 identical or different heteroatoms selected from nitrogen, oxygen, and sulfur; and
n is an integer of 0 to 3,
wherein when n is 2 or 3, $R^1$ may be identical or different from each other.

2. The method according to claim 1, wherein in Formula (I),
A is pyrazolyl substituted with n-number of $R^1$;
$R^1$ is
  halogen;
  cyano;
  C1-C6 alkyl that may be substituted with halogen or C1-C4 alkoxy;
  C3-C7 cycloalkyl;
  phenyl; or
  a C3-C6 monocyclic unsaturated heterocyclic group containing one oxygen atom or one sulfur atom;
$R^2$ is
  linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
  C3-C7 cycloalkyl that may be substituted with halogen, C1-C4 alkyl, halogeno C1-C4 alkyl, or C3-C5 cycloalkyl;
  C2-C6 alkenyl that may be substituted with halogen; or
  C4-C12 bridged cycloalkyl that may be substituted with C1-C4 alkyl;
X is
  $CR^3$, wherein $R^3$ is
    hydrogen;
    halogen;
    C1-C6 alkyl;
    C2-C4 alkynyl that may be substituted with
      C1-C6 alkyl that may be substituted with hydroxy,
      C3-C7 cycloalkyl that may be substituted with hydroxy,
      one or more C3-C6 monocyclic saturated heterocyclic groups containing 1 to 3 identical or different heteroatoms selected from nitrogen, oxygen, and sulfur, or
      one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
    C1-C4 alkoxy that may be substituted with one or more C3-C6 monocyclic saturated heterocyclic groups containing 1 to 3 identical or different heteroatoms selected from nitrogen, oxygen, and sulfur; and
n is an integer of 1 or 2,
wherein when n is 2, $R^1$ may be identical or different from each other.

3. The method according to claim 1, wherein the compound represented by Formula (I) or a salt thereof is a compound represented by Formula (II) below or a salt thereof:

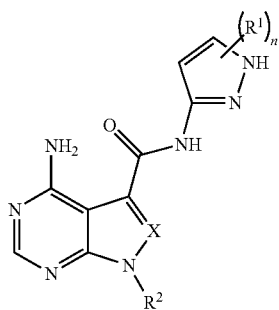

(II)

wherein R¹ is
halogen;
cyano;
C1-C6 alkyl that may be substituted with halogen;
C3-C7 cycloalkyl;
phenyl; or
a C3-C6 monocyclic unsaturated heterocyclic group containing one oxygen atom or one sulfur atom;
R² is
linear C1-C6 alkyl or branched C3-C8 alkyl that may be substituted with halogen, C3-C7 cycloalkyl that may be substituted with C1-C4 alkyl, phenyl, C1-C4 alkoxy, or one or more C3-C6 monocyclic unsaturated heterocyclic groups containing one oxygen atom or one sulfur atom;
C3-C7 cycloalkyl that may be substituted with halogen, C1-C4 alkyl, halogeno C1-C4 alkyl, or C3-C5 cycloalkyl;
C2-C6 alkenyl that may be substituted with halogen; or
C4-C12 bridged cycloalkyl;
X is
CR³, wherein R³ is
hydrogen;
halogen;
C1-C4 alkyl;
C2-C4 alkynyl that may be substituted with
C1-C6 alkyl that may be substituted with hydroxy,
C3-C7 cycloalkyl that may be substituted with hydroxy,
one or more C3-C6 monocyclic saturated heterocyclic groups containing 1 to 3 identical or different heteroatoms selected from nitrogen, oxygen, and sulfur, or
one or more C3-C10 monocyclic or polycyclic unsaturated heterocyclic groups that may be substituted with C1-C6 alkyl and contains 1 to 3 identical or different heteroatoms selected from nitrogen, oxygen, and sulfur; or
C1-C4 alkoxy; and
n is an integer of 1 or 2,
wherein when n is 2, R¹ may be identical or different from each other.

* * * * *